(12) United States Patent
Tanaka et al.

(10) Patent No.: US 11,420,944 B2
(45) Date of Patent: Aug. 23, 2022

(54) VOLTAGE-DEPENDENT T-TYPE CALCIUM CHANNEL BLOCKER

(71) Applicants: Nippon Chemiphar Co., Ltd., Tokyo (JP); Kinki University, Osaka (JP)

(72) Inventors: Hiroto Tanaka, Tokyo (JP); Isao Ooi, Misato (JP); Yuzo Mogi, Misato (JP); Masaaki Hirose, Misato (JP); Tsuyoshi Endo, Misato (JP); Toru Ogawa, Misato (JP); Atsufumi Kawabata, Kashiba (JP)

(73) Assignees: Nippon Chemiphar Co., Ltd., Tokyo (JP); Kinki University, Osaka (JP)

( * ) Notice: Subject to any disclaimer, the term of this patent is extended or adjusted under 35 U.S.C. 154(b) by 0 days.

(21) Appl. No.: 16/069,221

(22) PCT Filed: Jan. 12, 2017

(86) PCT No.: PCT/JP2017/000898
§ 371 (c)(1),
(2) Date: Sep. 27, 2018

(87) PCT Pub. No.: WO2017/122754
PCT Pub. Date: Jul. 20, 2017

(65) Prior Publication Data
US 2019/0077767 A1     Mar. 14, 2019

(30) Foreign Application Priority Data
Jan. 12, 2016   (JP) .............................. JP2016-003769

(51) Int. Cl.
| C07D 403/12 | (2006.01) |
| C07D 407/12 | (2006.01) |
| C07D 409/12 | (2006.01) |
| C07D 409/14 | (2006.01) |
| C07D 413/12 | (2006.01) |
| C07D 417/12 | (2006.01) |
| C07D 235/16 | (2006.01) |
| C07D 413/14 | (2006.01) |

(Continued)

(52) U.S. Cl.
CPC .......... *C07D 235/16* (2013.01); *A61K 31/343* (2013.01); *A61K 31/381* (2013.01); *A61K 31/4025* (2013.01); *A61K 31/4184* (2013.01); *A61K 31/423* (2013.01); *A61K 31/427* (2013.01); *A61K 31/428* (2013.01); *A61K 31/4245* (2013.01); *A61K 31/437* (2013.01); *A61K 31/4355* (2013.01); *A61K 31/454* (2013.01); *A61K 31/4709* (2013.01); *A61K 31/496* (2013.01); *A61K 31/5377* (2013.01); *A61K 31/55* (2013.01); *A61P 25/04* (2018.01); *C07D 307/81* (2013.01); *C07D 333/32* (2013.01); *C07D 401/12* (2013.01); *C07D 403/12* (2013.01); *C07D 405/12* (2013.01); *C07D 409/12* (2013.01); *C07D 409/14* (2013.01); *C07D 413/12* (2013.01); *C07D 413/14* (2013.01); *C07D 417/12* (2013.01); *C07D 417/14* (2013.01); *C07D 471/04* (2013.01); *C07D 491/048* (2013.01)

(58) Field of Classification Search
CPC .. C07D 403/12; C07D 407/12; C07D 409/12; C07D 409/14; C07D 413/12; C07D 417/12
See application file for complete search history.

(56) References Cited

U.S. PATENT DOCUMENTS 7,144,881 B2    12/2006   Wu et al.

FOREIGN PATENT DOCUMENTS

| JP | 2008535801 A | 9/2008 |
| JP | 2009534320 A | 9/2009 |

(Continued)

OTHER PUBLICATIONS

RN 1825360-74-4 in STN, 2015.*

(Continued)

*Primary Examiner* — Brian E McDowell
(74) *Attorney, Agent, or Firm* — Wood Herron & Evans LLP

(57) ABSTRACT

A compound represented by the following General Formula (I), a tautomer or a stereoisomer of the compound, a pharmaceutically acceptable salt thereof, or a solvate thereof, is used as a voltage-dependent T-type calcium channel blocker:

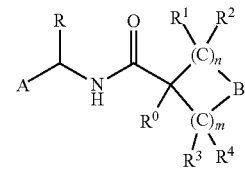

wherein A represents a 5-membered heteroaryl group or a fused ring of a 5-membered or 6-membered heterocyclic ring with a benzene ring or a pyridine ring, each of which may have a substituent; R represents a hydrogen atom or the like; B represents CR5(Q1) or NQ2, herein Q1 represents a benzimidazole group which may have a substituent, or the like; Q2 represents an alkyl group having 1 to 8 carbon atoms which may have a substituent, a heteroaryl group which may have a substituent, or the like; R0, R1, R2, R3, R4, and R5 each represent a hydrogen atom or the like; and n and m each represent 0, 1, or 2.

50 Claims, 1 Drawing Sheet

(51) Int. Cl.
| | |
|---|---|
| C07D 401/12 | (2006.01) |
| C07D 405/12 | (2006.01) |
| C07D 417/14 | (2006.01) |
| C07D 471/04 | (2006.01) |
| C07D 491/048 | (2006.01) |
| A61K 31/4184 | (2006.01) |
| A61K 31/4025 | (2006.01) |
| A61K 31/428 | (2006.01) |
| A61K 31/5377 | (2006.01) |
| A61K 31/427 | (2006.01) |
| C07D 333/32 | (2006.01) |
| A61K 31/4245 | (2006.01) |
| A61K 31/496 | (2006.01) |
| A61K 31/381 | (2006.01) |
| A61K 31/437 | (2006.01) |
| A61K 31/423 | (2006.01) |
| A61K 31/55 | (2006.01) |
| A61K 31/343 | (2006.01) |
| A61K 31/454 | (2006.01) |
| C07D 307/81 | (2006.01) |
| A61K 31/4355 | (2006.01) |
| A61K 31/4709 | (2006.01) |
| A61P 25/04 | (2006.01) |

(56) References Cited

FOREIGN PATENT DOCUMENTS

| | | | |
|---|---|---|---|
| JP | 2012528078 | A | 11/2012 |
| JP | 5269761 | B2 | 8/2013 |
| JP | 5309033 | B2 | 10/2013 |
| WO | 9931048 | A1 | 6/1999 |
| WO | 2008057856 | A2 | 5/2008 |
| WO | 2010060952 | A1 | 6/2010 |
| WO | 2010137351 | A1 | 12/2010 |
| WO | 2011053542 | A1 | 5/2011 |
| WO | 2011056744 | A1 | 5/2011 |
| WO | 2014086453 | A1 | 6/2014 |
| WO | 2015093534 | A1 | 6/2015 |
| WO | 2015103317 | A1 | 7/2015 |
| WO | 2015130905 | A1 | 9/2015 |
| WO | 2016036633 | A1 | 3/2016 |
| WO | 2016036636 | A1 | 3/2016 |
| WO | 2016036638 | A1 | 3/2016 |
| WO | WO 2016/036633 | * | 3/2016 |
| WO | WO 2016/036638 | * | 3/2016 |
| WO | 2017031204 | A1 | 2/2017 |

OTHER PUBLICATIONS

Jacus MO, Uebele VN, Renger JJ, Todorovic SM. ; Presynaptic Cav3.2 channels regulate excitatory neurotransmission in nociceptive dorsal horn neurons. J Neurosci. 2012, 32, 9374-82.
Choi S, Na HS, Kim J, Lee J, Lee S, Kim D, Park J, Chen CC, Campbell KP, Shin HS. ; Attenuated pain responses in mice lacking Cav3.2 T-type channels. Genes Brain Behav. 2007, 6, 425-431.
Jagodic MM, Pathirathna S, Joksovic PM, Lee W, Nelson MT, Naik AK, Su P, Jevtovic-Todorovic V, Todorovic SM. ; Upregulation of the T-type calcium current in small rat sensory neurons after chronic constrictive injury of the sciatic nerve. J Neurophysiol. 2008, 99, 3151-6.
Messinger RB, Naik AK, Jagodic MM, Nelson MT, Lee WY, Choe WJ, Orestes P, Latham JR, Todorovic SM, Jevtovic-Todorovic V. ; In vivo silencing of the Cav3.2 T-type calcium channels in sensory neurons alleviates hyperalgesia in rats with streptozocin-induced diabetic neuropathy. Pain. 2009, 145, 184-95.
Jagodic MM, Pathirathna S, Nelson MT, Mancuso S, Joksovic PM, Rosenberg ER, Bayliss DA, Jevtovic-Todorovic V, Todorovic SM. ; Cell-specific alterations of T-type calcium current in painful diabetic neuropathy enhance excitability of sensory neurons. J Neurosci. 2007, 27, 3305-16.
Marger F, Gelot A, Alloui A, Matricon J, Ferrer JF, Barrere C, Pizzoccaro A, Muller E, Nargeot J, Snutch TP, Eschalier A, Bourinet E, Ardid D. ; T-type calcium channels contribute to colonic hypersensitivity in a rat model of irritable bowel syndrome. Proc Natl Acad Sci USA. 2011, 5. 11268-73.
Shinzo Kagabu et al., Journal of Pesticide Science (Tokyo, Japan) (2009), 34(3), 161-172.
Yasumasa Hamada et al., Tetrahedron Letters (1985), 26(27), 3223-26.
Imbriglio, Jason E. et al., Discovery and Pharmacology of a Novel Class of Diacylglycerol Acyltransferase 2 Inhibitors, Journal of Medicinal Chemistry, 2015, 58 (23), pp. 9345-9353, ISSN: 0022-2623.
Database Registry [Online] Retrieved from STN, Entered STN: May 22, 2011, retrieval date: Mar. 15, 2017, CAS Registry No. 1298752-60-9, 1298683-74-5, 1298337-65-1, 1298337-61-7.
Database Registry [Online] Retrieved from STN, Entered STN: May 19, 2011, retrieval date: Mar. 15, 2017, CAS Registry No. 1297113-68-8.
Database Registry [Online] Retrieved from STN, Entered STN: Jan. 3, 2016, retrieval date: Mar. 15, 2017, CAS Registry No. 1840218-78-1.
Database Registry [Online] Retrieved from STN, Entered STN: May 15, 2015, retrieval date: Mar. 15, 2017, CAS Registry No. 1705544-88-2, 1705083-33-5.
Database Registry [Online] Retrieved from STN, Entered STN: Apr. 13, 2011, retrieval date: Mar. 15, 2017, CAS Registry No. 1278662-77-3.
Database Registry [Online] Retrieved from STN, Entered STN: Jul. 5, 2015, retrieval date: Mar. 15, 2017, CAS Registry No. 1795037-59-0.
Database Registry [Online] Retrieved from STN, Entered STN: Sep. 26, 2014, retrieval date: Mar. 15, 2017, CAS Registry No. 1626870-01-6.
Database Registry [Online] Retrieved from STN, Entered STN: Dec. 17, 2013, retrieval date: Mar. 15, 2017, CAS Registry No. 1496862-05-5.
Database Registry [Online] Retrieved from STN, Entered STN: Sep. 12, 2014, retrieval date: Mar. 15, 2017, CAS Registry No. 1622520-30-2.
Database Registry [Online] Retrieved from STN, Entered STN: Jun. 18, 2015, retrieval date: Mar. 15, 2017, CAS Registry No. 1783191-18-3.
Database Registry [Online] Retrieved from STN, Entered STN: Mar. 9, 2015, retrieval date: Mar. 15, 2017, CAS Registry No. 1658489-18-9.
Database Registry [Online] Retrieved from STN, Entered STN: Mar. 21, 2014, retrieval date: Mar. 15, 2017, CAS Registry No. 1571663-30-3.
Database Registry [Online] Retrieved from STN, Entered STN: Mar. 21, 2010, retrieval date: Mar. 15, 2017, CAS Registry No. 1212477-07-0.
Database Registry [Online] Retrieved from STN, Entered STN: May 13, 2011, retrieval date:Mar. 15, 2017, CAS Registry No. 1294097-04-3, 1294095-97-8.
Database Registry [Online] Retrieved from STN, Entered STN: Aug. 15, 2011, retrieval date:Mar. 15, 2017, CAS Registry No. 1318209-03-8.
PCT Office, International Search Report issued in PCT/JP2017/000898 dated Mar. 28, 2017, 11 pages.
European Patent Office, Search Report issued in EP 17738507.7 dated Aug. 9, 2019. 10 pages.
European Patent Office, Office Action issued in EP 17738507.7 dated Jul. 29, 2021.

* cited by examiner

***$P<0.001$ vs. Sham + Vehicle. ††$P<0.01$, †††$P<0.001$ vs. PSNL + Vehicle.

VOLTAGE-DEPENDENT T-TYPE CALCIUM CHANNEL BLOCKER

TECHNICAL FIELD

The present invention relates to a compound having a (cycloalkyl)carboxamide skeleton or a (saturated nitrogen-containing heterocyclic)carboxamide skeleton, and a voltage-dependent T-type calcium channel blocker containing this compound as an active ingredient.

BACKGROUND ART

Voltage-dependent T-type calcium channels are expressed at the dorsal root ganglions of primary afferent nerve fibers or the posterior horn of the spinal cord (Non-Patent Literature 1). Since it has been reported that in knockout mice in which a T-type calcium channel (Cav 3.2 channel) has been deleted, pain-related actions in acute pain, inflammatory pain, and visceral pain are reduced (Non-Patent Literature 2), Cav 3.2 channel is closely involved in the transmission of pain. Furthermore, it has been reported that in the dorsal root ganglions of a pathological animal model having pain, such as neuropathic pain (Non-Patent Literature 3), painful diabetic neuropathy (Non-Patent Literatures 4 and 5), and irritable bowel syndrome (Non-Patent Literature 6), the current density of the T-type calcium channels increases, and the T-type calcium channels become overactive. Thus, the T-type calcium channels can serve as a target for agents of pain therapy of a new mechanism. A T-type calcium channel inhibitor has an action mechanism that is different from the action mechanism of opioid receptor agonists or $\alpha_2\delta$ ligands, and therefore, it is expected that a T-type calcium channel inhibitor also exhibits an effect on chronic pain that is resistant to existing drugs.

Meanwhile, regarding a compound having a (cycloalkyl)carboxamide skeleton, Non-Patent Literature 7 describes a compound represented by the following Formula (A):

[Chemical Formula 1]

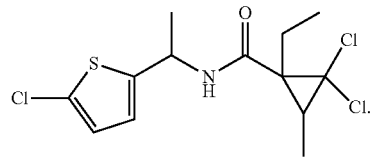

and Patent Literature 1 describes a compound represented by the following Formula (B):

[Chemical Formula 2]

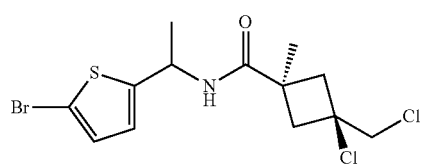

Regarding a compound having a (saturated nitrogen-containing heterocyclic)carboxamide skeleton, Non-Patent Literature 8 describes a compound represented by the following Formula (C):

[Chemical Formula 3]

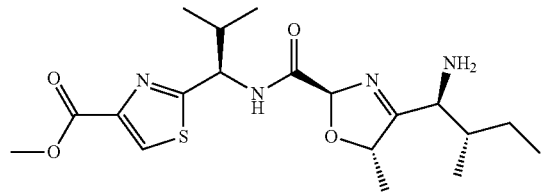

In Non-Patent Literatures 7 and 8 and Patent Literature 1, no description is given to the effect that any of the compounds represented by the above-described Formulae (A) to (C) has voltage-dependent T-type calcium channel inhibitory action.

Patent Literature 2, Patent Literature 3, and Patent Literature 4 also disclose compounds having a cyclopropanamide structure; however, the purpose of the compound described in Patent Literature 2 is to control a NO synthase, and no specific example is described therein for a compound in which a heteroarylalkyl is bonded to a nitrogen atom.

Patent Literature 3 also provides a glucocorticoid receptor modulator; however, a compound in which a heteroarylalkyl is bonded to a nitrogen atom is not described therein.

Patent Literature 4 provides a K channel opener, and a compound in which 1-(2,3-dihydrobenzofuran-5-yl)ethyl is bonded to a nitrogen atom is described.

Meanwhile, as a compound having voltage-dependent T-type calcium channel inhibitory action, Patent Literature 5 describes a compound represented by the following Formula (D) (RQ-00311651):

[Chemical Formula 4]

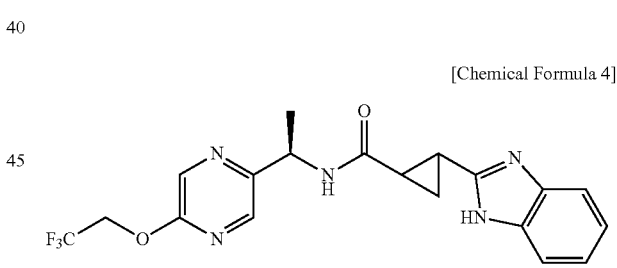

and Patent Literature 6 describes a compound represented by the following Formula (E):

[Chemical Formula 5]

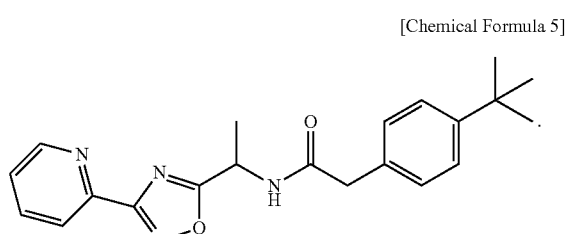

Patent Literature 7 describes a compound represented by the following Formula (F) (TTA-A2):

[Chemical Formula 6]

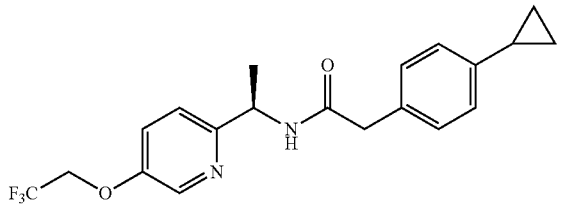

and Patent Literature 8 describes a compound represented by the following Formula (G):

[Chemical Formula 7]

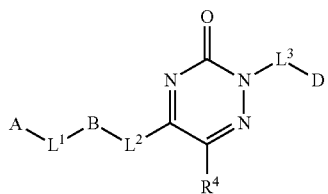

In Patent Literature 8, pain is mentioned as a target disease of a compound having voltage-dependent T-type calcium channel inhibitory action, and a limited example of the target disease may be chronic pain, while a more limited example of the target disease may be neuropathic pain.

It is further described in this patent literature that "pain is classified into chronic and acute pains including neuropathic, inflammatory, cancerous, and visceral pains, and causative diseases thereof include diabetic neuropathy, traumatic neuropathy, compression of nerve, strangulation, spinal cord injury, apoplexy, fibromyalgia, carpal tunnel syndrome, osteoarthritis, rheumatoid arthritis, multiple sclerosis, herpes zoster, herpes simplex, syphilis, neuropathy induced by cancer chemotherapy or HIV and HIV treatment, chronic arthralgia, post-herpetic neuralgia, neuroma pain, trigeminal neuralgia, phantom limb pain, post-operative pain, stump pain, toothache, nerve plexus neuropathy, glossopharyngeal neuralgia, laryngeal neuralgia, migraine, carcinomatous neuropathy, multiple neuropathy, causalgia, low back pain, complex regional pain syndrome (CRPS), and thalamic pain". It is also described to the effect that pains originating from causes other than the causes mentioned herein are also included in the target diseases of the active ingredients described in the Patent Literatures described above.

It is also described to the effect that "diseases other than pain include diseases associated with central nervous system (CNS) disorders, diseases associated with bladder dysfunction, apoplexy, pruritus, atopic dermatitis, hypertension, hyperaldosteronism, edema, ischemic heart diseases, age-related macular degeneration, cancer, diabetes mellitus, sterility and sexual incompetence, arrhythmia, and kidney diseases; the diseases associated with central nervous system (CNS) disorders include epilepsy, essential tremor, schizophrenia, Parkinson's disease, manic depressive psychosis, bipolar disorder, depression, anxiety, dementia, drug dependence, Huntington's disease, and sleep disorder; and the diseases associated with bladder dysfunction include overactive bladder."

CITATION LIST

Patent Literatures

Patent Literature 1: WO 99/31048
Patent Literature 2: Japanese Patent No. 5309033
Patent Literature 3: WO 2008/057856
Patent Literature 4: U.S. Pat. No. 7,144,881 B2
Patent Literature 5: WO 2010/137351
Patent Literature 6: WO 2011/053542
Patent Literature 7: Japanese Patent No. 5269761
Patent Literature 8: WO 2015/093534

Non-Patent Literatures

Non-Patent Literature 1: Jacus M O, Uebele V N, Renger J J, Todorovic S M.; Presynaptic Cav3.2 channels regulate excitatory neurotransmission in nociceptive dorsal horn neurons. J Neurosci. 2012, 32, 9374-82.
Non-Patent Literature 2: Choi S, Na H S, Kim J, Lee J, Lee S, Kim D, Park J, Chen C C, Campbell K P, Shin H S.; Attenuated pain responses in mice lacking CaV3.2 T-type channels. Genes Brain Behav. 2007, 6, 425-331.
Non-Patent Literature 3: Jagodic M M, Pathirathna S, Joksovic P M, Lee W, Nelson M T, Naik A K, Su P, Jevtovic-Todorovic V, Todorovic S M.; Upregulation of the T-type calcium current in small rat sensory neurons after chronic constrictive injury of the sciatic nerve. J Neurophysiol. 2008, 99, 3151-6.
Non-Patent Literature 4: Messinger R B, Naik A K, Jagodic M M, Nelson M T, Lee W Y, Choe W J, Orestes P, Latham J R, Todorovic S M, Jevtovic-Todorovic V.; In vivo silencing of the Ca(V)3.2 T-type calcium channels in sensory neurons alleviates hyperalgesia in rats with streptozocin-induced diabetic neuropathy. Pain. 2009, 145, 184-95.
Non-Patent Literature 5: Jagodic M M, Pathirathna S, Nelson M T, Mancuso S, Joksovic P M, Rosenberg E R, Bayliss D A, Jevtovic-Todorovic V, Todorovic S M.; Cell-specific alterations of T-type calcium current in painful diabetic neuropathy enhance excitability of sensory neurons. J Neurosci. 2007, 27, 3305-16.
Non-Patent Literature 6: Marger F, Gelot A, Alloui A, Matricon J, Ferrer J F, Barrere C, Pizzoccaro A, Muller E, Nargeot J, Snutch T P, Eschalier A, Bourinet E, Ardid D.; T-type calcium channels contribute to colonic hypersensitivity in a rat model of irritable bowel syndrome. Proc Natl Acad Sci USA. 2011, 5. 11268-73.
Non-Patent Literature 7: Journal of Pesticide Science (Tokyo, Japan) (2009), 34(3), 161-172.
Non-Patent Literature 8: Tetrahedron Letters (1985), 26(27), 3223-26.

SUMMARY OF INVENTION

Technical Problem

An object of the present invention is to provide a compound having a (cycloalkyl)carboxamide skeleton or a (saturated nitrogen-containing heterocyclic)carboxamide skeleton, the compound having voltage-dependent T-type calcium channel inhibitory action, and to provide a voltage-dependent T-type calcium channel blocker containing this compound as an active ingredient.

Another object of the present invention is to provide a compound having a (cycloalkyl)carboxamide skeleton or a (saturated nitrogen-containing heterocyclic)carboxamide skeleton, the compound having superior voltage-dependent T-type calcium channel inhibitory action in an inactivated state compared to a quiescent state or a closed state.

Solution to Problem

That is, the present invention relates to a compound represented by the following General Formula (IA), a tautomer or a stereoisomer of the compound, a pharmaceutically acceptable salt thereof, or a solvate thereof:

[Chemical Formula 8]

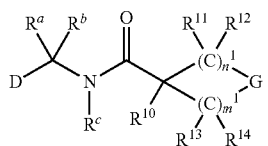

(IA)

wherein D represents a 5-membered heteroaryl group or a fused ring of a 5-membered or 6-membered heterocyclic ring with a benzene ring or a pyridine ring, the 5-membered heteroaryl group having one to three identical or different heteroatoms selected from the group consisting of an oxygen atom, a nitrogen atom, and a sulfur atom as a ring-constituting element(s), the 5-membered heteroaryl group having, as a substituent, at least one selected from the group consisting of a halogen atom, a cyano group, a carboxyl group, an alkyl group having 1 to 8 carbon atoms, a cyclopropyl group, an alkoxy group having 1 to 8 carbon atoms, a phenyl group which may have a substituent, a group represented by the following formula:

[Chemical Formula 9]

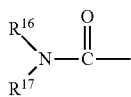

an alkyl group having 1 to 8 carbon atoms and substituted with 1 to 5 halogen atoms, an alkoxy group having 1 to 8 carbon atoms and substituted with 1 to 5 halogen atoms, and a (C1-C8 alkyloxy)carbonyl group, and the 5-membered or 6-membered heterocyclic ring having one or two identical or different heteroatoms selected from the group consisting of an oxygen atom, a nitrogen atom, and a sulfur atom as a ring-constituting element(s), the fused ring may have the above-described substituent carried by the 5-membered heteroaryl group, while D is bonded to $C(R^a)(R^b)N$ via a ring-constituting carbon atom;

wherein, $R^{16}$ and $R^{17}$, which may be identical or different, each represent a hydrogen atom, an alkyl group having 1 to 8 carbon atoms, or an aryl group which may have a substituent; or $R^{16}$, $R^{17}$, and the nitrogen atom to which $R^{16}$ and $R^{17}$ are bonded are joined together and represent a saturated nitrogen-containing saturated 4-membered to 7-membered heterocyclic ring which may further have one heteroatom selected from the group consisting of an oxygen atom, a nitrogen atom, and a sulfur atom as a ring-constituting element, and may have a substituent;

$R^a$ represents a hydrogen atom, a cyano group, an alkyl group having 1 to 8 carbon atoms, an alkyl group having 1 to 8 carbon atoms and substituted with 1 to 5 halogen atoms, a 3-membered to 7-membered cycloalkyl group, or a heteroaryl group which may have a substituent, and $R^b$ represents a hydrogen atom or an alkyl group having 1 to 8 carbon atoms;

alternatively, $R^a$, $R^b$, and the carbon atom to which $R^a$ and $R^b$ are bonded are joined together and form a 3-membered to 6-membered cycloalkyl ring;

$R^c$ represents a hydrogen atom or an alkyl group having 1 to 8 carbon atoms;

G represents $CR^{15}(W^1)$ or $NW^2$;

wherein, $W^1$ represents an alkyl group having 1 to 8 carbon atoms substituted with a phenyloxy group which may have any one selected from the group consisting of a trifluoromethyl group, a t-butyl group, and a methoxy group as a substituent of the phenyl group, a phenylaminocarbonyl group which may have any one selected from the group consisting of a trifluoromethyl group, a t-butyl group, and a methoxy group as a substituent of the phenyl group, a heteroaryl group which may have a substituent, or an aryl group which may have a substituent;

$W^2$ represents an alkylsulfonyl group having 1 to 8 carbon atoms; an arylsulfonyl group which may have a substituent; an alkyl group having 1 to 8 carbon atoms which may be substituted with any one selected from the group consisting of an alkylcarbonyl group having 1 to 8 carbon atoms, an adamantylaminocarbonyl group, an (optionally substituted C1-C8 alkyl)aminocarbonyl group, an optionally substituted arylaminocarbonyl group, and an optionally substituted heteroarylaminocarbonyl group as a substituent; a heteroaryl group which may have a substituent, or an aryl group which may have a substituent;

the substituent which may be carried by the heteroaryl group, aryl group, arylsulfonyl group, arylaminocarbonyl group, and heteroarylaminocarbonyl group of $W^1$ and $W^2$ is a halogen atom, a carboxyl group, a cyano group, a hydroxyl group, an alkyl group having 1 to 8 carbon atoms, an alkoxy group having 1 to 8 carbon atoms, an alkylsulfonyl group having 1 to 8 carbon atoms, an alkyl group having 1 to 8 carbon atoms and substituted with 1 to 5 halogen atoms, an alkoxy group having 1 to 8 carbon atoms and substituted with 1 to 5 halogen atoms, an amino group, an alkylamino group having 1 to 8 carbon atoms, a carboxamide, a phenyl group, a pyridyl group, or an alkyl group having 1 to 5 carbon atoms and substituted with a phenyl group;

$R^{10}$, $R^{11}$, $R^{12}$, $R^{13}$, $R^{14}$, and $R^{15}$, which may be identical or different, each represent a hydrogen atom, a cyano group, a hydroxyl group, a halogen atom, a carboxyl group, an amino group, an alkylamino group having 1 to 8 carbon atoms, a dialkylamino group having 2 to 12 carbon atoms, or an alkyl group having 1 to 8 carbon atoms;

$n^1$ and $m^1$ each represent 0, 1, or 2, provided that $n^1$ and $m^1$ are not 0 and 2 at the same time; and in a case where D is 2,3-dihydrobenzofuran which may have a substituent, $W^1$ is not a phenyl group which may have a substituent.

Furthermore, the present invention relates to a compound represented by the following General Formula (I), a tautomer or a stereoisomer of the compound, a pharmaceutically acceptable salt thereof, or a solvate thereof:

[Chemical Formula 10]

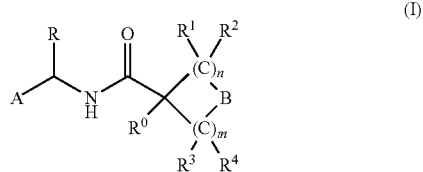

(I)

wherein A represents a 5-membered heteroaryl group or a fused ring of a 5-membered or 6-membered heterocyclic ring with a benzene ring or a pyridine ring, the 5-membered heteroaryl group having one to three identical or different heteroatoms selected from the group consisting of an oxygen atom, a nitrogen atom, and a sulfur atom as a ring-constituting element(s), the 5-membered heteroaryl group having, as a substituent, at least one selected from the group consisting of a halogen atom, a cyano group, a carboxyl group, an alkyl group having 1 to 8 carbon atoms, a cyclopropyl group, an alkoxy group having 1 to 8 carbon atoms, a phenyl group which may have a substituent, a group represented by the following formula:

[Chemical Formula 11]

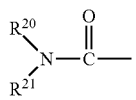

an alkyl group having 1 to 8 carbon atoms and substituted with 1 to 5 halogen atoms, an alkoxy group having 1 to 8 carbon atoms and substituted with 1 to 5 halogen atoms, and a (C1-C8 alkyloxy)carbonyl group, and the 5-membered or 6-membered heterocyclic ring having one or two identical or different heteroatoms selected from the group consisting of an oxygen atom, a nitrogen atom, and a sulfur atom as a ring-constituting element(s), the fused ring may have the above-described substituent carried by the 5-membered heteroaryl group, while A is bonded to CH(R)N via a ring-constituting carbon atom;

wherein, $R^{20}$ and $R^{21}$, which may be identical or different, each represent a hydrogen atom, an alkyl group having 1 to 8 carbon atoms, or an aryl group which may have a substituent; or $R^{20}$, $R^{21}$, and the nitrogen atom to which $R^{20}$ and $R^{21}$ are bonded are joined together and represent a saturated nitrogen-containing saturated 4-membered to 7-membered heterocyclic ring which may further have one heteroatom selected from the group consisting of an oxygen atom, a nitrogen atom, and a sulfur atom as a ring-constituting element, and may have a substituent;

R represents a hydrogen atom, a cyano group, an alkyl group having 1 to 8 carbon atoms, a 3-membered to 7-membered cycloalkyl group, or a heteroaryl group which may have a substituent;

B represents $CR^5(Q^1)$ or $NQ^2$;

wherein, $Q^1$ represents an alkyl group having 1 to 8 carbon atoms and substituted with a phenyloxy group which may have any one selected from the group consisting of a trifluoromethyl group, a t-butyl group, and a methoxy group as a substituent for the phenyl group, a phenylaminocarbonyl group which may have any one selected from the group consisting of a trifluoromethyl group, a t-butyl group, and a methoxy group as a substituent for the phenyl group; a heteroaryl group which may have a substituent; or an aryl group which may have a substituent;

$Q^2$ represents an alkylsulfonyl group having 1 to 8 carbon atoms; an arylsulfonyl group which may have a substituent; an alkyl group having 1 to 8 carbon atoms which may be substituted with any one selected from the group consisting of an alkylcarbonyl group having 1 to 8 carbon atoms, an adamantylaminocarbonyl group, an (optionally substituted C1-C8 alkyl)aminocarbonyl group, an optionally substituted arylaminocarbonyl group, and an optionally substituted heteroarylaminocarbonyl group as a substituent; a heteroaryl group which may have a substituent; or an aryl group which may have a substituent;

the substituent which may be carried by the heteroaryl group, aryl group, arylsulfonyl group, arylaminocarbonyl group, and heteroarylaminocarbonyl group of $Q^1$ and $Q^2$ is selected from the group consisting of a halogen atom, a carboxyl group, a cyano group, a hydroxyl group, an alkyl group having 1 to 8 carbon atoms, an alkoxy group having 1 to 8 carbon atoms, an alkylsulfonyl group having 1 to 8 carbon atoms, an alkyl group having 1 to 8 carbon atoms and substituted with 1 to 5 halogen atoms, an alkoxy group having 1 to 8 carbon atoms and substituted with 1 to 5 halogen atoms, an amino group, an alkylamino group having 1 to 8 carbon atoms, a carboxamide, a phenyl group, a pyridyl group, or an alkyl group having 1 to 5 carbon atoms and substituted with a phenyl group;

$R^0$, $R^1$, $R^2$, $R^3$, $R^4$, and $R^5$, which may be identical or different, each represent a hydrogen atom, a cyano group, a hydroxyl group, a halogen atom, a carboxy group, an amino group, an alkylamino group having 1 to 8 carbon atoms, a dialkylamino group having 2 to 12 carbon atoms, or an alkyl group having 1 to 8 carbon atoms;

n and m each represent 0, 1, or 2, provided that n and m are not 0 and 2 at the same time; and in a case in which A represents 2,3-dihydrobenzofuran which may have a substituent, $Q^1$ is not a phenyl group which may have a substituent.

Furthermore, the present invention relates to a compound represented by the following General Formula (II), a tautomer or a stereoisomer of the compound, a pharmaceutically acceptable salt thereof, or a solvate thereof:

[Chemical Formula 12]

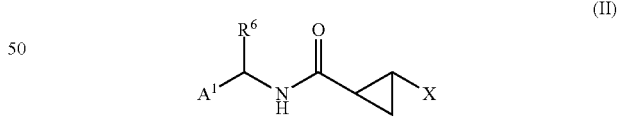

(II)

wherein $A^1$ represents a 5-membered heteroaryl group or a fused ring of a 5-membered or 6-membered heterocyclic ring with a benzene ring or a pyridine ring, the 5-membered heteroaryl group having one to three identical or different heteroatoms selected from the group consisting of an oxygen atom, a nitrogen atom, and a sulfur atom as a ring-constituting element(s), the 5-membered heteroaryl group having, as a substituent, at least one selected from the group consisting of a halogen atom, a cyano group, a carboxyl group, an alkyl group having 1 to 8 carbon atoms, a cyclopropyl group, an alkoxy group having 1 to 8 carbon atoms, a phenyl group which may have a substituent, a group represented by the following formula:

[Chemical Formula 13]

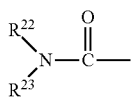

an alkyl group having 1 to 8 carbon atoms and substituted with 1 to 5 halogen atoms, an alkoxy group having 1 to 8 carbon atoms and substituted with 1 to 5 halogen atoms, and a (C1-C8 alkyloxy)carbonyl group, and the 5-membered or 6-membered heterocyclic ring having one or two identical or different heteroatoms selected from the group consisting of an oxygen atom, a nitrogen atom, and a sulfur atom as a ring-constituting element(s), the fused ring may have the above-described substituent carried by the 5-membered heteroaryl group, while $A^1$ is bonded to $CH(R^6)N$ via a ring-constituting carbon atom;

wherein, $R^{22}$ and $R^{23}$, which may be identical or different, each represent a hydrogen atom, an alkyl group having 1 to 8 carbon atoms, or an aryl group which may have a substituent; or $R^{22}$, $R^{23}$, and the nitrogen atom to which $R^{22}$ and $R^{23}$ are bonded are joined together and represent a saturated nitrogen-containing saturated 4-membered to 7-membered heterocyclic ring which may further have one heteroatom selected from the group consisting of an oxygen atom, a nitrogen atom, and a sulfur atom as a ring-constituting element, and may have a substituent;

$R^6$ represents a hydrogen atom, a cyano group, an alkyl group having 1 to 8 carbon atoms, a 3-membered to 7-membered cycloalkyl group, or a heteroaryl group which may have a substituent; and X represents a heteroaryl group which may have, as a substituent, any one selected from the group consisting of a halogen atom, a carboxyl group, a cyano group, a hydroxyl group, an alkyl group having 1 to 8 carbon atoms, an alkoxy group having 1 to 8 carbon atoms, an alkylsulfonyl group having 1 to 8 carbon atoms, an alkyl group having 1 to 8 carbon atoms and substituted with 1 to 5 halogen atoms, an alkoxy group having 1 to 8 carbon atoms and substituted with 1 to 5 halogen atoms, an amino group, an alkylamino group having 1 to 8 carbon atoms, a carboxamide, a phenyl group, a pyridyl group, or an alkyl group having 1 to 5 carbon atoms and substituted with a phenyl group.

Furthermore, the present invention relates to a compound represented by the following General Formula (III), a tautomer or a stereoisomer of the compound, a pharmaceutically acceptable salt thereof, or a solvate thereof:

[Chemical Formula 14]

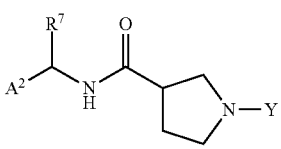

(III)

wherein $A^2$ represents a 5-membered heteroaryl group or a fused ring of a 5-membered or 6-membered heterocyclic ring with a benzene ring or a pyridine ring, the 5-membered heteroaryl group having one to three identical or different heteroatoms selected from the group consisting of an oxygen atom, a nitrogen atom, and a sulfur atom as a ring-constituting element(s), the 5-membered heteroaryl group having, as a substituent, at least one selected from the group consisting of a halogen atom, a carboxyl group, an alkyl group having 1 to 8 carbon atoms, a cyclopropyl group, an alkoxy group having 1 to 8 carbon atoms, a phenyl group, a group represented by the following formula:

[Chemical Formula 15]

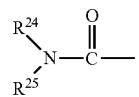

an alkyl group having 1 to 8 carbon atoms and substituted with 1 to 5 halogen atoms, an alkoxy group having 1 to 8 carbon atoms and substituted with 1 to 5 halogen atoms, and a (C1-C8 alkyloxy)carbonyl group, and the 5-membered or 6-membered heterocyclic ring having one or two identical or different heteroatoms selected from the group consisting of an oxygen atom, a nitrogen atom, and a sulfur atom as a ring-constituting element(s), the fused ring may have the above-described substituent carried by the 5-membered heteroaryl group, while $A^2$ is bonded to $CH(R^7)N$ via a ring-constituting carbon atom;

wherein, $R^{24}$ and $R^{25}$, which may be identical or different, each represent a hydrogen atom, an alkyl group having 1 to 8 carbon atoms, or an aryl group which may have a substituent; or $R^{24}$, $R^{25}$, and the nitrogen atom to which $R^{24}$ and $R^{25}$ are bonded are joined together and represent a saturated nitrogen-containing saturated 4-membered to 7-membered heterocyclic ring which may further have one heteroatom selected from the group consisting of an oxygen atom, a nitrogen atom, and a sulfur atom as a ring-constituting element, and may have a substituent;

$R^7$ represents a hydrogen atom, a cyano group, an alkyl group having 1 to 8 carbon atoms, a 3-membered to 7-membered cycloalkyl group, or a heteroaryl group which may have a substituent; and Y represents an alkylsulfonyl group having 1 to 8 carbon atoms, an arylsulfonyl group which may have a substituent, an alkyl group having 1 to 8 carbon atoms which may be substituted with any one selected from the group consisting of an alkylcarbonyl group having 1 to 8 carbon atoms, an adamantylaminocarbonyl group, an (optionally substituted C1-C8 alkyl)aminocarbonyl group, an optionally substituted arylaminocarbonyl group, and an optionally substituted heteroarylaminocarbonyl group as a substituent, a heteroaryl group which may have a substituent, or an aryl group which may have a substituent.

Furthermore, the present invention relates to a pharmaceutical composition including the compound represented by the above General Formula (IA), (I), (II), or (III), a tautomer or a stereoisomer of the compound, a pharmaceutically acceptable salt thereof, or a solvate thereof, as an active ingredient.

Furthermore, the present invention relates to a voltage-dependent T-type calcium channel blocker including the compound represented by the above General Formula (IA), (I), (II), or (III), a tautomer or a stereoisomer of the compound, a pharmaceutically acceptable salt thereof, or a solvate thereof, as an active ingredient.

Furthermore, the present invention relates to a therapeutic or prophylactic agent for a disease related to the voltage-dependent T-type calcium channel, the agent including the compound represented by the above General Formula (IA), (I), (II), or (III), a tautomer or a stereoisomer of the compound, a pharmaceutically acceptable salt thereof, or a solvate thereof, as an active ingredient.

Furthermore, the present invention relates to a prophylactic or therapeutic agent for acute pain, chronic pain, or neuropathic pain, the agent including the compound represented by the above General Formula (IA), (I), (II), or (III), a tautomer or a stereoisomer of the compound, a pharmaceutically acceptable salt thereof, or a solvate thereof, as an active ingredient.

Furthermore, the present invention relates to use of the compound represented by the above General Formula (IA), (I), (II), or (III), a tautomer or a stereoisomer of the compound, a pharmaceutically acceptable salt thereof, or a solvate thereof, for the prevention or treatment of acute pain, chronic pain, neuropathic pain.

Furthermore, the present invention relates to a method for treating acute pain, chronic pain, or neuropathic pain in a human, the method including a step of administering an effective amount of the compound represented by the above General Formula (IA), (I), (II), or (III), a tautomer or a stereoisomer of the compound, a pharmaceutically acceptable salt thereof, or a solvate thereof, to the human.

Advantageous Effects of Invention

The compound of the present invention has excellent voltage-dependent T-type calcium channel inhibitory action.

DESCRIPTION OF EMBODIMENTS

Figure 1:
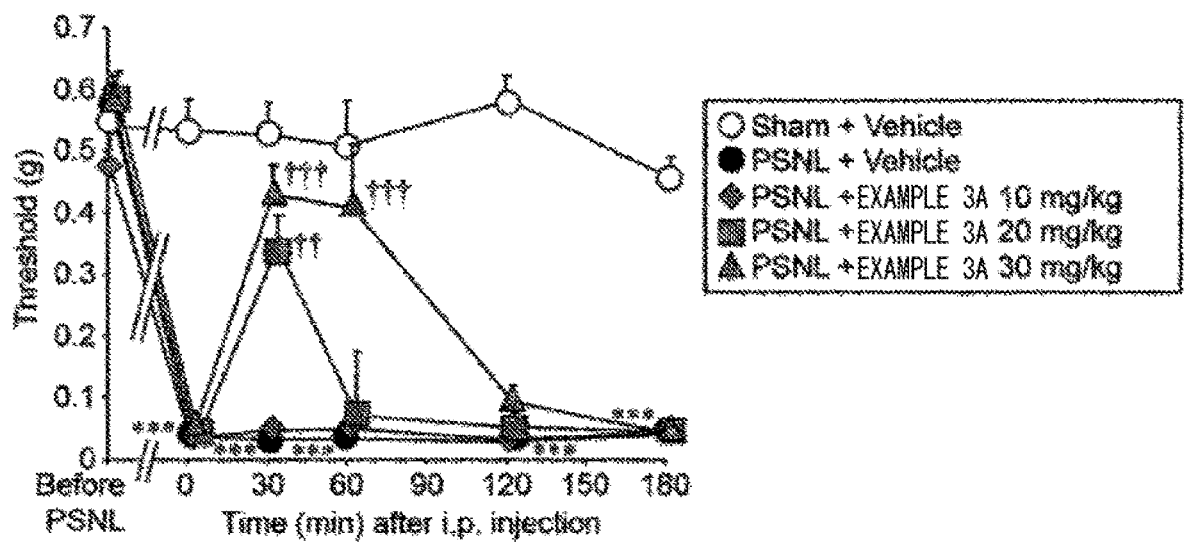
FIG. 1 is a diagram showing the test results for allodynia in a PSNL model using the diastereomer A of Example 3.

Next, the present invention will be described in more detail.

According to the present specification, examples of an alkyl group having 1 to 8 carbon atoms include linear, branched, or cyclic alkyl groups such as a methyl group, an ethyl group, a propyl group, an isopropyl group, a butyl group, a cyclopropyl group, a cyclopentyl group, a cyclohexyl group, an i-butyl group, a t-butyl group, a pentyl group, and a hexyl group.

Examples of an alkyl group having 1 to 8 carbon atoms and substituted with 1 to 5 halogen atoms include a methyl group, an ethyl group, a propyl group, an isopropyl group, a butyl group, and a t-butyl group, all of which are substituted by 1 to 5 halogen atoms, such as a fluorine atom, a chlorine atom, or a bromine atom. Preferred examples include a trifluoromethyl group, a chloromethyl group, a 2-chloroethyl group, a 2-bromoethyl group, and a 2-fluoroethyl group.

Examples of an alkoxy group having 1 to 8 carbon atoms include a methoxy group, an ethoxy group, a propoxy group, an isopropoxy group, a butoxy group, an i-butoxy group, a t-butoxy group, a pentyloxy group, and a hexyloxy group.

Examples of an alkoxy group having 1 to 8 carbon atoms and substituted with 1 to 5 halogen atoms include a methoxy group, an ethoxy group, a propoxy group, an isopropoxy group, a butoxy group, and a t-butoxy group, all of which are substituted with 1 to 3 halogen atoms, such as a fluorine atom, a chlorine atom, or a bromine atom. Preferred examples include a trifluoromethoxy group, a chloromethoxy group, a 2-chloroethoxy group, a 2-bromoethoxy group, a 2-fluoroethoxy group, and a 2,2,2-trifluoroethoxy group.

Examples of a halogen atom include a fluorine atom, a chlorine atom, and a bromine atom.

Examples of a (C1-C8 alkyloxy)carbonyl group include an ethoxycarbonyl group, an n-butoxycarbonyl group, and a t-butoxycarbonyl group.

Examples of a 5-membered heteroaryl group having one to three identical or different heteroatoms as a ring-constituting element(s) include a 5-membered heteroaryl group containing one sulfur atom as a ring-constituting element, and a 5-membered heteroaryl group containing one sulfur atom and one nitrogen atom. Preferred examples include thiophene and thiazole.

Examples of a fused ring of a 5-membered heteroaryl ring and a benzene ring or a 6-membered heteroaryl ring, the 5-membered heteroaryl ring having one to three identical or different heteroatoms, and the 6-membered heteroaryl ring having one to three identical or different heteroatoms as a ring-constituting element(s), include indole and pyrrolopyridine.

Examples of a fused ring of a benzene ring and a 5-membered heteroaryl ring having one or two identical or different heteroatoms as a ring-constituting element(s), include a fused ring of a benzene ring and a 5-membered heteroaryl ring containing one or two nitrogen atoms as a ring-constituting element. Preferred examples include indole.

Examples of an alkylsulfonyl group having 1 to 8 carbon atoms include a methylsulfonyl group and an ethylsulfonyl group.

Examples of a (C1-C8 alkyl)aminocarbonyl group include an ethylaminocarbonyl group.

Examples of a (C2-C12 dialkyl)aminocarbonyl group include an N,N-dimethylaminocarbonyl group and an N,N-diethylaminocarbonyl group.

(a) Examples of an aryl group which may have a substituent include a phenyl group which may have 1 to 3 substituents.

(b) Examples of a heteroaryl group which may have a substituent include a benzimidazole group and a benzothiazole group, both of which may have 1 to 4 substituents.

(c) Examples of an arylsulfonyl group which may have a substituent include a benzenesulfonyl group which may have 1 to 4 substituents.

(d) Examples of an arylaminocarbonyl group which may have a substituent include a benzeneaminocarbonyl group which may have 1 to 4 substituents.

(e) Examples of a heteroarylaminocarbonyl group which may have a substituent include a thiazol-2-ylaminocarbonyl group which may have 1 to 4 substituents.

(f) Examples of an alkyl group having 1 to 8 carbon atoms and substituted with an aryloxy which may have a substituent of $Q^1$, include a methyl group and an ethyl group, both being substituted with a phenyloxy which may have 1 to 3 substituents.

In regard to the above-described items (a) to (f), examples of the substituent for the aryl or heteroaryl group include a halogen atom, a carboxyl group, a cyano, a hydroxyl, an alkyl group having 1 to 8 carbon atoms, an alkoxy group having 1 to 8 carbon atoms, an alkylsulfonyl group having 1 to 8 carbon atoms, an alkyl group having 1 to 8 carbon atoms and substituted with 1 to 5 halogen atoms, an alkoxy group having 1 to 8 carbon atoms and substituted with 1 to 5 halogen atoms, and a carboxamide.

Furthermore, examples of an (optionally substituted C1-C8 alkyl)aminocarbonyl group include an ethylaminocarbonyl group which may have a substituent such as a halogen atom, a carboxyl group, a cyano, a hydroxyl, or an alkoxy group having 1 to 8 carbon atoms.

In regard to the compounds represented by General Formulae (IA), (I), (II), and (III), a 5-membered heteroaryl group or the fused ring of a benzene ring with a 5-membered heteroaryl ring, the 5-membered heteroaryl group having one to three identical or different heteroatoms as a ring-constituting element(s), and the 5-membered heteroaryl ring having one or two identical or different heteroatoms as a ring-constituting element(s), may have another substituent, in addition to the above-mentioned at least one substituent. The total number of substituents is 1 to 3 in the 5-membered heteroaryl group, and 1 to 5 in the benzene ring and the 5-membered heteroaryl ring.

Examples of a compound represented by General Formula (IA) described above, a tautomer or a stereoisomer of the compound, a pharmaceutically acceptable salt thereof, or a solvate thereof, include the following.

(1)
A compound represented by General Formula (IA) described above, a tautomer or a stereoisomer of the compound, a pharmaceutically acceptable salt thereof, or a solvate thereof.

(2)
The compound according to the item (1), a tautomer or a stereoisomer of the compound, a pharmaceutically acceptable salt thereof, or a solvate thereof, wherein the 5-membered heteroaryl group for D, having one to three identical or different heteroatoms selected from an oxygen atom, a nitrogen atom, and a sulfur atom as a ring-constituting element(s), is thiophene, thiazole, pyrazole, imidazole, furan, oxazole, oxadiazole, triazole, or pyrrole.

(3)
The compound according to the item (1), a tautomer or a stereoisomer of the compound, a pharmaceutically acceptable salt thereof, or a solvate thereof, wherein the 5-membered heteroaryl group for D, having one to three identical or different heteroatoms selected from an oxygen atom, a nitrogen atom, and a sulfur atom as a ring-constituting element(s), is thiophene or thiazole.

(4)
The compound according to the item (1), a tautomer or a stereoisomer of the compound, a pharmaceutically acceptable salt thereof, or a solvate thereof, wherein the fused ring of a 5-membered or 6-membered heterocyclic ring with a benzene ring or a pyridine ring, the 5-membered or 6-membered heterocyclic ring having one or two identical or different heteroatoms selected from the group consisting of an oxygen atom, a nitrogen atom, and a sulfur atom as a ring-constituting element(s), is any one selected from the group consisting of indole, benzofuran, furopyridine, pyrazolopyridine, benzoxazole, benzothiazole, benzimidazole, quinoline, dihydrobenzodioxine, and dihydrobenzofuran.

(5)
The compound according to the item (1), a tautomer or a stereoisomer of the compound, a pharmaceutically acceptable salt thereof, or a solvate thereof, wherein the fused ring of a 5-membered or 6-membered heterocyclic ring with a benzene ring or a pyridine ring, the 5-membered or 6-membered heterocyclic ring having one or two identical or different heteroatoms selected from the group consisting of an oxygen atom, a nitrogen atom, and a sulfur atom as a ring-constituting element(s), is benzofuran, benzothiophene, or benzoxazole.

(6)
The compound according to any one of the items (1) to (5), a tautomer or a stereoisomer of the compound, a pharmaceutically acceptable salt thereof, or a solvate thereof, wherein $R^a$ represents an alkyl group having 1 to 8 carbon atoms, and $R^b$ represents a hydrogen atom.

(7)
The compound according to any one of the items (1) to (6), a tautomer or a stereoisomer of the compound, a pharmaceutically acceptable salt thereof, or a solvate thereof, wherein $R^c$ represents a hydrogen atom.

(8)
The compound according to any one of the items (1) to (7), a tautomer or a stereoisomer of the compound, a pharmaceutically acceptable salt thereof, or a solvate thereof, wherein $R^{10}$, $R^{11}$, $R^{12}$, $R^{13}$, and $R^{14}$, which may be identical or different, each represent a hydrogen atom, a halogen atom, or a hydroxyl group.

(9)
The compound according to any one of the items (1) to (7), a tautomer or a stereoisomer of the compound, a pharmaceutically acceptable salt thereof, or a solvate thereof, wherein $R^{10}$, $R^{11}$, $R^{12}$, $R^{13}$, and $R^{14}$ each represent a hydrogen atom.

(10)
The compound according to any one of the items (1) to (9), a tautomer or a stereoisomer of the compound, a pharmaceutically acceptable salt thereof, or a solvate thereof, wherein $n^1$ represents 0, $m^1$ represents 1, and G represents $CR^{15}(W^1)$.

(11)
The compound according to the item (10), a tautomer or a stereoisomer of the compound, a pharmaceutically acceptable salt thereof, or a solvate thereof, wherein $R^{15}$ represents a hydrogen atom.

(12)
The compound according to any one of the items (1) to (11), a tautomer or a stereoisomer of the compound, a pharmaceutically acceptable salt thereof, or a solvate thereof, wherein $W^1$ represents a heteroaryl group which may have a substituent, and $W^1$ is bonded to $C(R^{15})$ via a carbon atom that constitutes the ring of the heteroaryl group.

(13)
The compound according to the item (1) or any one of the items (1) to (12), a tautomer or a stereoisomer of the compound, a pharmaceutically acceptable salt thereof, or a solvate thereof, wherein $W^1$ represents a fused ring of an optionally substituted 5-membered heteroaryl ring with an optionally substituted 6-membered heteroaryl ring or a benzene ring, the 5-membered heteroaryl ring having one or two nitrogen atoms as a ring-constituting element, and the 6-membered heteroaryl ring having one or two nitrogen atoms as a ring-constituting element.

(14)
The compound according to any one of the items (1) to (12), a tautomer or a stereoisomer of the compound, a pharmaceutically acceptable salt thereof, or a solvate thereof, wherein $W^1$ represents benzimidazole, imidazole, benzoxazole, quinoline, pyridine, imidazopyridine, or indole, all of which may have a substituent.

(15)
The compound according to any one of the items (1) to (12), a tautomer or a stereoisomer of the compound, a pharmaceutically acceptable salt thereof, or a solvate thereof, wherein $W^1$ represents benzimidazol-2-yl which may have a substituent, or indol-3-yl which may have a substituent.

(16)

The compound according to any one of the items (1) to (9), a tautomer or a stereoisomer of the compound, a pharmaceutically acceptable salt thereof, or a solvate thereof, wherein G represents $NW^2$.

(17)

The compound according to the item (16), a tautomer or a stereoisomer of the compound, a pharmaceutically acceptable salt thereof, or a solvate thereof, wherein $n^1$ represents 1, and $m^1$ represents 2.

(18)

The compound according to the item (16) or (17), a tautomer or a stereoisomer of the compound, a pharmaceutically acceptable salt thereof, or a solvate thereof, wherein $W^2$ represents an alkyl group having 1 to 8 carbon atoms which may be substituted with, as a substituent, any one selected from the group consisting of:

(1) a (C1-C8 alkyl)aminocarbonyl group;

(2) an arylaminocarbonyl group which may have a substituent selected from a halogen atom, a hydroxyl group, an alkyl group having 1 to 8 carbon atoms, an alkoxy group having 1 to 8 carbon atoms, an alkyl group having 1 to 8 and substituted with 1 to 5 halogen atom, and an alkoxy group having 1 to 8 carbon atoms and substituted with 1 to 5 halogen atoms; and (3) a heteroarylaminocarbonyl group which may have a substituent selected from a halogen atom, a hydroxyl group, an alkyl group having 1 to 8 carbon atoms, an alkoxy group having 1 to 8 carbon atoms, an alkyl group having 1 to 8 carbon atoms and substituted with 1 to 5 halogen atoms, and an alkoxy group having 1 to 8 carbon atoms and substituted with 1 to 5 halogen atoms.

(19)

The compound according to the item (16) or (17), a tautomer or a stereoisomer of the compound, a pharmaceutically acceptable salt thereof, or a solvate thereof, wherein $W^2$ represents a heteroaryl group which may have a substituent, or an aryl group which may have a substituent.

(20)

The compound according to the item (19), a tautomer or a stereoisomer of the compound, a pharmaceutically acceptable salt thereof, or a solvate thereof, wherein $W^2$ is bonded to a nitrogen atom of G via a carbon atom that constitutes the ring of a heteroaryl group which may have a substituent.

(21)

The compound according to any one of the items (16), (17), (19), and (20), a tautomer or a stereoisomer of the compound, a pharmaceutically acceptable salt thereof, or a solvate thereof, wherein the substituent for the heteroaryl group which may have a substituent, represented by $W^2$, is selected from a halogen atom, a carboxyl group, a cyano group, a hydroxyl group, an alkyl group having 1 to 8 carbon atoms, an alkoxy group having 1 to 8 carbon atoms, an alkylsulfonyl group having 1 to 8 carbon atoms, an alkyl group having 1 to 8 carbon atoms and substituted with 1 to 5 halogen atoms, an alkoxy group having 1 to 8 carbon atoms and substituted with 1 to 5 halogen atoms, and a carboxamide.

(22)

The compound according to any one of the items (16), (17), and (19) to (21), a tautomer or a stereoisomer of the compound, a pharmaceutically acceptable salt thereof, or a solvate thereof, wherein $W^2$ represents a fused ring of an optionally substituted 5-membered heteroaryl ring and a benzene ring, the heteroaryl ring having one nitrogen atom as a ring-constituting element and one nitrogen atom or sulfur atom as another heteroatom.

(23)

The compound according to any one of the items (16), (17), and (19) to (22), a tautomer or a stereoisomer of the compound, a pharmaceutically acceptable salt thereof, or a solvate thereof, wherein $W^2$ represents benzimidazol-2-yl which may have a substituent.

Examples of a compound represented by General Formula (I), a tautomer or a stereoisomer of the compound, a pharmaceutically acceptable salt thereof, or a solvate thereof, include the following.

(24)

A compound represented by General Formula (I) described above, a tautomer or a stereoisomer of the compound, a pharmaceutically acceptable salt thereof, or a solvate thereof.

(25)

The compound according to the item (24), a tautomer or a stereoisomer of the compound, a pharmaceutically acceptable salt thereof, or a solvate thereof, wherein A represents a 5-membered heteroaryl group or a fused ring of a 5-membered heteroaryl ring with a benzene ring or a 6-membered heteroaryl ring, the 5-membered heteroaryl group and the 5-membered heteroaryl ring having one to three identical or different heteroatoms as a ring-constituting element(s), the 5-membered heteroaryl group and the 5-membered heteroaryl ring having, as a substituent, at least one selected from the group consisting of a halogen atom, a carboxyl group, an alkyl group having 1 to 8 carbon atoms, an alkoxy group having 1 to 8 carbon atoms, a (C1-C8 alkyl)aminocarbonyl group, a (C2-C12 dialkyl)aminocarbonyl group, an alkyl group having 1 to 8 carbon atoms and substituted with 1 to 5 halogen atoms, an alkoxy group having 1 to 8 carbon atoms and substituted with 1 to 5 halogen atoms, and a (C1-C8 alkyloxy)carbonyl group, and the 6-membered heteroaryl ring having one to three identical or different heteroatoms as a ring-constituting element(s), the fused ring optionally having no substituent;

R represents a hydrogen atom, a cyano group, an alkyl group having 1 to 8 carbon atoms, or a heteroaryl group which may have a substituent;

$Q^1$ represents an alkyl group having 1 to 8 carbon atoms and substituted with an aryloxy group which may have a substituent, or a heteroaryl group or aryl group which may have a substituent;

$Q^2$ represents an alkylsulfonyl group having 1 to 8 carbon atoms, an arylsulfonyl group which may have a substituent, an alkyl group having 1 to 8 carbon atoms which may be substituted with an (optionally substituted C1-C8 alkyl) aminocarbonyl group, an optionally substituted arylaminocarbonyl group, and an optionally substituted heteroarylaminocarbonyl group as a substituent, or a heteroaryl group which may have a substituent; and $R^0$, $R^1$, $R^2$, $R^3$, $R^4$, and $R^5$, which may be identical or different, each represent a hydrogen atom, a cyano group, a hydroxyl group, a halogen atom, a carboxyl group, an amino group, an alkylamino group having 1 to 8 carbon atoms, or an alkyl group having 1 to 8 carbon atoms.

(26)

The compound according to the item (24) or (25), a tautomer or a stereoisomer of the compound, a pharmaceutically acceptable salt thereof, or a solvate thereof, wherein the heteroaryl group having a substituent for A represents thiophene, thiazole, pyrazole, imidazole, furan, oxazole, oxadiazole, triazole, or pyrrole.

(27)

The compound according to the item (24) or (25), a tautomer or a stereoisomer of the compound, a pharmaceutically acceptable salt thereof, or a solvate thereof, wherein A represents thiophene having a substituent, or thiazole having a substituent.

(28)

The compound according to the item (24) or (25), a tautomer or a stereoisomer of the compound, a pharmaceutically acceptable salt thereof, or a solvate thereof, wherein A represents indole, benzofuran, furopyridine, pyrazolopyridine, benzoxazole, benzothiazole, benzimidazole, quinoline, dihydrobenzodioxine, dihydrobenzofuranindole, benzofuran, benzo[d][1,3]dioxole, all of which may have a substituent.

(29)

The compound according to the item (24) or (25), a tautomer or a stereoisomer of the compound, a pharmaceutically acceptable salt thereof, or a solvate thereof, wherein A represents benzofuran, benzoxazole, benzothiophene, all of which may have a substituent.

(30)

The compound according to any one of the items (24) to (29), a tautomer or a stereoisomer of the compound, a pharmaceutically acceptable salt thereof, or a solvate thereof, wherein R represents an alkyl group having 1 to 8 carbon atoms.

(31)

The compound according to any one of the items (24) to (30), a tautomer or a stereoisomer of the compound, a pharmaceutically acceptable salt thereof, or a solvate thereof, wherein $R^0$, $R^1$, $R^2$, $R^3$, and $R^4$, which may be identical or different, each represent a hydrogen atom, a halogen atom, or a hydroxyl group.

(32)

The compound according to any one of the items (24) to (30), a tautomer or a stereoisomer of the compound, a pharmaceutically acceptable salt thereof, or a solvate thereof, wherein $R^0$, $R^1$, $R^2$, $R^3$, and $R^4$ each represent a hydrogen atom.

(33)

The compound according to any one of the items (24) to (32), a tautomer or a stereoisomer of the compound, a pharmaceutically acceptable salt thereof, or a solvate thereof, wherein n represents 0, m represents 1, or B represents $CR^5(Q^1)$.

(34)

The compound according to any one of the items (24) to (33), a tautomer or a stereoisomer of the compound, a pharmaceutically acceptable salt thereof, or a solvate thereof, wherein $R^5$ represents a hydrogen atom.

(35)

The compound according to any one of the items (24) to (34), a tautomer or a stereoisomer of the compound, a pharmaceutically acceptable salt thereof, or a solvate thereof, wherein $Q^1$ represents a heteroaryl group which may have a substituent, and $Q^1$ is bonded to $C(R^5)$ via a carbon atom that constitutes the ring of the heteroaryl group.

(36)

The compound according to any one of the items (24) to (35), a tautomer or a stereoisomer of the compound, a pharmaceutically acceptable salt thereof, or a solvate thereof, wherein $Q^1$ represents a fused ring of an optionally substituted 5-membered heteroaryl ring with an optionally substituted 6-membered heteroaryl ring or a benzene ring, the 5-membered heteroaryl ring having one or two nitrogen atoms as a ring-constituting element, and the 6-membered heteroaryl ring having one or two nitrogen atoms as a ring-constituting element.

(37)

The compound according to any one of the items (24) to (35), a tautomer or a stereoisomer of the compound, a pharmaceutically acceptable salt thereof, or a solvate thereof, wherein $Q^1$ represents benzimidazole, imidazole, benzoxazole, quinoline, pyridine, imidazopyridine, or indole, all of which may have a substituent.

(38)

The compound according to any one of the items (24) to (35), a tautomer or a stereoisomer of the compound, a pharmaceutically acceptable salt thereof, or a solvate thereof, wherein $Q^1$ represents benzimidazol-2-yl which may have a substituent, or indol-3-yl which may have a substituent.

(39)

The compound according to any one of the items (24) to (38), a tautomer or a stereoisomer of the compound, a pharmaceutically acceptable salt thereof, or a solvate thereof, wherein the substituent of the heteroaryl group which may have a substituent for $Q^1$ is selected from the group consisting of a halogen atom, a carboxyl group, a cyano group, a hydroxyl group, an alkyl group having 1 to 8 carbon atoms, an alkoxy group having 1 to 8 carbon atoms, an alkylsulfonyl group having 1 to 8 carbon atoms, an alkyl group having 1 to 8 carbon atoms and substituted with 1 to 5 halogen atoms, an alkoxy group having 1 to 8 carbon atoms and substituted with 1 to 5 halogen atoms, an amino group, an alkylamino group having 1 to 8 carbon atoms, and a carboxamide.

(40)

The compound according to any one of the items (24) to (32), a tautomer or a stereoisomer of the compound, a pharmaceutically acceptable salt thereof, or a solvate thereof, wherein B represents $NQ^2$.

(41)

The compound according to any one of the items (24) to (32) and (40), a tautomer or a stereoisomer of the compound, a pharmaceutically acceptable salt thereof, or a solvate thereof, wherein n represents 1, and m represents 2.

(42)

The compound according to any one of the items (24) to (32), (40), and (41), a tautomer or a stereoisomer of the compound, a pharmaceutically acceptable salt thereof, or a solvate thereof, wherein $Q^2$ represents an alkyl group having 1 to 8 carbon atoms which may be substituted with, as a substituent, any one selected from the group consisting of:

(1) a (C1-C8 alkyl)aminocarbonyl group;

(2) an arylaminocarbonyl group which may have a substituent selected from the group consisting of a halogen atom, a hydroxyl group, an alkyl group having 1 to 8 carbon atoms, an alkoxy group having 1 to 8 carbon atoms, an alkyl group having 1 to 8 carbon atoms and substituted with 1 to 5 halogen atoms, and an alkoxy group having 1 to 8 carbon atoms and substituted with 1 to 5 halogen atoms; and (3) a heteroarylaminocarbonyl group which may have a substituent selected from the group consisting of a halogen atom, a hydroxyl group, an alkyl group having 1 to 8 carbon atoms, an alkoxy group having 1 to 8 carbon atoms, an alkyl group having 1 to 8 carbon atoms and substituted with 1 to 5 halogen atoms, and an alkoxy group having 1 to 8 carbon atoms and substituted with 1 to 5 halogen atoms.

(43)

The compound according to any one of the items (24) to (32), (40), and (41), a tautomer or a stereoisomer of the compound, a pharmaceutically acceptable salt thereof, or a solvate thereof, wherein $Q^2$ represents a heteroaryl group which may have a substituent.

(44)

The compound according to the item (43), a tautomer or a stereoisomer of the compound, a pharmaceutically acceptable salt thereof, or a solvate thereof, wherein the substituent for the heteroaryl group which may have a substituent, represented by $Q^2$, is selected from the group consisting of a halogen atom, a carboxyl group, a cyano group, a hydroxyl group, an alkyl group having 1 to 8 carbon atoms, an alkoxy group having 1 to 8 carbon atoms, an alkylsulfonyl group having 1 to 8 carbon atoms, an alkyl group having 1 to 8 carbon atoms and substituted with 1 to 5 halogen atoms, an alkoxy group having 1 to 8 carbon atoms and substituted with 1 to 5 halogen atoms, and a carboxamide.

(45)

The compound according to the item (43) or (44), a tautomer or a stereoisomer of the compound, a pharmaceutically acceptable salt thereof, or a solvate thereof, wherein $Q^2$ is bonded to a nitrogen atom of B via a carbon atom that constitutes the ring of an optionally substituted heteroaryl group.

(46)

The compound according to any one of the items (43) to (45), a tautomer or a stereoisomer of the compound, a pharmaceutically acceptable salt thereof, or a solvate thereof, wherein $Q^2$ represents a fused ring of a 5-membered heteroaryl ring and a benzene ring, the heteroaryl ring having one nitrogen atom as a ring-constituting element which may have a substituent and also having one nitrogen atom or sulfur atom as another heteroatom.

(47)

The compound according to any one of the items (43) to (45), a tautomer or a stereoisomer of the compound, a pharmaceutically acceptable salt thereof, or a solvate thereof, wherein $Q^2$ represents benzimidazol-2-yl which may have a substituent.

Examples of a compound represented by General Formula (II) described above, a tautomer or a stereoisomer of the compound, a pharmaceutically acceptable salt thereof, or a solvate thereof, include the following.

(48)

A compound represented by General Formula (II) described above, a tautomer or a stereoisomer of the compound, a pharmaceutically acceptable salt thereof, or a solvate thereof.

(49)

The compound according to the item (48), a tautomer or a stereoisomer of the compound, a pharmaceutically acceptable salt thereof, or a solvate thereof, wherein $A^1$ represents a fused ring of a 5-membered heteroaryl group having one to three identical or different heteroatoms as a ring-constituting element(s) with a 5-membered heteroaryl ring having one or two identical or different heteroatoms as a ring-constituting element(s), or a fused ring of a benzene ring with a 5-membered heteroaryl ring having one or two identical or different heteroatoms as a ring-constituting element(s), the fused ring having, as a substituent, at least one selected from the group consisting of a halogen atom, an alkyl group having 1 to 8 carbon atoms, an alkoxy group having 1 to 8 carbon atoms, a (C1-C8 alkyl)aminocarbonyl group, a (C2-C12 dialkyl)aminocarbonyl group, an alkyl group having 1 to 8 carbon atoms and substituted with 1 to 5 halogen atoms, an alkoxy group having 1 to 8 carbon atoms and substituted with 1 to 5 halogen atoms, an a (C1-C8 alkyloxy)carbonyl group;

$R^6$ represents a hydrogen atom, a cyano group, or an alkyl group having 1 to 8 carbon atoms; and X represents a fused ring of a 5-membered heteroaryl ring and a benzene ring which may have a substituent.

(50)

The compound according to the item (48) or (49), a tautomer or a stereoisomer of the compound, a pharmaceutically acceptable salt thereof, or a solvate thereof, wherein $A^1$ represents a fused ring of a 5-membered heteroaryl group having one to three identical or different heteroatoms as a ring-constituting element(s) with a 5-membered heteroaryl ring having one or two identical or different heteroatoms as a ring-constituting element(s), or a fused ring of a benzene ring with a 5-membered heteroaryl ring having one or two identical or different heteroatoms as a ring-constituting element(s), the fused ring having, as a substituent, at least one selected from the group consisting of a halogen atom, an alkyl group having 1 to 8 carbon atoms, an alkoxy group having 1 to 8 carbon atoms, an alkyl group having 1 to 8 carbon atoms and substituted with 1 to 5 halogen atoms, an alkoxy group having 1 to 8 carbon atoms and substituted with 1 to 5 halogen atoms, and a (C1-C8 alkyloxy)carbonyl group, and the 5-membered heteroaryl ring having one or two identical or different heteroatoms as a ring-constituting element(s).

(51)

The compound according to any one of the items (48) to (50), a tautomer or a stereoisomer of the compound, a pharmaceutically acceptable salt thereof, or a solvate thereof, wherein the heteroaryl group having a substituent for $A^1$ is thiophene, thiazole, pyrazole, imidazole, furan, oxazole, oxadiazole, triazole, or pyrrole.

(52)

The compound according to any one of the items (48) to (50), a tautomer or a stereoisomer of the compound, a pharmaceutically acceptable salt thereof, or a solvate thereof, wherein $A^1$ represents thiophene having a substituent, or thiazole having a substituent.

(53)

The compound according to any one of the items (48) to (50), a tautomer or a stereoisomer of the compound, a pharmaceutically acceptable salt thereof, or a solvate thereof, wherein $A^1$ represents thiophene or thiazole, both of which are substituted with at least one alkoxy group having 1 to 4 carbon atoms which is substituted with 1 to 3 halogen atoms.

(54)

The compound according to the item (48), a tautomer or a stereoisomer of the compound, a pharmaceutically acceptable salt thereof, or a solvate thereof, wherein $A^1$ represents indole, benzofuran, pyrazolopyridine benzoxazole, benzothiazole, benzimidazole, dihydrobenzodioxine, or dihydrobenzofuran, all of which may have a substituent.

(55)

The compound according to the item (48), a tautomer or a stereoisomer of the compound, a pharmaceutically acceptable salt thereof, or a solvate thereof, wherein $A^1$ represents benzofuran, benzoxazole, benzothiophene, all of which may have a substituent.

(56)

The compound according to any one of the items (48) to (55), a tautomer or a stereoisomer of the compound, a pharmaceutically acceptable salt thereof, or a solvate thereof, wherein X is bonded to cyclopropyl via a carbon atom that constitutes the heteroaryl ring of the fused ring.

(57)

The compound according to any one of the items (48) to (56), a tautomer or a stereoisomer of the compound, a pharmaceutically acceptable salt thereof, or a solvate thereof, wherein the substituent of the fused ring for X is selected from a halogen atom, a carboxyl group, a cyano group, a hydroxyl group, an alkyl group having 1 to 8 carbon atoms, an alkoxy group having 1 to 8 carbon atoms, an alkylsulfonyl group having 1 to 8 carbon atoms, an alkyl group having 1 to 8 carbon atoms and substituted with 1 to 5 halogen atoms, an alkoxy group having 1 to 8 carbon atoms and substituted with 1 to 5 halogen atoms, and a carboxamide.

(58)

The compound according to any one of the items (48) to (57), a tautomer or a stereoisomer of the compound, a pharmaceutically acceptable salt thereof, or a solvate thereof, wherein X represents a fused ring of a 5-membered heteroaryl ring and a benzene ring, the heteroaryl ring having one or two nitrogen atoms as a ring-constituting element which may have a substituent.

(59)

The compound according to any one of the items (48) to (57), a tautomer or a stereoisomer of the compound, a pharmaceutically acceptable salt thereof, or a solvate thereof, wherein X represents benzimidazol-2-yl which may have a substituent, or indol-3-yl which may have a substituent.

(60)

The compound according to any one of the items (48) to (57), a tautomer or a stereoisomer of the compound, a pharmaceutically acceptable salt thereof, or a solvate thereof, wherein X represents benzimidazol-2-yl.

(61)

The compound according to any one of the items (48) to (60), a tautomer or a stereoisomer of the compound, a pharmaceutically acceptable salt thereof, or a solvate thereof, wherein $R^6$ represents a methyl group.

Examples of a compound represented by General Formula (III) described above, a tautomer or a stereoisomer of the compound, a pharmaceutically acceptable salt thereof, or a solvate thereof, include the following.

(62)

A compound represented by General Formula (III) described above, a tautomer or a stereoisomer of the compound, a pharmaceutically acceptable salt thereof, or a solvate thereof.

(63)

The compound according to the item (62), a tautomer or a stereoisomer of the compound, a pharmaceutically acceptable salt thereof, or a solvate thereof, wherein $A^2$ represents a fused ring of a 5-membered heteroaryl group having one to three identical or different heteroatoms as a ring-constituting element(s) with a 5-membered heteroaryl ring having one or two identical or different heteroatoms as a ring-constituting element(s), or a fused ring of a benzene ring with a 5-membered heteroaryl ring having one or two identical or different heteroatoms as a ring-constituting element(s), the fused ring having, as a substituent, at least one selected from the group consisting of a halogen atom, an alkyl group having 1 to 8 carbon atoms, an alkoxy group having 1 to 8 carbon atoms, an alkyl group having 1 to 8 carbon atoms and substituted with 1 to 5 halogen atoms, an alkoxy group having 1 to 8 carbon atoms and substituted with 1 to 5 halogen atoms, and a (C1-C8 alkyloxy)carbonyl group;

$R^7$ represents a hydrogen atom, a cyano group, or an alkyl group having 1 to 8 carbon atoms; and Y represents an alkyl group having 1 to 8 carbon atoms which may be substituted with, as a substituent, any one selected from a (C1-C8 alkyl)aminocarbonyl group, an arylaminocarbonyl group which may have a substituent, and a heteroarylaminocarbonyl group which may have a substituent, or a fused ring of a 5-membered heteroaryl ring and a benzene ring which may have a substituent.

(64)

The compound according to the item (62) or (63), a tautomer or a stereoisomer of the compound, a pharmaceutically acceptable salt thereof, or a solvate thereof, wherein $A^2$ represents thiophene, thiazole, pyrazole, imidazole, or pyrrole, all of which have a substituent.

(65)

The compound according to the item (62) or (63), a tautomer or a stereoisomer of the compound, a pharmaceutically acceptable salt thereof, or a solvate thereof, wherein $A^2$ represents thiophene having a substituent, or thiazole having a substituent.

(66)

The compound according to the item (62) or (63), a tautomer or a stereoisomer of the compound, a pharmaceutically acceptable salt thereof, or a solvate thereof, wherein $A^2$ represents any one of thiophene and thiazole, both of which are substituted with at least one alkoxy group having 1 to 4 carbon atoms which is substituted with 1 to 3 halogen atoms.

(67)

The compound according to the item (62) or (63), a tautomer or a stereoisomer of the compound, a pharmaceutically acceptable salt thereof, or a solvate thereof, wherein $A^2$ represents indole, benzofuran, pyrazolopyridine, benzoxazole, benzothiazole, benzimidazole, dihydrobenzodioxine, or dihydrobenzofuran, all of which may have a substituent.

(68)

The compound according to the item (62) or (63), a tautomer or a stereoisomer of the compound, a pharmaceutically acceptable salt thereof, or a solvate thereof, wherein $A^2$ represents indole, benzothiophene, benzoxazole, benzofuran, all of which may have a substituent.

(69)

The compound according to any one of the items (62) to (68), a tautomer or a stereoisomer of the compound, a pharmaceutically acceptable salt thereof, or a solvate thereof, wherein Y represents an alkyl group having 1 to 8 carbon atoms which may be substituted with, as a substituent, any one selected from the group consisting of:

(1) a (C1-C8 alkyl)aminocarbonyl group;

(2) an arylaminocarbonyl group which may have a substituent selected from the group consisting of a halogen atom, a hydroxyl group, an alkyl group having 1 to 8 carbon atoms, an alkoxy group having 1 to 8 carbon atoms, an alkyl group having 1 to 8 carbon atoms and substituted with 1 to 5 halogen atoms, and an alkoxy group having 1 to 8 carbon atoms and substituted with 1 to 5 halogen atoms; and (3) a heteroarylaminocarbonyl group which may have a substituent selected from the group consisting of a halogen atom, a hydroxyl group, an alkyl group having 1 to 8 carbon atoms, an alkoxy group having 1 to 8 carbon atoms, an alkyl group having 1 to 8 carbon atoms and substituted with 1 to 5 halogen atoms, and an alkoxy group having 1 to 8 carbon atoms and substituted with 1 to 5 halogen atoms.

(70)

The compound according to any one of the items (62) to (68), a tautomer or a stereoisomer of the compound, a pharmaceutically acceptable salt thereof, or a solvate thereof, wherein Y represents a methyl group substituted with, as a substituent, any one selected from the group consisting of:

(1) a (C3-C5 alkyl)aminocarbonyl group;
(2) a phenylaminocarbonyl group; and
(3) a (thiazole or oxazole)aminocarbonyl group.

(71)

The compound according to any one of the items (62) to (68), a tautomer or a stereoisomer of the compound, a pharmaceutically acceptable salt thereof, or a solvate thereof, wherein Y represents a fused ring of a 5-membered heteroaryl group and a benzene ring which may have a substituent.

(72)

The compound according to the item (71), a tautomer or a stereoisomer of the compound, a pharmaceutically acceptable salt thereof, or a solvate thereof, wherein the substituent of the fused ring of a benzene ring and a 5-membered heteroaryl group which may have a substituent, for Y, is selected from the group consisting of a halogen atom, a carboxyl group, a cyano group, a hydroxyl group, an alkyl group having 1 to 8 carbon atoms, an alkoxy group having 1 to 8 carbon atoms, an alkylsulfonyl group having 1 to 8 carbon atoms, an alkyl group having 1 to 8 carbon atoms and substituted with 1 to 5 halogen atoms, an alkoxy group having 1 to 8 carbon atoms and substituted with 1 to 5 halogen atoms, and a carboxamide.

(73)

The compound according to the item (71) or (72), a tautomer or a stereoisomer of the compound, a pharmaceutically acceptable salt thereof, or a solvate thereof, wherein Y represents a fused ring of a benzene ring and a 5-membered heteroaryl group which may have a substituent, and is bonded to a nitrogen atom of pyrrolidine via a carbon atom that constitutes the heteroaryl ring.

(74)

The compound according to the item (71) or (72), a tautomer or a stereoisomer of the compound, a pharmaceutically acceptable salt thereof, or a solvate thereof, wherein Y represents a fused ring of a 5-membered heteroaryl ring and a benzene ring, the heteroaryl ring having one nitrogen atom as a ring-constituting element which may have a substituent and one nitrogen atom or sulfur atom as another heteroatom.

(75)

The compound according to any one of the items (71) to (74), a tautomer or a stereoisomer of the compound, a pharmaceutically acceptable salt thereof, or a solvate thereof, wherein Y represents a benzimidazole which may have a substituent.

(76)

The compound according to any one of the items (62) to (75), a tautomer or a stereoisomer of the compound, a pharmaceutically acceptable salt thereof, or a solvate thereof, wherein $R^7$ represents a methyl group.

Furthermore, preferred examples of the compound of the present invention include the following compounds, a tautomer or a stereoisomer of the compound, a pharmaceutically acceptable salt thereof, or a solvate thereof.

A compound selected from the following, a tautomer or a stereoisomer of the compound, a pharmaceutically acceptable salt thereof, or a solvate thereof:

(1S,2S)-2-(1H-benzo[d]imidazol-2-yl)-N—((R)-1-(4-methyl-5-(2,2,2-trifluoroethoxy)thiophen-2-yl)ethyl)cyclopropane-1-carboxamide, (1R,2R)-2-(1H-benzo[d]imidazol-2-yl)-N—((R)-1-(4-methyl-5-(2,2,2-trifluoroethoxy)thiophen-2-yl)ethyl)cyclopropane-1-carboxamide, (1S,2S)-2-(1H-benzo[d]imidazol-2-yl)-N—((S)-1-(5-(2,2,2-trifluoroethoxy)thiophen-2-yl)ethyl)cyclopropane-1-carboxamide, (1R,2R)-2-(1H-benzo[d]imidazol-2-yl)-N—((S)-1-(5-(2,2,2-trifluoroethoxy)thiophen-2-yl)ethyl)cyclopropane-1-carboxamide, (1S,2S)-2-(1H-benzo[d]imidazol-2-yl)-N—((R)-1-(5-(2,2,2-trifluoroethoxy)thiophen-2-yl)ethyl)cyclopropane-1-carboxamide, (1R,2R)-2-(1H-benzo[d]imidazol-2-yl)-N—((R)-1-(5-(2,2,2-trifluoroethoxy)thiophen-2-yl)ethyl)cyclopropane-1-carboxamide, (1S,2S)-2-(1-methyl-1H-benzo[d]imidazol-2-yl)-N—((R)-1-(5-(2,2,2-trifluoroethoxy)thiophen-2-yl)ethyl)cyclopropane-1-carboxamide, (1R,2R)-2-(1-methyl-1H-benzo[d]imidazol-2-yl)-N—((R)-1-(5-(2,2,2-trifluoroethoxy)thiophen-2-yl)ethyl)cyclopropane-1-carboxamide, (1S,2S)-2-(1H-benzo[d]imidazol-2-yl)-N—((R)-1-(5-(trifluoromethyl)thiophen-2-yl)ethyl)cyclopropane-1-carboxamide, (1R,2R)-2-(1H-benzo[d]imidazol-2-yl)-N—((R)-1-(5-(trifluoromethyl)thiophen-2-yl)ethyl)cyclopropane-1-carboxamide, (1S,2S)-2-(1H-benzo[d]imidazol-2-yl)-N—((R)-1-(5-bromothiophen-2-yl)ethyl)cyclopropane-1-carboxamide, (1R,2R)-2-(1H-benzo[d]imidazol-2-yl)-N—((R)-1-(5-bromothiophen-2-yl)ethyl)cyclopropane-1-carboxamide, (1S,2S)-2-(1H-benzo[d]imidazol-2-yl)-N—((S)-1-(2-(2,2,2-trifluoroethoxy)thiazol-5-yl)ethyl)cyclopropane-1-carboxamide, (1R,2R)-2-(1H-benzo[d]imidazol-2-yl)-N—((S)-1-(2-(2,2,2-trifluoroethoxy)thiazol-5-yl)ethyl)cyclopropane-1-carboxamide, (1S,2S)-2-(1H-benzo[d]imidazol-2-yl)-N—((R)-1-(2-(2,2,2-trifluoroethoxy)thiazol-2-yl)ethyl)cyclopropane-1-carboxamide, (1R,2R)-2-(1H-benzo[d]imidazol-2-yl)-N—((R)-1-(2-(2,2,2-trifluoroethoxy)thiazol-2-yl)ethyl)cyclopropane-1-carboxamide, (1S,2S)-2-(1H-benzo[d]imidazol-2-yl)-N—((R)-1-(5-(3,3,3-trifluoropropyl)-1H-pyrazol-4-yl)ethyl)cyclopropane-1-carboxamide, (1R,2R)-2-(1H-benzo[d]imidazol-2-yl)-N—((R)-1-(5-(3,3,3-trifluoropropyl)-1H-pyrazol-4-yl)ethyl)cyclopropane-1-carboxamide, (1S,2S)-3-(1-(2-(1H-benzo[d]imidazol-2-yl)cyclopropanecarboxamido)ethyl)-1H-indole-1-carboxylic acid tert-butyl ester, (1R,2R)-3-(1-(2-(1H-benzo[d]imidazol-2-yl)cyclopropanecarboxamido)ethyl)-1H-indole-1-carboxylic acid tert-butyl ester, (1S,2S)-2-(1H-benzo[d]imidazol-2-yl)-N—((R)-1-(5-bromothiazol-2-yl)ethyl)cyclopropane-1-carboxamide, (1R,2R)-2-(1H-benzo[d]imidazol-2-yl)-N—((R)-1-(5-bromothiazol-2-yl)ethyl)cyclopropane-1-carboxamide, (R)-1-(1H-benzo[d]imidazol-2-yl)-N—((R)-1-(5-(2,2,2-trifluoroethoxy)thiophen-2-yl)ethyl)pyrrolidine-3-carboxamide, (R)-1-(benzo[d]thiazol-2-yl)-N—((R)-1-(5-(2,2,2-trifluoroethoxy)thiophen-2-yl)ethyl)pyrrolidine-3-carboxamide, (S)-1-(2-(tert-butylamino)-2-oxoethyl)-N—((R)-1-(5-(2,2,2-trifluoroethoxy)thiophen-2-yl)ethyl)pyrrolidine-3-carboxamide, (R)-1-(2-(tert-butylamino)-2-oxoethyl)-N—((R)-1-(5-(2,2,2-trifluoroethoxy)thiophen-2-yl)ethyl)pyrrolidine-3-carboxamide, (R)-1-(2-oxoethyl-2-(thiazol-2-ylamino)ethyl)-N—((R)-1-(5-(2,2,2-trifluoroethoxy)thiophen-2-yl)ethyl)pyrrolidine-3-carboxamide, (R)-1-(2-oxoethyl-2-(phenylamino)ethyl)-N—((R)-1-(5-(2,2,2-trifluoroethoxy)thiophen-2-yl)ethyl)pyrrolidine-3-carboxamide, (R)-1-(3,3-dimethylbutyl)-N—((R)-1-(5-(2,2,2-trifluoroethoxy)thiophen-2-yl)ethyl)pyrrolidine-3-carboxamide, (1S,2S)-2-(3,5-difluorophenyl)-N—((R)-1-(5-(2,2,2-trifluoroethoxy)thiophen-2-yl)ethyl)cyclopropane-1-carboxamide, (1R,2R)-2-(3,5-difluorophenyl)-N—((R)-1-(5-(2,2,2-trifluoroethoxy)thiophen-2-yl)ethyl)cyclopropane-1-carboxamide, (1S,2S)-2-(1-methyl-1H-imidazol-2-yl)-N—((R)-1-(5-(2,2,2-trifluoroethoxy)thiophen-2-yl)ethyl)cyclopropane-1-carboxamide, (1R,2R)-2-(1-methyl-1H-imidazol-2-yl)-N—((R)-1-(5-(2,2,2-trifluoroethoxy)thiophen-2-yl)ethyl)cyclopropane-1-carboxamide, (1S,2S)-2-(1H-indol-3-yl)-N—((R)-1-(5-(2,2,2-trifluoroethoxy)thiophen-2-yl)ethyl)cyclopropane-1-carboxamide, (1R,2R)-2-(1H-indol-3-yl)-N—((R)-1-(5-(2,2,2-trifluoroethoxy)thiophen-2-yl)ethyl)cyclopropane-1-carboxamide, (1S,2S)-2-(1-methyl-1H-indazol-6-yl)-N—((R)-1-(5-(2,2,2-trifluoroethoxy)thiophen-2-yl)ethyl)cyclopropanecarboxamide, (1R,2R)-2-(1-methyl-1H-indazol-6-yl)-N—((R)-1-(5-(2,2,2-trifluoroethoxy)thiophen-2-yl)ethyl)cyclopropanecarboxamide, (1S,2S)-2-(pyridin-2-yl)-N—((R)-1-(5-(2,2,2-trifluoroethoxy)thiophen-2-yl)ethyl)cyclopropane-1-carboxamide, (1R,2R)-2-(pyridin-2-yl)-N—((R)-1-(5-(2,2,2-trifluoroethoxy)thiophen-2-yl)ethyl)cyclopropane-1-carboxamide, (3R)-1-(1-oxo-1-(phenylamino)propan-2-yl)-N—((R)-1-(5-(2,2,2-trifluoroethoxy)thiophen-2-yl)ethyl)pyrrolidine-3-carboxamide, (1S,2S)-5-(((1R)-1-(2-(1H-benzo[d]imidazol-2-yl)cyclopropane-1-carboxamido)ethyl)thiophene-2-carboxylic acid tert-butyl ester, (1R,2R)-5-(((1R)-1-(2-(1H-benzo[d]imidazol-2-yl)cyclopropane-1-carboxamido)ethyl)thiophene-2-carboxylic acid tert-butyl ester, (1S,2S)-5-(((1R)-1-(2-(1H-benzo[d]imidazol-2-yl)cyclopropane-1-carboxamido)ethyl)thiophene-2-carboxylic acid, (1R,2R)-5-(((1R)-1-(2-(1H-benzo[d]imidazol-2-yl)cyclopropane-1-carboxamido)ethyl)thiophene-2-carboxylic acid, (1S,2S)-2-(1H-imidazo[4,5-c]pyridin-2-yl)-N—((R)-1-(5-(2,2,2-trifluoroethoxy)thiophen-2-yl)ethyl)cyclopropane-1-carboxamide, (1R,2R)-2-(1H-imidazo[4,5-c]pyridin-2-yl)-N—((R)-1-(5-(2,2,2-trifluoroethoxy)thiophen-2-yl)ethyl)cyclopropane-1-carboxamide, (1S,2S)-2-(1-methyl-1H-indol-3-yl)-N—((R)-1-(5-(2,2,2-trifluoroethoxy)thiophen-2-yl)ethyl)cyclopropane-1-carboxamide, (1R,2R)-2-(1-methyl-1H-indol-3-yl)-N—((R)-1-(5-(2,2,2-trifluoroethoxy)thiophen-2-yl)ethyl)cyclopropane-1-carboxamide, (1S,2S)-5-(((1R)-1-(2-(1H-benzo[d]imidazol-2-yl)cyclopropane-1-carboxamido)ethyl)thiophene-2-carboxamide, (1R,2R)-5-(((1R)-1-(2-(1H-benzo[d]imidazol-2-yl)cyclopropane-1-carboxamido)ethyl)thiophene-2-carboxamide, (1S,2S)-2-(4-phenyl-1H-imidazol-2-yl)-N—((R)-1-(5-(2,2,2-trifluoroethoxy)thiophen-2-yl)ethyl)cyclopropane-1-carboxamide, (1R,2R)-2-(4-phenyl-1H-imidazol-2-yl)-N—((R)-1-(5-(2,2,2-trifluoroethoxy)thiophen-2-yl)ethyl)cyclopropane-1-carboxamide, (1S,2S)-5-((1R)-1-(2-(1H-benzo[d]imidazol-2-yl)cyclopropane-1-carboxamido)ethyl)-N,N-diethylthiophene-2-carboxamide, (1R,2R)-5-((1R)-1-(2-(1H-benzo[d]imidazol-2-yl)cyclopropane-1-carboxamido)ethyl)-N,N-diethylthiophene-2-carboxamide, (1S,2S)-2-(1H-benzo[d]imidazol-2-yl)-N—((R)-1-(5-(pyrrolidine-1-carbonyl)thiophen-2-yl)ethyl)cyclopropane-1-carboxamide, (1R,2R)-2-(1H-benzo[d]imidazol-2-yl)-N—((R)-1-(5-(pyrrolidine-1-carbonyl)thiophen-2-yl)ethyl)cyclopropane-1-carboxamide, (1S,2S)-2-(quinolin-2-yl)-N—((R)-1-(5-(2,2,2-trifluoroethoxy)thiophen-2-yl)ethyl)cyclopropane-1-carboxamide, (1R,2R)-2-(quinolin-2-yl)-N—((R)-1-(5-(2,2,2-trifluoroethoxy)thiophen-2-yl)ethyl)cyclopropane-1-carboxamide, (1S,2S)-2-(3H-imidazo[4,5-b]pyridin-2-yl)-N—((R)-1-(5-(2,2,2-trifluoroethoxy)thiophen-2-yl)ethyl)cyclopropane-1-carboxamide, (1R,2R)-2-(3H-imidazo[4,5-b]pyridin-2-yl)-N—((R)-1-(5-(2,2,2-trifluoroethoxy)thiophen-2-yl)ethyl)cyclopropane-1-carboxamide, (R)-1-(2-(adamantan-1-ylamino)-2-oxoethyl)-N—((R)-1-(5-(2,2,2-trifluoroethoxy)thiophen-2-yl)ethyl)pyrrolidine-3-carboxamide, (R)-1-(2-oxo-2-(pyrazin-2-ylamino)ethyl)-N—((R)-1-(5-(2,2,2-trifluoroethoxy)thiophen-2-yl)ethyl)pyrrolidine-3-carboxamide, (1S,2S)-2-(1-benzyl-1H-imidazol-2-yl)-N—((R)-1-(5-(2,2,2-trifluoroethoxy)thiophen-2-yl)ethyl)cyclopropane-1-carboxamide, (1R,2R)-2-(1-benzyl-1H-imidazol-2-yl)-N—((R)-1-(5-(2,2,2-trifluoroethoxy)thiophen-2-yl)ethyl)cyclopropane-1-carboxamide, (1S,2S)-2-(4-(pyridin-2-yl)-1H-imidazol-2-yl)-N—((R)-1-(5-(2,2,2-trifluoroethoxy)thiophen-2-yl)ethyl)cyclopropane-1-carboxamide, (1R,2R)-2-(4-(pyridin-2-yl)-1H-imidazol-2-yl)-N—((R)-1-(5-(2,2,2-trifluoroethoxy)thiophen-2-yl)ethyl)cyclopropane-1-carboxamide, (1S,2S)-2-(benzo[d]oxazol-2-yl)-N—((R)-1-(5-(2,2,2-trifluoroethoxy)thiophen-2-yl)ethyl)cyclopropane-1-carboxamide, (1R,2R)-2-(benzo[d]oxazol-2-yl)-N—((R)-1-(5-(2,2,2-trifluoroethoxy)thiophen-2-yl)ethyl)cyclopropane-1-carboxamide, (R)—N—((R)-1-(5-(2,2,2-trifluoroethoxy)thiophen-2-yl)ethyl)-1-(5-(trifluoromethyl)pyridin-2-yl)pyrrolidine-3-carboxamide, (R)-1-(2-((3,5-dichlorophenyl)amino)-2-oxoethyl)-N—((R)-1-(5-(2,2,2-trifluoroethoxy)thiophen-2-yl)ethyl)pyrrolidine-3-carboxamide, (R)-1-(3,3-dimethyl-2-oxobutyl)-N—((R)-1-(5-(2,2,2-trifluoroethoxy)thiophen-2-yl)ethyl)pyrrolidine-3-carboxamide, (1S,2S)-2-(1H-benzo[d]imidazol-2-yl)-N—((R)-2-methyl-1-(5-(2,2,2-trifluoroethoxy)thiophen-2-yl)propyl)cyclopropane-1-carboxamide, (1R,2R)-2-(1H-benzo[d]imidazol-2-yl)-N—((R)-2-methyl-1-(5-(2,2,2-trifluoroethoxy)thiophen-2-yl)propyl)cyclopropane-1-carboxamide, (1S,2S)—N—((R)-1-(5-bromothiophen-2-yl)ethyl)-2-(quinolin-2-yl)cyclopropane-1-carboxamide,
(1R,2R)—N—((R)-1-(5-bromothiophen-2-yl)ethyl)-2-(quinolin-2-yl)cyclopropane-1-carboxamide,
(3R)-1-(1-((adamantan-1-yl)amino)-1-oxopropan-2-yl)-N—((R)-1-(2-(2,2,2-trifluoroethoxy)thiazol-5-yl)ethyl)pyrrolidine-3-carboxamide,
(1S,2S)-2-(1-methyl-1H-indol-3-yl)-N—((R)-1-(2-(2,2,2-trifluoroethoxy)thiazol-5-yl)ethyl)cyclopropane-1-carboxamide,
(1R,2R)-2-(1-methyl-1H-indol-3-yl)-N—((R)-1-(2-(2,2,2-trifluoroethoxy)thiazol-5-yl)ethyl)cyclopropane-1-carboxamide,
(1S,2S)-2-(1H-indol-3-yl)-N—((R)-1-(2-(2,2,2-trifluoroethoxy)thiazol-5-yl)ethyl)cyclopropane-1-carboxamide,
(1R,2R)-2-(1H-indol-3-yl)-N—((R)-1-(2-(2,2,2-trifluoroethoxy)thiazol-5-yl)ethyl)cyclopropane-1-carboxamide,
(1S,2S)-2-(1H-benzo[d]imidazol-2-yl)-N—((R)-2-methyl-1-(5-(trifluoromethyl)thiophen-2-yl)propyl)cyclopropane-1-carboxamide,
(1S,2S)-2-(1H-benzo[d]imidazol-2-yl)-N—((R)-1-(4-methyl-2-(2,2,2-trifluoroethoxy)thiazol-5-yl)ethyl)cyclopropane-1-carboxamide,
(1S,2S)-2-(1H-benzo[d]imidazol-2-yl)-N—((R)-1-(quinolin-2-yl)ethyl)cyclopropane-1-carboxamide,
(1S,2S)-2-(5-chloro-1H-benzo[d]imidazol-2-yl)-N—((R)-1-(5-(2,2,2-trifluoroethoxy)thiophen-2-yl)ethyl)cyclopropane-1-carboxamide,
(1R,2R)-2-(5-chloro-1H-benzo[d]imidazol-2-yl)-N—((R)-1-(5-(2,2,2-trifluoroethoxy)thiophen-2-yl)ethyl)cyclopropane-1-carboxamide,
(1S,2S)-2-(1-ethyl-1H-benzo[d]imidazol-2-yl)-N—((R)-1-(5-(2,2,2-trifluoroethoxy)thiophen-2-yl)ethyl)cyclopropane-1-carboxamide,
(1R,2R)-2-(1-ethyl-1H-benzo[d]imidazol-2-yl)-N—((R)-1-(5-(2,2,2-trifluoroethoxy)thiophen-2-yl)ethyl)cyclopropane-1-carboxamide,
(1S,2S)—N—((R)-1-(benzo[d][1,3]dioxol-5-yl)ethyl)-2-(1H-benzo[d]imidazol-2-yl)cyclopropane-1-carboxamide,
(1S,2S)-2-(1H-benzo[d]imidazol-2-yl)-N—((R)-1-(5-(morpholine-4-carbonyl)thiophen-2-yl)ethyl)cyclopropane-1-carboxamide,
(1R,2R)-2-(1H-benzo[d]imidazol-2-yl)-N—((R)-1-(5-(morpholine-4-carbonyl)thiophen-2-yl)ethyl)cyclopropane-1-carboxamide,
(1S,2S)-2-(1-ethyl-1H-benzo[d]imidazol-2-yl)-N—((R)-1-(2-(2,2,2-trifluoroethoxy)thiazol-5-yl)ethyl)cyclopropane-1-carboxamide,
(1R,2R)-2-(1-ethyl-1H-benzo[d]imidazol-2-yl)-N—((R)-1-(2-(2,2,2-trifluoroethoxy)thiazol-5-yl)ethyl)cyclopropane-1-carboxamide,
(1S,2S)—N—((R)-1-(1H-indol-6-yl)ethyl)-2-(1H-benzo[d]imidazol-2-yl)cyclopropane-1-carboxamide,
(1S,2S)-2-(1H-benzo[d]imidazol-2-yl)-N—((R)-cyclohexyl(5-(trifluoromethyl)thiophen-2-yl)methyl)cyclopropane-1-carboxamide,
(1S,2S)-2-(1H-benzo[d]imidazol-2-yl)-N—((R)-1-(5-(3,3-difluoropyrrolidine-1-carbonyl)thiophen-2-yl)ethyl)cyclopropane-1-carboxamide,
(1R,2R)-2-(1H-benzo[d]imidazol-2-yl)-N—((R)-1-(5-(3,3-difluoropyrrolidine-1-carbonyl)thiophen-2-yl)ethyl)cyclopropane-1-carboxamide,
(1S,2S)-2-(1H-benzo[d]imidazol-2-yl)-N—((R)-1-(5-(piperidine-1-carbonyl)thiophen-2-yl)ethyl)cyclopropane-1-carboxamide,
(1R,2R)-2-(1H-benzo[d]imidazol-2-yl)-N—((R)-1-(5-(piperidine-1-carbonyl)thiophen-2-yl)ethyl)cyclopropane-1-carboxamide,
(1S,2S)-5-((1R)-1-(2-(1H-benzo[d]imidazol-2-yl)cyclopropane-1-carboxamido)ethyl)-N-(4-fluorophenyl)-N-methylthiophene-2-carboxamide,
(1R,2R)-5-((1R)-1-(2-(1H-benzo[d]imidazol-2-yl)cyclopropane-1-carboxamido)ethyl)-N-(4-fluorophenyl)-N-methylthiophene-2-carboxamide,
(1S,2S)-2-(1H-benzo[d]imidazol-2-yl)-N—((R)-1-(5-fluoro-1H-indol-2-yl)ethyl)cyclopropane-1-carboxamide,
(1S,2S)-2-(5-chloro-1H-benzo[d]imidazol-2-yl)-N—((R)-1-(2-(2,2,2-trifluoroethoxy)thiazol-5-yl)ethyl)cyclopropane-1-carboxamide,
(1R,2R)-2-(5-chloro-1H-benzo[d]imidazol-2-yl)-N—((R)-1-(2-(2,2,2-trifluoroethoxy)thiazol-5-yl)ethyl)cyclopropane-1-carboxamide,
(1S,2S)-2-(1H-benzo[d]imidazol-2-yl)-N—((R)-1-(5-fluorobenzofuran-2-yl)ethyl)cyclopropane-1-carboxamide,
(1S,2S)-2-(1H-benzo[d]imidazol-2-yl)-N—((R)-1-(5-fluorobenzo[b]thiophen-2-yl)ethyl)cyclopropane-1-carboxamide,
(1S,2S)-2-(1H-benzo[d]imidazol-2-yl)-N—((R)-1-(5-(2,2-dimethylpyrrolidine-1-carbonyl)thiophen-2-yl)ethyl)cyclopropane-1-carboxamide,
(1R,2R)-2-(1H-benzo[d]imidazol-2-yl)-N—((R)-1-(5-(2,2-dimethylpyrrolidine-1-carbonyl)thiophen-2-yl)ethyl)cyclopropane-1-carboxamide,
(1S,2S)-2-(1H-benzo[d]imidazol-2-yl)-N—((R)-1-(5-(4-methylpiperazine-1-carbonyl)thiophen-2-yl)ethyl)cyclopropane-1-carboxamide,
(1R,2R)-2-(1H-benzo[d]imidazol-2-yl)-N—((R)-1-(5-(4-methylpiperazine-1-carbonyl)thiophen-2-yl)ethyl)cyclopropane-1-carboxamide,
(1S,2S)-2-(1H-benzo[d]imidazol-2-yl)-N—((R)-cyclopropyl(5-(trifluoromethyl)thiophen-2-yl)methyl)cyclopropane-1-carboxamide,
(1S,2S)-2-(1H-benzo[d]imidazol-2-yl)-N—((R)-1-(2,3-dihydrobenzo[b][1,4]dioxin-6-yl)ethyl)cyclopropane-1-carboxamide,
(1S,2S)-2-(5-methoxy-1H-benzo[d]imidazol-2-yl)-N—((R)-1-(5-(2,2,2-trifluoroethoxy)thiophen-2-yl)ethyl)cyclopropane-1-carboxamide,
(1R,2R)-2-(5-methoxy-1H-benzo[d]imidazol-2-yl)-N—((R)-1-(5-(2,2,2-trifluoroethoxy)thiophen-2-yl)ethyl)cyclopropane-1-carboxamide,
(1S,2S)-2-(1H-benzo[d]imidazol-2-yl)-N—((R)-1-(3-cyclopropyl-1,2,4-oxadiazol-5-yl)ethyl)cyclopropane-1-carboxamide,
(1S,2S)-2-(1H-benzo[d]imidazol-2-yl)-N—((R)-1-(2,2-difluorobenzo[d][1,3]dioxol-5-yl)ethyl)cyclopropane-1-carboxamide,
(1S,2S)-2-(1H-benzo[d]imidazol-2-yl)-N—((R)-1-(5-cyclopropylfuran-2-yl)ethyl)cyclopropane-1-carboxamide,
(1S,2S)-2-(1H-benzo[d]imidazol-2-yl)-N—((R)-1-(5-(piperazine-1-carbonyl)thiophen-2-yl)ethyl)cyclopropane-1-carboxamide,
(1R,2R)-2-(1H-benzo[d]imidazol-2-yl)-N—((R)-1-(5-(piperazine-1-carbonyl)thiophen-2-yl)ethyl)cyclopropane-1-carboxamide,
(1S,2S)-2-(1H-benzo[d]imidazol-2-yl)-N—((R)-1-(benzofuran-2-yl)ethyl)cyclopropane-1-carboxamide,
(1S,2S)-2-(5-chloro-1H-benzo[d]imidazol-2-yl)-N—((R)-1-(3-cyclopropyl-1,2,4-oxadiazol-5-yl)ethyl)cyclopropane-1-carboxamide, (1R,2R)-2-(5-chloro-1H-benzo[d]imidazol-2-yl)-N—((R)-1-(3-cyclopropyl-1,2,4-oxadiazol-5-yl)ethyl)cyclopropane-1-carboxamide, (1S,2S)-2-(1H-benzo[d]imidazol-2-yl)-N—((R)-1-(2,3-dihydrobenzofuran-5-yl)ethyl)cyclopropane-1-carboxamide, (1S,2S)-2-(1H-benzo[d]imidazol-2-yl)-N—((R)-1-(5-methoxybenzofuran-2-yl)ethyl)cyclopropane-1-carboxamide, (1S,2S)-2-(1H-benzo[d]imidazol-2-yl)-N—((R)-1-(furo[3,2-b]pyridin-2-yl)ethyl)cyclopropane-1-carboxamide, (1S,2S)-2-(1H-benzo[d]imidazol-2-yl)-N—((S)-1-(furo[3,2-b]pyridin-2-yl)ethyl)cyclopropane-1-carboxamide, (1S,2S)-2-(5-chloro-1H-benzo[d]imidazol-2-yl)-N—((R)-1-(5-fluorobenzofuran-2-yl)ethyl)cyclopropane-1-carboxamide, (1S,2S)-2-(1H-benzo[d]imidazol-2-yl)-N—((R)-1-(5-chlorobenzofuran-2-yl)ethyl)cyclopropane-1-carboxamide, (1S,2S)-2-(1H-benzo[d]imidazol-2-yl)-N—((R)-1-(5-(3,3-difluoroazetidine-1-carbonyl)thiophen-2-yl)ethyl)cyclopropane-1-carboxamide, (1R,2R)-2-(1H-benzo[d]imidazol-2-yl)-N—((R)-1-(5-(3,3-difluoroazetidine-1-carbonyl)thiophen-2-yl)ethyl)cyclopropane-1-carboxamide, 5-((R)-1-((1S,2S)-2-(1H-benzo[d]imidazol-2-yl)cyclopropane-1-carboxamido)ethyl)-N,N-dimethylthiophene-2-carboxamide, 5-((R)-1-((1R,2R)-2-(1H-benzo[d]imidazol-2-yl)cyclopropane-1-carboxamido)ethyl)-N,N-dimethylthiophene-2-carboxamide, (1S,2S)-2-(6-chloro-3H-imidazo[4,5-b]pyridin-2-yl)-N—((R)-1-(5-(2,2,2-trifluoroethoxy)thiophen-2-yl)ethyl)cyclopropane-1-carboxamide, (1R,2R)-2-(6-chloro-3H-imidazo[4,5-b]pyridin-2-yl)-N—((R)-1-(5-(2,2,2-trifluoroethoxy)thiophen-2-yl)ethyl)cyclopropane-1-carboxamide, (1S,2S)-2-(1H-benzo[d]imidazol-2-yl)-N—((R)-1-(1-methyl-1H-indol-6-yl)ethyl)cyclopropane-1-carboxamide, (1S,2S)—N—((R)-1-(5-(azepane-1-carbonyl)thiophen-2-yl)ethyl)-2-(1H-benzo[d]imidazol-2-yl)cyclopropane-1-carboxamide, (1R,2R)—N—((R)-1-(5-(azepane-1-carbonyl)thiophen-2-yl)ethyl)-2-(1H-benzo[d]imidazol-2-yl)cyclopropane-1-carboxamide, (1S,2S)-2-(1H-benzo[d]imidazol-2-yl)-N—((R)-1-(5,7-difluorobenzofuran-2-yl)ethyl)cyclopropane-1-carboxamide, (1S,2S)-2-(1H-benzo[d]imidazol-2-yl)-N—((R)-1-(2-phenylthiazol-5-yl)ethyl)cyclopropane-1-carboxamide, (1S,2S)-2-(benzo[d]oxazol-2-yl)-N—((R)-1-(2-(2,2,2-trifluoroethoxy)thiazol-5-yl)ethyl)cyclopropane-1-carboxamide, (1R,2R)-2-(benzo[d]oxazol-2-yl)-N—((R)-1-(2-(2,2,2-trifluoroethoxy)thiazol-5-yl)ethyl)cyclopropane-1-carboxamide, (1S,2S)-2-(1H-benzo[d]imidazol-2-yl)-N—((R)-1-(5,6-difluorobenzofuran-2-yl)ethyl)cyclopropane-1-carboxamide, (1S,2S)-2-(1H-benzo[d]imidazol-2-yl)-N—((R)-1-(4,6-difluorobenzofuran-2-yl)ethyl)cyclopropane-1-carboxamide, (1S,2S)-2-(1H-benzo[d]imidazol-2-yl)-N—((R)-1-(pyrazolo[1,5-a]pyridin-2-yl)ethyl)cyclopropane-1-carboxamide, (1S,2S)-2-(1H-benzo[d]imidazol-2-yl)-N—((R)-1-(5-(4,4-difluoropiperidine-1-carbonyl)thiophen-2-yl)ethyl)cyclopropane-1-carboxamide, (1R,2R)-2-(1H-benzo[d]imidazol-2-yl)-N—((R)-1-(5-(4,4-difluoropiperidine-1-carbonyl)thiophen-2-yl)ethyl)cyclopropane-1-carboxamide, (1S,2S)-2-(1H-benzo[d]imidazol-2-yl)-N-((1R)-1-(5-(3-fluoropiperidine-1-carbonyl)thiophen-2-yl)ethyl)cyclopropane-1-carboxamide, (1R,2R)-2-(1H-benzo[d]imidazol-2-yl)-N-((1R)-1-(5-(3-fluoropiperidine-1-carbonyl)thiophen-2-yl)ethyl)cyclopropane-1-carboxamide, (1S,2S)-2-(1H-benzo[d]imidazol-2-yl)-N—((R)-1-(7-fluorobenzofuran-2-yl)ethyl)cyclopropane-1-carboxamide, (1S,2S)-2-(1H-benzo[d]imidazol-2-yl)-N—((R)-1-(4-fluorobenzofuran-2-yl)ethyl)cyclopropane-1-carboxamide, (1S,2S)—N—((R)-1-(5-fluorobenzofuran-2-yl)ethyl)-2-(1H-indol-3-yl)cyclopropane-1-carboxamide, (1R,2R)—N—((R)-1-(5-fluorobenzofuran-2-yl)ethyl)-2-(1H-indol-3-yl)cyclopropane-1-carboxamide, (1S,2S)-2-(1H-benzo[d]imidazol-2-yl)-N—((R)-1-(furo[3,2-c]pyridin-2-yl)ethyl)cyclopropane-1-carboxamide, (1S,2S)-2-(1H-benzo[d]imidazol-2-yl)-N—((S)-1-(furo[3,2-c]pyridin-2-yl)ethyl)cyclopropane-1-carboxamide, (1S,2S)-2-(1H-benzo[d]imidazol-2-yl)-N—((R)-1-(6-fluorobenzofuran-2-yl)ethyl)cyclopropane-1-carboxamide, (1S,2S)-2-(1H-benzo[d]imidazol-2-yl)-N—((R)-1-(5-fluoro-3-methylbenzofuran-2-yl)ethyl)cyclopropane-1-carboxamide, (1S,2S)-2-(1-ethyl-1H-benzo[d]imidazol-2-yl)-N—((R)-1-(5-fluorobenzofuran-2-yl)ethyl)cyclopropane-1-carboxamide, (1S,2S)—N—((R)-1-(5-fluorobenzofuran-2-yl)ethyl)-2-(1-methyl-1H-indazol-6-yl)cyclopropane-1-carboxamide, (1R,2R)—N—((R)-1-(5-fluorobenzofuran-2-yl)ethyl)-2-(1-methyl-1H-indazol-6-yl)cyclopropane-1-carboxamide, (1S,2S)-2-(1H-benzo[d]imidazol-2-yl)-N—((R)-1-(5-fluorobenzo[d]thiazol-2-yl)ethyl)cyclopropane-1-carboxamide, (1S,2S)-2-(1H-benzo[d]imidazol-2-yl)-N—((S)-1-(5-fluorobenzo[d]thiazol-2-yl)ethyl)cyclopropane-1-carboxamide, (1S,2S)-2-(1H-benzo[d]imidazol-2-yl)-N—((R)-1-(5-fluorobenzo[d]oxazol-2-yl)ethyl)cyclopropane-1-carboxamide, (1S,2S)-2-(5-methyl-3H-imidazo[4,5-b]pyridin-2-yl)-N—((R)-1-(5-(2,2,2-trifluoroethoxy)thiophen-2-yl)ethyl)cyclopropane-1-carboxamide, (1R,2R)-2-(5-methyl-3H-imidazo[4,5-b]pyridin-2-yl)-N—((R)-1-(5-(2,2,2-trifluoroethoxy)thiophen-2-yl)ethyl)cyclopropane-1-carboxamide, (1S,2S)-2-(1H-benzo[d]imidazol-2-yl)-N—((R)-1-(5-cyanobenzofuran-2-yl)ethyl)cyclopropane-1-carboxamide, (1S,2S)-2-(5-chlorobenzo[d]oxazol-2-yl)-N—((R)-1-(5-fluorobenzofuran-2-yl)ethyl)cyclopropane-1-carboxamide, (1R,2R)-2-(5-chlorobenzo[d]oxazol-2-yl)-N—((R)-1-(5-fluorobenzofuran-2-yl)ethyl)cyclopropane-1-carboxamide, (1S,2S)-2-(1H-benzo[d]imidazol-2-yl)-N—((R)-1-(5-(trifluoromethyl)benzofuran-2-yl)ethyl)cyclopropane-1-carboxamide, (1S,2S)-2-(1-ethyl-1H-benzo[d]imidazol-2-yl)-N—((R)-1-(6-fluorobenzofuran-2-yl)ethyl)cyclopropane-1-carboxamide, (1S,2S)-2-(1H-benzo[d]imidazol-2-yl)-N—((S)-1-(5-fluorobenzofuran-2-yl)ethyl)cyclopropane-1-carboxamide, (1S,2S)—N—((R)-1-(5-fluorobenzofuran-2-yl)ethyl)-2-((4-fluorophenoxy)methyl)cyclopropane-1-carboxamide,
(1R,2R)—N—((R)-1-(5-fluorobenzofuran-2-yl)ethyl)-2-((4-fluorophenoxy)methyl)cyclopropane-1-carboxamide,
(1S,2S)-2-(1H-benzo[d]imidazol-2-yl)-N—((5-fluorobenzofuran-2-yl)methyl)cyclopropane-1-carboxamide,
(1S,2S)-2-(1H-benzo[d]imidazol-2-yl)-N—((R)-1-(6-fluorobenzo[d]oxazol-2-yl)ethyl)cyclopropane-1-carboxamide,
(1S,2S)-2-(1H-benzo[d]imidazol-2-yl)-N—((S)-2-methyl-1-(5-(trifluoromethyl)thiophen-2-yl)propyl)cyclopropane-1-carboxamide,
(1S,2S)-2-(1H-benzo[d]imidazol-2-yl)-N—((S)-cyclohexyl(5-(trifluoromethyl)thiophen-2-yl)methyl)cyclopropane-1-carboxamide,
(1S,2S)—N—((R)-1-(5-fluorobenzofuran-2-yl)ethyl)-2-(imidazo[1,5-a]pyridin-3-yl)cyclopropane-1-carboxamide,
(1R,2R)—N—((R)-1-(5-fluorobenzofuran-2-yl)ethyl)-2-(imidazo[1,5-a]pyridin-3-yl)cyclopropane-1-carboxamide,
(1S,2R)—N—((R)-1-(5-fluorobenzofuran-2-yl)ethyl)-2-(imidazo[1,5-a]pyridin-3-yl)cyclopropane-1-carboxamide,
(1R,2S)—N—((R)-1-(5-fluorobenzofuran-2-yl)ethyl)-2-(imidazo[1,5-a]pyridin-3-yl)cyclopropane-1-carboxamide,
(1S,2S)-2-(5-fluoro-1H-benzo[d]imidazol-2-yl)-N—((R)-1-(5-(2,2,2-trifluoroethoxy)thiophen-2-yl)ethyl)cyclopropane-1-carboxamide,
(1S,2S)-2-(1H-benzo[d]imidazol-2-yl)-N—((R)-1-(6-fluorobenzo[b]thiophen-2-yl)ethyl)cyclopropane-1-carboxamide,
(1S,2S)-2-(1H-benzo[d]imidazol-2-yl)-N—((R)-1-(6-fluorobenzo[b]thiophen-2-yl)-2-methylpropyl)cyclopropane-1-carboxamide,
(R)—N—((R)-1-(5-fluorobenzofuran-2-yl)ethyl)-1-(5-(trifluoromethyl)pyridin-2-yl)pyrrolidine-3-carboxamide,
(1S,2S)-2-(4-chloro-1H-benzo[d]imidazol-2-yl)-N—((R)-1-(5-(2,2,2-trifluoroethoxy)thiophen-2-yl)ethyl)cyclopropane-1-carboxamide,
(1R,2R)-2-(4-chloro-1H-benzo[d]imidazol-2-yl)-N—((R)-1-(5-(2,2,2-trifluoroethoxy)thiophen-2-yl)ethyl)cyclopropane-1-carboxamide,
(1S,2S)-2-(1H-benzo[d]imidazol-2-yl)-N—((R)-1-(6-(trifluoromethyl)benzofuran-2-yl)ethyl)cyclopropane-1-carboxamide,
(1S,2S)-2-(1H-benzo[d]imidazol-2-yl)-N—((R)-1-(6-fluorobenzofuran-2-yl)-2-methylpropyl)cyclopropane-1-carboxamide,
(1S,2S)-2-(5-fluoro-1H-benzo[d]imidazol-2-yl)-N—((R)-1-(5-fluorobenzofuran-2-yl)ethyl)cyclopropane-1-carboxamide,
(R)-1-(benzo[d]thiazol-2-yl)-N—((R)-1-(5-fluorobenzofuran-2-yl)ethyl)pyrrolidine-3-carboxamide,
(1S,2S)-2-(1H-benzo[d]imidazol-2-yl)-N—((R)-1-(6-fluoro-1H-benzo[d]imidazol-2-yl)ethyl)cyclopropane-1-carboxamide,
(1S,2S)-2-(1H-benzo[d]imidazol-2-yl)-N—((S)-1-(6-fluoro-1H-benzo[d]imidazol-2-yl)ethyl)cyclopropane-1-carboxamide,
(1S,2S)-2-(1H-benzo[d]imidazol-2-yl)-N-(1-(5-fluorobenzofuran-2-yl)cyclopropyl)cyclopropane-1-carboxamide,
(1S,2S)-2-(1H-benzo[d]imidazol-2-yl)-N—((R)-1-(6-fluorobenzofuran-2-yl)ethyl)-N-methylcyclopropane-1-carboxamide,
(1S,2S)—N$^1$—((R)-1-(5-fluorobenzofuran-2-yl)ethyl)-N$^2$-(3-(trifluoromethyl)phenyl)cyclopropane-1,2-dicarboxamide,
(1R,2R)—N$^1$—((R)-1-(5-fluorobenzofuran-2-yl)ethyl)-N$^2$-(3-(trifluoromethyl)phenyl)cyclopropane-1,2-dicarboxamide,
(R)—N—((R)-1-(5-fluorobenzofuran-2-yl)ethyl)-1-(3-(trifluoromethyl)phenyl)pyrrolidine-3-carboxamide,
(S)—N—((R)-1-(5-fluorobenzofuran-2-yl)ethyl)-1-(3-(trifluoromethyl)phenyl)pyrrolidine-3-carboxamide,
(1S,2S)-2-(1H-benzo[d]imidazol-2-yl)-N—((R)-1-(3,6-difluorobenzo[b]thiophen-2-yl)ethyl)cyclopropane-1-carboxamide,
(1S,2S)-2-(1H-benzo[d]imidazol-2-yl)-N—((R)-1-(5-fluoro-1-methyl-1H-indol-2-yl)ethyl)cyclopropane-1-carboxamide,
(1S,2S)-2-(1H-benzo[d]imidazol-2-yl)-N—((S)-1-(5-fluoro-1-methyl-1H-indol-2-yl)ethyl)cyclopropane-1-carboxamide,
(1S,2S)-2-(1H-benzo[d]imidazol-2-yl)-N—((R)-1-(5-fluorobenzofuran-2-yl)ethyl-2,2,2-d$_3$)cyclopropane-1-carboxamide,
(1S,2S)-2-(1H-benzo[d]imidazol-2-yl)-N—((S)-1-(5-fluorobenzofuran-2-yl)ethyl-2,2,2-d$_3$)cyclopropane-1-carboxamide,
(1S,2S)—N—((R)-1-(5-fluorobenzofuran-2-yl)ethyl)-2-((3-(trifluoromethyl)phenoxy)methyl)cyclopropane-1-carboxamide,
(1R,2R)—N—((R)-1-(5-fluorobenzofuran-2-yl)ethyl)-2-((3-(trifluoromethyl)phenoxy)methyl)cyclopropane-1-carboxamide,
(1S,2S)-2-(1H-benzo[d]imidazol-2-yl)-N—((R)-1-(5-fluorobenzofuran-2-yl)butyl)cyclopropane-1-carboxamide,
(1S,2S)-2-(1H-benzo[d]imidazol-2-yl)-N—((S)-1-(5-fluorobenzofuran-2-yl)butyl)cyclopropane-1-carboxamide,
(1S,2S)-2-(1-ethyl-1H-benzo[d]imidazol-2-yl)-N—((R)-1-(6-fluoro-1H-benzo[d]imidazol-2-yl)ethyl)cyclopropane-1-carboxamide, and
(1S,2S)-2-(1-ethyl-1H-benzo[d]imidazol-2-yl)-N—((S)-1-(6-fluoro-1H-benzo[d]imidazol-2-yl)ethyl)cyclopropane-1-carboxamide.

Examples of the pharmaceutically acceptable salt of the compound represented by General Formula (IA), (I), (II), or (III) include acid addition salts with mineral acids such as hydrochloric acid, sulfuric acid, and phosphoric acid; acid addition salts with organic acids such as formic acid, acetic acid, citric acid, tartaric acid, and methanesulfonic acid; salts with inorganic bases such as sodium salt, potassium salt, lithium salt, and calcium salt; and base addition salts with organic bases such as arginine and piperazine.

Furthermore, the compound of the present invention may include stereoisomers including cis/trans isomers, optically active substances and racemates, and all of them are included in the present invention, while mixtures of enantiomers or diastereomers are also included in the present invention.

The compound of the present invention also includes stable isotopes.

The compound of the present invention may be a tautomer, a hydrate, a solvate with an organic solvent such as an alcohol, a derivative substituted with a stable isotope such as deuterium, or a prodrug.

In the present specification, the following abbreviations may be used.

M: molar concentration, N: normal, MS: mass spectrometry, [M+H]$^+$: molecular ion peak, [M−H]$^-$: molecular ion peak, CDCl$_3$: deuterated chloroform, DMSO-d$_6$: deuterated dimethyl sulfoxide, CD₃OD: deuterated methanol, ¹H NMR: proton nuclear magnetic resonance, Me: methyl group, Et: ethyl group, t-Bu: tert-buyl group, CN: cyano group, CF₃: trifluoromethyl group, Ts: p-toluenesulfonyl group, Boc: tert-butoxycarbonyl group, DMF: N,N-dimethylformamide, THF: tetrahydrofuran, DME: 1,2-dimethoxyethane, HATU: O-(7-azabenzotriazol-1-yl)-N,N,N',N'-tetramethyluronium hexafluorophosphate, HOBT: 1-hydroxybenzotriazole, WSC: 1-ethyl-3-(dimethylaminopropyl)carbodiimide, DMT-MM: 4-(4,6-dimethoxy-1,3,5-triazin-2-yl)-4-methylmorpholinium chloride, DMAP: N,N-dimethyl-4-aminopyridine, DIBAL-H: diisobutylaluminum hydride, L-selectride: lithium tri(sec-butyl)borohydride, DIPEA: N,N-diisopropylethylamine, BINAP: 2,2'-bis(diphenylphosphino)-1,1'-binaphthyl, DMSO: dimethyl sulfoxide, FBS: fetal bovine serum, DMEM: Dulbecco's Modified Eagle Medium, CO₂: carbon dioxide, NaCl: sodium chloride, KCl: potassium chloride, MgCl₂: magnesium chloride, CaCl₂: calcium chloride, CsCl: cesium chloride, CsF: cesium fluoride, HEPES: 4-(2-hydroxyethyl)-1-piperazineethanesulfonic acid, EGTA: glycol ether diamine tetraacetic acid, CYP: Cytochrome P450, NADP or NADP⁺: nicotinamide adenine dinucleotide phosphate, G-6-P DH(Y): glucose-6-phosphate, G-6-P DH(Y): glucose-6-phosphate dehydrogenase (derived from yeast), and PSNL: partial sciatic nerve ligation Next, methods for producing the compounds of the present invention represented by General Formula (IA), (I), (II), or (III) described above will be described below; however, the methods for producing the compounds of the present invention are not limited to the following methods.

The compounds of the present invention can be produced using commercially available compounds as raw materials and using a known method or a method described below. Regarding known methods, the methods described in Jikken Kagaku Koza (Lectures on Experimental Chemistry), 5$^{th}$ Edition (published by Maruzen Publishing Co., Ltd.); Shinpen Hetero Kan Kagobutsu (New Edition: Heterocyclic Compounds) (Kodansha, Ltd.), Protective Groups in Organic Synthesis (John Wiley & Sons, Inc.), and the like are available.

Depending on the compound to be produced using the present production methods, protection or deprotection, conversion, or introduction of a functional group may be effective in the various stages of production. In such a case, the processes are not limited to the operation or procedure of the described production method, and any appropriate operation or procedure can be applied using known methods.

A prodrug of the compound of the present invention can be produced by applying known methods such as amidation, esterification, and alkylation in the various stages of the production.

Depending on the compound to be produced using the present production method, the compound may include various salts, hydrates, and crystal polymorphisms. Furthermore, in a case in which optical isomers, geometric isomers, or tautomers may exist, the compound may include a mixture thereof at any ratio, without any particular limitations. Such a mixture of isomers can be separated by a known method.

In the following description, a method for producing the compound of the present invention will be described; however, the method for producing the compound of the present invention is not intended to be limited to the methods described below.

[Chemical Formula 16]

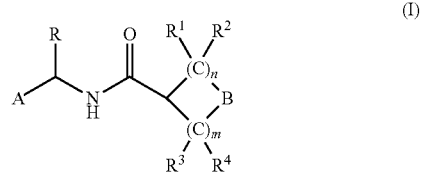

[Chemical Formula 17]

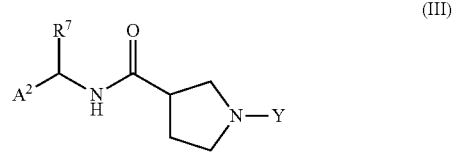

Production Method 1
Method for Producing Compound (I)
Compound (I) of the present invention can be produced by, for example, a method described below.

[Chemical Formula 18]

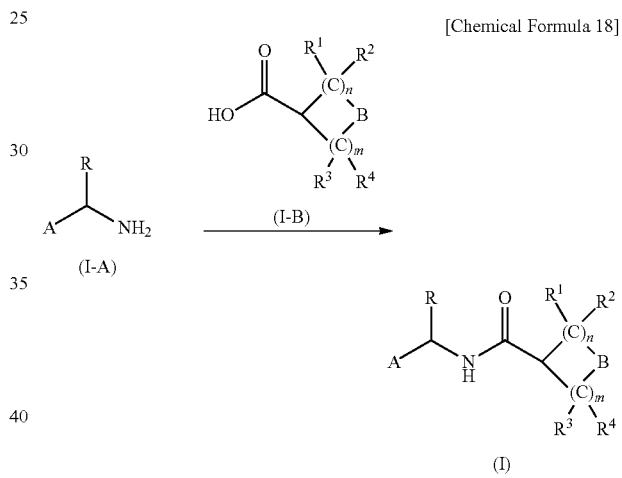

wherein the reference signs have the same meanings as described above.

Compound (I) of the present invention can be produced by reacting Compound (I-A) with Compound (I-B) in an appropriate solvent such as DMF in the presence of a condensing agent such as HATU or WSC, optionally an additive such as HOBT or DMAP, and optionally a base such as triethylamine or DIPEA, at 0° C. to 100° C.

Furthermore, Compound (I) can be produced by reacting Compound (I-B) with a corresponding carboxylic acid chloride or carboxylic acid anhydride in an appropriate solvent such as THF and in the presence of a base such as triethylamine, DIPEA, or pyridine as necessary, at 0° C. to 100° C.

In addition to those, Compound (I) can be produced from Compound (I-A) and Compound (I-B), or from respectively corresponding derivatives thereof, using the condensation reaction described in Christian A. G. N. MontalbettiChristian A. G. N. Montalbetti, Christian A. G. N. Montalbetti, et al., Tetrahedron, 61(46), 2005, 10827-10852, or a condensation reaction equivalent thereto.

Compound (I-A) can be produced by, for example, a method described below.

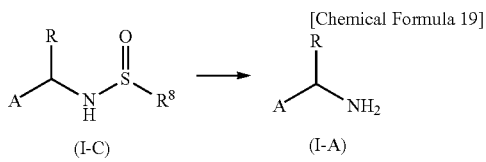

wherein R[8] represents a C1-C6 alkyl group or a substituted aryl group; and other reference signs have the same meanings as described above.

Compound (I-A) can be produced by reacting Compound (I-C) with an acid such as hydrogen chloride or trifluoroacetic acid in an appropriate solvent such as methanol, or without solvent, at −10° C. to 100° C.

Compound (I-C) can be produced by, for example, a method described below.

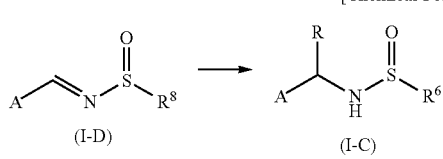

wherein R[8] represents a C1-C6 alkyl group or a substituted aryl group; and other reference signs have the same meanings as described above.

Compound (I-C) can be produced by reacting Compound (I-D) with a nucleophilic agent such as a Grignard reagent in an appropriate solvent such as THF at −78° C. to 60° C.

In addition to that, Compound (I-C) can also be produced from Compound (I-D) using the nucleophilic addition reaction described in Jonathan A. Ellman, Pure Appl. Chem., 75(1), 2003, 39-46, or a nucleophilic addition reaction equivalent thereto.

Furthermore, Compound (I-C) can be produced by reacting Compound (I-D) with a reducing agent such as sodium borohydride in an appropriate solvent such as THF at −78° C. to 100° C.

Compound (I-D) can be produced by, for example, a method described below.

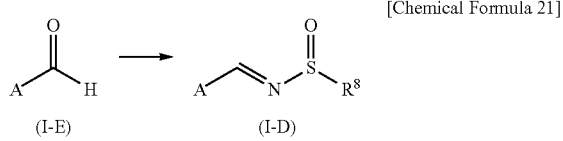

wherein R[8] represents a C1-C6 alkyl group or a substituted aryl group; and other reference signs have the same meanings as described above.

Compound (I-D) can be produced from Compound (I-E) by reacting Compound (I-E) with a sulfinamide derivative such as t-butyl sulfonamide or p-toluene sulfonamide, or with an acidic dehydrating agent such as titanium (IV) ethoxide or copper sulfate, in an appropriate solvent such as THF at room temperature to 100° C.

In addition to that, Compound (I-D) can also be produced from Compound (I-E) using the imine synthesis reaction described in Sara Morales, et al., J. Am. Chem. Soc., 136(3), 2014, 1082-1089, or an imine synthesis reaction equivalent thereto.

Compound (I-E) can be a commercially available product, or can be produced by a known method from a commercially available product. For example, Compound (I-E) can be produced according to the synthesis methods described in known patent literatures including WO 2013/192352, WO 2011/053542, WO 2010/059922, and the like, or according to synthesis methods equivalent thereto, from appropriate starting raw materials by combining known methods.

Compound (I-C) can also be produced by, for example, a method described below.

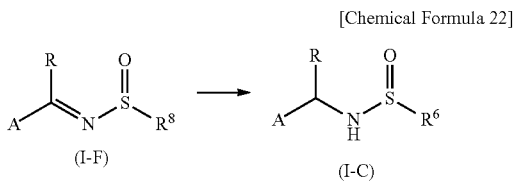

wherein R[8] represents a C1-C6 alkyl group or a substituted aryl group; and other reference signs have the same meanings as described above.

Compound (I-C) can be produced from Compound (I-F) by reacting Compound (I-F) with a reducing agent such as DIBAL-H or L-selectride in an appropriate solvent such as THF at −78° C. to 60° C.

In addition to that, Compound (I-C) can be produced from Compound (I-F) using the reduction reactions described in Jonathan A. Ellman, Pure Appl. Chem., 75(1), 2003, 39-46; Example 42 of Patent Literature WO 2011/123751; and the like, or reduction reactions equivalent thereto.

Compound (I-F) can be produced by, for example, a method described below.

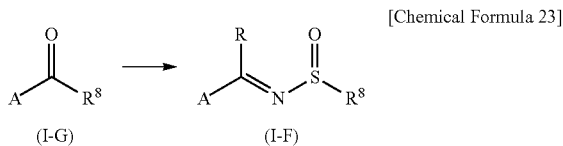

wherein R[8] represents a C1-C6 alkyl group or a substituted aryl group; and other reference signs have the same meanings as described above.

Compound (I-F) can be produced from Compound (I-G) by a method similar to the method for producing Compound (I-D), using Compound (I-G).

Compound (I-G) can be a commercially available product, or can be produced by a known method from a commercially available product. For example, Compound (I-G) can be produced according to the synthesis methods described in known patent literatures including WO 2014/201327, WO 2010/019910, WO 2006/137019, and the like or according to synthesis methods equivalent thereto, from appropriate starting raw materials by combining known methods.

Compound (I-A) can also be produced according to the synthesis methods described in, for example, known patent literatures including WO 2014/144100, WO 2011/106627, WO 2009/005076, and the like, or according to synthesis methods equivalent thereto, from appropriate starting raw materials by combining known methods.

Compound (I-B) can be produced by, for example, a method described below.

[Chemical Formula 24]

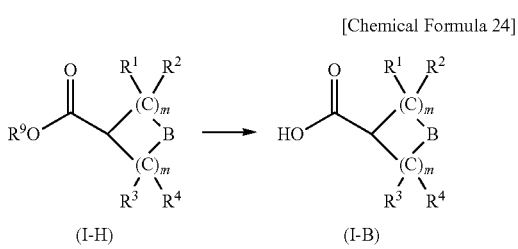

wherein $R^9$ represents an arbitrary functional group that can be converted to H by a deprotection reaction; and other reference signs have the same meanings as described above.

Compound (I-B) can be produced from Compound (I-H) by reacting Compound (I-H) with a base such as lithium hydroxide or sodium hydroxide in an appropriate solvent such as a mixed solvent of water and methanol or THF, at 0° C. to 100° C.

In addition to that, Compound (I-B) can be produced from Compound (I-H) using the deprotection reactions for a protective group as described in Protective groups in Organic Synthesis (John Wiley & Sons, Inc.) and the like, or deprotection reactions equivalent thereto.

Compound (I-H) can be a commercially available product, or can be produced according to a known method from a commercially available product. For example, Compound (I-H) can be produced according to the synthesis methods described in known patent literatures including WO 2010/137351 and JP 2008/280297, or academic literatures including Jason A. Miller, J. Org. Chem., 68(20), 2003, 7884-7886 and the like, or according to synthesis methods equivalent thereto, from appropriate starting raw materials by combining known methods.

Production Method 2
Method for Producing Compound (III)
Compound (III) of the present invention can be produced by, for example, a method described below.

[Chemical Formula 25]

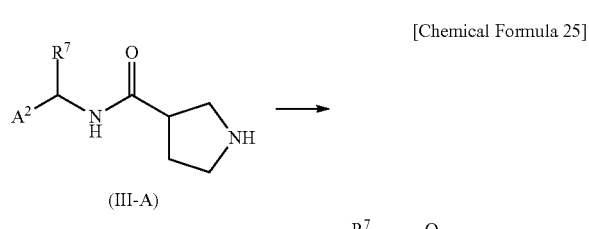

wherein the reference signs have the same meanings as described above.

Compound (III) of the present invention can be produced from Compound (III-A) by reacting Compound (III-A) with a corresponding aldehyde (Y—CHO) in an appropriate solvent such as acetonitrile, in the presence of a reducing agent such as sodium triacetoxyborohydride or sodium cyanoborohydride, optionally an additive such as acetic acid, and optionally a base such as triethylamine or DIPEA, at 0° C. to 100° C.

Furthermore, Compound (III) can be produced from Compound (III-A) by reacting Compound (III-A) with a corresponding alkylating agent (Y-L: L represents a halogen such as Cl, Br, or I, or an appropriate leaving group such as OMs or OTs) in an appropriate solvent such as DMF or acetonitrile, optionally an additive such as potassium iodide, and optionally a base such as potassium carbonate, at 0° C. to 150° C.

In addition to that, introduction of a Y group into Compound (III-A) is not limited to the reactions described above, and Compound (III) can be produced from Compound (III-A) using a generally known reaction for introducing a functional group into an amino group, or a reaction equivalent thereto.

Compound (III-A) can be produced by, for example, a method described below.

[Chemical Formula 26]

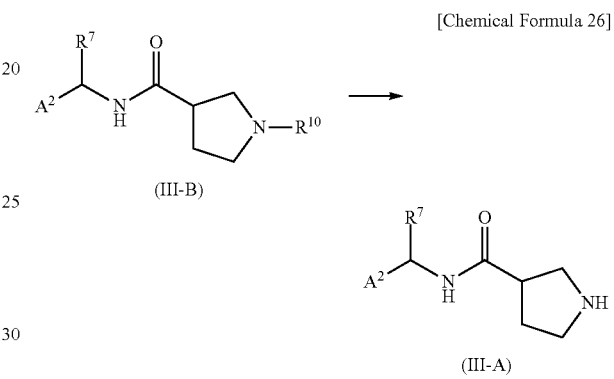

wherein $R^{10}$ represents an arbitrary functional group that can be converted to H by a deprotection reaction; and other reference signs have the same meanings as described above.

Compound (III-A) can be produced from Compound (III-B) by reacting Compound (III-B) with an acid such as hydrochloric acid or trifluoroacetic acid in an appropriate solvent such as methanol or chloroform, at −10° C. to 100° C.

In addition to that, Compound (III-A) can be produced from Compound (III-B) using the deprotection reactions for a protective group as described in Protective Groups in Organic Synthesis (John Wiley & Sons, Inc.) and the like, or deprotection reactions equivalent thereto.

Compound (III-B) can be produced by, for example, a method described below.

[Chemical Formula 27]

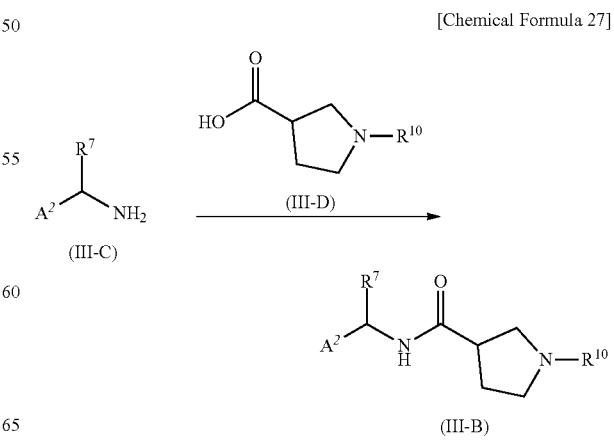

wherein $R^{10}$ represents an arbitrary functional group that can be converted to H by a deprotection reaction; and other reference signs have the same meanings as described above.

Compound (III-B) can be produced from Compound (III-C) using Compound (III-D) by a method similar to the method for producing Compound (I).

The compound of the present invention represented by General Formula (I), (II), or (III) as described above can be produced by referring to the production methods described in the present specification, as well as Reference examples and Examples, academic literatures, patent literatures, and the like.

The compounds of the present invention other than the compound represented by General Formula (IA), (I), (II), or (III) can be produced by referring to the synthesis schemes described above, Synthesis Examples that will be described below, patent literatures described above, and the like.

Next, the pharmacological action of the compound of the present invention will be described.

In Examples 140 and 141 described below, the results for a pharmacological experiment on the voltage-dependent T-type calcium inhibitory action of the compound of the present invention carried out by using stable cells expressing human Cav3.2 channels and measuring the intracellular calcium concentration are described.

As is obvious from Tables 1 to 6, it was found that the compound of the present invention has excellent voltage-dependent T-type calcium inhibitory action.

However, it is known that Ca channels have a property called state (status)-dependency.

That is, Ca channels adopt three states, namely, a closed state, an activated or open state, and an inactivated state, depending on the difference in the membrane voltage.

As described in Examples 140 given below, it has been disclosed that among the compounds of the present invention, diastereomer A of Example 1, diastereomers A and B of Example 2, diastereomer A of Example 3, diastereomers A and B of Example 4, diastereomers A and B of Example 6, diastereomers A and B of Example 7, diastereomer A described in Example 8, diastereomer A of Example 11, diastereomers A of Example 12, Examples 15 to 17, and particularly Example 1, diastereomer A of Example 3, diastereomer A of Example 4, and diastereomer A of Example 8 exhibit excellent voltage-dependent T-type calcium channel inhibitory action in an inactivated state, compared to a resting state or a closed state. Therefore, the compound of the present invention is expected to exhibit selective voltage-dependent T-type calcium inhibitory action.

Furthermore, an electrophysiological evaluation using an automatic patch clamp system is described in Example 142, and the results are described in Tables 7 and 8. The compound of the present invention exhibited excellent voltage-dependent T-type calcium inhibitory action.

Neuropathic pain is a state in which depolarization is repeated; however, the compound of the present invention also includes a compound having a property by which the blocking effect is enhanced in such a state (frequency-dependence).

Furthermore, an evaluation of the CYP3A4 activity inhibitory action is described in Example 143. From Table 9, the compound of the present invention also includes compounds having weak CYP3A4 activity inhibitory action.

In Example 144 that is described below, in a pharmacological experiment for mechanical allodynia in a mouse partial sciatic nerve ligation (PSNL) model, mechanical allodynia could be suppressed in a statistically meaningful manner compared to a vehicle group, by intraperitoneally administering 20 to 30 mg/kg of diastereomer A of Example 3, as is obvious from FIG. 1. Similarly, it is shown in Example 145 that the compound of Example 65 could suppress mechanical allodynia in a statistically meaningful manner by oral administration (FIG. 2).

Therefore, the compound of the present invention is a highly safe voltage-dependent T-type calcium channel blocker that has excellent voltage-dependent T-type calcium inhibitory action and exhibits stronger affinity in the inactivated state compared to the resting state, without causing serious adverse side effects such as cardiac toxicity (hERG). The compound of the present invention can be used for the diseases such as neuropathic pain described in Patent Literatures 2 to 4 that have been mentioned above.

That is, the target diseases of the compound of the present invention include pain, as described in Patent Literature 4, and limited target diseases include chronic pain, while further limited target diseases include neuropathic pain.

Furthermore, as described in the patent literatures mentioned above, examples of the "pain are classified into chronic and acute pains including neuropathic, inflammatory, cancerous, and visceral pains, and causative diseases thereof include diabetic neuropathy, traumatic neuropathy, compression of nerve, strangulation, spinal cord injury, apoplexy, fibromyalgia, carpal tunnel syndrome, osteoarthritis, rheumatoid arthritis, multiple sclerosis, herpes zoster, herpes simplex, syphilis, neuropathy induced by cancer chemotherapy or HIV and HIV treatment, chronic arthralgia, post-herpetic neuralgia, neuroma pain, trigeminal neuralgia, phantom limb pain, post-operative pain, stump pain, toothache, nerve plexus neuropathy, glossopharyngeal neuralgia, laryngeal neuralgia, migraine, carcinomatous neuropathy, multiple neuropathy, causalgia, low back pain, complex regional pain syndrome (CRPS), and thalamic pain". Pains originating from causes other than the causes listed here are also included in the target diseases of the present invention. As described in those literatures, examples of the target disease other than pain include "diseases associated with central nervous system (CNS) disorders, diseases associated with bladder dysfunction, apoplexy, pruritus, atopic dermatitis, hypertension, hyperaldosteronism, edema, ischemic heart diseases, age-related macular degeneration, cancer, diabetes mellitus, sterility and sexual incompetence, arrhythmia, and kidney diseases; the diseases associated with central nervous system (CNS) disorders include epilepsy, essential tremor, schizophrenia, Parkinson's disease, manic depressive psychosis, bipolar disorder, depression, anxiety, dementia, drug dependence, Huntington's disease, and sleep disorder; and the diseases associated with bladder dysfunction include overactive bladder."

The compound of the present invention can also be used in combination with known pain treating agents.

The compound of the present invention can be administered to a human by an appropriate administration method such as oral administration or parenteral administration; however, oral administration is preferred.

In order to formulate the compound of the present invention, the compound can be produced into formulations such as a tablet, a granular preparation, a powder preparation, a capsule, a suspension, an injectable preparation, and a suppository, by the methods conventionally used in the field of formulation technology.

For the preparation of these formulations, for example, in the case of a tablet, an excipient, a disintegrant, a binder, a lubricating agent, a colorant, and the like, which are conventionally used, are used. Here, examples of the excipient include lactose, D-mannitol, crystalline cellulose, and glucose; examples of the disintegrant include starch and carboxymethyl cellulose calcium (CMC-Ca); examples of the lubricating agent include magnesium stearate and talc; and examples of the binder include hydroxypropyl cellulose (HPC), gelatin, and polyvinylpyrrolidone (PVP). For the production of an injectable preparation, a solvent, a stabilizer, a dissolution aid, a suspending agent, an emulsifier, a soothing agent, a buffering agent, a preservative, and the like are used.

The amount of administration for an adult is usually about 0.01 mg to 100 mg of the compound of the present invention per day as an active ingredient in an injectable preparation, and 1 mg to 2,000 mg per day by oral administration. However, the amount of administration can be increased or decreased depending on the age, symptoms, and the like.

Next, the present invention will be explained in more detail by way of Reference Examples and Examples; however, the present invention is not intended to be limited to these.

Regarding the columns and TLC used in the Reference Examples and Examples, unless particularly stated otherwise, any one or both of silica gel and NH silica gel were used. For an analysis of a synthesized compound, $^1$H-NMR (400 MHz), atmospheric pressure ionization high-resolution time-of-flight mass spectrometry (ESI), and other appropriate analysis methods were used. Furthermore, a compound synthesized in a Reference Example or a compound equivalent thereto was subjected to structure determination by New Mosher's method using an amide obtainable by a method similar to Reference Example 11-1 and Reference Example 11-2 as necessary. Naming of compounds was carried out based on ChemBioDraw ver. 14.

Reference Example 1-1

4-Methyl-5-(2,2,2-trifluoroethoxy)thiophene-2-carboaldehyde

In a nitrogen atmosphere, 5-bromo-4-methylthiophene (200 mg, 0.98 mmol), 2,2,2-trifluoroethan-1-ol (142 μL, 2.0 mmol) and potassium carbonate (404 mg, 2.9 mmol) were dissolved in DMF (2.0 mL), and the solution was stirred for one day at 100° C. The reaction liquid was left to cool to room temperature, water was added thereto, and the mixture was stirred for a while. Subsequently, the mixture was extracted with diethyl ether. The organic layer was washed with saturated brine and was dried over anhydrous sodium sulfate, and insoluble matters were filtered. Subsequently, the solvent was distilled off under reduced pressure. A residue thus obtained was purified by silica gel column chromatography (hexane:ethyl acetate) (concentration gradient: 0% to 30%), and thus the title compound (yellow crystals, 94 mg, 43%) was obtained.

$^1$H NMR (CDCl$_3$, 400 MHz): δ=2.15 (s, 3H), 4.45 (q, 2H, J=8 Hz), 7.43 (s, 1H), 9.68 (s, 1H).

Reference Example 1-2

(S)-2-methyl-N-((4-methyl-5-(2,2,2-trifluoroethoxy)thiophen-2-yl)methylene)propane-2-sulfinamide In a nitrogen atmosphere, 4-methyl-5-(2,2,2-trifluoroethoxy)thiophene-2-carboaldehyde (1.69 g, 7.5 mmol) synthesized in Reference Example 1-1, (S)-2-methylpropane-2-sulfinamide (0.96 g, 7.9 mmol), and tetraethyl titanate (3.8 mL, 18 mmol) were dissolved in THF (170 mL), and the solution was stirred for one day at 75° C. The reaction liquid was left to cool to room temperature, saturated brine was added thereto, and the mixture was stirred for a while. Subsequently, insoluble matters were filtered and washed with ethyl acetate and methanol. The filtrate was concentrated under reduced pressure and then dissolved in ethyl acetate. The solution was washed with saturated brine. The organic layer was dried over anhydrous sodium sulfate, insoluble matters were filtered, and then the solvent was distilled off under reduced pressure. Thus, the title compound (yellow oily material, 197 g, 80%) was obtained.

$^1$H NMR (CDCl$_3$, 400 MHz): δ=1.23 (s, 9H), 2.12 (s, 3H), 4.43 (q, 2H, J=8 Hz), 7.14 (s, 1H), 8.48 (s, 1H).

Reference Example 1-3

(S)-2-methyl-N—((R)-1-(4-methyl-5-(2,2,2-trifluoroethoxy)thiophen-2-yl)ethyl)propane-2-sulfinamide In a nitrogen atmosphere, (S)-2-methyl-N-((4-methyl-5-(2,2,2-trifluoroethoxy)thiophen-2-yl)methylene)propane-2-sulfinamide (1.97 g, 6.0 mmol) synthesized in Reference Example 1-2 was dissolved in THF, and the solution was stirred for a while at −40° C. Subsequently, a THF solution of methylmagnesium bromide (31 mL, 28 mmol, 0.9 M) was added thereto, and the mixture was stirred for one hour at the same temperature. The temperature of the reaction liquid was increased to room temperature, and the reaction liquid was stirred for one day. Subsequently, a saturated solution of ammonium chloride and water were added thereto, and the mixture was extracted with ethyl acetate. The organic layer was washed with saturated brine and was dried over anhydrous sodium sulfate. Insoluble matters were filtered, and then the solvent was distilled off under reduced pressure. A residue thus obtained was purified by silica gel column chromatography (hexane:ethyl acetate) (concentration gradient: 0% to 60%), and thus the title compound (yellow oily material, 1.49 g, 72%) was obtained.

$^1$H NMR (CDCl$_3$, 400 MHz): δ=1.23 (s, 9H), 1.59 (d, 3H, J=6 Hz), 2.05 (s, 3H), 3.32 (d, 1H, J=5 Hz), 4.29 (q, 2H, J=8 Hz), 4.6-4.7 (m, 1H), 6.50 (s, 1H).

Reference Example 1-4

(R)-1-(4-methyl-5-(2,2,2-trifluoroethoxy)thiophen-2-yl)ethan-1-amine hydrochloride (S)-2-methyl-N—((R)-1-(4-methyl-5-(2,2,2-trifluoroethoxy)thiophen-2-yl)ethyl)propane-2-sulfinamide (1.49 g, 4.3 mmol) synthesized in Reference Example 1-3 was dissolved in 2 N hydrochloric acid-methanol (19 mL), and the solution was stirred for 3 hours at room temperature. The reaction liquid was concentrated under reduced pressure, water was added thereto, and the mixture was washed with ethyl acetate. A 10% aqueous solution of potassium carbonate was added to the aqueous layer to make the aqueous layer basic, and the aqueous layer was extracted with ethyl acetate. The organic layer was washed with saturated brine and was dried over anhydrous sodium sulfate. Insoluble matters were filtered, and then the solvent was distilled off under reduced pressure. 2 N hydrochloric acid-methanol (4 mL) was added to a residue thus obtained, and the mixture was stirred for 2 hours at room temperature. The reaction liquid was concentrated under reduced pressure. A suspension liquid obtained by adding diethyl ether to the concentrate was filtered, and crystals thus obtained were dried. Thus, the title compound (white crystals, 603 mg, 50%) was obtained.

¹H NMR (DMSO-d₆, 400 MHz): δ=1.52 (d, 3H, J=7 Hz), 2.02 (s, 3H), 4.53 (q, 1H, J=7 Hz), 4.73 (q, 2H, J=9 Hz), 6.86 (s, 1H), 8.51 (br s, 3H).

Reference Example 2-1

(R)-2-methyl-N—((S)-1-(5-(2,2,2-trifluoroethoxy)thiophen-2-yl)ethyl)propane-2-sulfinamide According to a technique similar to that of Reference Example 1-2, (R)-2-methyl-N-((5-(2,2,2-trifluoroethoxy)thiophen-2-yl)methylene)propane-2-sulfinamide was obtained using 5-(2,2,2-trifluoroethoxy)thiophene-2-carboaldehyde (150 mg, 0.71 mmol) and (R)-2-methylpropane-2-sulfinamide (91 mg, 75 mmol). According to a technique similar to that of Reference Example 1-3, the title compound (90 mg, 38%) was obtained using (R)-2-methyl-N-((5-(2,2,2-trifluoroethoxy)thiophen-2-yl)methylene)propane-2-sulfinamide thus obtained.

¹H NMR (CDCl₃, 400 MHz): δ=1.23 (s, 9H), 1.60 (d, 3H, J=6 Hz), 3.34 (d, 1H, J=5 Hz), 4.35 (q, 2H, J=8 Hz), 4.6-4.7 (m, 1H), 6.15 (d, 1H, J=4 Hz), 6.59 (dd, 1H, J=1, 4 Hz).

Reference Example 2-2

(S)-1-(5-(2,2,2-trifluoroethoxy)thiophen-2-yl)ethan-1-amine

2 N hydrochloric acid-methanol was added to (R)-2-methyl-N—((S)-1-(5-(2,2,2-trifluoroethoxy)thiophen-2-yl)ethyl)propane-2-sulfinamide (90 mg, 0.27 mmol) synthesized in Reference Example 2-1, and the mixture was stirred for one hour at room temperature. Subsequently, the solvent was distilled off under reduced pressure. Water was added to a residue thus obtained, and the mixture was washed with ethyl acetate. Subsequently, an aqueous solution of potassium carbonate was added to the aqueous layer, and the aqueous layer was extracted with ethyl acetate. The organic layer thus collected was dried over sodium sulfate, insoluble matters were separated by filtration, and then the filtrate was concentrated under reduced pressure. Thus, the title compound (pale yellow oil, 61 mg, 100%) was obtained.

¹H NMR (CDCl₃, 400 MHz): δ=1.43 (d, 3H, J=6 Hz), 4.22 (dq, 1H, J=1, 6 Hz), 4.34 (q, 2H, J=8 Hz), 6.17 (d, 1H, J=4 Hz), 6.51 (dq, 1H, J=1, 4 Hz). 2H portion is not observable.

Reference Example 3-1

(S)-2-methyl-N—((R)-1-(5-(2,2,2-trifluoroethoxy)thiophen-2-yl)ethyl)propane-2-sulfinamide According to a technique similar to that of Reference Example 1-2, (S)-2-methyl-N-((5-(2,2,2-trifluoroethoxy)thiophen-2-yl)methylene)propane-2-sulfinamide was obtained using 5-(2,2,2-trifluoroethoxy)thiophene-2-carboaldehyde (500 mg, 2.38 mmol). According to a technique similar to that of Reference Example 1-3, the title compound (403 mg, 51%) was obtained using (R)-2-methyl-N-((5-(2,2,2-trifluoroethoxy)thiophen-2-yl)methylene)propane-2-sulfinamide thus obtained.

¹H NMR (CDCl₃, 400 MHz): δ=1.23 (s, 9H), 1.60 (d, 3H, J=7 Hz), 3.34 (d, 1H, J=5 Hz), 4.35 (q, 2H, J=8 Hz), 4.6-4.7 (m, 1H), 6.15 (d, 1H, J=4 Hz), 6.59 (dd, 1H, J=1, 4 Hz).

Reference Example 3-2

(R)-1-(5-(2,2,2-trifluoroethoxy)thiophen-2-yl)ethan-1-amine

According to a technique similar to that of Reference Example 2-2, the title compound (280 mg, 100%) was obtained using (S)-2-methyl-N—((R)-1-(5-(2,2,2-trifluoroethoxy)thiophen-2-yl)ethyl)propane-2-sulfinamide (403 mg, 1.22 mmol) synthesized in Reference Example 3-1.

¹H NMR (CDCl₃, 400 MHz): δ=1.43 (d, 3H, J=6 Hz), 4.22 (dq, 1H, J=1, 6 Hz), 4.34 (q, 2H, J=8 Hz), 6.17 (d, 1H, J=4 Hz), 6.51 (dq, 1H, J=1, 4 Hz). 2H portion is not observable.

Reference Example 4

(R)-1-(5-(2,2,2-trifluoroethoxy)thiophen-2-yl)ethan-1-amine hydrochloride

According to a technique similar to that of Reference Example 1-4, the title compound (milky white crystals, 3.16 g, 61%) was obtained using (S)-2-methyl-N—((R)-1-(5-(2,2,2-trifluoroethoxy)thiophen-2-yl)ethyl)propane-2-sulfinamide (6.49 g, 20 mmol) synthesized in Reference Example 3-1.

¹H NMR (DMSO-d₆, 400 MHz): δ=1.50 (d, 3H, J=7 Hz), 4.56 (q, 1H, J=7 Hz), 4.85 (q, 2H, J=9 Hz), 6.48 (d, 1H, J=4 Hz), 6.89 (s, 1H), 8.21 (br s, 3H).

Reference Example 5-1

(R)-2-methyl-N—((S)-1-(2-(2,2,2-trifluoroethoxy)thiazol-5-yl)ethyl)propane-2-sulfinamide According to a technique similar to that of Reference Example 1-2, (R)-2-methyl-N-((2-(2,2,2-trifluoroethoxy)thiazol-5-yl)methylene)propane-2-sulfinamide was obtained using 2-(2,2,2-trifluoroethoxy) thiazole-5-carboaldehyde (205 mg, 0.97 mmol) and (R)-2-methylpropane-2-sulfinamide (124 mg, 1.02 mmol). According to a technique similar to that of Reference Example 1-3, the title compound (lower spot in TLC (ethyl acetate/hexane=1/5), 49 mg, 16%) was obtained using (R)-2-methyl-N-((2-(2,2,2-trifluoroethoxy)thiazol-5-yl)methylene)propane-2-sulfinamide thus obtained.

¹H NMR (CDCl₃, 400 MHz): δ=1.22 (s, 9H), 1.61 (d, 3H, J=7 Hz), 3.41 (d, 1H, J=4 Hz), 4.6-4.9 (m, 3H), 6.99 (s, 1H).

Reference Example 5-2

(S)-1-(2-(2,2,2-trifluoroethoxy) thiazol-5-yl) ethan-1-amine

According to a technique similar to that of Reference Example 2-2, the title compound (22 mg, 66%) was obtained using (R)-2-methyl-N—((S)-1-(2-(2,2,2-trifluoroethoxy)thiazol-5-yl)ethyl)propane-2-sulfinamide (49 mg, 0.15 mmol) synthesized in Reference Example 5-1.

¹H NMR (CDCl₃, 400 MHz): δ=1.45 (d, 3H, J=6 Hz), 4.27 (d, 1H, J=6 Hz), 4.77 (q, 2H, J=8 Hz), 6.92 (s, 1H). 2H portion is not observable.

Reference Example 6-1

(R)-2-methyl-N—((R)-1-(2-(2,2,2-trifluoroethoxy)thiazol-5-yl)ethyl)propane-2-sulfinamide According to a technique similar to that of Reference Example 1-2, (R)-2-methyl-N-((2-(2,2,2-trifluoroethoxy)

thiazol-5-yl)methylene)propane-2-sulfinamide was obtained using 2-(2,2,2-trifluoroethoxy) thiazole-5-carboaldehyde (205 mg, 0.97 mmol) and (R)-2-methylpropane-2-sulfinamide (124 mg, 1.02 mmol). According to a technique similar to that of Reference Example 1-3, the title compound (lower spot in TLC (ethyl acetate/hexane=1/5), 23 mg, 8%) was obtained using (R)-2-methyl-N-((2-(2,2,2-trifluoroethoxy)thiazol-5-yl)methylene)propane-2-sulfinamide thus obtained.

¹H NMR (CDCl₃, 400 MHz): δ=1.23 (s, 9H), 1.58 (d, 3H, J=6 Hz), 3.51 (d, 1H, J=4 Hz), 4.6-4.8 (m, 1H), 4.78 (q, 2H, J=8 Hz), 7.03 (s, 1H).

Reference Example 6-2

(R)-1-(2-(2,2,2-trifluoroethoxy)thiazol-5-yl)ethan-1-amine

According to a technique similar to that of Reference Example 2-2, the title compound (14 mg, 91%) was obtained using (R)-2-methyl-N—((R)-1-(2-(2,2,2-trifluoroethoxy)thiazol-5-yl)ethyl)propane-2-sulfinamide (23 mg, 0.07 mmol) synthesized in Reference Example 6-1.

¹H NMR (CDCl₃, 400 MHz): δ=1.44 (d, 3H, J=6 Hz), 4.26 (dq, 1H, J=1, 6 Hz), 4.77 (q, 2H, J=8 Hz), 6.91 (d, 1H, J=1 Hz). 2H portion is not observable.

Reference Example 7-1

(S)-2-methyl-N-((1-(3,3,3-trifluoropropyl)-1H-pyrazol-4-yl)methylene)propane-2-sulfinamide According to a technique similar to that of Reference Example 1-2, the title compound (colorless oily material, 126 mg, 85%) was obtained using 1-(3,3,3-trifluoropropyl)-1H-pyrazole-4-carboaldehyde (147 mg, 0.50 mmol).

¹H NMR (CDCl₃, 400 MHz): δ=1.23 (s, 9H), 2.7-2.9 (m, 2H), 4.41 (t, 2H, J=7 Hz), 7.86 (s, 1H), 7.96 (s, 1H), 8.49 (s, 1H).

Reference Example 7-2

(S)-2-methyl-N—((R)-1-(3,3,3-trifluoropropyl)-1H-pyrazol-4-yl)ethyl)propane-2-sulfinamide According to a technique similar to that of Reference Example 1-3, the title compound (colorless oily material, 62 mg, 47%) was obtained using (S)-2-methyl-N-((1-(3,3,3-trifluoropropyl)-1H-pyrazol-4-yl)methylene)propane-2-sulfinamide (126 mg, 0.43 mmol) synthesized in Reference Example 7-1.

¹H NMR (CDCl₃, 400 MHz): δ=1.27 (s, 9H), 1.56 (d, 3H, J=6 Hz), 2.6-2.8 (m, 2H), 3.26 (d, 1H, J=5 Hz), 4.33 (t, 2H, J=7 Hz), 4.5-4.6 (m, 1H), 7.34 (s, 1H), 7.47 (s, 1H).

Reference Example 7-3

(R)-1-(1-(3,3,3-trifluoropropyl)-1H-pyrazol-4-yl)ethan-1-amine

According to a technique similar to that of Reference Example 1-4, a free form of the title compound was obtained using (S)-2-methyl-N—((R)-1-(1-(3,3,3-trifluoropropyl)-1H-pyrazol-4-yl)ethyl)propane-2-sulfinamide (62 mg, 0.20 mmol) synthesized in Reference Example 7-2. Subsequently, the free form was converted to a hydrochloride salt using a 2 N hydrochloric acid-methanol solution before concentration, and then the solution was concentrated. Thus, the title compound (white powder, 38 mg, 78%) was obtained.

Reference Example 8-1

3-(−1-(((S)-tert-butylsulfinyl)amino)ethyl)-1H-indole-1-carboxylic acid tert-butyl ester According to a technique similar to that of Reference Example 1-2, (S)-3-(((tert-butylsulfinyl)imino)methyl)-1H-indole-1-carboxylic acid tert-butyl ester was obtained using 3-formyl-1H-indole-1-carboxylic acid tert-butyl ester (200 mg, 0.82 mmol). According to a technique similar to that of Reference Example 1-3, the title compound (130 mg, 44%) was obtained using (S)-3-(((tert-butylsulfinyl)imino)methyl)-1H-indole-1-carboxylic acid tert-butyl ester thus obtained.

¹H NMR (CDCl₃, 400 MHz): δ=1.21 (s, 9H), 1.66 (s, 9H), 1.71 (d, 3H, J=7 Hz), 3.38 (d, 1H, J=5 Hz), 4.7-4.9 (m, 1H), 7.1-7.4 (m, 2H), 7.54 (s, 1H), 7.61 (dd, 1H, J=1, 7 Hz), 8.15 (d, 1H, J=7 Hz).

Reference Example 8-2

3-(1-Aminoethyl)-1H-indole-1-carboxylic acid tert-butyl ester

According to a technique similar to that of Reference Example 2-2, the title compound (7 mg, 8%) was obtained using 3-(−1-(((S)-tert-butylsulfinyl)amino)ethyl)-1H-indole-1-carboxylic acid tert-butyl ester (130 mg, 0.36 mmol) synthesized in Reference Example 8-1.

¹H NMR (CDCl₃, 400 MHz): δ=1.56 (d, 3H, J=7 Hz), 1.66 (s, 9H), 4.43 (q, 1H, J=7 Hz), 7.24 (dt, 1H, J=1, 8 Hz), 7.32 (dt, 1H, J=1, 8 Hz), 7.54 (s, 1H), 7.62 (d, 1H, J=8 Hz), 8.14 (d, 1H, J=8 Hz). 2H portion is not observable.

Reference Example 9-1

(R)-3-(((R)-1-(5-(2,2,2-trifluoroethoxy)thiophen-2-yl)ethyl)carbamoyl)pyrrolidine-1-carboxylic acid tert-butyl ester (R)-1-(5-(2,2,2-trifluoroethoxy)thiophen-2-yl)ethan-1-amine hydrochloride (50 mg, 0.19 mmol) synthesized in Reference Example 4, (R)-1-(tert-butoxycarbonyl)pyrrolidine-3-carboxylic acid (49 mg, 0.23 mmol), N,N-diisopropylethylamine (100 µL, 0.57 mmol), and HATU (102 mg, 0.27 mmol) were dissolved in DMF (2.0 mL), and the solution was stirred for one hour at room temperature. A saturated aqueous solution of sodium hydrogen carbonate and water were added to the reaction liquid, and the mixture was stirred for a while. Subsequently, the mixture was extracted with ethyl acetate. The organic layer was washed with saturated brine and was dried over anhydrous sodium sulfate. Insoluble matters were filtered, and then the solvent was distilled off under reduced pressure. A residue thus obtained was purified by silica gel column chromatography (hexane:ethyl acetate) (concentration gradient: 5% to 80%), and thus the title compound (yellow oily material, 57 mg, 70%) was obtained.

¹H NMR (CDCl₃, 400 MHz): δ=1.44 (s, 9H), 1.51 (d, 3H, J=7 Hz), 1.9-2.3 (m, 2H), 2.8-2.9 (m, 1H), 3.2-3.7 (m, 4H), 4.34 (q, 2H, J=8 Hz), 5.21 (quint, 1H, J=7 Hz), 6.1-6.3 (m, 1H), 6.16 (d, 1H, J=3 Hz), 6.56 (s, 1H).

Reference Example 9-2

(R)—N—((R)-1-(5-(2,2,2-trifluoroethoxy)thiophen-2-yl)ethyl)pyrrolidine-3-carboxamide hydrochloride (R)-3-(((R)-1-(5-(2,2,2-trifluoroethoxy)thiophen-2-yl)ethyl)carbamoyl)pyrrolidine-1-carboxylic acid tert-butyl ester (57 mg, 0.13 mmol) synthesized in Reference Example 9-1 was dissolved in 2 N hydrochloric acid-methanol (2.0 mL), and the solution was stirred for 2 hours at room temperature. The reaction liquid was concentrated under reduced pressure. A suspension liquid obtained by adding diethyl ether to the concentrate was filtered, and crystals thus obtained were dried. Thus, the title compound (white crystals, 38 mg, 79%) was obtained.

$^1$H NMR (DMSO-d$_6$, 400 MHz): δ=1.40 (d, 3H, J=7 Hz), 1.8-4.2 (m, 7H), 4.77 (q, 2H, J=9 Hz), 5.00 (quint, 1H, J=7 Hz), 6.35 (d, 1H, J=4 Hz), 6.5-6.7 (m, 1H), 8.4-8.7 (m, 2H). 1H portion is not observable.

Reference Example 10-1

(S)-3-(((R)-1-(5-(2,2,2-trifluoroethoxy)thiophen-2-yl)ethyl)carbamoyl)pyrrolidine-1-carboxylic acid tert-butyl ester According to a technique similar to that of Reference Example 9-1, the title compound (77 mg, 95%) was obtained using (R)-1-(5-(2,2,2-trifluoroethoxy)thiophen-2-yl)ethan-1-amine hydrochloride (50 mg, 0.19 mmol) synthesized in Reference Example 4-1 and (S)-1-(tert-butoxycarbonyl)pyrrolidine-3-carboxylic acid (49 mg, 0.23 mmol).

$^1$H NMR (CDCl$_3$, 400 MHz): δ=1.45 (s, 9H), 1.51 (d, 3H, J=6 Hz), 2.0-2.1 (m, 2H), 2.7-2.9 (m, 1H), 3.2-3.4 (m, 1H), 3.4-3.6 (m, 3H), 4.34 (q, 2H, J=8 Hz), 5.1-5.3 (m, 1H), 6.1-6.3 (m, 1H), 6.17 (d, 1H, J=4 Hz), 6.56 (dd, 1H, J=1, 4 Hz).

Reference Example 10-2

(S)—N—((R)-1-(5-(2,2,2-trifluoroethoxy)thiophen-2-yl)ethyl)pyrrolidine-3-carboxamide hydrochloride According to a technique similar to that of Reference Example 9-2, the title compound (52 mg, 80%) was obtained using (S)-3-(((R)-1-(5-(2,2,2-trifluoroethoxy)thiophen-2-yl)ethyl)carbamoyl)pyrrolidine-1-carboxylic acid tert-butyl ester (77 mg, 0.18 mmol) synthesized in Reference Example 10-1.

$^1$H NMR (DMSO-d$_6$, 400 MHz): δ=1.41 (d, 3H, J=7 Hz), 1.8-2.0 (m, 1H), 2.0-2.2 (m, 1H), 3.0-3.4 (m, 5H), 4.77 (q, 2H, J=9 Hz), 5.00 (quint, 1H, J=7 Hz), 6.34 (d, 1H, J=4 Hz), 6.60 (dd, 1H, J=1, 4 Hz), 8.72 (d, 1H, J=8 Hz), 9.13 (br s, 2H).

Reference Example 11-1

(R)-3,3,3-trifluoro-2-methoxy-2-phenyl-N—((R)-1-(5-(2,2,2-trifluoroethoxy)thiophen-2-yl)ethyl)propanamide (R)-1-(5-(2,2,2-trifluoroethoxy)thiophen-2-yl)ethan-1-amine (10 mg, 0.04 mmol) synthesized in Reference Example 3-2, (+)-Mosher's acid (13 mg, 0.05 mmol), N,N-diisopropylethylamine (16 μL, 0.09 mmol), and HATU (20 mg, 0.05 mmol) were dissolved in THF (2 mL), and the solution was stirred for 2 hours at room temperature. A saturated solution of sodium hydrogen carbonate was added to the reaction liquid, and then the reaction liquid was extracted with hexane. The organic layer was washed with saturated brine and was dried over anhydrous sodium sulfate. Insoluble matters were filtered, and then the solvent was distilled off under reduced pressure. Thus, the title compound (10 mg, 51%) was obtained.

$^1$H NMR (CDCl$_3$, 400 MHz): δ=1.52 (d, 3H, J=7 Hz), 3.4-3.4 (m, 3H), 4.34 (q, 2H, J=8 Hz), 5.2-5.4 (m, 1H), 6.19 (d, 1H, J=4 Hz), 6.61 (dd, 1H, J=1, 4 Hz), 6.91 (d, 1H, J=8 Hz), 7.3-7.6 (m, 5H).

Reference Example 11-2

(S)-3,3,3-trifluoro-2-methoxy-2-phenyl-N—((R)-1-(5-(2,2,2-trifluoroethoxy)thiophen-2-yl)ethyl)propanamide (R)-1-(5-(2,2,2-trifluoroethoxy)thiophen-2-yl)ethan-1-amine (10 mg, 0.04 mmol) synthesized in Reference Example 3-2, (−)-Mosher's acid (13 mg, 0.05 mmol), N,N-diisopropylethylamine (16 μL, 0.09 mmol), HATU (20 mg, 0.05 mmol) were dissolved in THF (2 mL), and the solution was stirred for 2 hours at room temperature. A saturated solution of sodium hydrogen carbonate was added to the reaction liquid, and then the mixture was extracted with hexane. The organic layer was washed with saturated brine and was dried over anhydrous sodium sulfate. Insoluble matters were filtered, and then the solvent was distilled off under reduced pressure. Thus, the title compound (10 mg, 51%) was obtained.

$^1$H NMR (CDCl$_3$, 400 MHz): δ=1.58 (d, 3H, J=7 Hz), 3.38 (s, 3H), 4.33 (q, 2H, J=8 Hz), 5.2-5.4 (m, 1H), 6.16 (d, 1H, J=4 Hz), 6.57 (d, 1H, J=4 Hz), 6.91 (d, 1H, J=8 Hz), 7.3-7.6 (m, 5H).

Reference Example 12-1

(R)-3-(((R)-1-(2-(2,2,2-trifluoroethoxy) thiazol-5-yl)ethyl)carbamoyl)pyrrolidine-1-carboxylic acid tert-butyl ester According to a technique similar to that of Reference Example 9-1, the title compound (153 mg, 100%) was obtained using (R)-1-(2-(2,2,2-trifluoroethoxy)thiazol-5-yl)ethan-1-amine (70 mg, 0.31 mmol) and (R)-1-(tert-butoxycarbonyl)pyrrolidine-3-carboxylic acid (80 mg, 0.37 mmol).

$^1$H NMR (CDCl$_3$, 400 MHz): δ=1.45 (s, 9H), 1.5-1.6 (m, 3H), 2.0-2.3 (m, 2H), 2.81 (quint, 1H, J=8 Hz), 3.2-3.7 (m, 4H) 4.7-4.9 (m, 2H), 5.25 (quint, 1H, J=7 Hz), 5.6-5.8 (m, 1H), 6.97 (s, 1H).

Reference Example 12-2

(R)—N—((R)-1-(2-(2,2,2-trifluoroethoxy)thiazol-5-yl)ethyl)pyrrolidine-3-carboxamide (R)-3-(((R)-1-(2-(2,2,2-trifluoroethoxy)thiazol-5-yl)ethyl)carbamoyl)pyrrolidine-1-carboxylic acid tert-butyl ester (130 mg, 0.31 mmol) synthesized in Reference Example 12-1 was dissolved in 2 N hydrochloric acid-methanol, and the solution was stirred for 10 minutes at room temperature. The reaction liquid was concentrated under reduced pressure, and a suspension liquid obtained by adding diethyl ether to the concentrate was filtered. Ammonia-methanol was added to crystals thus obtained, and a suspension liquid thus produced was filtered. The crystals thus obtained were washed with chloroform and dried, and thus the title compound (51.9 mg, 52%) was obtained.

$^1$H NMR (CDCl$_3$, 400 MHz): δ=1.53 (d, 3H, J=7 Hz), 1.8-2.2 (m, 2H), 2.6-3.0 (m, 3H), 3.0-3.2 (m, 2H), 4.7-4.9 (m, 2H), 5.1-5.3 (m, 1H), 6.53 (d, 1H, J=8 Hz), 6.94 (d, 1H, J=1 Hz).

Reference Example 13-1

4-Methyl-2-(2,2,2-trifluoroethoxy)thiazole-5-carboxylic acid ethyl ester

According to a technique similar to that of Reference Example 1-1, the title compound (colorless oily material, 3.13 g, 73%) was obtained using 2-bromo-4-methylthiazole-5-carboxylic acid ethyl ester (4.00 g, 16 mmol).

$^1$H NMR (CDCl$_3$, 400 MHz): δ=1.35 (t, 3H, J=7 Hz), 2.58 (s, 3H), 4.30 (q, 2H, J=7 Hz), 4.82 (q, 2H, J=8 Hz).

Reference Example 13-2

(4-Methyl-2-(2,2,2-trifluoroethoxy)thiazol-5-yl) methanol

In a nitrogen atmosphere, 4-methyl-2-(2,2,2-trifluoroethoxy) thiazole-5-carboxylic acid ethyl ester (1.01 g, 3.7 mmol) synthesized in Reference Example 13-1 was dissolved in THF (20 mL), and the solution was stirred for a while at 0° C. Subsequently, lithium aluminum hydride (215 mg, 5.7 mmol) was added thereto, and the mixture was stirred for 40 minutes at the same temperature. A saturated aqueous solution of Rochelle salt was added to the reaction liquid, and the mixture was stirred for a while. Subsequently, the mixture was extracted with ethyl acetate. The organic layer was washed with saturated brine and was dried over anhydrous sodium sulfate. Insoluble matters were filtered, and then the solvent was distilled off under reduced pressure. A residue thus obtained was purified by silica gel column chromatography (hexane:ethyl acetate) (concentration gradient: 10% to 36%), and thus the title compound (pale yellow oily material, 713 mg, 85%) was obtained.

$^1$H NMR (CDCl$_3$, 400 MHz): δ=1.69 (t, 1H, J=5 Hz), 2.23 (s, 3H), 4.66 (d, 2H, J=5 Hz), 4.77 (q, 2H, J=8 Hz).

Reference Example 13-3

4-Methyl-2-(2,2,2-trifluoroethoxy)thiazole-5-carboaldehyde

In a nitrogen atmosphere, (4-methyl-2-(2,2,2-trifluoroethoxy)thiazol-5-yl)methanol (713 mg, 3.1 mmol) synthesized in Reference Example 13-2 was dissolved in THF (16 mL), and the solution was stirred for a while at 0° C. Subsequently, Dess-Martin periodinane (1.62 g, 3.8 mmol) was added thereto, and the mixture was stirred for 80 minutes at the same temperature. A saturated aqueous solution of sodium thiosulfate was added to the reaction liquid, and the mixture was stirred for a while. Subsequently, the mixture was extracted with ethyl acetate. The organic layer was washed with saturated brine and was dried over anhydrous sodium sulfate. Insoluble matters were filtered, and then the solvent was distilled off under reduced pressure. A residue thus obtained was purified by silica gel column chromatography (hexane:ethyl acetate) (concentration gradient: 0% to 20%), and thus the title compound (pale yellow oily material, 571 mg, 81%) was obtained.

$^1$H NMR (CDCl$_3$, 400 MHz): δ=2.59 (s, 3H), 4.87 (q, 2H, J=8 Hz), 9.95 (s, 1H).

Reference Example 13-4

(S)-2-methyl-N-((4-methyl-2-(2,2,2-trifluoroethoxy) thiazol-5-yl)methylene)propane-2-sulfinamide According to a technique similar to that of Reference Example 1-2, the title compound (pale yellow oily material, 732 mg, 88%) was obtained using 4-methyl-2-(2,2,2-trifluoroethoxy)thiazole-5-carboaldehyde (571 mg, 2.5 mmol) synthesized in Reference Example 13-3.

$^1$H NMR (CDCl$_3$, 400 MHz): δ=1.22 (s, 9H), 2.48 (s, 3H), 4.7-4.9 (m, 2H), 8.62 (s, 1H).

Reference Example 13-5

(S)-2-methyl-N—((R)-1-(4-methyl-2-(2,2,2-trifluoroethoxy)thiazol-5-yl)ethyl)propane-2-sulfinamide According to a technique similar to that of Reference Example 1-3, the title compound (pale yellow oily material, 389 mg, 51%) was obtained using (S)-2-methyl-N-((4-methyl-2-(2,2,2-trifluoroethoxy)thiazol-5-yl)methylene) propane-2-sulfinamide (732 mg, 2.2 mmol) synthesized in Reference Example 13-4.

$^1$H NMR (CDCl$_3$, 400 MHz): δ=1.21 (s, 9H), 1.49 (d, 3H, J=6 Hz), 2.25 (s, 3H), 3.33 (s, 1H), 4.7-4.8 (m, 3H).

Reference Example 13-6

(R)-1-(4-methyl-2-(2,2,2-trifluoroethoxy)thiazol-5-yl)ethan-1-amine

According to a technique similar to that of Reference Example 2-2, the title compound (pale yellow oily material, 309 mg, 100%) was obtained using (S)-2-methyl-N—((R)-1-(4-methyl-2-(2,2,2-trifluoroethoxy)thiazol-5-yl)ethyl)propane-2-sulfinamide (384 mg, 1.1 mmol) synthesized in Reference Example 13-5.

$^1$H NMR (CDCl$_3$, 400 MHz): δ=1.36 (d, 3H, J=6 Hz), 2.18 (s, 3H), 4.36 (q, 1H, J=6 Hz), 4.74 (q, 2H, J=8 Hz). 2H portion is not observable.

Reference Example 14-1

(S)—N-((5-bromothiophen-2-yl)methylene)-2-methylpropane-2-sulfinamide

According to a technique similar to that of Reference Example 1-2, the title compound (pale yellow crystals, 1.65 g, 100%) was obtained using 5-bromothiophene-2-carboaldehyde (1.00 g, 5.2 mmol) and (S)-2-methylpropane-2-sulfinamide (0.67 g, 5.5 mmol).

$^1$H NMR (CDCl$_3$, 400 MHz): δ=1.24 (s, 9H), 7.12 (d, 1H, J=4 Hz), 7.27 (d, 1H, J=3 Hz), 8.54 (s, 1H).

Reference Example 14-2

(S)—N—((R)-1-(5-bromothiophen-2-yl) ethyl)-2-methyl propane-2-sulfinamide

According to a technique similar to that of Reference Example 1-3, the title compound (0.61 g, 38%) was obtained using (S)—N-((5-bromothiophen-2-yl)methylene)-2-methylpropane-2-sulfinamide (1.54 g, 5.2 mmol) synthesized in Reference Example 14-1.

¹H NMR (CDCl₃, 400 MHz): δ=1.24 (s, 9H), 1.63 (d, 3H, J=6 Hz), 3.37 (d, 1H, J=5 Hz), 4.7-4.8 (m, 1H), 6.72 (dd, 1H, J=1, 5 Hz), 6.89 (d, 1H, J=4 Hz).

Reference Example 14-3

(R)-1-(5-bromothiophen-2-yl)ethan-1-amine hydrochloride

According to a technique similar to that of Reference Example 1-4, the title compound (324 mg, 68%) was obtained using (S)—N—((R)-1-(5-bromothiophen-2-yl) ethyl)-2-methylpropane-2-sulfinamide (0.61 g, 2.0 mmol) synthesized in Reference Example 14-2.

¹H NMR (DMSO-d₆, 400 MHz): δ=1.56 (d, 3H, J=7 Hz), 4.66 (q, 1H, J=7 Hz), 7.13 (d, 1H, J=4 Hz), 7.19 (d, 1H, J=4 Hz), 8.66 (br s, 3H).

Reference Example 15-1

(S)—N—((R)-1-(5-cyclopropylfuran-2-yl)ethyl)-2-methylpropane-2-sulfinamide

According to a technique similar to that of Reference Example 2-1, the title compound (pale yellow oily material, 114 mg, 42%) was obtained using 5-cyclopropylfuran-2-carboaldehyde (145 mg, 1.1 mmol).

¹H NMR (CDCl₃, 400 MHz): δ=0.7-0.9 (m, 4H), 1.20 (s, 9H), 1.57 (d, 3H, J=7 Hz), 1.8-1.9 (m, 1H), 3.22 (d, 1H, J=7 Hz), 4.51 (quint, 1H, J=7 Hz), 5.86 (d, 1H, J=3 Hz), 6.06 (d, 1H, J=3 Hz).

Reference Example 15-2

(R)-1-(5-cyclopropylfuran-2-yl)ethan-1-amine

According to a technique similar to that of Reference Example 2-2, the title compound (pale yellow crystals, 32 mg, 48%) was obtained using (S)—N—((R)-1-(5-cyclopropylfuran-2-yl)ethyl)-2-methylpropane-2-sulfinamide (114 mg, 0.45 mmol) synthesized in Reference Example 15-1.

¹H NMR (CDCl₃, 400 MHz): δ=0.7-0.9 (m, 4H), 1.39 (d, 3H, J=6 Hz), 1.8-1.9 (m, 1H), 4.00 (q, 1H, J=6 Hz), 5.83 (d, 1H, J=3 Hz), 5.95 (d, 1H, J=3 Hz). 2H portion is not observable.

Reference Example 16-1

(R)-(1-(3-cyclopropyl-1,2,4-oxadiazol-5-yl)ethyl) carbamic acid tert-butyl ester In a nitrogen atmosphere, N-hydroxycyclopropane carboximidamide (304 mg, 3.0 mmol), (tert-butoxycarbonyl)-D-alanine (690 mg, 3.7 mmol), and DIPEA (1.0 mL, 5.9 mmol) were dissolved in DMF (15 mL), and the solution was stirred for a while at room temperature. Subsequently, HATU (1.37 g, 3.6 mmol) was added thereto, and the mixture was stirred for 3 hours at the same temperature and for 2 hours at 100° C. The reaction liquid was left to cool to room temperature, and a saturated aqueous solution of sodium hydrogen carbonate and water were added thereto. The mixture was stirred for a while and then was extracted with ethyl acetate. The organic layer was washed with saturated brine and was dried over anhydrous sodium sulfate. Insoluble matters were filtered, and then the solvent was distilled off under reduced pressure. A residue thus obtained was purified by silica gel column chromatography (hexane:ethyl acetate) (concentration gradient: 0% to 40%), and thus the title compound (yellow oily material, 546 mg, 71%) was obtained.

¹H NMR (CDCl₃, 400 MHz): δ=1.0-1.1 (m, 4H), 1.45 (s, 9H), 1.53 (d, 3H, J=7 Hz), 2.0-2.1 (m, 1H), 4.7-5.2 (m, 2H).

Reference Example 16-2

(R)-1-(3-cyclopropyl-1,2,4-oxadiazol-5-yl)ethan-1-amine hydrochloride

According to a technique similar to that of Reference Example 9-2, the title compound (pale green crystals, 463 mg, 100%) was obtained using (R)-(1-(3-cyclopropyl-1,2, 4-oxadiazol-5-yl)ethyl)carbamic acid tert-butyl ester (546 mg, 2.2 mmol) synthesized in Reference Example 16-1.

¹H NMR (DMSO-d₆, 400 MHz): δ=0.9-1.0 (m, 2H), 1.1-1.2 (m, 2H), 1.60 (d, 3H, J=7 Hz), 2.1-2.2 (m, 1H), 4.79 (q, 1H, J=7 Hz), 9.01 (br s, 2H).

Reference Example 17-1

(S)-2-methyl-N—((R)-2-methyl-1-(5-(2,2,2-trifluoroethoxy)thiophen-2-yl)propyl)propane-2-sulfinamide (S)-2-methyl-N—((S)-2-methyl-1-(5-(2,2,2-trifluoroethoxy)thiophen-2-yl)propyl)propane-2-sulfinamide According to a technique similar to that of Reference Example 1-2, (S)-2-methyl-N-((5-(2,2,2-trifluoroethoxy) thiophen-2-yl)methylene)propane-2-sulfinamide (6.93 g, 100%) was obtained using 5-(2,2,2-trifluoroethoxy)thiophene-2-carboaldehyde (4.64 g, 22.0 mmol). According to a technique similar to that of Reference Example 1-3, the R-form of the title compound (pale yellow liquid, 59 mg, 26%) and the S-form of the title compound (pale yellow liquid, 124 mg, 55%) were obtained using (S)-2-methyl-N-((5-(2,2,2-trifluoroethoxy)thiophen-2-yl)methylene)propane-2-sulfinamide (200 mg, 0.64 mmol) thus obtained and a THF solution of isopropylmagnesium bromide (3 mL, 2.93 mmol, 1.0 M).

R-Form

¹H NMR (CDCl₃, 400 MHz): δ=0.91 (d, 3H, J=6 Hz), 1.01 (d, 3H, J=6 Hz), 1.23 (s, 9H), 1.8-2.0 (m, 1H), 3.48 (d, 1H, J=2 Hz), 4.29 (dd, 1H, J=2, 7 Hz), 4.35 (q, 2H, J=8 Hz), 6.16 (d, 1H, J=4 Hz), 6.60 (d, 1H, J=4 Hz).

S-Form

¹H NMR (CDCl₃, 400 MHz): δ=0.94 (d, 6H, J=7 Hz), 1.25 (s, 9H), 2.1-2.2 (m, 1H), 3.35 (d, 1H, J=6 Hz), 4.29 (t, 1H, J=6 Hz), 4.34 (q, 2H, J=8 Hz), 6.18 (d, 1H, J=4 Hz), 6.66 (d, 1H, J=4 Hz).

Reference Example 17-2

(R)-2-methyl-1-(5-(2,2,2-trifluoroethoxy) thiophen-2-yl) propan-1-amine hydrochloride According to a technique similar to that of Reference Example 1-4, a crude form of the title compound was obtained using (S)-2-methyl-N—((R)-2-methyl-1-(5-(2,2,2- trifluoroethoxy)thiophen-2-yl)propyl)propane-2-sulfinamide (59 mg, 0.17 mmol) synthesized in Reference Example 17-1.

$^1$H NMR (CD$_3$OD, 400 MHz): δ=0.93 (d, 3H, J=6 Hz), 1.21 (d, 3H, J=7 Hz), 2.0-2.3 (m, 1H), 4.15 (d, 1H, J=9 Hz), 4.62 (q, 2H, J=8 Hz), 6.41 (d, 1H, J=4 Hz), 6.88 (d, 1H, J=4 Hz). 2H portion is not observable.

Reference Example 18-1

(S)-2-methyl-N-((5-(trifluoromethyl)thiophen-2-yl) methylene)propane-2-sulfinamide In a nitrogen atmosphere, 5-(trifluoromethyl)thiophene-2-carboxylic acid (503 mg, 2.6 mmol) was dissolved in THF (5 mL), and a THF solution of a borane-THF complex (12 mL, 10 mmol, 0.9 M) was added thereto. The mixture was stirred for 30 minutes at 80° C. The reaction liquid was cooled to 0° C., methanol was added thereto, and the mixture was stirred for a while. Subsequently, the solvent was distilled off under reduced pressure, and (5-(trifluoromethyl) thiophen-2-yl)methanol was obtained. According to a technique similar to that of Reference Example 13-3, 5-(trifluoromethyl)thiophene-2-carboaldehyde was obtained using (5-(trifluoromethyl)thiophen-2-yl)methanol thus obtained. According to a technique similar to that of Reference Example 1-2, the title compound (yellow oily material, 571 mg, 79%) was obtained using 5-(trifluoromethyl)thiophene-2-carboaldehyde thus obtained.

$^1$H NMR (CDCl$_3$, 400 MHz): δ=1.26 (s, 9H), 7.47 (s, 2H), 8.68 (s, 1H).

Reference Example 18-2

(S)—N—((R)-cyclopropyl(5-(trifluoromethyl)thiophen-2-yl)methyl)-2-methylpropane-2-sulfinamide According to a technique similar to that of Reference Example 1-3, the title compound (pale yellow oily material, 55 mg, 28%) was obtained using (S)-2-methyl-N-((5-(trifluoromethyl)thiophen-2-yl)methylene)propane-2-sulfinamide (168 mg, 0.59 mmol) synthesized in Reference Example 18-1 and a THF solution of cyclopropylmagnesium bromide (2.5 mL, 1.8 mmol, 0.7 M).

$^1$H NMR (CDCl$_3$, 400 MHz): δ=0.4-0.8 (m, 4H), 1.2-1.3 (m, 10H), 3.71 (d, 1H, J=4 Hz), 3.84 (dd, 1H, J=4, 10 Hz), 6.99 (d, 1H, J=4 Hz), 7.31 (dd, 1H, J=1, 4 Hz).

Reference Example 18-3

(R)-cyclopropyl(5-(trifluoromethyl)thiophen-2-yl) methanamine

According to a technique similar to that of Reference Example 2-2, the title compound (pale yellow oily material, 25 mg, 67%) was obtained using (S)—N—((R)-cyclopropyl (5-(trifluoromethyl)thiophen-2-yl)methyl)-2-methylpropane-2-sulfinamide (55 mg, 0.17 mmol) synthesized in Reference Example 18-2.

$^1$H NMR (CDCl$_3$, 400 MHz): δ=0.3-0.5 (m, 2H), 0.6-0.7 (m, 2H), 1.1-1.2 (m, 1H) 3.42 (d, 1H, J=9 Hz) 6.9-7.0 (m, 1H), 7.2-7.3 (m, 1H). 2H portion is not observable.

Reference Example 19-1

(S)-2-methyl-N—((R)-2-methyl-1-(5-(trifluoromethyl)thiophen-2-yl)propyl)propane-2-sulfinamide (S)-2-methyl-N—((S)-2-methyl-1-(5-(trifluoromethyl)thiophen-2-yl)propyl)propane-2-sulfinamide According to a technique similar to that of Reference Example 1-3, the R-form of the title compound (pale brown oily material, 254 mg, 46%) and the S-form of the title compound (pale brown oily material, 189 mg, 34%) were obtained using (S)-2-methyl-N-((5-(trifluoromethyl)thiophen-2-yl)methylene)propane-2-sulfinamide (482 mg, 1.7 mmol) synthesized in Reference Example 18-1 and a THF solution of isopropylmagnesium chloride (2.6 mL, 5.2 mmol, 2 M).

R-Form
$^1$H NMR (CDCl$_3$, 400 MHz): δ=0.93 (d, 3H, J=7 Hz), 1.01 (d, 3H, J=7 Hz), 1.25 (s, 9H), 1.9-2.1 (m, 1H), 3.56 (d, 1H, J=2 Hz), 4.52 (dd, 1H, J=2, 6 Hz), 6.91 (d, 1H, J=4 Hz), 7.31 (dd, 1H, J=1, 4 Hz).

S-Form
$^1$H NMR (CDCl$_3$, 400 MHz): δ=0.94 (d, 3H, J=7 Hz), 0.96 (d, 3H, J=7 Hz), 1.26 (s, 9H), 2.2-2.3 (m, 1H), 3.45 (d, 1H, J=6 Hz), 4.48 (dd, 1H, J=6, 6 Hz), 7.01 (dd, 1H, J=1, 4 Hz), 7.31 (dd, 1H, J=1, 4 Hz).

Reference Example 19-2

(R)-2-methyl-1-(5-(trifluoromethyl)thiophen-2-yl) propan-1-amine hydrochloride

According to a technique similar to that of Reference Example 1-4, the title compound (pale yellow crystals, 197 mg, 98%) was obtained using (S)-2-methyl-N—((R)-2-methyl-1-(5-(trifluoromethyl)thiophen-2-yl)propyl)propane-2-sulfinamide (253 mg, 0.77 mmol) synthesized in Reference Example 19-1.

$^1$H NMR (DMSO-d$_6$, 400 MHz): δ=0.80 (d, 3H, J=7 Hz), 1.01 (d, 3H, J=7 Hz), 2.1-2.2 (m, 1H), 4.47 (br s, 1H), 7.37 (d, 1H, J=4 Hz), 7.72 (dd, 1H, J=2, 4 Hz), 8.73 (br s, 2H).

Reference Example 20

(S)-2-methyl-1-(5-(trifluoromethyl)thiophen-2-yl) propan-1-amine

According to a technique similar to that of Reference Example 2-2, the title compound (yellow-brown oily material, 19 mg, 78%) was obtained using (S)-2-methyl-N—((S)-2-methyl-1-(5-(trifluoromethyl)thiophen-2-yl)propyl)propane-2-sulfinamide (35 mg, 0.11 mmol) synthesized in Reference Example 19-1.

$^1$H NMR (CDCl$_3$, 400 MHz): δ=0.91 (d, 3H, J=7 Hz), 0.97 (d, 3H, J=7 Hz), 1.8-2.0 (m, 1H), 4.00 (d, 1H, J=6 Hz), 6.85 (d, 1H, J=3 Hz), 7.29 (d, 1H, J=3 Hz). 2H portion is not observable.

Reference Example 21-1

(S)—N—((R)-cyclohexyl(5-(trifluoromethyl)thiophen-2-yl)methyl)-2-methylpropane-2-sulfinamide (S)—N—((S)-cyclohexyl(5-(trifluoromethyl)thiophen-2-yl)methyl)-2-methylpropane-2-sulfinamide According to a technique similar to that of Reference Example 1-3, the R-form of the title compound (yellow oily material, 178 mg, 24%) and the S-form of the title compound (yellow oily material, 216 mg, 29%) were obtained using (S)-2-methyl-N-((5-(trifluoromethyl)thiophen-2-yl)methylene)propane-2-sulfinamide (571 mg, 2.0 mmol) synthesized in Reference Example 18-1 and a THF solution of cyclohexylmagnesium bromide (4.0 mL, 4.0 mmol, 1 M).

R-Form
$^1$H NMR (CDCl$_3$, 400 MHz): δ=1.0-1.3 (m, 14H), 1.5-1.9 (m, 6H), 3.62 (d, 1H, J=2 Hz), 4.50 (dd, 1H, J=2, 7 Hz), 6.89 (d, 1H, J=4 Hz), 7.29 (dd, 1H, J=1, 4 Hz).

S-Form
$^1$H NMR (CDCl$_3$, 400 MHz): δ=0.9-1.3 (m, 14H), 1.6-1.9 (m, 6H), 3.43 (d, 1H, J=7 Hz), 4.44 (dd, 1H, J=7, 7 Hz), 6.99 (d, 1H, J=4 Hz), 7.30 (dd, 1H, J=1, 4 Hz).

Reference Example 21-2

(R)-cyclohexyl(5-(trifluoromethyl)thiophen-2-yl)methanamine

According to a technique similar to that of Reference Example 2-2, the title compound (pale yellow oily material, 121 mg, 95%) was obtained using (S)—N—((R)-cyclohexyl(5-(trifluoromethyl)thiophen-2-yl)methyl)-2-methylpropane-2-sulfinamide (178 mg, 0.48 mmol) synthesized in Reference Example 21-1.
$^1$H NMR (CDCl$_3$, 400 MHz): δ=0.9-2.0 (m, 11H), 3.98 (d, 1H, J=6 Hz), 6.82 (d, 1H, J=4 Hz), 7.28 (dd, 1H, J=1, 4 Hz). 2H portion is not observable.

Reference Example 22

(S)-cyclohexyl(5-(trifluoromethyl)thiophen-2-yl)methanamine

According to a technique similar to that of Reference Example 2-2, the title compound (45 mg, 100%) was obtained using (S)—N—((S)-cyclohexyl(5-(trifluoromethyl)thiophen-2-yl)methyl)-2-methylpropane-2-sulfinamide (40 mg, 0.11 mmol) synthesized in Reference Example 21-1.
$^1$H NMR (CDCl$_3$, 400 MHz): δ=0.9-1.9 (m, 11H), 3.98 (d, 1H, J=6 Hz), 6.83 (d, 1H, J=4 Hz), 7.28 (d, 1H, J=4H z). 2H portion is not observable.

Reference Example 23-1

(R)—N-((5-fluorobenzofuran-2-yl)methylene)-2-methylpropane-2-sulfinamide

According to a technique similar to that of Reference Example 1-2, the title compound (pale yellow powder, 3.96 g, 96%) was obtained using 5-fluorobenzofuran-2-carboaldehyde (2.54 g, 15.5 mmol) and (R)-2-methylpropane-2-sulfinamide (2.44 g, 20.1 mmol).
$^1$H NMR (CDCl$_3$, 400 MHz): δ=11.31 (s, 9H), 7.18 (ddd, 1H, J=2, 9, 9 Hz), 7.31 (s, 1H), 7.34 (dd, 1H, J=2, 8 Hz), 7.54 (dd, 1H, J=4, 9 Hz), 8.55 (s, 1H).

Reference Example 23-2

(R)—N—((R)-1-(5-fluorobenzofuran-2-yl)ethyl)-2-methylpropane-2-sulfinamide (R)—N—((S)-1-(5-fluorobenzofuran-2-yl)ethyl)-2-methylpropane-2-sulfinamide According to a technique similar to that of Reference Example 1-3, the R-form of the title compound (pale yellow crystals, 1.55 g, 49%) and the S-form of the title compound (white crystals, 1.56 g, 49%) were obtained using (R)—N-((5-fluorobenzofuran-2-yl)methylene)-2-methylpropane-2-sulfinamide (3.0 g, 11.2 mmol) synthesized in Reference Example 23-1.

R-Form
$^1$H NMR (CDCl$_3$, 400 MHz): δ=1.24 (s, 9H), 1.63 (d, 3H, J=7 Hz), 3.61 (d, 1H, J=6 Hz), 4.68 (quint, 1H, J=6 Hz), 6.66 (s, 1H), 6.98 (ddd, 1H, J=3, 9, 9 Hz), 7.18 (dd, 1H, J=3, 9 Hz), 7.37 (dd, 1H, J=4, 9 Hz).

S-Form
$^1$H NMR (CDCl$_3$, 400 MHz): δ=1.23 (s, 9H), 1.70 (d, 3H, J=7 Hz), 3.36 (d, 1H, J=6 Hz), 4.71 (quint, 1H, J=7 Hz), 6.57 (s, 1H), 6.98 (ddd, 1H, J=3, 9, 9 Hz), 7.18 (dd, 1H, J=3, 9 Hz), 7.36 (dd, 1H, J=4, 9 Hz).

Reference Example 23-3

(R)-1-(5-fluorobenzofuran-2-yl)ethan-1-amine

According to a technique similar to that of Reference Example 2-2, the title compound (pale yellow oily material, 341 mg, 100%) was obtained using ((R)—N—((R)-1-(5-fluorobenzofuran-2-yl)ethyl)-2-methylpropane-2-sulfinamide (540 mg, 1.91 mmol) synthesized in Reference Example 23-2.
$^1$H NMR (CDCl$_3$, 400 MHz): δ=1.51 (d, 3H, J=6 Hz), 4.19 (q, 1H, J=6 Hz), 6.48 (s, 1H), 6.95 (ddd, 1H, J=2, 9, 9 Hz), 7.16 (dd, 1H, J=2, 9 Hz), 7.35 (dd, 1H, J=4, 9 Hz). 2H portion is not observable.

Reference Example 24

(S)-1-(5-fluorobenzofuran-2-yl)ethan-1-amine

According to a technique similar to that of Reference Example 2-2, the title compound (pale yellow oily material, 20 mg, 100%) was obtained using ((R)—N—((S)-1-(5-fluorobenzofuran-2-yl)ethyl)-2-methylpropane-2-sulfinamide (31 mg, 0.11 mmol) synthesized in Reference Example 23-2.

Reference Example 25-1

(S)—N-((4-fluorobenzofuran-2-yl)methylene)-2-methylpropane-2-sulfinamide

According to a technique similar to that of Reference Example 27-1, 4-fluorobenzofuran-2-carboxylic acid methyl ester was obtained using 2-fluoro-6-hydroxybenzaldehyde (1.00 g, 7.1 mmol). In a nitrogen atmosphere, 4-fluorobenzofuran-2-carboxylic acid methyl ester (866 mg, 4.5 mmol) thus obtained was dissolved in THF (23 mL), and the solution was stirred for a while at 0° C. Subsequently, a THF solution of lithium borohydride (3.0 mL, 9.0 mmol, 3 M) was added thereto, and the mixture was stirred for 6.5 hours at room temperature. A saturated aqueous solution of ammonium chloride was added to the reaction liquid, and the mixture was stirred for a while. Subsequently, the mixture was extracted with ethyl acetate. The organic layer was washed with saturated brine and was dried over anhydrous sodium sulfate. Insoluble matters were filtered, and then the solvent was distilled off under reduced pressure. Thus, (4-fluorobenzofuran-2-yl)methanol was obtained. According to a technique similar to that of Reference Example 13-3, 4-fluorobenzofuran-2-carboaldehyde was obtained using (4-fluorobenzofuran-2-yl)methanol thus obtained. According to a technique similar to that of Reference Example 1-2, the title compound (yellow crystals, 754 mg, 39%) was obtained using 4-fluorobenzofuran-2-carboaldehyde thus obtained.

$^1$H NMR (CDCl$_3$, 400 MHz): δ=1.31 (s, 9H), 6.9-7.1 (m, 1H), 7.3-7.5 (m, 3H), 8.56 (s, 1H).

Reference Example 25-2

(S)—N—((R)-1-(4-fluorobenzofuran-2-yl)ethyl)-2-methylpropane-2-sulfinamide

According to a technique similar to that of Reference Example 1-3, the title compound (pale yellow oily material, 308 mg, 39%) was obtained using (S)—N-((4-fluorobenzofuran-2-yl)methylene)-2-methylpropane-2-sulfinamide (754 mg, 2.8 mmol) synthesized in Reference Example 25-1.

$^1$H NMR (CDCl$_3$, 400 MHz): δ=1.24 (s, 9H), 1.71 (d, 3H, J=7 Hz), 3.38 (d, 1H, J=7 Hz), 4.73 (quint, 1H, J=7 Hz), 6.69 (s, 1H), 6.91 (ddd, 1H, J=1, 9, 9 Hz), 7.1-7.3 (m, 2H).

Reference Example 25-3

(R)-1-(4-fluorobenzofuran-2-yl)ethan-1-amine

According to a technique similar to that of Reference Example 2-2, the title compound (pale yellow oily material, 214 mg, 100%) was obtained using (S)—N—((R)-1-(4-fluorobenzofuran-2-yl)ethyl)-2-methylpropane-2-sulfinamide (308 mg, 1.1 mmol) synthesized in Reference Example 25-2.

$^1$H NMR (CDCl$_3$, 400 MHz): δ=1.52 (d, 3H, J=6 Hz), 4.21 (q, 1H, J=6 Hz), 6.59 (s, 1H), 6.89 (ddd, 1H, J=1, 8, 9 Hz), 7.17 (ddd, 1H, J=5, 8, 8 Hz), 7.24 (d, 1H, J=8 Hz). 2H portion is not observable.

Reference Example 26-1

(S)—N-((7-fluorobenzofuran-2-yl)methylene)-2-methylpropane-2-sulfinamide

According to a technique similar to that of Reference Example 25-1, the title compound (pale yellow oily material, 572 mg, 30%) was obtained using 3-fluoro-2-hydroxybenzaldehyde (1.00 g, 7.1 mmol).

$^1$H NMR (CDCl$_3$, 400 MHz): δ=1.31 (s, 9H), 7.19 (ddd, 1H, J=1, 8, 10 Hz), 7.25 (ddd, 1H, J=5, 8, 8 Hz), 7.36 (d, 1H, J=3 Hz), 7.47 (dd, 1H, J=1, 8 Hz), 8.5 8 (s, 1H).

Reference Example 26-2

(S)—N—((R)-1-(7-fluorobenzofuran-2-yl)ethyl)-2-methylpropane-2-sulfinamide

According to a technique similar to that of Reference Example 1-3, the title compound (pale yellow oily material, 302 mg, 50%) was obtained using (S)—N-((7-fluorobenzofuran-2-yl)methylene)-2-methylpropane-2-sulfinamide (572 mg, 2.1 mmol) synthesized in Reference Example 26-1.

$^1$H NMR (CDCl$_3$, 400 MHz): δ=1.24 (s, 9H), 1.72 (d, 3H, J=7 Hz), 3.41 (d, 1H, J=7 Hz), 4.75 (quint, 1H, J=7 Hz), 6.65 (d, 1H, J=2 Hz), 7.00 (ddd, 1H, J=1, 8, 10 Hz), 7.13 (ddd, 1H, J=4, 8, 8 Hz), 7.29 (dd, 1H, J=1, 8 Hz).

Reference Example 26-3

(R)-1-(7-fluorobenzofuran-2-yl)ethan-1-amine

According to a technique similar to that of Reference Example 2-2, the title compound (pale yellow oily material, 188 mg, 98%) was obtained using (S)—N—((R)-1-(7-fluorobenzofuran-2-yl)ethyl)-2-methylpropane-2-sulfinamide (302 mg, 1.1 mmol) synthesized in Reference Example 26-2.

$^1$H NMR (CDCl$_3$, 400 MHz): δ=1.53 (d, 3H, J=7 Hz), 4.23 (q, 1H, J=7 Hz), 6.54 (dd, 1H, J=1, 3 Hz), 6.98 (ddd, 1H, J=1, 8, 10 Hz), 7.11 (ddd, 1H, J=5, 8, 8 Hz), 7.27 (dd, 1H, J=1, 8 Hz). 2H portion is not observable.

Reference Example 27-1

6-Fluorobenzofuran-2-carboxylic acid methyl ester

4-Fluoro-2-hydroxybenzaldehyde (1.00 g, 7.1 mmol) and methyl bromoacetate (0.79 mL, 8.6 mmol) were dissolved in DMF (19 mL), and potassium carbonate (1.97 g, 14 mmol) was added thereto. The mixture was stirred for 15 minutes at room temperature and for 5 hours at 80° C. The reaction liquid was left to cool to room temperature, water was added thereto, and the mixture was stirred for a while. Subsequently, the mixture was extracted with ethyl acetate. The organic layer was washed with saturated brine and was dried over anhydrous sodium sulfate. Insoluble matters were filtered, and then the solvent was distilled off under reduced pressure. A residue thus obtained was purified by silica gel column chromatography (hexane:ethyl acetate) (concentration gradient: 2% to 30%), and thus the title compound (white crystals, 471 mg, 34%) was obtained.

$^1$H NMR (CDCl$_3$, 400 MHz): δ=3.98 (s, 3H), 7.09 (ddd, 1H, J=2, 9, 9 Hz), 7.30 (dd, 1H, J=2, 9 Hz), 7.51 (d, 1H, J=1 Hz), 7.63 (dd, 1H, J=6, 9 Hz).

Reference Example 27-2

(S)—N-((6-fluorobenzofuran-2-yl)methylene)-2-methylpropane-2-sulfinamide

In a nitrogen atmosphere, 6-fluorobenzofuran-2-carboxylic acid methyl ester (471 mg, 2.4 mmol) synthesized in Reference Example 27-1 was dissolved in THF (16 mL), and the solution was stirred for a while at 0° C. Subsequently, a THF solution of lithium borohydride (1.6 mL, 4.8 mmol, 3 M) was added thereto, and the mixture was stirred for 4 hours at room temperature. A THF solution of lithium borohydride (0.80 mL, 2.4 mmol, 3 M) was added to the reaction liquid, and the mixture was stirred for 20 hours. A saturated aqueous solution of ammonium chloride was added to the reaction liquid, and the mixture was stirred for a while. Subsequently, the mixture was extracted with ethyl acetate. The organic layer was washed with saturated brine and was dried over anhydrous sodium sulfate. Insoluble matters were filtered, and then the solvent was distilled off under reduced pressure. Thus, (6-fluorobenzofuran-2-yl) methanol was obtained. According to a technique similar to that of Reference Example 13-3, 6-fluorobenzofuran-2-carboaldehyde was obtained using (6-fluorobenzofuran-2-yl) methanol thus obtained. According to a technique similar to that of Reference Example 1-2, the title compound (pale yellow oily material, 477 mg, 73%) was obtained using 6-fluorobenzofuran-2-carboaldehyde thus obtained.

$^1$H NMR (CDCl$_3$, 400 MHz): δ=1.30 (s, 9H), 7.09 (ddd, 1H, J=2, 8, 8 Hz), 7.2-7.4 (m, 2H), 7.63 (dd, 1H, J=5, 8 Hz), 8.53 (s, 1H).

Reference Example 27-3

(S)—N—((R)-1-(6-fluorobenzofuran-2-yl)ethyl)-2-methylpropane-2-sulfinamide

According to a technique similar to that of Reference Example 1-3, the title compound (white crystals, 228 mg, 45%) was obtained using (S)—N-((6-fluorobenzofuran-2-yl)methylene)-2-methylpropane-2-sulfinamide (477 mg, 1.8 mmol) synthesized in Reference Example 27-2.

$^1$H NMR (CDCl$_3$, 400 MHz): δ=1.23 (s, 9H), 1.69 (d, 3H, J=7 Hz), 3.36 (d, 1H, J=7 Hz), 4.70 (quint, 1H, J=7 Hz), 6.58 (s, 1H), 6.98 (ddd, 1H, J=2, 8, 10 Hz), 7.16 (dd, 1H, J=2, 9 Hz), 7.43 (dd, 1H, J=5, 8 Hz).

Reference Example 27-4

(R)-1-(6-fluorobenzofuran-2-yl)ethan-1-amine

According to a technique similar to that of Reference Example 2-2, the title compound (pale yellow oily material, 162 mg, 100%) was obtained using (S)—N—((R)-1-(6-fluorobenzofuran-2-yl)ethyl)-2-methylpropane-2-sulfinamide (228 mg, 0.81 mmol) synthesized in Reference Example 27-3.

$^1$H NMR (CDCl$_3$, 400 MHz): δ=1.51 (d, 3H, J=6 Hz), 4.19 (q, 1H, J=6 Hz), 6.47 (s, 1H), 6.96 (ddd, 1H, J=2, 8, 10 Hz), 7.15 (dd, 1H, J=2, 8 Hz), 7.41 (dd, 1H, J=6, 8 Hz). 2H portion is not observable.

Reference Example 28-1

5,7-Difluorobenzofuran-2-carboxylic acid methyl ester

According to a technique similar to that of Reference Example 27-1, the title compound (white crystals, 898 mg, 45%) was obtained using 3,5-difluoro-2-hydroxybenzaldehyde (1.50 g, 9.5 mmol).

$^1$H NMR (CDCl$_3$, 400 MHz): δ=4.00 (s, 3H), 7.00 (ddd, 1H, J=2, 9, 10 Hz), 7.17 (dd, 1H, J=2, 8 Hz), 7.53 (d, 1H, J=3 Hz).

Reference Example 28-2

(S)—N—((R)-1-(5,7-difluorobenzofuran-2-yl)ethyl)-2-methylpropane-2-sulfinamide

In a nitrogen atmosphere, 5,7-difluorobenzofuran-2-carboxylic acid methyl ester (898 mg, 4.2 mmol) synthesized in Reference Example 28-1 was dissolved in THF (20 mL), and the solution was stirred for a while at 0° C. Subsequently, a THF solution of lithium borohydride (2.2 mL, 6.6 mmol, 3 M) was added thereto, and the mixture was stirred for 3 hours at room temperature. A THF solution of lithium borohydride (0.70 mL, 2.1 mmol, 3 M) was added to the reaction liquid, and the mixture was stirred for 17 hours. A saturated aqueous solution of ammonium chloride was added to the reaction liquid, and the mixture was stirred for a while. Subsequently, the mixture was extracted with ethyl acetate. The organic layer was washed with saturated brine and was dried over anhydrous sodium sulfate. Insoluble matters were filtered, and then the solvent was distilled off under reduced pressure. Thus, (5,7-difluorobenzofuran-2-yl)methanol was obtained. According to a technique similar to that of Reference Example 13-3, 5,7-difluorobenzofuran-2-carboaldehyde was obtained using (5,7-difluorobenzofuran-2-yl)methanol thus obtained. According to a technique similar to that of Reference Example 1-2, (S)—N-((5,7-difluorobenzofuran-2-yl)methylene)-2-methylpropane-2-sulfinamide was obtained using 5,7-difluorobenzofuran-2-carboaldehyde thus obtained. According to a technique similar to Reference Example 1-3, the title compound (yellow oily material, 333 mg, 26%) was obtained using (S)—N-((5,7-difluorobenzofuran-2-yl)methylene)-2-methylpropane-2-sulfinamide thus obtained.

$^1$H NMR (CDCl$_3$, 400 MHz): δ=1.24 (s, 9H), 1.71 (d, 3H, J=7 Hz), 3.40 (d, 1H, J=7 Hz), 4.74 (quint, 1H, J=7 Hz), 6.62 (d, 1H, J=3 Hz), 6.81 (ddd, 1H, J=2, 9, 10 Hz), 6.99 (dd, 1H, J=2, 8 Hz).

Reference Example 28-3

(R)-1-(5,7-difluorobenzofuran-2-yl)ethan-1-amine

According to a technique similar to that of Reference Example 2-2, the title compound (pale yellow oily material, 255 mg, 100%) was obtained using (S)—N—((R)-1-(5,7-difluorobenzofuran-2-yl)ethyl)-2-methylpropane-2-sulfinamide (333 mg, 1.1 mmol) synthesized in Reference Example 28-2.

$^1$H NMR (CDCl$_3$, 400 MHz): δ=1.53 (d, 3H, J=7 Hz), 4.22 (q, 1H, J=7 Hz), 6.52 (d, 1H, J=2 Hz), 6.78 (dddd, 1H, J=2, 10, 11 Hz), 6.98 (dd, 1H, J=2, 9 Hz). 2H portion is not observable.

Reference Example 29-1

5,6-Difluorobenzofuran-2-carboxylic acid methyl ester

According to a technique similar to that of Reference Example 27-1, the title compound (white crystals, 618 mg, 46%) was obtained using 4,5-difluoro-2-hydroxybenzaldehyde (1.00 g, 6.3 mmol).

$^1$H NMR (CDCl$_3$, 400 MHz): δ=3.98 (s, 3H), 7.4-7.5 (m, 3H).

Reference Example 29-2

(S)—N—((R)-1-(5,6-difluorobenzofuran-2-yl)ethyl)-2-methylpropane-2-sulfinamide

According to a technique similar to that of Reference Example 28-2, the title compound (pale yellow crystals, 823 mg, 32%) was obtained using 5,6-difluorobenzofuran-2-carboxylic acid methyl ester (618 mg, 2.9 mmol) synthesized in Reference Example 29-1.

$^1$H NMR (CDCl$_3$, 400 MHz): δ=1.23 (s, 9H), 1.68 (d, 3H, J=7 Hz), 3.37 (d, 1H, J=7 Hz), 4.70 (quint, 1H, J=7 Hz), 6.56 (s, 1H), 7.2-7.3 (m, 2H).

Reference Example 29-3

(R)-1-(5,6-difluorobenzofuran-2-yl)ethan-1-amine

According to a technique similar to that of Reference Example 2-2, the title compound (pale yellow oily material, 195 mg, 100%) was obtained using (S)—N—((R)-1-(5,6-difluorobenzofuran-2-yl)ethyl)-2-methylpropane-2-sulfinamide (277 mg, 0.92 mmol) synthesized in Reference Example 29-2.

$^1$H NMR (CDCl$_3$, 400 MHz): δ=1.50 (d, 3H, J=6 Hz), 4.19 (q, 1H, J=6 Hz), 6.46 (s, 1H), 7.2-7.3 (m, 2H). 2H portion is not observable.

Reference Example 30-1

4,6-Difluorobenzofuran-2-carboxylic acid methyl ester

According to a technique similar to that of Reference Example 27-1, the title compound (white crystals, 522 mg, 40%) was obtained using 2,4-difluoro-6-hydroxybenzaldehyde (967 mg, 6.1 mmol).

$^1$H NMR (CDCl$_3$, 400 MHz): δ=3.99 (s, 3H), 6.83 (ddd, 1H, J=2, 9, 9 Hz), 7.1-7.2 (m, 1H), 7.57 (d, 1H, J=1 Hz).

Reference Example 30-2

(S)—N—((R)-1-(4,6-difluorobenzofuran-2-yl)ethyl)-2-methylpropane-2-sulfinamide

According to a technique similar to that of Reference Example 28-2, the title compound (yellow oily material, 260 mg, 35%) was obtained using 4,6-difluorobenzofuran-2-carboxylic acid methyl ester (522 mg, 2.5 mmol) synthesized in Reference Example 30-1.

$^1$H NMR (CDCl$_3$, 400 MHz): δ=1.23 (s, 9H), 1.69 (d, 3H, J=6 Hz), 3.37 (d, 1H, J=6 Hz), 4.70 (quint, 1H, J=6 Hz), 6.65 (s, 1H), 6.73 (ddd, 1H, J=2, 10, 10 Hz), 6.9-7.1 (m, 1H).

Reference Example 30-3

(R)-1-(4,6-difluorobenzofuran-2-yl)ethan-1-amine

According to a technique similar to that of Reference Example 2-2, the title compound (pale yellow oily material, 165 mg, 97%) was obtained using (S)—N—((R)-1-(4,6-difluorobenzofuran-2-yl)ethyl)-2-methylpropane-2-sulfinamide (260 mg, 0.86 mmol) synthesized in Reference Example 30-2.

$^1$H NMR (CDCl$_3$, 400 MHz): δ=1.51 (d, 3H, J=7 Hz), 4.19 (q, 1H, J=7 Hz), 6.55 (s, 1H), 6.72 (ddd, 1H, J=2, 10, 10 Hz), 6.9-7.0 (m, 1H). 2H portion is not observable.

Reference Example 31-1

(S)—N-((5-fluoro-3-methylbenzofuran-2-yl)methylene)-2-methylpropane-2-sulfinamide According to a technique similar to that of Reference Example 27-2, the title compound (yellow oily material, 419 mg, 81%) was obtained using 5-fluoro-3-methylbenzofuran-2-carboxylic acid methyl ester (385 mg, 1.9 mmol).

$^1$H NMR (CDCl$_3$, 400 MHz): δ=1.30 (s, 9H), 2.51 (s, 3H), 7.17 (ddd, 1H, J=2, 9, 9 Hz), 7.27 (dd, 1H, J=2, 9 Hz), 7.49 (dd, 1H, J=4, 9 Hz), 8.66 (s, 1H).

Reference Example 31-2

(S)—N—((R)-1-(5-fluoro-3-methylbenzofuran-2-yl)ethyl)-2-methylpropane-2-sulfinamide According to a technique similar to that of Reference Example 1-3, the title compound (colorless oily material, 222 mg, 50%) was obtained using (S)—N-((5-fluoro-3-methylbenzofuran-2-yl)methylene)-2-methylpropane-2-sulfinamide (419 mg, 1.5 mmol) synthesized in Reference Example 31-1.

$^1$H NMR (CDCl$_3$, 400 MHz): δ=1.15 (s, 9H), 1.65 (d, 3H, J=7 Hz), 2.23 (s, 3H), 3.41 (d, 1H, J=4 Hz), 4.7-4.9 (m, 1H), 6.98 (ddd, 1H, J=2, 9, 9 Hz), 7.12 (dd, 1H, J=2, 9 Hz), 7.32 (d d, 1H, J=4, 9 Hz).

Reference Example 31-3

(R)-1-(5-fluoro-3-methylbenzofuran-2-yl)ethan-1-amine

According to a technique similar to that of Reference Example 2-2, the title compound (pale yellow oily material, 150 mg, 100%) was obtained using (S)—N—((R)-1-(5-fluoro-3-methylbenzofuran-2-yl)ethyl)-2-methylpropane-2-sulfinamide (222 mg, 0.75 mmol) synthesized in Reference Example 31-2.

$^1$H NMR (CDCl$_3$, 400 MHz): δ=1.49 (d, 3H, J=7 Hz), 2.18 (s, 3H), 4.29 (q, 1H, J=7 Hz), 6.94 (ddd, 1H, J=3, 9, 9 Hz), 7.08 (dd, 1H, J=3, 9 Hz), 7.31 (dd, 1H, J=4, 9 Hz). 2H portion is not observable.

Reference Example 32-1

(S)—N-((5-methoxybenzofuran-2-yl)methylene)-2-methylpropane-2-sulfinamide

According to a technique similar to that of Reference Example 27-2, the title compound (pale yellow crystals, 556 mg, 80%) was obtained using 5-methoxybenzofuran-2-carboxylic acid methyl ester (516 mg, 2.5 mmol).

$^1$H NMR (CDCl$_3$, 400 MHz): δ=1.30 (s, 9H), 3.86 (s, 3H), 7.0-7.1 (m, 2H), 7.27 (d, 1H, J=2 Hz), 7.49 (d, 1H, J=9 Hz), 8.53 (s, 1H).

Reference Example 32-2

(S)—N—((R)-1-(5-methoxybenzofuran-2-yl)ethyl)-2-methylpropane-2-sulfinamide

According to a technique similar to that of Reference Example 1-3, the title compound (pale yellow crystals, 280 mg, 48%) was obtained using (S)—N-((5-methoxybenzofuran-2-yl)methylene)-2-methylpropane-2-sulfinamide (556 mg, 2.0 mmol) synthesized in Reference Example 32-1.

$^1$H NMR (CDCl$_3$, 400 MHz): δ=1.22 (s, 9H), 1.69 (d, 3H, J=7 Hz), 3.36 (d, 1H, J=7 Hz), 3.83 (s, 3H), 4.70 (quint, 1H, J=7 Hz), 6.54 (s, 1H), 6.86 (dd, 1H, J=2, 9 Hz), 6.99 (d, 1H, J=2 Hz), 7.32 (d, 1H, J=9 Hz).

Reference Example 32-3

(R)-1-(5-methoxybenzofuran-2-yl)ethan-1-amine

According to a technique similar to that of Reference Example 2-2, the title compound (pale yellow oily material, 224 mg, 100%) was obtained using (S)—N—((R)-1-(5-methoxybenzofuran-2-yl)ethyl)-2-methylpropane-2-sulfinamide (280 mg, 0.95 mmol) synthesized in Reference Example 32-2.

$^1$H NMR (CDCl$_3$, 400 MHz): δ=1.51 (d, 3H, J=7 Hz), 3.84 (s, 3H), 4.18 (q, 1H, J=7 Hz), 6.44 (s, 1H), 6.84 (dd, 1H, J=3, 9 Hz), 6.98 (d, 1H, J=3 Hz), 7.32 (d, 1H, J=9 Hz). 2H portion is not observable.

Reference Example 33-1

3-(3,3-Diethoxyprop-1-yn-1-yl)-4-hydroxybenzonitrile

In a nitrogen atmosphere, 4-hydroxy-3-iodobenzonitrile (600 mg, 2.5 mmol), 3,3-diethoxypropyne (388 μL, 2.7 mmol), triethylamine (374 μL, 2.7 mmol), copper(I) iodide (19 mg, 0.10 mmol), and bis(triphenylphosphine)palladium (II) dichloride (34 mg, 0.048 mmol) were dissolved in DMF (2.5 mL), and the solution was stirred for 16 hours at room temperature. Water was added to the reaction liquid, the mixture was stirred for a while, and then the mixture was extracted with ethyl acetate. The organic layer was washed with saturated brine and was dried over anhydrous sodium sulfate. Insoluble materials were filtered, and then the solvent was distilled off under reduced pressure. A residue thus obtained was purified by silica gel column chromatography (hexane:ethyl acetate) (concentration gradient: 29% to 50%), and thus the title compound (brown oily material, 356 mg, 59%) was obtained.

$^1$H NMR (CDCl$_3$, 400 MHz): δ=1.28 (t, 6H, J=7 Hz), 3.6-3.8 (m, 4H), 5.67 (s, 1H), 6.87 (s, 1H), 7.57 (s, 2H), 7.9-8.0 (m, 1H).

Reference Example 33-2

(S)—N-((5-cyanobenzofuran-2-yl)methylene)-2-methylpropane-2-sulfinamide 3-(3,3-Diethoxyprop-1-yn-1-yl)-4-hydroxybenzonitrile (356 mg, 1.5 mmol) synthesized in Reference Example 33-1 was dissolved in THF (5 mL) and water (1 mL), and trifluoroacetic acid (1 mL) was added to the solution. The mixture was stirred for 80 minutes at 60° C. The reaction liquid was left to cool to room temperature, a saturated aqueous solution of sodium hydrogen carbonate was added thereto, and the mixture was stirred for a while. Subsequently, the mixture was extracted with ethyl acetate. The organic layer was washed with saturated brine and was dried over anhydrous sodium sulfate. Insoluble matters were filtered, and then the solvent was distilled off under reduced pressure. Thus, 2-formylbenzofuran-5-carbonitrile was obtained. According to a technique similar to that of Reference Example 1-2, the title compound (yellow crystals, 245 mg, 62%) was obtained using 2-formylbenzofuran-5-carbonitrile thus obtained.

$^1$H NMR (CDCl$_3$, 400 MHz): δ=1.31 (s, 9H), 7.39 (s, 1H), 7.6-7.8 (m, 2H), 8.0-8.1 (m, 1H), 8.60 (s, 1H).

Reference Example 33-3

(S)—N-((R)-1-(5-cyanobenzofuran-2-yl)ethyl)-2-methylpropane-2-sulfinamide

According to a technique similar to that of Reference Example 1-3, the title compound (pale yellow oily material, 63 mg, 24%) was obtained using (S)—N-((5-cyanobenzofuran-2-yl)methylene)-2-methylpropane-2-sulfinamide (245 mg, 0.89 mmol) synthesized in Reference Example 33-2.

$^1$H NMR (CDCl$_3$, 400 MHz): δ=1.24 (s, 9H), 1.71 (d, 3H, J=6 Hz), 3.39 (d, 1H, J=6 Hz), 4.75 (quint, 1H, J=6 Hz), 6.68 (s, 1H), 7.52 (d, 1H, J=8 Hz), 7.55 (dd, 1H, J=1, 8 Hz), 7.87 (d, 1H, J=1 Hz).

Reference Example 33-4

(R)-2-(1-aminoethyl)benzofuran-5-carbonitrile

According to a technique similar to that of Reference Example 2-2, the title compound (pale yellow crystals, 40 mg, 99%) was obtained using (S)—N-((R)-1-(5-cyanobenzofuran-2-yl)ethyl)-2-methylpropane-2-sulfinamide (63 mg, 0.22 mmol) synthesized in Reference Example 33-3.

$^1$H NMR (CDCl$_3$, 400 MHz): δ=1.53 (d, 3H, J=6 Hz), 4.25 (q, 1H, J=6 Hz), 6.58 s, 1H), 7.5-7.6 (m, 2H), 7.85 (s, 1H). 2H portion is not observable.

Reference Example 34-1

(S)-2-methyl-N-((5-(trifluoromethyl)benzofuran-2-yl)methylene)propane-2-sulfinamide According to a technique similar to that of Reference Example 1-2, the title compound (pale yellow crystals, 248 mg, 81%) was obtained using 5-(trifluoromethyl)benzofuran-2-carboaldehyde (206 mg, 0.96 mmol).

$^1$H NMR (CDCl$_3$, 400 MHz): δ=1.31 (s, 9H), 7.40 (s, 1H), 7.70 (s, 2H), 8.01 (s, 1H), 8.60 (s, 1H).

Reference Example 34-2

(S)-2-methyl-N-((R)-1-(5-(trifluoromethyl)benzofuran-2-yl)ethyl)propane-2-sulfinamide According to a technique similar to that of Reference Example 1-3, the title compound (pale yellow oily material, 151 mg, 58%) was obtained using (S)-2-methyl-N-((5-(trifluoromethyl)benzofuran-2-yl)methylene)propane-2-sulfinamide (248 mg, 0.78 mmol) synthesized in Reference Example 34-1.

$^1$H NMR (CDCl$_3$, 400 MHz): δ=1.23 (s, 9H), 1.71 (d, 3H, J=6 Hz), 3.38 (d, 1H, J=6 Hz), 4.75 (quint, 1H, J=6 Hz), 6.68 (s, 1H), 7.5-7.6 (m, 2H), 7.83 (s, 1H).

Reference Example 34-3

(R)-1-(5-(trifluoromethyl)benzofuran-2-yl)ethan-1-amine

According to a technique similar to that of Reference Example 2-2, the title compound (pale yellow oily material, 97 mg, 94%) was obtained using (S)-2-methyl-N-((R)-1-(5-(trifluoromethyl)benzofuran-2-yl)ethyl)propane-2-sulfinamide (151 mg, 0.45 mmol) synthesized in Reference Example 34-2.

$^1$H NMR (CDCl$_3$, 400 MHz): δ=1.53 (d, 3H, J=7 Hz), 4.24 (q, 1H, J=7 Hz), 6.58 (s, 1H), 7.4-7.5 (m, 2H), 7.81 (s, 1H). 2H portion is not observable.

Reference Example 35-1

(S)-2-methyl-N-((6-(trifluoromethyl)benzofuran-2-yl)methylene)propane-2-sulfinamide According to a technique similar to that of Reference Example 27-2, the title compound (yellow oily material, 552 mg, 84%) was obtained using 6-(trifluoromethyl)benzofuran-2-carboxylic acid ethyl ester (537 mg, 2.1 mmol).

$^1$H NMR (CDCl$_3$, 400 MHz): δ=1.31 (s, 9H), 7.38 (s, 1H), 7.57 (d, 1H, J=8 Hz), 7.81 (d, 1H, J=8 Hz), 7.88 (s, 1H), 8.60 (s, 1H).

Reference Example 35-2

(S)-2-methyl-N—((R)-1-(6-(trifluoromethyl)benzofuran-2-yl)ethyl)propane-2-sulfinamide According to a technique similar to that of Reference Example 1-3, the title compound (white crystals, 271 mg, 47%) was obtained using (S)-2-methyl-N-((6-(trifluoromethyl)benzofuran-2-yl)methylene)propane-2-sulfinamide (522 mg, 1.7 mmol) synthesized in Reference Example 35-1.
$^1$H NMR (CDCl$_3$, 400 MHz): δ=1.24 (s, 9H), 1.71 (d, 3H, J=6 Hz), 3.39 (d, 1H, J=6 Hz), 4.76 (quint, 1H, J=6 Hz), 6.68 (s, 1H), 7.48 (d, 1H, J=8 Hz), 7.62 (d, 1H, J=8 Hz), 7.72 (s, 1H).

Reference Example 35-3

(R)-1-(6-(trifluoromethyl)benzofuran-2-yl)ethan-1-amine

According to a technique similar to that of Reference Example 2-2, the title compound (pale yellow oily material, 171 mg, 92%) was obtained using (S)-2-methyl-N—((R)-1-(6-(trifluoromethyl)benzofuran-2-yl)ethyl)propane-2-sulfinamide (271 mg, 0.81 mmol) synthesized in Reference Example 35-2.
$^1$H NMR (CDCl$_3$, 400 MHz): δ=1.53 (d, 3H, J=7 Hz), 4.24 (q, 1H, J=7 Hz), 6.58 (s, 1H), 7.46 (d, 1H, J=8 Hz), 7.60 (d, 1H, J=8 Hz), 7.71 (s, 1H). 2H portion is not observable.

Reference Example 36-1

(S)—N—((R)-1-(6-fluorobenzofuran-2-yl)-2-methylpropyl)-2-methylpropane-2-sulfinamide According to a technique similar to that of Reference Example 1-3, the title compound (pale yellow oily material, 107 mg, 26%) was obtained using (S)—N-((6-fluorobenzofuran-2-yl)methylene)-2-methylpropane-2-sulfinamide (350 mg, 1.3 mmol) synthesized in Reference Example 27-2 and a THF solution of isopropylmagnesium chloride (1.3 mL, 2.6 mmol, 2 M).
$^1$H NMR (CDCl$_3$, 400 MHz): δ=0.97 (d, 3H, J=7 Hz), 1.04 (d, 3H, J=7 Hz), 1.20 (s, 9H), 2.2-2.3 (m, 1H), 3.49 (d, 1H, J=4 Hz), 4.34 (dd, 1H, J=4, 6 Hz), 6.57 (s, 1H), 6.98 (ddd, 1H, J=2, 9, 10 Hz), 7.16 (dd, 1H, J=2, 9 Hz), 7.44 (dd, 1H, J=6, 9 Hz).

Reference Example 36-2

(R)-1-(6-fluorobenzofuran-2-yl)-2-methylpropan-1-amine

According to a technique similar to that of Reference Example 2-2, the title compound (pale yellow oily material, 74 mg, 100%) was obtained using (S)—N—((R)-1-(6-fluorobenzofuran-2-yl)-2-methylpropyl)-2-methylpropane-2-sulfinamide (107 mg, 0.34 mmol) synthesized in Reference Example 36-1.
$^1$H NMR (CDCl$_3$, 400 MHz): δ=0.94 (d, 3H, J=7 Hz), 0.99 (d, 3H, J=7 Hz), 2.0-2.2 (m, 1H), 3.80 (d, 1H, J=5 Hz), 6.49 (s, 1H), 6.96 (ddd, 1H, J=2, 9, 10 Hz), 7.15 (dd, 1H, J=2, 9 Hz), 7.41 (dd, 1H, J=6, 9 Hz). 2H portion is not observable.

Reference Example 37-1

(R)—N-((5-fluorobenzofuran-2-yl)methyl)-2-methylpropane-2-sulfinamide (R)—N-((5-fluorobenzofuran-2-yl)methylene)-2-methylpropane-2-sulfinamide (250 mg, 0.94 mmol) synthesized in Reference Example 23-1 was dissolved in methanol (5.0 mL), and sodium borohydride (106 mg, 2.81 mmol) was added thereto. The mixture was stirred for one hour at room temperature. Water was added to the reaction liquid, and the mixture was stirred for a while. Subsequently, the mixture was extracted with ethyl acetate. The organic layer was washed with saturated brine and was dried over anhydrous sodium sulfate. Insoluble matters were filtered, and then the solvent was distilled off under reduced pressure. A residue thus obtained was purified by silica gel column chromatography (hexane:ethyl acetate) (concentration gradient: 0% to 100%), and thus the title compound (white crystals, 250 mg, 99%) was obtained.
$^1$H NMR (CDCl$_3$, 400 MHz): δ=1.25 (s, 9H), 3.60 (t, 1H, J=6 Hz), 4.39 (ddd, 1H, J=1, 6, 16 Hz), 4.74 (ddd, 1H, J=1, 6, 16 Hz), 6.65 (d, 1H, J=1 Hz), 6.98 (ddd, 1H, J=2, 9, 9 Hz), 7.18 (dd, 1H, J=2, 9 Hz), 7.36 (dd, 1H, J=4, 9 Hz).

Reference Example 37-2

(5-Fluorobenzofuran-2-yl)methanamine

According to a technique similar to that of Reference Example 2-2, the title compound (yellow oily material, 46 mg, 100%) was obtained using (R)—N-((5-fluorobenzofuran-2-yl)methyl)-2-methylpropane-2-sulfinamide (75 mg, 0.28 mmol) synthesized in Reference Example 37-1.
$^1$H NMR (CDCl$_3$, 400 MHz): δ=3.97 (s, 2H), 6.51 (d, 1H, J=1 Hz), 6.95 (td, 1H, J=3, 9 Hz), 7.17 (dd, 1H, J=3, 9 Hz), 7.35 (dd, 1H, J=5, 9 Hz). 2H portion is not observable.

Reference Example 38-1

2-(3,3-DIethoxyprop-1-yn-1-yl)pyridin-3-ol

According to a technique similar to that of Reference Example 33-1, the title compound (pale brown oily material, 415 mg, 83%) was obtained using 2-iodopyridin-3-ol (501 mg, 2.3 mmol).
$^1$H NMR (CDCl$_3$, 400 MHz): δ=1.29 (t, 6H, J=7 Hz), 3.6-3.8 (m, 4H), 5.69 (s, 1H), 7.02 (s, 1H), 7.22 (dd, 1H, J=5, 9 Hz), 7.7-7.8 (m, 1H), 8.54 (dd, 1H, J=2, 5 Hz).

Reference Example 38-2

(S)—N-(1-(furo[3,2-b]pyridin-2-yl)ethyl)-2-methylpropane-2-sulfinamide

According to a technique similar to that of Reference Example 33-2, (S)—N-(furo[3,2-b]pyridin-2-ylmethylene)-2-methylpropane-2-sulfinamide was obtained using 2-(3,3-diethoxyprop-1-yn-1-yl)pyridin-3-ol (415 mg, 1.9 mmol) synthesized in Reference Example 38-1. According to a technique similar to that of Reference Example 1-3, the title compound (pale yellow crystals, 252 mg, 50%) was obtained using (S)—N-(furo[3,2-b]pyridin-2-ylmethylene)-2-methylpropane-2-sulfinamide thus obtained.
$^1$H NMR (CDCl$_3$, 400 MHz): δ=1.24 (s, 9H), 1.67 (d, 1.2H, J=7 Hz), 1.73 (d, 1.8H, J=7 Hz), 3.40 (d, 0.6H, J=6

Hz), 3.67 (d, 0.4H, J=5 Hz), 4.7-4.8 (m, 1H), 6.81 (s, 0.6H), 6.87 (s, 0.4H), 7.1-7.3 (m, 1H), 7.6-7.8 (m, 1H), 8.5-8.6 (m, 1H).

Reference Example 38-3

1-(Furo[3,2-b]pyridin-2-yl)ethan-1-amine

According to a technique similar to that of Reference Example 2-2, the title compound (brown oily material, 113 mg, 87%) was obtained using (S)—N-(1-(furo[3,2-b]pyridin-2-yl)ethyl)-2-methylpropane-2-sulfinamide (252 mg, 0.95 mmol) synthesized in Reference Example 38-2.
$^1$H NMR (CDCl$_3$, 400 MHz): δ=1.55 (d, 3H, J=7 Hz), 4.25 (q, 1H, J=7 Hz), 6.73 (s, 1H), 7.17 (dd, 1H, J=5, 8 Hz), 7.69 (d, 1H, J=8 Hz), 8.49 (dd, 1H, J=1.5 Hz). 2H portion is not observable.

Reference Example 39-1

3-(3,3-Diethoxyprop-1-yn-1-yl)pyridin-4-ol

According to a technique similar to that of Reference Example 33-1, the title compound (brown oily material, 686 mg, 70%) was obtained using 3-iodopyridin-4-ol (982 mg, 4.4 mmol).
$^1$H NMR (CDCl$_3$, 400 MHz): δ=1.28 (t, 6H, J=7 Hz), 3.6-3.8 (m, 4H), 5.68 (s, 1H), 6.89 (d, 1H, J=1 Hz), 7.4-7.5 (m, 1H), 8.49 (d, 1H, J=5 Hz), 8.91 (d, 1H, J=1 Hz).

Reference Example 39-2

(S)—N-(furo[3,2-c]pyridin-2-ylmethylene)-2-methylpropane-2-sulfinamide

According to a technique similar to that of Reference Example 33-2, the title compound (pale yellow crystals, 556 mg, 72%) was obtained using 3-(3,3-diethoxyprop-1-yn-1-yl)pyridin-4-ol (432 mg, 2.9 mmol) synthesized in Reference Example 39-1.
$^1$H NMR (CDCl$_3$, 400 MHz): δ=1.31 (s, 9H), 7.40 (d, 1H, J=1 Hz), 7.5-7.6 (m, 1H), 8.60 (s, 1H), 8.63 (d, 1H, J=6 Hz), 9.06 (s, 1H).

Reference Example 39-3

(S)—N-(1-(furo[3,2-c]pyridin-2-yl)ethyl)-2-methylpropane-2-sulfinamide

According to a technique similar to that of Reference Example 1-3, the title compound (yellow oily material, 550 mg, 93%) was obtained using (S)—N-(furo[3,2-c]pyridin-2-ylmethylene)-2-methyl propane-2-sulfinamide (556 mg, 2.2 mmol) synthesized in Reference Example 39-2.
$^1$H NMR (CDCl$_3$, 400 MHz): δ=1.24 (s, 5.4H), 1.25 (s, 3.6H), 1.66 (d, 1.2H, J=7 Hz), 1.72 (d, 1.8H, J=7 Hz), 3.40 (d, 0.6H, J=6 Hz), 3.63 (d, 0.4H, J=6 Hz), 4.6-4.8 (m, 1H), 6.69 (s, 0.6H), 6.78 (s, 0.4H), 7.3-7.5 (m, 1H), 8.47 (d, 1H, J=6 Hz), 8.87 (s, 1H).

Reference Example 39-4

1-(Furo[3,2-c]pyridin-2-yl)ethan-1-amine

According to a technique similar to that of Reference Example 2-2, the title compound (pale yellow oily material, 126 mg, 38%) was obtained using (S)—N-(1-(furo[3,2-c]pyridin-2-yl)ethyl)-2-methylpropane-2-sulfinamide (550 mg, 2.1 mmol) synthesized in Reference Example 39-3.
$^1$H NMR (CDCl$_3$, 400 MHz): δ=1.54 (d, 3H, J=6 Hz), 4.23 (q, 1H, J=6 Hz), 6.58 (s, 1H), 7.38 (d, 1H, J=5 Hz), 8.45 (d, 1H, J=5 Hz), 8.84 (s, 1H). 2H portion is not observable.

Reference Example 40-1

(S)—N—((R)-1-(5-fluorobenzo[b]thiophen-2-yl)ethyl)-2-methylpropane-2-sulfinamide According to a technique similar to that of Reference Example 18-1, (S)—N-((5-fluorobenzo[b]thiophen-2-yl)methylene)-2-methylpropane-2-sulfinamide was obtained using 5-fluorobenzo[b]thiophene-2-carboxylic acid (500 mg, 2.6 mmol) and lithium aluminum hydride (128 mg, 3.4 mmol). According to a technique similar to that of Reference Example 1-3, the title compound (pale yellow crystals, 189 mg, 25%) was obtained using (S)—N-((5-fluorobenzo[b]thiophen-2-yl)methylene)-2-methylpropane-2-sulfinamide thus obtained.
$^1$H NMR (CDCl$_3$, 400 MHz): δ=1.26 (s, 9H), 1.71 (d, 3H, J=7 Hz), 3.46 (d, 1H, J=5 Hz), 4.8-5.0 (m, 1H), 7.06 (ddd, 1H, J=3, 9, 9 Hz), 7.16 (s, 1H), 7.37 (dd, 1H, J=3, 9 Hz), 7.70 (dd, 1H, J=5, 9 Hz).

Reference Example 40-2

(R)-1-(5-fluorobenzo[b]thiophen-2-yl)ethan-1-amine

According to a technique similar to that of Reference Example 2-2, the title compound (pale yellow oily material, 140 mg, 100%) was obtained using (S)—N—((R)-1-(5-fluorobenzo[b]thiophen-2-yl)ethyl)-2-methylpropane-2-sulfinamide (189 mg, 0.63 mmol) synthesized in Reference Example 40-1.
$^1$H NMR (CDCl$_3$, 400 MHz): δ=1.54 (d, 3H, J=6 Hz), 4.43 (q, 1H, J=6 Hz), 7.03 (ddd, 1H, J=2, 9, 9 Hz), 7.09 (s, 1H), 7.34 (dd, 1H, J=2, 9 Hz), 7.70 (dd, 1H, J=5, 9 Hz). 2H portion is not observable.

Reference Example 41-1

(S)—N-((6-fluorobenzo[b]thiophen-2-yl)methylene)-2-methylpropane-2-sulfinamide

According to a technique similar to that of Reference Example 27-2, the title compound (yellow crystals, 5.44 g, 65%) was obtained using 6-fluorobenzo[b]thiophene-2-carboxylic acid methyl ester (6.14 g, 32 mmol).
$^1$H NMR (CDCl$_3$, 400 MHz): δ=1.28 (s, 9H), 7.16 (ddd, 1H, J=2, 9, 9 Hz), 7.53 (dd, 1H, J=2, 8 Hz), 7.72 (s, 1H), 7.82 (dd, 1H, J=6, 9 Hz), 8.77 (s, 1H).

Reference Example 41-2

(S)—N—((R)-1-(6-fluorobenzo[b]thiophen-2-yl)-2-methylpropyl)-2-methylpropane-2-sulfinamide According to a technique similar to that of Reference Example 1-3, the title compound (colorless oily material, 245 mg, 40%) was obtained using (S)—N-((6-fluorobenzo[b]thiophen-2-yl)methylene)-2-methylpropane-2-sulfinamide (537 mg, 1.9 mmol) synthesized in Reference Example 41-1 and a THF solution of isopropylmagnesium chloride (1.9 mL, 3.8 mmol, 2 M).

¹H NMR (CDCl₃, 400 MHz): δ=0.95 (d, 3H, J=7 Hz), 1.07 (d, 3H, J=7 Hz), 1.24 (s, 9H), 2.0-2.1 (m, 1H), 3.59 (d, 1H, J=2 Hz), 4.50 (dd, 1H, J=2, 7 Hz), 7.08 (ddd, 1H, J=2, 9, 9 Hz), 7.18 (s, 1H), 7.47 (dd, 1H, J=2, 9 Hz), 7.65 (dd, 1H, J=5, 9H z).

Reference Example 41-3

(R)-1-(6-fluorobenzo[b]thiophen-2-yl)-2-methylpropan-1-amine

According to a technique similar to that of Reference Example 2-2, the title compound (pale yellow oily material, 175 mg, 100%) was obtained using (S)—N—((R)-1-(6-fluorobenzo[b]thiophen-2-yl)-2-methylpropyl)-2-methylpropane-2-sulfinamide (245 mg, 0.75 mmol) synthesized in Reference Example 41-2.
¹H NMR (CDCl₃, 400 MHz): δ=0.93 (d, 3H, J=7 Hz), 1.01 (d, 3H, J=7 Hz), 1.9-2.0 (m, 1H), 3.99 (d, 1H, J=7 Hz), 7.06 (ddd, 1H, J=2, 9, 9 Hz), 7.08 (s, 1H), 7.48 (dd, 1H, J=2, 9 Hz), 7.61 (dd, 1H, J=5, 9 Hz). 2H portion is not observable.

Reference Example 42-1

(E)-2-(5-fluorobenzo[d]oxazol-2-yl)-N,N-dimethylethen-1-amine

5-Fluoro-2-methylbenzo[d]oxazole (2.00 g, 13 mmol) and N,N-dimethylformamide dimethyl acetal (3.5 mL, 26 mmol) were dissolved in DMF (13 mL), and the solution was stirred for 23 hours at 125° C. The reaction liquid was left to cool to room temperature, and the solvent was distilled off under reduced pressure. A residue thus obtained was purified by silica gel column chromatography (hexane: ethyl acetate) (concentration gradient: 28% to 49%), and the title compound (brown crystals, 2.29 g, 84%) was obtained.
¹H NMR (CDCl₃, 400 MHz): δ=2.98 (s, 6H), 5.03 (d, 1H, J=13 Hz), 6.81 (ddd, 1H, J=3, 9, 9 Hz), 7.14 (dd, 1H, J=3, 9 Hz), 7.21 (dd, 1H, J=4, 9 Hz), 7.56 (d, 1H, J=13 Hz).

Reference Example 42-2

(R)—N-((5-fluorobenzo[d]oxazol-2-yl)methylene)-2-methylpropane-2-sulfinamide (E)-2-(5-fluorobenzo[d]oxazol-2-yl)-N,N-dimethylethen-1-amine (2.29 g, 11 mmol) synthesized in Reference Example 42-1 was dissolved in THF (34 mL), and an aqueous solution of sodium periodate (34 mL, 34 mmol, 1 M) was added to the solution. The mixture was stirred for one hour at 45° C. The reaction liquid was left to cool to room temperature, and insoluble matters were filtered. Subsequently, the filtrate was extracted with ethyl acetate. The organic layer was washed with a 1 M aqueous solution of sodium hydrogen carbonate and saturated brine and was dried over anhydrous sodium sulfate. Insoluble matters were filtered, and the solvent was distilled off under reduced pressure. Thus, 5-fluorobenzo[d]oxazole-2-carboaldehyde was obtained. According to a technique similar to that of Reference Example 1-2, the title compound (pale yellow crystals, 559 mg, 19%) was obtained using 5-fluorobenzo[d]oxazole-2-carboaldehyde thus obtained and (R)-2-methylpropane-2-sulfinamide (467 mg, 3.9 mmol).
¹H NMR (CDCl₃, 400 MHz): δ=1.34 (s, 9H), 7.25 (ddd, 1H, J=2, 9, 9 Hz), 7.57 dd, 1H, J=2, 8 Hz), 7.61 (dd, 1H, J=4, 9 Hz), 8.67 (s, 1H).

Reference Example 42-3

(R)—N—((R)-1-(5-fluorobenzo[d]oxazol-2-yl)ethyl)-2-methylpropane-2-sulfinamide

According to a technique similar to that of Reference Example 1-3, the title compound (pale yellow oily material, 436 mg, 74%) was obtained using (R)—N-((5-fluorobenzo[d]oxazol-2-yl)methylene)-2-methylpropane-2-sulfinamide (559 mg, 2.1 mmol) synthesized in Reference Example 42-2.
¹H NMR (CDCl₃, 400 MHz): δ=1.27 (s, 9H), 1.70 (d, 3H, J=7 Hz), 4.18 (d, 1H, J=7 Hz), 4.79 (quint, 1H, J=7 Hz), 7.07 (ddd, 1H, J=3, 9, 9 Hz), 7.39 (dd, 1H, J=3, 9 Hz), 7.46 (dd, 1H, J=4, 9 Hz).

Reference Example 42-4

(R)-1-(5-fluorobenzo[d]oxazol-2-yl)ethan-1-amine

According to a technique similar to that of Reference Example 2-2, the title compound (pale yellow oily material, 150 mg, 100%) was obtained using (R)—N—((R)-1-(5-fluorobenzo[d]oxazol-2-yl)ethyl)-2-methylpropane-2-sulfinamide (222 mg, 0.75 mmol) synthesized in Reference Example 42-3.
¹H NMR (CDCl₃, 400 MHz): δ=1.61 (d, 3H, J=7 Hz), 4.32 (q, 1H, J=7 Hz), 7.06 (ddd, 1H, J=3, 9, 9 Hz), 7.38 (dd, 1H, J=3, 8 Hz), 7.43 (dd, 1H, J=4, 9 Hz). 2H portion is not observable.

Reference Example 43-1

(R)-2-methyl-N—((R)-1-(pyrazolo[1,5-a]pyridin-2-yl)ethyl)propane-2-sulfinamide

Pyrazolo[1,5-a]pyridine-2,3-dicarboxylic acid dimethyl ester (3.35 g, 14 mmol) was dissolved in 50% sulfuric acid (110 mL), and the solution was stirred for 2.5 hours at 80° C. The reaction liquid was cooled to 0° C., and a 8 M aqueous solution of sodium hydroxide was added thereto to adjust the pH to 9. Subsequently, the pH was adjusted to 3 with 6 M hydrochloric acid. A suspension liquid thus produced was separated by filtration, and crystals were washed with water and then dried under reduced pressure. Thus, pyrazolo[1,5-a]pyridine-2-carboxylic acid (pale brown crystals, 1.88 g, 81%) was obtained. In a nitrogen atmosphere, pyrazolo[1,5-a]pyridine-2-carboxylic acid (941 mg, 5.8 mmol) thus obtained was dissolved in THF (30 mL), and the solution was stirred for a while at room temperature. Subsequently, a THF solution of a borane-THF complex (20 mL, 18 mmol, 0.9 M) was added to the solution, and the mixture was stirred for 3.5 hours at 70° C. The reaction liquid was cooled to 0° C., water was added thereto, and the mixture was stirred for a while. Subsequently, 6 N hydrochloric acid was added thereto, and the mixture was heated to reflux for one hour. The solvent was distilled off under reduced pressure, subsequently methanol was added thereto, and the solvent was distilled off again. A residue thus obtained was diluted with ethyl acetate, and the organic layer was washed with a 1 N aqueous solution of sodium hydroxide, water, and saturated brine. The organic layer was dried over anhydrous sodium sulfate, insoluble matters were filtered, and then the solvent was distilled off under reduced pressure. Thus, pyrazolo[1,5-a]pyridin-2-ylmethanol was obtained. According to a technique similar to that of Reference Example 13-3, pyrazolo[1,5-a]pyridine-2-carboaldehyde was obtained using pyrazolo[1,5-a]pyridin-2-ylmethanol thus obtained. According to a technique similar to that of Reference Example 1-2, (R)-2-methyl-N-(pyrazolo[1,5-a]pyridin-2-yl-methylene)propane-2-sulfinamide was obtained using pyrazolo[1,5-a]pyridine-2-carboaldehyde thus obtained and (R)-2-methylpropane-2-sulfinamide. According to a technique similar to that of Reference Example 1-3, the title compound (pale yellow oily material, 498 mg, 65%) was obtained using (R)-2-methyl-N-(pyrazolo[1,5-a]pyridin-2-ylmethylene)propane-2-sulfinamide thus obtained.

$^1$H NMR (CDCl$_3$, 400 MHz): δ=1.26 (s, 9H), 1.63 (d, 3H, J=7 Hz), 3.98 (d, 1H, J=4 Hz), 4.7-4.9 (m, 1H), 6.48 (s, 1H), 6.72 (dd, 1H, J=7, 7 Hz), 7.08 (dd, 1H, J=7, 9 Hz), 7.46 (d, 1H, J=9 Hz), 8.39 (d, 1H, J=7 Hz).

Reference Example 43-2

(R)-1-(pyrazolo[1,5-a]pyridin-2-yl)ethan-1-amine

According to a technique similar to that of Reference Example 2-2, the title compound (pale yellow oily material, 185 mg, 61%) was obtained using (R)-2-methyl-N—((R)-1-(pyrazolo[1,5-a]pyridin-2-yl)ethyl)propane-2-sulfinamide (498 mg, 1.9 mmol) synthesized in Reference Example 43-1.

$^1$H NMR (CDCl$_3$, 400 MHz): δ=1.54 (d, 3H, J=7 Hz), 4.36 (q, 1H, J=7 Hz), 6.41 (s, 1H), 6.70 (ddd, 1H, J=1, 7, 7 Hz), 7.07 (ddd, 1H, J=1, 7, 9 Hz), 7.46 (d, 1H, J=9 Hz), 8.38 (dd, 1H, J=1, 7 Hz). 2H portion is not observable.

Reference Example 44-1

(S)-2-methyl-N—((R)-1-(1-methyl-1H-indol-6-yl)ethyl)propane-2-sulfinamide

According to a technique similar to that of Reference Example 2-1, the title compound (pale yellow crystals, 393 mg, 60%) was obtained using 1-methyl-1H-indole-6-carboaldehyde (374 mg, 2.4 mmol).

$^1$H NMR (CDCl$_3$, 400 MHz): δ=1.20 (s, 9H), 1.60 (d, 3H, J=7 Hz), 3.39 (d, 1H, J=3 Hz), 3.79 (s, 3H), 4.6-4.8 (m, 1H), 6.46 (d, 1H, J=3 Hz), 7.05 (d, 1H, J=3 Hz), 7.09 (dd, 1H, J=1, 8 Hz), 7.30 (s, 1H), 7.58 (d, 1H, J=8 Hz).

Reference Example 44-2

(R)-1-(1-methyl-1H-indol-6-yl)ethan-1-amine

According to a technique similar to that of Reference Example 2-2, the title compound (pale yellow oily material, 234 mg, 95%) was obtained using (S)-2-methyl-N—((R)-1-(1-methyl-1H-indol-6-yl)ethyl)propane-2-sulfinamide (393 mg, 1.4 mmol) synthesized in Reference Example 44-1.

$^1$H NMR (CDCl$_3$, 400 MHz): δ=1.51 (d, 3H, J=7 Hz), 3.73 (s, 3H), 4.31 (q, 1H, J=7 Hz), 6.45 (d, 1H, J=3 Hz), 7.01 (d, 1H, J=3 Hz), 7.08 (dd, 1H, J=1, 8 Hz), 7.39 (s, 1H), 7.56 (d, 1H, J=8 Hz). 2H portion is not observable.

Reference Example 45-1

(S)—N—((R)-1-(2,3-dihydrobenzofuran-5-yl)ethyl)-2-methylpropane-2-sulfinamide

According to a technique similar to that of Reference Example 2-1, the title compound (white crystals, 515 mg, 64%) was obtained using 2,3-dihydrobenzofuran-5-carboaldehyde (448 mg, 3.0 mmol).

$^1$H NMR (CDCl$_3$, 400 MHz): δ=1.20 (s, 9H), 1.50 (d, 3H, J=7 Hz), 3.20 (t, 2H, J=9 Hz), 3.29 (d, 1H, J=3 Hz), 4.4-4.5 (m, 1H), 4.57 (t, 2H, J=9 Hz), 6.74 (d, 1H, J=8 Hz), 7.07 (dd, 1H, J=2, 8 Hz), 7.16 (d, 1H, J=2 Hz).

Reference Example 45-2

(R)-1-(2,3-dihydrobenzofuran-5-yl)ethan-1-amine

According to a technique similar to that of Reference Example 2-2, the title compound (pale yellow oily material, 150 mg, 48%) was obtained using (S)—N—((R)-1-(2,3-dihydrobenzofuran-5-yl)ethyl)-2-methylpropane-2-sulfinamide (515 mg, 1.9 mmol) synthesized in Reference Example 45-1.

$^1$H NMR (CDCl$_3$, 400 MHz): δ=1.39 (d, 3H, J=6 Hz), 3.20 (t, 2H, J=9 Hz), 4.09 (q, 1H, J=6 Hz), 4.56 (t, 2H, J=9 Hz), 6.73 (d, 1H, J=8 Hz), 7.08 (dd, 1H, J=2, 8 Hz), 7.22 (s, 1H). 2H portion is not observable.

Reference Example 46-1

5-Fluorobenzofuran-2-carbonitrile

According to a technique similar to that of Reference Example 27-1, the title compound (yellow crystals, 164 mg, 6%) was obtained using 5-fluoro-2-hydroxybenzaldehyde (3.00 g, 21 mmol) and bromoacetonitrile (1.2 mL, 17 mmol).

$^1$H NMR (CDCl$_3$, 400 MHz): δ=7.25 (ddd, 1H, J=2, 9, 9 Hz), 7.34 (dd, 1H, J=2.8 Hz), 7.43 (d, 1H, J=1 Hz), 7.52 (dd, 1H, J=4, 9 Hz).

Reference Example 46-2

1-(5-Fluorobenzofuran-2-yl)cyclopropan-1-amine

5-Fluorobenzofuran-2-carbonitrile (213 mg, 1.3 mmol) synthesized in Reference Example 46-1 was dissolved in THF (7 mL), and tetraisopropyl titanate (464 μL, 1.6 mmol) was added to the solution. The mixture was stirred for 10 minutes at room temperature. A THF solution of ethylmagnesium bromide (3.3 mL, 3.2 mmol, 1 M) was added to the reaction liquid, and the mixture was stirred for 5.5 hours at the same temperature. Subsequently, a boron trifluoride-diethyl ether complex (0.25 mL, 2.0 mmol) was added to the mixture, and the mixture was stirred for another 30 minutes. A 1 N aqueous solution of sodium hydroxide was added to the reaction liquid, and the mixture was stirred for a while. Subsequently, insoluble matters were removed by filtration through Celite, and the filtrate was extracted with ethyl acetate. The organic layer was washed with saturated brine and was dried over anhydrous sodium sulfate. Insoluble matters were filtered, and then the solvent was distilled off under reduced pressure. A residue thus obtained was purified by silica gel column chromatography (hexane:ethyl acetate) (concentration gradient: 5% to 100%), and thus the title compound (brown crystals, 52 mg, 21%) was obtained.

$^1$H NMR (CDCl$_3$, 400 MHz): δ=1.1-1.3 (m, 4H), 6.46 (d, 1H, J=1 Hz), 6.90 (ddd, 1H, J=3, 9, 9 Hz), 7.12 (dd, 1H, J=3, 9 Hz), 7.28 (dd, 1H, J=4, 9 Hz). 2H portion is not observable.

Reference Example 47-1

(3,6-Difluorobenzo[b]thiophen-2-yl)methanol

According to a technique similar to that of Reference Example 54-3, 6-fluorobenzo[b]thiophene-2-carboxylic acid (pale yellow crystals, 1.18 g, 94%) was obtained using 6-fluorobenzo[b]thiophene-2-carboxylic acid methyl ester (1.34 g, 6.4 mmol). 6-Fluorobenzo[b]thiophene-2-carboxylic acid (500 mg, 2.6 mmol) thus obtained was dissolved in THF (10 mL), and the solution was cooled to −78° C. A hexane solution of butyllithium (3.5 mL, 5.6 mmol, 1.6 M) was added to the solution, and the mixture was stirred for one hour at the same temperature. A THF solution (5 mL) of N-fluorobenzenesulfonimide (967 mg, 3.1 mmol) was added to the reaction liquid, and the mixture was heated to room temperature and was stirred for 1.5 hours. 3 N hydrochloric acid was added to the reaction liquid, and the mixture was stirred for a while. Subsequently, the mixture was extracted with ethyl acetate. The organic layer was washed with water and saturated brine, and the organic layer was dried over anhydrous sodium sulfate. Insoluble matters were filtered, and then the solvent was distilled off under reduced pressure. Thus, 3,6-difluorobenzo[b]thiophene-2-carboxylic acid was obtained. In a nitrogen atmosphere, 3,6-difluorobenzo[b]thiophene-2-carboxylic acid thus obtained was dissolved in THF (25 mL), and a THF solution of a borane-THF complex (5.6 mL, 5.0 mmol, 0.9 M) was added thereto. The mixture was stirred for 7 hours at room temperature. A THF solution of a borane-THF complex (5.6 mL, 5.0 mmol, 0.9 M) was added to the reaction liquid, and the mixture was stirred for another 22 hours. Water and a 2 N aqueous solution of sodium hydroxide were added to the reaction liquid, and the mixture was stirred for a while. Subsequently, the mixture was extracted with ethyl acetate. The organic layer was washed with saturated brine and was dried over anhydrous sodium sulfate. Insoluble matters were filtered, and then the solvent was distilled off under reduced pressure. A residue thus obtained was purified by silica gel column chromatography (hexane:ethyl acetate) (concentration gradient: 5% to 40%), and thus the title compound (yellow crystals, 355 mg, 69%) was obtained.

$^1$H NMR (CDCl$_3$, 400 MHz): δ=1.86 (t, 1H, J=6 Hz), 4.91 (dd, 2H, J=2, 6 Hz), 7.16 (ddd, 1H, J=2, 9, 9 Hz), 7.44 (ddd, 1H, J=2, 2, 8 Hz), 7.67 (dd, 1H, J=5, 9 Hz).

Reference Example 47-2

(S)—N-((3,6-difluorobenzo[b]thiophen-2-yl)methylene)-2-methylpropane-2-sulfinamide According to a technique similar to that of Reference Example 13-3, 3,6-difluorobenzo[b]thiophene-2-carboaldehyde was obtained using (3,6-difluorobenzo[b]thiophen-2-yl)methanol (355 mg, 1.8 mmol) synthesized in Reference Example 47-1. According to a technique similar to that of Reference Example 1-2, the title compound (415 mg, 78%) was obtained using 3,6-difluorobenzo[b]thiophene-2-carboaldehyde thus obtained.

$^1$H NMR (CDCl$_3$, 400 MHz): δ=1.27 (s, 9H), 7.20 (ddd, 1H, J=2, 9, 9 Hz), 7.45 ddd, 1H, J=2, 2, 8 Hz), 7.81 (dd, 1H, J=5, 9 Hz), 8.92 (s, 1H).

Reference 47-3

(S)—N—((R)-1-(3,6-difluorobenzo[b]thiophen-2-yl)ethyl)-2-methylpropane-2-sulfinamide According to a technique similar to that of Reference Example 1-3, the title compound (white crystals, 273 mg, 62%) was obtained using (S)—N-((3,6-difluorobenzo[b]thiophen-2-yl)methylene)-2-methylpropane-2-sulfinamide (415 mg, 1.4 mmol) synthesized in Reference Example 47-2.

$^1$H NMR (CDCl$_3$, 400 MHz): δ=1.23 (s, 9H), 1.66 (d, 3H, J=6 Hz), 3.39 (d, 1H, J=3 Hz), 5.0-5.2 (m, 1H), 7.14 (ddd, 1H, J=2, 9, 9 Hz), 7.40 (ddd, 1H, J=2, 2, 9 Hz), 7.6 5 (dd, 1H, J=5, 9 Hz).

Reference Example 47-4

(R)-1-(3,6-difluorobenzo[b]thiophen-2-yl)ethan-1-amine

According to a technique similar to that of Reference Example 2-2, the title compound (pale yellow oily material, 209 mg, 100%) was obtained using (S)—N—((R)-1-(3,6-difluorobenzo[b]thiophen-2-yl)ethyl)-2-methylpropane-2-sulfinamide (273 mg, 0.86 mmol) synthesized in Reference Example 47-3.

$^1$H NMR (CDCl$_3$, 400 MHz): δ=1.51 (d, 3H, J=6 Hz), 4.63 (q, 1H, J=6 Hz), 7.13 (ddd, 1H, J=2, 9, 9 Hz), 7.42 (ddd, 1H, J=2, 2, 9 Hz), 7.61 (dd, 1H, J=5, 9 Hz). 2H Reference Example 48-1

(R)—N-((5-fluoro-1-methyl-1H-indol-2-yl)methylene)-2-methylpropane-2-sulfinamide According to a technique similar to that of Reference Example 54-2, 5-fluoro-1-methyl-1H-indole-2-carboxylic acid methyl ester was obtained using 5-fluoro-1H-indole-2-carboxylic acid (747 mg, 4.2 mmol), methyl iodide (1.58 mL, 25 mmol), and potassium carbonate (1.73 g, 13 mmol). In a nitrogen atmosphere, 5-fluoro-1-methyl-1H-indole-2-carboxylic acid methyl ester thus obtained was dissolved in THF (20 mL), and the solution was stirred for a while at 0° C. Subsequently, a THF solution of lithium borohydride (2.6 mL, 7.8 mmol, 3 M) was added to the solution, and the mixture was stirred for 3.5 hours at room temperature and for 17 hours at 65° C. The reaction liquid was left to cool to room temperature, a saturated aqueous solution of ammonium chloride was added thereto, and the mixture was stirred for a while. Subsequently, the mixture was extracted with ethyl acetate. The organic layer was washed with saturated brine and was dried over anhydrous sodium sulfate. Insoluble matters were filtered, and then the solvent was distilled off under reduced pressure. Thus, (5-fluoro-1-methyl-1H-indol-2-yl)methanol was obtained. According to a technique similar to that of Reference Example 13-3, 5-fluoro-1-methyl-1H-indole-2-carbaldehyde was obtained using (5-fluoro-1-methyl-1H-indol-2-yl)methanol thus obtained. According to a technique similar to that of Reference Example 1-2, the title compound (pale yellow crystals, 876 mg, 75%) was obtained using 5-fluoro-1-methyl-1H-indole-2-carboaldehyde thus obtained and (R)-2-methylpropane-2-sulfinamide.

$^1$H NMR (CDCl$_3$, 400 MHz): δ=1.28 (s, 9H), 4.11 (s, 3H), 7.04 (s, 1H), 7.13 (d dd, 1H, J=3, 9, 9 Hz), 7.3-7.4 (m, 2H), 8.62 (s, 1H).

Reference Example 48-2

(R)—N-(1-(5-fluoro-1-methyl-1H-indol-2-yl)ethyl)-2-methylpropane-2-sulfinamide

According to a technique similar to that of Reference Example 1-3, the title compound (white crystals, 886 mg, 96%) was obtained using (R)—N-((5-fluoro-1-methyl-1H-indol-2-yl)methylene)-2-methylpropane-2-sulfinamide (876 mg, 3.1 mmol) synthesized in Reference Example 48-1.

Diastereomer mixture (1:1)
$^1$H NMR (CDCl$_3$, 400 MHz): δ=1.22 (s, 4.5H), 1.23 (s, 4.5H), 1.66 (d, 1.5H, J=7 Hz), 1.79 (d, 1.5H, J=7 Hz), 3.24 (d, 0.5H, J=8 Hz), 3.45 (d, 0.5H, J=2 Hz), 3.73 (s, 1.5H), 3.79 (s, 1.5H), 4.7-4.8 (m, 1H), 6.43 (s, 0.5H), 6.47 (s, 0.5H), 6.9-7.0 (m, 1H), 7.2-7.3 (m, 2H).

Reference Example 48-3

1-(5-Fluoro-1-methyl-1H-indol-2-yl)ethan-1-amine

According to a technique similar to that of Reference Example 2-2, the title compound (pale yellow oily material, 522 mg, 91%) was obtained using (R)—N-(1-(5-fluoro-1-methyl-1H-indol-2-yl)ethyl)-2-methylpropane-2-sulfinamide (886 mg, 3.0 mmol) synthesized in Reference Example 48-2.
$^1$H NMR (CDCl$_3$, 400 MHz): δ=1.54 (d, 3H, J=7H), 3.77 (s, 3H), 4.26 (q, 1H, J=7 Hz), 6.37 (s, 1H), 6.92 (ddd, 1H, J=3, 9, 9 Hz), 7.1-7.3 (m, 2H). 2H portion is not observable.

Reference Example 49-1

(R)—N—((R)-1-(5-fluorobenzofuran-2-yl)ethyl-2,2,2-d$_3$)-2-methylpropane-2-sulfinamide (R)—N—((S)-1-(5-fluorobenzofuran-2-yl)ethyl-2,2,2-d$_3$)-2-methylpropane-2-sulfinamide According to a technique similar to that of Reference Example 1-3, the R-form of the title compound (pale yellow oily material, 630 mg, 44%) and the S-form of the title compound (white crystals, 800 mg, 56%) were obtained using (R)-N-((5-fluorobenzofuran-2-yl)methylene)-2-methylpropane-2-sulfinamide (1.33 g, 5.0 mmol) synthesized in Reference Example 23-1 and a diethyl ether solution of methyl-d$_3$-magnesium iodide (15 mL, 15 mmol, 1 M).
R-Form
$^1$H NMR (CDCl$_3$, 400 MHz): δ=1.24 (s, 9H), 3.61 (d, 1H, J=6 Hz), 4.66 (d, 1H, J=6 Hz), 6.65 (s, 1H), 6.98 (td, 1H, J=3, 9 Hz), 7.18 (dd, 1H, J=3, 9 Hz), 7.37 (dd, 1H, J=4, 9 Hz).
S-Form
$^1$H NMR (CDCl$_3$, 400 MHz): δ=1.23 (s, 9H), 3.36 (d, 1H, J=6 Hz), 4.70 (d, 1H, J=6 Hz), 6.57 (s, 1H), 6.98 (td, 1H, J=3, 9 Hz), 7.18 (dd, 1H, J=3, 9 Hz), 7.36 (dd, 1H, J=4, 9 Hz).

Reference Example 49-2

(R)-1-(5-fluorobenzofuran-2-yl)ethan-2,2,2-d$_3$-1-amine

According to a technique similar to that of Reference Example 2-2, the title compound (colorless oily material, 38 mg, 92%) was obtained using (R)—N—((R)-1-(5-fluorobenzofuran-2-yl)ethyl-2,2,2-d$_3$)-2-methylpropane-2-sulfinamide (65 mg, 0.23 mmol) synthesized in Reference Example 49-1.
$^1$H NMR (CDCl$_3$, 400 MHz): δ=4.18 (s, 1H), 6.47 (s, 1H), 6.95 (ddd, 1H, J=3, 9, 9 Hz), 7.16 (dd, 1H, J=3, 9 Hz), 7.35 (dd, 1H, J=4, 9 Hz). 2H portion is not observable.

Reference Example 50

(S)-1-(5-fluorobenzofuran-2-yl)ethan-2,2,2-d$_3$-1-amine

According to a technique similar to that of Reference Example 2-2, the title compound (50 mg, 100%) was obtained using (R)—N—((S)-1-(5-fluorobenzofuran-2-yl)ethyl-2,2,2-d$_3$)-2-methylpropane-2-sulfinamide (65 mg, 0.23 mmol) synthesized in Reference Example 49-1.
$^1$H NMR (CDCl$_3$, 400 MHz): δ=4.18 (s, 1H), 6.47 (s, 1H), 6.95 (td, 1H, J=3, 9 Hz), 7.16 (dd, 1H, J=3, 9 Hz), 7.34 (dd, 1H, J=4, 9 Hz). 2H portion is not observable.

Reference Example 51-1

(R)—N—((R)-1-(5-fluorobenzofuran-2-yl)butyl)-2-methylpropane-2-sulfinamide (R)—N—((S)-1-(5-fluorobenzofuran-2-yl)butyl)-2-methylpropane-2-sulfinamide According to a technique similar to that of Reference Example 1-3, the R-form of the title compound (white crystals, 880 mg, 74%) and the S-form of the title compound (white crystals, 310 mg, 26%) were obtained using (R)—N-((5-fluorobenzofuran-2-yl)methylene)-2-methylpropane-2-sulfinamide (1.00 g, 3.8 mmol) synthesized in Reference Example 23-1 and a THF solution of propylmagnesium bromide (10 mL, 9.4 mmol, 0.9 M).
R-Form
$^1$H NMR (CDCl$_3$, 400 MHz): δ=0.95 (t, 3H, J=7 Hz), 1.24 (s, 9H), 1.3-1.5 (m, 2H), 1.8-2.1 (m, 2H), 3.53 (d, 1H, J=7 Hz), 4.47 (q, 1H, J=7 Hz), 6.67 (s, 1H), 6.96 (td, 1H, J=3, 9 Hz), 7.17 (dd, 1H, J=3, 9 Hz), 7.36 (dd, 1H, J=4, 9 Hz).
S-Form
$^1$H NMR (CDCl$_3$, 400 MHz): δ=0.95 (t, 3H, J=7 Hz), 1.20 (s, 9H), 1.3-1.5 (m, 2H), 1.8-2.1 (m, 2H), 3.41 (d, 1H, J=5 Hz), 4.56 (q, 1H, J=7 Hz), 6.58 (s, 1H), 6.97 (td, 1H, J=3, 9 Hz), 7.18 (dd, 1H, J=3, 9 Hz), 7.36 (dd, 1H, J=4, 9 Hz).

Reference Example 51-2

(R)-1-(5-fluorobenzofuran-2-yl)butan-1-amine

According to a technique similar to that of Reference Example 2-2, the title compound (colorless oily material, 47 mg, 100%) was obtained using (R)—N—((R)-1-(5-fluorobenzofuran-2-yl)butyl)-2-methylpropane-2-sulfinamide (60 mg, 0.19 mmol) synthesized in Reference Example 51-1.
$^1$H NMR (CDCl$_3$, 400 MHz): δ=0.95 (t, 3H, J=7 Hz), 1.3-1.5 (m, 2H), 1.6-2.0 (m, 2H), 4.03 (t, 1H, J=7 Hz), 6.48 (s, 1H), 6.95 (td, 1H, J=3, 9 Hz), 7.16 (dd, 1H, J=3, 9 Hz), 7.35 (dd, 1H, J=4, 9 Hz). 2H portion is not observable.

Reference Example 52

(S)-1-(5-fluorobenzofuran-2-yl)butan-1-amine

According to a technique similar to that of Reference Example 2-2, the title compound (46 mg, 100%) was obtained using (R)—N—((S)-1-(5-fluorobenzofuran-2-yl)butyl)-2-methylpropane-2-sulfinamide (60 mg, 0.19 mmol) synthesized in Reference Example 51-1.

¹H NMR (CDCl₃, 400 MHz): δ=0.95 (t, 3H, J=7 Hz), 1.3-1.5 (m, 2H), 1.6-2.0 (m, 2H), 4.02 (t, 1H, J=7 Hz), 6.48 (s, 1H), 6.94 (td, 1H, J=3, 9 Hz), 7.16 (dd, 1H, J=3, 9 Hz), 7.34 (dd, 1H, J=4, 9 Hz). 2H

Reference Example 53-1

(S)-2-methyl-N—((R)-1-(2-phenylthiazol-5-yl)ethyl) propane-2-sulfinamide

According to a technique similar to that of Reference Example 3-1, the title compound (yellow crystals, 543 mg, 33%) was obtained using 2-phenylthiazole-5-carboaldehyde (1.00 g, 5.3 mmol).

¹H NMR (CDCl₃, 400 MHz): δ=1.24 (s, 9H), 1.71 (d, 3H, J=6 Hz), 3.45 (d, 1H, J=5 Hz), 4.8-5.0 (m, 1H), 7.4-7.5 (m, 3H), 7.70 (s, 1H), 7.8-8.0 (m, 2H).

Reference Example 53-2

(R)-1-(2-phenylthiazol-5-yl)ethan-1-amine

According to a technique similar to that of Reference Example 2-2, the title compound (yellow oily material, 12 mg, 91%) was obtained using (S)-2-methyl-N—((R)-1-(2-phenylthiazol-5-yl)ethyl)propane-2-sulfinamide (20 mg, 0.065 mmol) synthesized in Reference Example 53-1.

¹H NMR (CDCl₃, 400 MHz): δ=1.54 (d, 3H, J=6 Hz), 4.45 (q, 1H, J=6 Hz), 7.3-7.5 (m, 3H), 7.64 (s, 1H), 7.8-8.0 (m, 2H). 2H

Reference Example 54-1

Trans-2-(1H-benzo[d]imidazol-2-yl)cyclopropane-1-carboxylic acid ethyl ester

Trans-2-(ethoxycarbonyl)cyclopropane-1-carboxylic acid (4.68 g, 29.6 mmol), 1,2-phenylenediamine (3.84 g, 35.5 mmol), DIPEA (25.5 mL, 148.0 mmol), and HATU (14.6 g, 38.5 mmol) were dissolved in DMF (99 mL), and the solution was stirred overnight at room temperature. A saturated aqueous solution of sodium hydrogen carbonate and water were added to the reaction liquid, and the mixture was stirred for a while. Subsequently, the mixture was extracted with ethyl acetate. The organic layer was washed with saturated brine and was dried over anhydrous sodium sulfate. Insoluble materials were filtered, and then the solvent was distilled off under reduced pressure. Acetic acid (62 mL) was added to a residue thus obtained, and the mixture was stirred overnight at 100° C. Toluene was added to the reaction liquid, and the solvent was distilled off under reduced pressure. An aqueous solution of potassium carbonate was added to a residue thus obtained to neutralize the residue, and the mixture was extracted with ethyl acetate. The organic layer was washed with saturated brine and was dried over anhydrous sodium sulfate. Insoluble materials were filtered, and then the solvent was distilled off under reduced pressure. A residue thus obtained was purified by silica gel column chromatography (hexane:ethyl acetate) (concentration gradient: 40% to 80%) and recrystallization (hexane:ethyl acetate), and thus the title compound (2.78 g, 41%) was obtained.

¹H NMR (DMSO-d₆, 400 MHz): δ=1.22 (t, 3H, J=7 Hz), 1.56 (ddd, 1H, J=4, 5, 9 Hz), 1.65 (d dd, 1H, J=4, 6, 9 Hz), 2.22 (ddd, 1H, J=4, 5, 9 Hz), 2.61 (ddd, 1H, J=4, 6.9 Hz), 4.13 (q, 2H, J=7 Hz), 7.1-7.2 (m, 2H), 7.46 (dd, 2H, J=3, 6 Hz), 12.43 (br s, 1H).

Reference Example 54-2

Trans-2-(1-ethyl-1H-benzo[d]imidazol-2-yl)cyclopropane-1-carboxylic acid ethyl ester Trans-2-(1H-benzo[d]imidazol-2-yl)cyclopropane-1-carboxylic acid ethyl ester (750 mg, 3.26 mmol) synthesized in Reference Example 54-1 and cesium carbonate (1.70 g, 5.21 mmol) were dissolved in DMF (7.5 mL), and then bromoethane (290 μL, 3.91 mmol) was added thereto. The mixture was stirred overnight at room temperature. A saturated aqueous solution of ammonium chloride and water were added to the reaction liquid, and the mixture was extracted with ethyl acetate. The organic layer was washed with saturated brine and was dried over anhydrous sodium sulfate. Insoluble materials were filtered, and then the solvent was distilled off under reduced pressure. A residue thus obtained was purified by silica gel column chromatography (hexane:ethyl acetate) (concentration gradient: 10% to 60%), and thus the title compound (colorless oily material, 833 mg, 99%) was obtained.

¹H NMR (CDCl₃, 400 MHz): δ=1.30 (t, 3H, J=7 Hz), 1.45 (t, 3H, J=7 Hz), 1.70 (ddd, 1H, J=4, 6, 9 Hz), 1.80 (dddd, 1H, J=4, 6, 9 Hz), 2.43 (ddd, 1H, J=4, 6, 9 Hz), 2.60 (ddd, 1H, J=4, 6, 9 Hz), 4.1-4.4 (m, 4H), 7.2-7.4 (m, 3H), 7.6-7.7 (m, 1H).

Reference Example 54-3

Trans-2-(1-ethyl-1H-benzo[d]imidazol-2-yl)cyclopropane-1-carboxylic acid

Trans-2-(1-ethyl-1H-benzo[d]imidazol-2-yl)cyclopropane-1-carboxylic acid ethyl ester (830 mg, 3.21 mmol) synthesized in Reference Example 54-2 was dissolved in methanol (14 mL) and water (4 mL), and then sodium hydroxide (200 mg, 4.82 mmol) was added thereto. The mixture was stirred overnight at 50° C. 3 N hydrochloric acid was added to the reaction liquid to neutralize the reaction liquid, and then the mixture was washed with diethyl ether. The aqueous layer was concentrated under reduced pressure, and thus a crude form (white crystals, 770 mg) of the title compound was obtained.

¹H NMR (DMSO-d₆, 400 MHz): δ=1.41 (t, 3H, J=7 Hz), 1.6-1.8 (m, 1H), 1.9-2.1 (m, 1H), 2.5-2.6 (m, 1H), 2.9-3.0 (m, 1H), 4.5-4.6 (m, 2H), 7.4-7.6 (m, 2H), 7.7-7.8 (m, 1H), 7.93 (d, 1H, J=7 Hz). 1H portion is not observable.

Reference Example 55-1

Trans-2-(5-chloro-1H-benzo[d]imidazol-2-yl)cyclopropane-1-carboxylic acid ethyl ester According to a technique similar to that of Reference Example 54-1, the title compound (pale yellow crystals, 3.11 g, 74%) was obtained using (trans-2-(ethoxycarbonyl)cyclopropane-1-carboxylic acid (2.50 g, 15.8 mmol) and 4-chloro-1,2-phenylenediamine (2.70 g, 19.0 mmol).

¹H NMR (CDCl₃, 400 MHz): δ=1.29 (t, 3H, J=7 Hz), 1.70 (ddd, 1H, J=4, 6, 9 Hz), 1.79 (ddd, 1H, J=4, 6, 9 Hz), 2.41 (ddd, 1H, J=4, 6, 9 Hz), 2.58 (ddd, 1H, J=4, 6, 9 Hz), 4.19 (q, 2H, J=7 Hz), 7.19 (dd, 1H, J=2, 8 Hz), 7.2-7.4 (m, 1H), 7.5-7.7 (m, 1H), 9.44 (br s, 1H).

Reference Example 55-2

Trans-2-(5-chloro-1H-benzo[d]imidazol-2-yl)cyclopropane-1-carboxylic acid

According to a technique similar to that of Reference Example 54-3, the title compound (white crystals, 1.88 g, 70%) was obtained using trans-2-(5-chloro-1H-benzo[d]imidazol-2-yl)cyclopropane-1-carboxylic acid ethyl ester (3.00 g, 11.3 mmol) synthesized in Reference Example 55-1.
$^1$H NMR (DMSO-d$_6$, 400 MHz): δ=1.5-1.8 (m, 2H), 2.2-2.4 (m, 1H), 2.69 (ddd, 1H, J=4, 6, 10 Hz), 7.31 (d, 1H, J=9 Hz), 7.59 (d, 1H, J=9 Hz), 7.67 (s, 1H). 2H portion is not observable.

Reference Example 56-1

Trans-2-(5-methoxy-1H-benzo[d]imidazol-2-yl)cyclopropane-1-carboxylic acid ethyl ester According to a technique similar to that of Reference Example 54-1, the title compound (1.71 g, 69%) was obtained using trans-2-(ethoxycarbonyl)cyclopropane-1-carboxylic acid (1.50 g, 9.49 mmol) and 4-methoxy-1,2-phenylenediamine (2.40 mg, 11.4 mmol).
$^1$H NMR (DMSO-d$_6$, 400 MHz): δ=1.21 (t, 3H, J=7 Hz), 1.53 (ddd, 1H, J=4, 6, 9 Hz), 1.62 (d dd, 1H, J=4, 6, 9 Hz), 2.18 (ddd, 1H, J=4, 6, 9 Hz), 2.57 (ddd, 1H, J=4, 6.9 Hz), 3.75 (s, 3H), 4.13 (q, 2H, J=7 Hz), 6.75 (dd, 1H, J=3, 9 Hz), 6.97 (s, 1H), 7.33 (d, 1H, J=9 Hz), 12.25 (br s, 1H).

Reference Example 56-2

2-(5-Methoxy-1H-benzo[d]imidazol-2-yl)cyclopropane-1-carboxylic acid

According to a technique similar to that of Reference Example 54-3, the title compound (white crystals, 719 mg, 47%) was obtained using trans-2-(5-methoxy-1H-benzo[d]imidazol-2-yl)cyclopropane-1-carboxylic acid ethyl ester (1.70 g, 6.53 mmol) synthesized in Reference Example 56-1.
$^1$H NMR (DMSO-d$_6$, 400 MHz): δ=1.59 (ddd, 1H, J=4, 6, 9 Hz), 1.71 (ddd, 1H, J=4, 6, 9 Hz), 2.26 (ddd, 1H, J=4, 6, 9 Hz), 2.66 (ddd, 1H, J=4, 6, 9 Hz), 3.80 (s, 3H), 6.90 (dd, 1H, J=2, 9 Hz), 7.06 (d, 1H, J=2 Hz), 7.46 (d, 1H, J=9 Hz). 2H portion is not observable.

Reference Example 57-1

Trans-2-(3H-imidazo[4,5-b]pyridin-2-yl)cyclopropane-1-carboxylic acid ethyl ester According to a technique similar to that of Reference Example 54-1, the title compound (pale yellow solid, 12 mg, 6%) was obtained using trans-2-(ethoxycarbonyl)cyclopropane-1-carboxylic acid (150 mg, 0.95 mmol) and pyridine-2,3-diamine (124 mg, 1.14 mmol).
$^1$H NMR (CDCl$_3$, 400 MHz): δ=1.30 (t, 3H, J=7 Hz), 1.7-1.9 (m, 2H), 2.4-2.5 (m, 1H), 2.7-2.8 (m, 1H), 4.21 (q, 2H, J=7 Hz), 7.24 (dd, 1H, J=4, 7 Hz), 7.98 (d, 1H, J=7 Hz), 8.33 (d, 1H, J=4 Hz), 11.82 (br s, 1H).

Reference Example 57-2

Trans-2-(3H-imidazo[4,5-b]pyridin-2-yl)cyclopropane-1-carboxylic acid

According to a technique similar to that of Reference Example 54-3, a crude form of the title compound was obtained using trans-2-(3H-imidazo[4,5-b]pyridin-2-yl)cyclopropane-1-carboxylic acid ethyl ester (12 mg, 0.05 mmol) synthesized in Reference Example 57-1.
$^1$H NMR (CD$_3$OD, 400 MHz): δ=1.4-1.6 (m, 2H), 2.0-2.2 (m, 1H), 2.5-2.7 (m, 1H), 6.87 (dd, 1H, J=5, 8 Hz), 7.65 (dd, 1H, J=2, 8 Hz), 7.95 (dd, 1H, J=2, 5 Hz). 2H portion is not observable.

Reference Example 58-1

Trans-2-(6-chloro-3H-imidazo[4,5-b]pyridin-2-yl)cyclopropane-1-carboxylic acid ethyl ester According to a technique similar to that of Reference Example 54-1, the title compound (715 mg, 46%) was obtained using trans-2-(ethoxycarbonyl)cyclopropane-1-carboxylic acid (920 mg, 5.80 mmol) and 5-chloropyridine-2,3-diamine (1.00 g, 6.97 mmol).
$^1$H NMR (DMSO-d$_6$, 400 MHz): δ=1.22 (t, 3H, J=7 Hz), 1.61 (ddd, 1H, J=4, 6, 9 Hz), 1.69 (d dd, 1H, J=4, 6, 9 Hz), 2.29 (ddd, 1H, J=4, 6, 9 Hz), 2.63 (ddd, 1H, J=4, 6.9 Hz), 4.13 (q, 2H, J=7 Hz), 8.03 (d, 1H, J=2 Hz), 8.27 (d, 1H, J=2 Hz) 0.1H portion is not observable.

Reference Example 58-2

Trans-2-(6-chloro-3H-imidazo[4,5-b]pyridin-2-yl)cyclopropane-1-carboxylic acid

According to a technique similar to that of Reference Example 54-3, the title compound (white crystals, 270 mg, 42%) was obtained using trans-2-(6-chloro-3H-imidazo[4,5-b]pyridin-2-yl)cyclopropane-1-carboxylic acid ethyl ester (715 mg, 2.69 mmol) synthesized in Reference Example 58-1.
$^1$H NMR (DMSO-d$_6$, 400 MHz): δ=1.56 (ddd, 1H, J=4, 6, 9 Hz), 1.64 (ddd, 1H, J=4, 6, 9 Hz), 2.18 (ddd, 1H, J=4, 6, 9 Hz), 2.58 (ddd, 1H, J=4, 6, 9 Hz), 8.04 (d, 1H, J=2 Hz), 8.27 (d, 1H, J=2 Hz), 12.91 (br s, 1H), 13.25 (br s, 1H).

Reference Example 59-1

Trans-2-(1H-imidazo[4,5-c]pyridin-2-yl)cyclopropane-1-carboxylic acid ethyl ester According to a technique similar to that of Reference Example 54-1, the title compound (83 mg, 57%) was obtained using trans-2-(ethoxycarbonyl)cyclopropane-1-carboxylic acid (100 mg, 0.63 mmol) and pyridine-3,4-diamine (83 mg, 0.76 mmol).
$^1$H NMR (CDCl$_3$, 400 MHz): δ=1.25 (t, 3H, J=7 Hz), 1.7-1.9 (m, 2H), 2.4-2.6 (m, 1H), 2.7-2.8 (m, 1H), 4.15 (q, 2H, J=7 Hz), 7.40 (d, 1H, J=6 Hz), 8.37 (d, 1H, J=5 Hz), 8.91 (s, 1H), 11.35 (br s, 1H).

Reference Example 59-2

Trans-2-(1H-imidazo[4,5-c]pyridin-2-yl)cyclopropane-1-carboxylic acid

According to a technique similar to that of Reference Example 54-3, a crude form of the title compound was obtained using trans-2-(1H-imidazo[4,5-c]pyridin-2-yl)cyclopropane-1-carboxylic acid ethyl ester (83 mg, 0.36 mmol) synthesized in Reference Example 59-1.

¹H NMR (CD₃OD, 400 MHz): δ=1.7-1.9 (m, 2H), 2.4-2.5 (m, 1H), 2.8-2.9 (m, 1H), 8.04 (d, 1H, J=7 Hz), 8.49 (d, 1H, J=7 Hz), 9.12 (s, 1H). 2H portion is not observable.

Reference Example 60-1

Trans-2-(5-methyl-3H-imidazo[4,5-b]pyridin-2-yl)cyclopropane-1-carboxylic acid ethyl ester According to a technique similar to that of Reference Example 54-1, the title compound (218 mg, 22%) was obtained using trans-2-(ethoxycarbonyl)cyclopropane-1-carboxylic acid (631 mg, 3.99 mmol) and 6-methylpyridine-2,3-diamine (590 mg, 4.79 mmol).

¹H NMR (DMSO-d₆, 400 MHz): 5=1.22 (t, 3H, J=7 Hz), 1.57 (ddd, 1H, J=4, 6, 9 Hz), 1.65 (d dd, 1H, J=4, 6, 9 Hz), 2.24 (ddd, 1H, J=4, 6, 9 Hz), 2.50 (s, 3H), 2.59 (ddd, 1H, J=4, 6, 9 Hz), 4.13 (q, 2H, J=7 Hz), 7.03 (d, 1H, J=8 Hz), 7.73 (d, 1H, J=8 Hz). 1H portion is not observable.

Reference Example 60-2

Trans-2-(5-methyl-3H-imidazo[4,5-b]pyridin-2-yl)cyclopropane-1-carboxylic acid

According to a technique similar to that of Reference Example 54-3, a crude form (335 mg) of the title compound was obtained using trans-2-(5-methyl-3H-imidazo[4,5-b]pyridin-2-yl)cyclopropane-1-carboxylic acid ethyl ester (218 mg, 0.89 mmol) synthesized in Reference Example 60-1.

¹H NMR (DMSO-d₆, 400 MHz): δ=1.6-1.9 (m, 2H), 2.3-2.5 (m, 1H), 2.68 (s, 3H) 2.7-2.9 (m, 1H), 7.42 (dd, 1H, J=3, 8 Hz), 8.27 (d, 1H, J=8 Hz), 12.84 (br s, 1H). 1H portion is not observable.

Reference Example 61-1

Trans-2-(4-chloro-1H-benzo[d]imidazol-2-yl)cyclopropane-1-carboxylic acid ethyl ester According to a technique similar to that of Reference Example 54-1, the title compound (white crystals, 662 mg, 82%) was obtained using trans-2-(ethoxycarbonyl)cyclopropane-1-carboxylic acid (480 mg, 3.04 mmol) and 3-chloro-1,2-phenylenediamine (520 mg, 3.64 mmol).

¹H NMR (CDCl₃, 400 MHz): δ=1.29 (t, 3H, J=7 Hz), 1.6-1.9 (m, 2H), 2.3-2.5 (m, 1H), 2.65 (ddd, 1H, J=4, 6, 9 Hz), 4.20 (q, 2H, J=7 Hz), 7.1-7.3 (m, 2H), 7.55 (d, 1H, J=7 Hz), 9.58 (br s, 1H).

Reference Example 61-2

Trans-2-(4-chloro-1H-benzo[d]imidazol-2-yl)cyclopropane-1-carboxylic acid

According to a technique similar to that of Reference Example 54-3, a crude form (white crystals, 831 mg) of the title compound was obtained using trans-2-(4-chloro-1H-benzo[d]imidazol-2-yl)cyclopropane-1-carboxylic acid ethyl ester (600 mg, 2.27 mmol) synthesized in Reference Example 61-1.

¹H NMR (DMSO-d₆, 400 MHz): δ=1.6-1.8 (m, 1H), 1.9-2.0 (m, 1H), 2.4-2.6 (m, 1H), 2.8-3.0 (m, 1H), 7.3-7.7 (m, 3H). 2H portion is not observable.

Reference Example 62-1

(1S,2S)-2-(1H-benzo[d]imidazol-2-yl)cyclopropane-1-carboxylic acid (1R,2S,5R)-2-isopropyl-5-methylcyclohexyl ester Into a 200-mL round bottom flask, (1S,2S)-2-((((1R,2S,5R)-2-isopropyl-5-methylcyclohexyl)oxy)carbonyl)cyclopropane-1-carboxylic acid (9.51 g, 35.4 mmol), 1,2-phenylenediamine (4.60 g, 42.5 mmol), and DIPEA (30.6 mL, 177.6 mmol) were introduced, and the contents were suspended in DMF (119 mL). Subsequently, HATU (17.5 g, 46.0 mmol) was added thereto, and the mixture was stirred for 23 hours at room temperature. A saturated aqueous solution of sodium hydrogen carbonate was added to the reaction liquid, and then the mixture was extracted four times with ethyl acetate. The organic layer thus combined was dried over sodium sulfate, and insoluble matters were separated by filtration. Subsequently, the filtrate was concentrated under reduced pressure. Toluene was added to a residue thus obtained, and the mixture was distilled off while water was azeotropically boiled. Subsequently, acetic acid (62 mL) was added to the residue, and the mixture was stirred for 3 hours at 80° C. Acetic acid was distilled off under reduced pressure, and then an aqueous solution of potassium carbonate was added to a residue thus obtained so as to neutralize the residue. The mixture was extracted three times with ethyl acetate. The organic layer thus combined was dried over anhydrous sodium sulfate, and insoluble matters were separated by filtration. Subsequently, the filtrate was concentrated under reduced pressure. A residue thus obtained was subjected to origin removal with hexane:ethyl acetate=1:1 using silica gel, and a solid was deposited using the same hexane:ethyl acetate=1:1. A solid thus obtained was collected by filtration, and thus the title compound (8.34 g, 70%) was obtained.

¹H NMR (CD₃OD, 400 MHz): δ=0.80 (d, 3H, J=7 Hz), 0.8-1.6 (m, 11H), 1.6-1.8 (m, 4H), 1.8-2.0 (m, 2H), 2.2-2.3 (m, 1H), 2.6-2.7 (m, 1H), 4.74 (td, 1H, J=4, 10 Hz), 7.1-7.3 (m, 2H), 7.4-7.6 (m, 2H). 1H portion is not observable.

Reference Example 62-2

(1S,2S)-2-(1H-benzo[d]imidazol-2-yl)cyclopropane-1-carboxylic acid

Into a 200-mL round bottom flask, (1S,2S)-2-(1H-benzo[d]imidazol-2-yl)cyclopropane-1-carboxylic acid (1R,2S,5R)-2-isopropyl-5-methylcyclohexyl ester (7.34 g, 21.6 mmol) synthesized in Reference Example 62-1 was introduced, and the compound was suspended in isopropanol (58 mL) and water (4.6 mL). Subsequently, sodium hydroxide (1.72 g, 43.0 mmol) was added thereto, and the mixture was stirred overnight at 80° C. The solvent was distilled off under reduced pressure, and then water was added to a residue thus obtained. The mixture was washed two times with diethyl ether. 3 N hydrochloric acid was added to the aqueous layer, and the solvent was distilled off. A residue thus obtained was suspended by adding ethyl acetate and water thereto. A solid thus obtained was collected by filtration and was dried under reduced pressure at room temperature. Thus, the title compound (light brown powder, 2.44 g, 56%) was obtained.

¹H NMR (DMSO-d₆, 400 MHz): δ=1.4-1.7 (m, 2H), 2.0-2.2 (m, 1H), 2.5-2.6 (m, 1H), 7.0-7.2 (m, 2H), 7.3-7.6 (m, 2H), 12.41 (br s, 1H). 1H portion is not observable.

Reference Example 63-1

(1S,2S)-2-(1-ethyl-1H-benzo[d]imidazol-2-yl)cyclopropane-1-carboxylic acid (1R,2S,5R)-2-isopropyl-5-methyl cyclohexyl ester According to a technique similar to that of Reference Example 54-2, the title compound (colorless oily material, 451 mg) was obtained using (1S,2S)-2-(1H-benzo[d]imidazol-2-yl)cyclopropane-1-carboxylic acid (1R,2S,5R)-2-isopropyl-5-methyl cyclohexyl ester (400 mg, 1.2 mmol) synthesized in Reference Example 62-1.

$^1$H NMR (CDCl$_3$, 400 MHz): δ=0.80 (d, 3H, J=7 Hz), 0.8-1.2 (m, 9H), 1.4-1.6 (m, 2H), 1.45 (t, 3H, J=7 Hz), 1.6-1.8 (m, 3H), 1.8-2.1 (in, 3H), 2.3-2.4 (m, 1H), 2.5-2.7 (m, 1H), 4.29 (q, 2H, J=7 Hz), 4.74 (dt, 1H, J=4, 11 Hz), 7.2-7.4 (m, 3H), 7.6-7.7 (m, 1H).

Reference Example 63-2

(1S,2S)-2-(1-ethyl-1H-benzo[d]imidazol-2-yl)cyclopropane-1-carboxylic acid

According to a technique similar to that of Reference Example 54-3, a crude form (white crystals, 433 mg) of the title compound was obtained using (1S,2S)-2-(1-ethyl-1H-benzo[d]imidazol-2-yl)cyclopropane-1-carboxylic acid (1R,2S,5R)-2-isopropyl-5-methyl cyclohexyl ester (451 mg) synthesized in Reference Example 63-1.

$^1$H NMR (DMSO-d$_6$, 400 MHz): δ=1.42 (t, 3H, J=7 Hz), 1.7-1.8 (m, 1H), 2.0-2.1 (m, 1H), 2.5-2.7 (m, 1H), 2.9-3.0 (min, 1H), 4.5-4.7 (m, 2H), 7.5-7.6 (m, 2H), 7.7-7.8 (m, 1H), 7.9-8.0 (m, 1H), 12.94 (br s, 1H).

Reference Example 64-1

(1S,2S)-2-(5-fluoro-1H-benzo[d]imidazol-2-yl)cyclopropane-1-carboxylic acid (1R,2S,5R)-2-isopropyl-5-methyl cyclohexyl ester According to a technique similar to that of Reference Example 54-1, the title compound (white crystals, 894 mg, 84%) was obtained using (1S,2S)-2-((((1R,2S,5R)-2-isopropyl-5-methylcyclohexyl)oxy)carbonyl)cyclopropane-1-carboxylic acid (800 mg, 2.98 mmol) and 4-fluoro-1,2-phenylenediamine (450 mg, 3.58 mmol).

$^1$H NMR (CDCl$_3$, 400 MHz): δ=0.7-1.2 (m, 12H), 1.3-1.5 (m, 2H), 1.6-2.0 (m, 6H), 2.3-2.5 (m, 1H), 2.57 (ddd, 1H, J=4, 6, 10 Hz), 4.71 (td, 1H, J=4, 11 Hz), 6.97 (td, 1H, J=3, 9 Hz), 7.06 (d, 0.5H, J=8 Hz), 7.2-7.4 (m, 1H), 7.56 (dd, 0.5H, J=5, 9 Hz), 9.49 (d, 1H, J=5 Hz).

Reference Example 64-2

(1S,2S)-2-(5-fluoro-1H-benzo[d]imidazol-2-yl)cyclopropane-1-carboxylic acid

According to a technique similar to that of Reference Example 54-3, a crude form of the title compound was obtained using (1S,2S)-2-(5-fluoro-1H-benzo[d]imidazol-2-yl)cyclopropane-1-carboxylic acid (1R,2S,5R)-2-isopropyl-5-methyl cyclohexyl ester (220 mg, 0.61 mmol) synthesized in Reference Example 64-1.

$^1$H NMR (DMSO-d$_6$, 400 MHz): δ=1.4-1.6 (m, 2H), 2.0-2.1 (m, 1H), 2.4-2.6 (m, 1H), 6.95 (td, 1H, J=2, 9 Hz), 7.25 (dd, 1H, J=2, 9 Hz), 7.42 (dd, 1H, J=5, 9 Hz), 12.59 (br s, 1H). 1H

Reference Example 65-1

(1S,2S)-2-(5-chloro-1H-benzo[d]imidazol-2-yl)cyclopropane-1-carboxylic acid (1R,2S,5R)-2-isopropyl-5-methyl cyclohexyl ester According to a technique similar to that of Reference Example 54-1, the title compound (pale yellow crystals, 890 mg, 77%) was obtained using (1S,2S)-2-((((1R,2S,5R)-2-isopropyl-5-methylcyclohexyl)oxy)carbonyl)cyclopropane-1-carboxylic acid (830 mg, 3.1 mmol) and 4-chloro-1,2-phenylenediamine (529 mg, 3.7 mmol).

$^1$H NMR (DMSO-d$_6$, 400 MHz): δ=0.75 (d, 3H, J=7 Hz), 0.8-1.2 (m, 9H), 1.2-1.3 (m, 1H), 1.3-1.7 (m, 6H), 1.7-2.0 (in, 1H), 2.1-2.3 (m, 1H), 2.5-2.6 (m, 1H), 4.64 (dt, 1H, J=4, 11 Hz), 7.15 (dd, 1H, J=2, 8 Hz), 7.46 (d, 1H, J=8 Hz), 7.52 (d, 1H, J=2 Hz) 0.1H portion is not observable.

Reference Example 65-2

(1S,2S)-2-(5-chloro-1H-benzo[d]imidazol-2-yl)cyclopropane-1-carboxylic acid

According to a technique similar to that of Reference Example 54-3, the title compound (white crystals, 225 mg, 40%) was obtained using (1S,2S)-2-(5-chloro-1H-benzo[d]imidazol-2-yl)cyclopropane-1-carboxylic acid (1R,2S,5R)-2-isopropyl-5-methylcyclohexyl ester (890 mg, 2.4 mmol) synthesized in Reference Example 65-1.

$^1$H NMR (DMSO-d$_6$, 400 MHz): δ=1.5-1.7 (m, 2H), 2.1-2.2 (m, 1H), 2.5-2.6 (m, 1H), 7.15 (dd, 1H, J=2, 8 Hz), 7.46 (d, 1H, J=8 Hz), 7.52 (s, 1H), 12.61 (br s, 2H).

Reference Example 66-1

(1S,2S)-cyclopropane-1,2-dicarboxylic acid 1-((1R,2S,5R)-2-isopropyl-5-methylcyclohexyl) 2-(2-oxo-2-(pyridin-2-yl)ethyl) diester (1S,2S)-2-((((1R,2S,5R)-2-isopropyl-5-methylcyclohexyl)oxy)carbonyl)cyclopropane-1-carboxylic acid (300 mg, 1.12 mmol), 2-(bromoacetayl)pyridine (314 mg, 1.12 mmol), and DIPEA (195 mL, 1.12 mmol) were dissolved in acetonitrile (12 mL), and the solution was stirred overnight at 50° C. Subsequently, DIPEA (389 mL, 2.24 mmol) was added thereto, and the mixture was stirred for 5 hours at 80° C. The solvent was distilled off under reduced pressure, and then water was added to a residue thus obtained. The organic layer was dried over anhydrous sodium sulfate, insoluble matters were filtered, and then the solvent was distilled off under reduced pressure. A residue thus obtained was purified by silica gel column chromatography (hexane:ethyl acetate) (concentration gradient: 10% to 40%), and thus the title compound (350 mg, 77%) was obtained.

Reference Example 66-2

(1S,2S)-2-(4-(pyridin-2-yl)-1H-imidazol-2-yl)cyclopropane-1-carboxylic acid (1R,2S,5R)-2-isopropyl-5-methyl cyclohexyl ester (1S,2S)-cyclopropane-1,2-dicarboxylic acid 1-((1R,2S,5R)-2-isopropyl-5-methylcyclohexyl) 2-(2-oxo-2-(pyridin-2-yl)ethyl) diester (350 mg, 0.90 mmol) synthesized in Reference Example 66-1 and ammonium acetate (1.39 g, 18.06 mmol) were dissolved in toluene (10 mL), and the solution was stirred overnight at 130° C. The reaction liquid was returned to room temperature, and water and a saturated aqueous solution of sodium hydrogen carbonate were added to the reaction liquid. Subsequently, the mixture was extracted with ethyl acetate. The organic layer was dried over anhydrous sodium sulfate, insoluble matters were filtered, and then the solvent was distilled off under reduced pressure. Thus, the title compound (342 mg, 100%) was obtained.

Reference Example 66-3

(1S,2S)-2-(4-(pyridin-2-yl)-1H-imidazol-2-yl)cyclopropane-1-carboxylic acid (1S,2S)-2-(4-(pyridin-2-yl)-1H-imidazol-2-yl)cyclopropane-1-carboxylic acid (1R,2S,5R)-2-isopropyl-5-methyl cyclohexyl ester (342 mg, 0.90 mmol) synthesized in Reference Example 66-2 was suspended in methanol (1 mL) and water (1 mL), and then sodium hydroxide (180 mg, 4.65 mmol) was added to the suspension liquid. The mixture was stirred at 80° C. The solvent was distilled off under reduced pressure, and then water was added to a residue thus obtained. The mixture was washed two times with diethyl ether, and water was distilled off under reduced pressure. Thus, a crude form of the title compound was obtained.

$^1$H NMR (CD$_3$OD, 400 MHz): δ=1.7-2.0 (m, 2H), 2.4-2.6 (m, 1H), 2.8-2.9 (m, 1H), 7.8-7.9 (m, 1H), 8.29 (s, 1H), 8.30 (d, 1H, J=8 Hz), 8.47 (td, 1H, J=2, 8 Hz), 8.72 (td, 1H, J=2, 6 Hz). 2H portion is not observable.

Reference Example 67-1

Trans-2-(benzo[d]oxazol-2-yl)cyclopropane-1-carboxylic acid ethyl ester

Trans-2-(ethoxycarbonyl)cyclopropane-1-carboxylic acid (1.00 g, 6.32 mmol), 2-bromoaniline (1.31 g, 7.59 mmol), DIPEA (3.3 mL, 19.0 mmol), and HATU (3.37 g, 8.85 mmol) were dissolved in DMF (63 mL), and the solution was stirred overnight at room temperature. A saturated solution of sodium hydrogen carbonate and water were added to the reaction liquid, and the mixture was stirred for a while. Subsequently, the mixture was extracted with ethyl acetate. The organic layer was washed with saturated brine and was dried over anhydrous sodium sulfate. Insoluble matters were filtered, and then the solvent was distilled off under reduced pressure. A residue thus obtained (1.05 g), 1,10-phenanthroline (61 mg, 0.34 mmol), and copper(I) iodide (32 mg, 0.17 mmol) were dissolved in DME (27 mL), and then cesium carbonate (1.64 g, 5.05 mmol) was added to the solution. The mixture was heated to reflux overnight. Water was added to the reaction liquid, and the mixture was extracted with ethyl acetate. The organic layer was dried over anhydrous sodium sulfate, insoluble matters were filtered, and then the solvent was distilled off under reduced pressure. A residue thus obtained was purified by silica gel column chromatography (hexane:ethyl acetate) (concentration: 0% to 10%), and thus the title compound (616 mg, 79%) was obtained.

$^1$H NMR (CDCl$_3$, 400 MHz): δ=1.29 (t, 3H, J=7 Hz), 1.7-1.08 (m, 2H), 2.3-2.5 (m, 1H), 2.7-2.9 (m, 1H), 4.20 (q, 2H, J=7 Hz), 7.2-7.4 (m, 2H), 7.4-7.5 (m, 1H), 7.6-7.7 (m, 1H).

Reference Example 67-2

Trans-2-(benzo[d]oxazol-2-yl)cyclopropane-1-carboxylic acid

According to a technique similar to that of Reference Example 54-3, the title compound (white crystals, 221 mg, 41%) was obtained using trans-2-(benzo[d]oxazol-2-yl)cyclopropane-1-carboxylic acid ethyl ester (615 mg, 2.66 mmol) synthesized in Reference Example 67-1.

$^1$H NMR (DMSO-d$_6$, 400 MHz): δ=1.61 (ddd, 1H, J=4, 6, 9 Hz), 1.67 (ddd, 1H, J=4, 6, 9 Hz), 2.27 (ddd, 1H, J=4, 6, 9 Hz), 2.67 (ddd, 1H, J=4, 6, 9 Hz), 7.3-7.4 (m, 2H), 7.6-7.7 (m, 2H) 0.1H portion is not observable.

Reference Example 68-1

Trans-2-(5-chlorobenzo[d]oxazol-2-yl)cyclopropane-1-carboxylic acid ethyl ester

According to a technique similar to that of Reference Example 67-1, the title compound (19 mg, 17%) was obtained using 2-bromo-5-chloroaniline (287 mg, 1.39 mmol).

$^1$H NMR (CDCl$_3$, 400 MHz): δ=1.28 (t, 3H, J=7 Hz), 1.7-1.8 (m, 2H), 2.3-2.5 (m, 1H), 2.7-2.8 (m, 1H), 4.20 (q, 2H, J=7 Hz), 7.26 (dd, 1H, J=2, 8 Hz), 7.37 (d, 1H, J=8 Hz), 7.60 (d, 1H, J=2 Hz).

Reference Example 68-2

Trans-2-(5-chlorobenzo[d]oxazol-2-yl)cyclopropane-1-carboxylic acid lithium salt Trans-2-(5-chlorobenzo[d]oxazol-2-yl)cyclopropane-1-carboxylic acid ethyl ester (19 mg, 0.07 mmol) synthesized in Reference Example 68-1 was suspended in methanol (1 mL) and water (1 mL), and then lithium hydroxide monohydrate (4 mg, 0.9 mmol) was added thereto. The mixture was stirred for 30 minutes at room temperature. The solvent was distilled off under reduced pressure, and thus a crude form of the title compound was obtained.

$^1$H NMR (CD$_3$OD, 400 MHz): δ=1.5-1.7 (m, 2H), 2.1-2.3 (m, 1H), 2.5-2.7 (m, 1H), 7.31 (dd, 1H, J=2, 9 Hz), 7.50 (d, 1H, J=9 Hz), 7.56 (d, 1H, J=2 Hz). 1H portion is not observable.

Reference Example 69-1

(1S,2S)-2-((pyridin-2-ylmethyl)carbamoyl)cyclopropane-1-carboxylic acid (1R,2S,5R)-2-isopropyl-5-methyl cyclohexyl ester According to a technique similar to that of Reference Example 9-1, the title compound (135 mg, 12%) was obtained using 2-(aminomethyl)pyridine (370 μL, 3.05 mmol) and (1S,2S)-2-((((1R,2S,5R)-2-isopropyl-5-methylcyclohexyl)oxy)carbonyl)cyclopropane-1-carboxylic acid (817 mg, 3.04 mmol).

$^1$H NMR (CDCl$_3$, 400 MHz): δ=0.76 (dd, 3H, J=5, 7 Hz), 0.8-1.1 (m, 9H), 1.3-1.7 (m, 6H), 1.8-2.3 (m, 4H), 4.5-4.8 (m, 3H), 7.0-7.1 (m, 1H), 7.2-7.3 (m, 2H), 7.68 (td, 1H, J=2, 8 Hz), 8.56 (d, 1H, J=5 Hz).

Reference Example 69-2

2-(Imidazo[1,5-a]pyridin-3-yl)cyclopropane-1-carboxylic acid (1R,2S,5R)-2-isopropyl-5-methyl cyclohexyl ester (1S,2S)-2-((pyridin-2-ylmethyl)carbamoyl)cyclopropane-1-carboxylic acid (1R,2S,5R)-2-isopropyl-5-methyl cyclohexyl ester (111 mg, 0.31 mmol) synthesized in Reference Example 69-1 was dissolved in toluene (1 mL), and phosphoryl chloride (0.5 mL) was added to the solution. In a nitrogen atmosphere, the mixture was heated to reflux overnight. The solvent was distilled off under reduced pressure, and then water was added to a residue thus obtained. The mixture was washed three times with ethyl acetate. The organic layer was dried over anhydrous sodium sulfate, insoluble matters were filtered, and then the solvent was distilled off under reduced pressure. A residue thus obtained was purified by silica gel column chromatography (hexane:ethyl acetate) (concentration gradient: 25% to 40%), and thus the title compound (yellow solid, 54 mg, 51%) was obtained.

$^1$H NMR (CDCl$_3$, 400 MHz): δ=0.80 (d, 3H, J=7 Hz), 0.8-1.2 (m, 9H), 1.3-1.6 (m, 2H), 1.6-1.8 (m, 4H), 1.8-2.3 (m, 3H), 2.6-2.7 (m, 1H), 4.7-4.8 (m, 1H), 6.5-6.8 (m, 2H), 7.2-7.3 (m, 1H), 7.3-7.5 (m, 1H), 7.8-7.9 (m, 1H).

Reference Example 69-3

2-(Imidazo[1,5-a]pyridin-3-yl)cyclopropane-1-carboxylic acid

According to a technique similar to that of Reference Example 54-3, a crude form (white powder, 75 mg) of the title compound was obtained using 2-(imidazo[1,5-a]pyridin-3-yl)cyclopropane-1-carboxylic acid (1R,2S,5R)-2-isopropyl-5-methylcyclohexyl ester (54 mg, 0.16 mmol) synthesized in Reference Synthesis Example 69-2.

$^1$H NMR (DMSO-d$_6$, 400 MHz): δ=1.3-1.5 (m, 2H), 1.8-2.0 (m, 1H), 2.6-2.8 (m, 1H), 6.6-6.8 (m, 2H), 7.23 (s, 1H), 7.50 (dd, 1H, J=1, 9 Hz), 8.25 (d, 1H, J=7 Hz). 1H portion is not observable.

Reference Example 70-1

Trans-2-(l-methyl-1H-imidazol-2-yl)cyclopropane-1-carboxylic acid ethyl ester

In an ice bath, trimethylsulfoxonium iodide (169 mg, 1.11 mmol) was dissolved in DMSO (3 mL), and sodium hydride (31 mg, 0.78 mmol, dispersed in 60% liquid paraffin) was added to the solution. The mixture was stirred for one hour at room temperature. (E)-3-(1-methyl-1H-imidazol-2-yl) acrylic acid ethyl ester (125 mg, 0.69 mmol) dissolved in DMSO (1.5 mL) and THF (1.5 mL) was added to the mixture, and the mixture was stirred overnight at 60° C. The reaction liquid was returned to room temperature, and then the reaction liquid was poured into an ice bath. The mixture was extracted with ethyl acetate. The organic layer was dried over anhydrous sodium sulfate, insoluble matters were filtered, and then the solvent was distilled off under reduced pressure. A residue thus obtained was purified by silica gel column chromatography (hexane:ethyl acetate) (concentration gradient: 60% to 100%), and thus the title compound (colorless liquid, 35 mg, 26%) was obtained.

$^1$H NMR (CDCl$_3$, 400 MHz): δ=1.29 (t, 3H, J=7 Hz), 1.5-1.7 (m, 2H), 2.1-2.2 (m, 1H), 2.3-2.5 (m, 1H), 3.67 (s, 3H), 4.1-4.3 (m, 2H), 6.79 (d, 1H, J=1 Hz), 6.86 (d, 1H, J=1 Hz).

Reference Example 70-2

Trans-2-(1-methyl-1H-imidazol-2-yl)cyclopropane-1-carboxylic acid

According to a technique similar to that of Reference Example 54-3, a crude form of the title compound was obtained using trans-2-(1-methyl-1H-imidazol-2-yl)cyclopropane-1-carboxylic acid ethyl ester (35 mg, 0.18 mmol) synthesized in Reference Example 70-1.

$^1$H NMR (CD$_3$OD, 400 MHz): δ=1.3-1.5 (m, 2H), 1.7-1.9 (m, 1H), 2.3-2.4 (m, 1H), 3.73 (s, 3H), 6.77 (d, 1H, J=1 Hz), 6.98 (d, 1H, J=1 Hz). 1H portion is not observable.

Reference Example 71-1

Trans-cyclopropane-1,2-dicarboxylic acid 1-ethyl 2-(2-oxo-2-(pyridin-2-yl)ethyl) diester According to a technique similar to that of Reference Example 66-1, a crude form of the title compound was obtained using trans-2-(ethoxycarbonyl)cyclopropane-1-carboxylic acid (100 mg, 0.63 mmol).

Reference Example 71-2

Trans-2-(4-(pyridin-2-yl)-1H-imidazol-2-yl)cyclopropane-1-carboxylic acid ethyl ester According to a technique similar to that of Reference Example 66-2, a crude form of the title compound was obtained using trans-cyclopropane-1,2-dicarboxylic acid 1-ethyl 2-(2-oxo-2-(pyridin-2-yl)ethyl) diester synthesized in Reference Example 71-1.

$^1$H NMR (CDCl$_3$, 400 MHz): δ=1.29 (t, 3H, J=7 Hz), 1.5-1.7 (m, 2H), 2.1-2.3 (m, 1H), 2.5-2.6 (m, 1H), 4.18 (q, 2H, J=7 Hz), 7.0-7.2 (m, 1H), 7.3-7.7 (m, 2H), 7.68 (td, 1H, J=2, 8 Hz), 8.50 (d, 1H, J=5 Hz), 10.21 (br s, 1H).

Reference Example 71-3

Trans-2-(4-(pyridin-2-yl)-1H-imidazol-2-yl)cyclopropane-1-carboxylic acid

According to a technique similar to that of Reference Example 66-3, a crude form of the title compound was obtained using trans-2-(4-(pyridin-2-yl)-1H-imidazol-2-yl)cyclopropane-1-carboxylic acid ethyl ester synthesized in Reference Example 71-2.

$^1$H NMR (CD$_3$OD, 400 MHz): δ=1.6-1.9 (m, 2H), 2.3-2.5 (m, 1H), 2.7-2.9 (m, 1H), 7.76 (ddd, 1H, J=1, 5, 8 Hz), 8.18 (s, 1H), 8.20 (d, 1H, J=8 Hz), 8.37 (td, 1H, J=1, 8 Hz), 8.72 (td, 1H, J=1, 5 Hz). 2H Reference Example 72-1

Trans-cyclopropane-1,2-dicarboxylic acid 1-ethyl 2-(2-oxo-2-phenylethyl) diester According to a technique similar to that of Reference Example 66-1, the title compound (87 mg, 100%) was obtained using trans-2-(ethoxycarbonyl)cyclopropane-1-carboxylic acid (50 mg, 0.32 mmol) and phenacyl chloride (49 mg, 0.32 mmol).

$^1$H NMR (CDCl$_3$, 400 MHz): δ=1.29 (t, 3H, J=7 Hz), 1.5-1.6 (m, 2H), 2.2-2.4 (m, 2H), 4.17 (q, 2H, J=7 Hz), 5.37 (s, 2H), 7.4-7.6 (m, 2H), 7.62 (td, 1H, J=2, 8 Hz), 7.8-8.0 (m, 2H).

Reference Example 72-2

Trans-2-(4-phenyl-1H-imidazol-2-yl)cyclopropane-1-carboxylic acid ethyl ester

According to a technique similar to that of Reference Example 66-2, the title compound (37 mg, 45%) was obtained using trans-cyclopropane-1,2-dicarboxylic acid 1-ethyl 2-(2-oxo-2-phenylethyl) diester (87 mg, 0.32 mmol) synthesized in Reference Example 72-1.

$^1$H NMR (CDCl$_3$, 400 MHz): δ=1.25 (t, 3H, J=7 Hz), 1.5-1.6 (m, 1H), 1.6-1.7 (m, 1H), 2.2-2.3 (m, 1H), 2.4-2.6 (m, 1H), 4.0-4.2 (m, 2H), 7.18 (s, 1H), 7.22 (t, 1H, J=7 Hz), 7.35 (d, 1H, J=8 Hz), 7.63 (br s, 2H), 7.62 (td, 1H, J=2, 8 Hz), 9.9-10.5 (m, 1H).

Reference Example 72-3

Trans-2-(4-phenyl-1H-imidazol-2-yl)cyclopropane-1-carboxylic acid

According to a technique similar to that of Reference Example 54-3, a crude form of the title compound was obtained using trans-2-(4-phenyl-1H-imidazol-2-yl)cyclopropane-1-carboxylic acid ethyl ester (37 mg, 0.14 mmol) synthesized in Reference Example 72-2.

Reference Example 73-1

Trans-2-(1-benzyl-1H-imidazol-2-yl)cyclopropane-1-carboxylic acid ethyl ester

According to a technique similar to that of Reference Example 70-1, the title compound (colorless liquid, 91 mg, 77%) was obtained using ethyl trans-3-(1-benzyl-1H-imidazol-2-yl)acrylate (112 mg, 0.44 mmol).

$^1$H NMR (CDCl$_3$, 400 MHz): δ=1.23 (t, 3H, J=7 Hz), 1.4-1.7 (m, 2H), 2.0-2.1 (m, 1H), 2.3-2.4 (m, 1H), 4.0-4.2 (m, 2H), 5.16 (s, 2H), 6.86 (d, 1H, J=1 Hz), 6.92 (d, 1H, J=Hz), 7.08 (d, 2H, J=7 Hz), 7.2-7.4 (m, 3H).

Reference Example 73-2

Trans-2-(1-benzyl-1H-imidazol-2-yl)cyclopropane-1-carboxylic acid

According to a technique similar to that of Reference Example 54-3, a crude form of the title compound was obtained using trans-2-(1-benzyl-1H-imidazol-2-yl)cyclopropane-1-carboxylic acid ethyl ester (91 mg, 0.34 mmol) synthesized in Reference Example 73-1.

$^1$H NMR (CD$_3$OD, 400 MHz): δ=1.6-1.8 (m, 2H), 2.1-2.3 (m, 1H), 2.6-2.8 (m, 1H), 5.51 (s, 2H), 7.2-7.5 (m, 5H), 7.47 (d, 1H, J=2 Hz), 7.6-7.7 (m, 1H). 2H portion is not observable.

Reference Example 74-1

Trans-2-((tosyloxy)methyl)cyclopropane-1-carboxylic acid ethyl ester

Trans-2-(ethoxycarbonyl)cyclopropane-1-carboxylic acid (200 mg, 1.26 mmol) was dissolved in THF (4 mL), and then in an ice bath, a THF solution of a borane-THF complex (1.52 mL, 1.51 mmol, 1.0 M) was added to the solution. The mixture was stirred overnight at room temperature. Water was added to the reaction liquid, the mixture was stirred for a while, and then the mixture was extracted with ethyl acetate. The organic layer was dried over anhydrous sodium sulfate, insoluble matters were filtered, and then the solvent was distilled off under reduced pressure. A residue thus obtained was dissolved in dichloromethane (6 mL), and then DMAP (154 mg, 1.26 mmol), DIPEA (439 mL, 2.52 mmol), and tosyl chloride (480 mg, 2.52 mmol) were added to the solution. The mixture was stirred for 4 hours at room temperature. Water was added to the reaction liquid, and the mixture was stirred for a while. Subsequently, the mixture was extracted with ethyl acetate. The organic layer was dried over anhydrous sodium sulfate, insoluble matters were filtered, and then the solvent was distilled off under reduced pressure. A residue thus obtained was purified by silica gel column chromatography (hexane:ethyl acetate) (concentration gradient: 5% to 30%), and thus the title compound (colorless liquid, 121 mg, 32%) was obtained.

$^1$H NMR (CDCl$_3$, 400 MHz): δ=0.8-0.9 (m, 1H), 1.1-1.3 (m, 1H), 1.25 (t, 3H, J=7 Hz), 1.5-1.6 (m, 1H), 1.6-1.8 (m, 1H), 2.46 (s, 3H), 3.86 (dd, 1H, J=8, 11 Hz), 4.02 (dd, 1H, J=7.11 Hz), 4.0-4.2 (m, 2H), 7.3-7.4 (m, 2H), 7.7-7.9 (m, 2H).

Reference Example 74-2

Trans-2-((4-fluorophenoxy)methyl)cyclopropane-1-carboxylic acid ethyl ester

Trans-2-((tosyloxy)methyl)cyclopropane-1-carboxylic acid ethyl ester (84 mg, 0.28 mmol) synthesized in Reference Example 74-1 and para-fluorophenol (126 mg, 1.13 mmol) were dissolved in DMF (4 mL), and then cesium carbonate (551 mg, 1.69 mmol) was added to the solution. The mixture was stirred overnight at 80° C. Water was added to the reaction liquid, the mixture was stirred for a while, and then the mixture was extracted with ethyl acetate. The organic layer was dried over anhydrous sodium sulfate, insoluble matters were filtered, and then the solvent was distilled off under reduced pressure. A residue thus obtained was purified by silica gel column chromatography (hexane:ethyl acetate) (concentration gradient: 5% to 30%), and the title compound (colorless liquid, 46 mg, 69%) was obtained.

$^1$H NMR (CDCl$_3$, 400 MHz): δ=0.9-1.1 (m, 1H), 1.2-1.4 (m, 1H), 1.27 (t, 3H, J=7 Hz), 1.6-1.8 (m, 1H), 1.8-2.0 (m, 1H), 3.83 (dd, 1H, J=6, 10 Hz), 3.91 (dd, 1H, J=6, 10 Hz), 4.1-4.2 (m, 2H), 6.7-6.9 (m, 2H), 6.9-7.0 (m, 2H).

Reference Example 74-3

2-((4-Fluorophenoxy)methyl)cyclopropane-1-carboxylic acid lithium salt

According to a technique similar to that of Reference Example 68-2, a crude form of the title compound was obtained using trans-2-((4-fluorophenoxy)methyl)cyclopropane-1-carboxylic acid ethyl ester (46 mg, 0.19 mmol) synthesized in Reference Example 74-2.

$^1$H NMR (CD$_3$OD, 400 MHz): δ=0.7-0.8 (m, 1H), 1.0-1.2 (m, 1H), 1.4-1.6 (m, 1H), 1.6-1.8 (m, 1H), 3.78 (dd, 1H, J=7, 10 Hz), 3.88 (dd, 1H, J=6, 10 Hz), 6.8-6.9 (m, 2H), 6.9-7.1 (m, 2H). 1H portion is not observable.

Reference Example 75-1

Ethyl trans-2-((3-(trifluoromethyl)phenyl)carbamoyl)cyclopropane-1-carboxylate

According to a technique similar to that of Reference Example 9-1, the title compound (colorless liquid, 82 mg, 86%) was obtained using trans-2-(ethoxycarbonyl)cyclopropane-1-carboxylic acid (50 mg, 0.32 mmol) and 3-aminobenzotrifluoride (61 mg, 0.38 mmol).

$^1$H NMR (CDCl$_3$, 400 MHz): δ=1.29 (t, 3H, J=7 Hz), 1.4-1.5 (m, 1H), 1.5-1.7 (m, 1H), 2.0-2.2 (m, 1H), 2.2-2.4

(m, 1H), 4.18 (q, 2H, J=7 Hz), 7.37 (d, 1H, J=8 Hz), 7.44 (d, 1H, J=8 Hz), 7.6-7.8 (m, 2H), 7.84 (s, 1H).

Reference Example 75-2

Trans-2-((3-(trifluoromethyl)phenyl)carbamoyl)cyclopropane-1-carboxylic acid

According to a technique similar to that of Reference Example 54-3, a crude form (colorless liquid, 75 mg, 100%) of the title compound was obtained using ethyl trans-2-((3-(trifluoromethyl)phenyl)carbamoyl)cyclopropane-1-carboxylate (82 mg, 0.27 mmol) synthesized in Reference Example 75-1.
$^1$H NMR (CD$_3$OD, 400 MHz): δ=1.3-1.5 (m, 2H), 2.0-2.2 (m, 1H), 2.2-2.4 (m, 1H), 7.36 (d, 1H, J=8 Hz), 7.49 (t, 1H, J=8 Hz), 7.74 (d, 1H, J=8 Hz), 8.01 (s, 1H). 2H portion is not observable.

Reference Example 76-1

Trans-2-((3-(trifluoromethyl)phenoxy)methyl)cyclopropane-1-carboxylic acid ethyl ester According to a technique similar to that of Reference Example 74-2, the title compound (colorless liquid, 56 mg, 95%) was obtained using 3-hydroxybenzotrifluoride (132 mg, 0.82 mmol).
$^1$H NMR (CDCl$_3$, 400 MHz): δ=0.9-1.1 (m, 1H), 1.2-1.4 (m, 1H), 1.28 (t, 3H, J=7 Hz), 1.6-1.8 (m, 1H), 1.8-2.0 (m, 1H), 3.89 (dd, 1H, J=6, 10 Hz), 3.99 (dd, 1H, J=6, 10 Hz), 4.1-4.2 (m, 2H), 7.05 (d, 1H, J=8 Hz), 7.10 (s, 1H), 7.21 (d, 1H, J=8 Hz), 7.38 (t, 1H, J=8 Hz).

Reference Example 76-2

Trans-2-((3-(trifluoromethyl)phenoxy)methyl)cyclopropane-1-carboxylic acid

According to a technique similar to that of Reference Example 54-3, a crude form (colorless liquid, 49 mg, 96%) of the title compound was obtained using trans-2-((3-(trifluoromethyl)phenoxy)methyl)cyclopropane-1-carboxylic acid ethyl ester (56 mg, 0.19 mmol) synthesized in Reference Example 76-1.
$^1$H NMR (CD$_3$OD, 400 MHz): δ=0.9-1.2 (m, 1H), 1.3-1.5 (m, 1H), 1.7-1.8 (m, 1H), 1.8-2.1 (m, 1H), 3.8-4.1 (m, 2H), 7.05 (d, 1H, J=8 Hz), 7.10 (s, 1H), 7.21 (d, 1H, J=8 Hz), 7.38 (t, 1H, J=8 Hz). 1H portion is not observable.

Reference Example 77-1

(R)-1-(5-fluorobenzofuran-2-yl)ethan-1-amine hydrochloride

According to a technique similar to that of Reference Example 1-4, a crude form of the title compound was obtained using (R)—N—((R)-1-(5-fluorobenzofuran-2-yl)ethyl)-2-methylpropane-2-sulfinamide (50 mg, 0.18 mmol) synthesized in Reference Example 23-2.
$^1$H NMR (CDCl$_3$, 400 MHz): δ=0.58 (d, 1H, J=6 Hz), 3.47 (br s, 1H), 5.67 (s, 1H), 5.81 (td, 1H, J=2, 9 Hz), 5.98 (dd, 1H, J=2, 8 Hz), 6.19 (d, 1H, J=4, 9 Hz), 7.64 (br s, 3H).

Reference Example 77-2

(R)-3-(((R)-1-(5-fluorobenzofuran-2-yl)ethyl)carbamoyl)pyrrolidine-1-carboxylic acid tert-butyl ester According to a technique similar to that of Reference Example 9-1, the title compound (white amorphous material, 66 mg, 100%) was obtained using (R)-1-(5-fluorobenzofuran-2-yl)ethan-1-amine hydrochloride synthesized in Reference Example 77-1 and (R)-1-(tert-butoxycarbonyl)pyrrolidine-3-carboxylic acid (46 mg, 0.18 mmol).
$^1$H NMR (CDCl$_3$, 400 MHz): δ=1.44 (s, 9H), 1.57 (d, 3H, J=7 Hz), 2.0-2.2 (m, 2H), 2.8-2.9 (m, 1H), 3.3-2.7 (m, 3H), 5.35 (quint, 1H, J=7 Hz), 5.83 (d, 1H, J=8 Hz), 6.53 (s, 1H), 6.98 (td, 1H, J=3, 9 Hz), 6.98 (td, 1H, J=3, 9 Hz), 7.17 (dd, 1H, J=3, 8 Hz), 7.35 (dd, 1H, J=4, 9 Hz).

Reference Example 77-3

(R)—N—((R)-1-(5-fluorobenzofuran-2-yl)ethyl)pyrrolidine-3-carboxamide hydrochloride According to a technique similar to that of Reference Example 9-2, a crude form (white solid, 58 mg, 100%) of the title compound was obtained using (R)-3-(((R)-1-(5-fluorobenzofuran-2-yl)ethyl)carbamoyl)pyrrolidine-1-carboxylic acid tert-butyl ester (66 mg, 0.18 mmol) synthesized in Reference Example 77-2.
$^1$H NMR (CD$_3$OD, 400 MHz): δ=1.57 (d, 3H, J=7 Hz), 2.1-2.4 (m, 2H), 3.1-3.6 (m, 5H), 5.22 (q, 1H, J=7 Hz), 6.67 (s, 1H), 7.00 (td, 1H, J=3, 9 Hz), 7.24 (dd, 1H, J=3, 9 Hz), 7.40 (dd, 1H, J=4, 9 Hz) 0.3H Reference Example 78-1

(S)—N—((R)-1-(6-fluorobenzofuran-2-yl)ethyl)-N,2-dimethylpropane-2-sulfinamide

In a nitrogen atmosphere, (S)—N—((R)-1-(6-fluorobenzofuran-2-yl)ethyl)-2-methylpropane-2-sulfinamide (208 mg, 0.73 mmol) synthesized in Reference Example 27-3 was dissolved in DMF (3.5 mL), and the solution was stirred for a while at 0° C. Subsequently, sodium hydride (45 mg, 1.1 mmol, dispersed in 60% liquid paraffin) was added to the solution, and the mixture was stirred for 10 minutes. Next, methyl iodide (137 μL, 2.2 mmol) was added thereto, and the mixture was stirred for 80 minutes at room temperature. Subsequently, water was added to the reaction liquid, and the mixture was extracted with ethyl acetate. The organic layer was washed with saturated brine and was dried over anhydrous sodium sulfate. Insoluble matters were filtered, and then the solvent was distilled off under reduced pressure. A residue thus obtained was purified by silica gel column chromatography (hexane:ethyl acetate) (concentration gradient: 5% to 50%), and thus the title compound (pale yellow oily material, 215 mg, 99%) was obtained.
$^1$H NMR (CDCl$_3$, 400 MHz): δ=1.25 (s, 9H), 1.62 (d, 3H, J=7 Hz), 2.52 (s, 3H), 4.67 (q, 1H, J=7 Hz), 6.62 (s, 1H), 6.98 (ddd, 1H, J=2, 9, 10 Hz), 7.16 (dd, 1H, J=2, 9 Hz), 7.44 (dd, 1H, J=5, 9 Hz).

Reference Example 78-2

(R)-1-(6-fluorobenzofuran-2-yl)-N-methylethan-1-amine

According to a technique similar to that of Reference Example 2-2, the title compound (pale yellow oily material, 155 mg, 100%) was obtained using (S)—N—((R)-1-(6-fluorobenzofuran-2-yl)ethyl)-N,2-dimethylpropane-2-sulfinamide (215 mg, 0.72 mmol) synthesized in Reference Example 78-1.

$^1$H NMR (CDCl$_3$, 400 MHz): δ=1.49 (d, 3H, J=7 Hz), 2.39 (s, 3H), 3.86 (q, 1H, J=7 Hz), 6.51 (s, 1H), 6.96 (ddd, 1H, J=2, 9, 10 Hz), 7.16 (dd, 1H, J=2, 9 Hz), 7.42 (dd, 1H, J=5, 9 Hz) 0.1H portion is not observable.

Example 1

Trans-2-(1H-benzo[d]imidazol-2-yl)-N—((R)-1-(4-methyl-5-(2,2,2-trifluoroethoxy)thiophen-2-yl)ethyl)cyclopropane-1-carboxamide

[Chemical Formula 28]

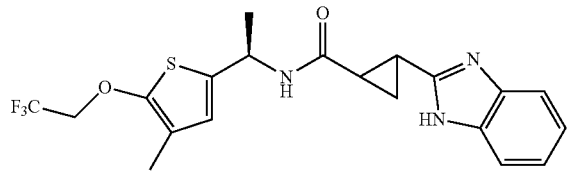

((R)-1-(4-methyl-5-(2,2,2-trifluoroethoxy)thiophen-2-yl)ethan-1-amine hydrochloride (65 mg, 0.24 mmol) synthesized in Reference Example 1-4, trans-2-(1H-benzo[d]imidazol-2-yl)cyclopropane-1-carboxylic acid (57 mg, 0.28 mmol), N,N-diisopropylethylamine (123 μL, 0.71 mmol), and HATU (126 mg, 0.33 mmol) were dissolved in DMF (2.4 mL), and the solution was stirred for 4 hours at room temperature. A saturated aqueous solution of sodium hydrogen carbonate and water were added to the reaction liquid, and the mixture was stirred for a while. Subsequently, the mixture was extracted with ethyl acetate. The organic layer was washed with saturated brine and was dried over anhydrous sodium sulfate. Insoluble matters were filtered, and then the solvent was distilled off under reduced pressure. A residue thus obtained was purified by silica gel column chromatography (hexane:ethyl acetate) (concentration gradient: 40% to 100%), and thus diastereomer A of the title compound (upper spot in TLC (ethyl acetate), white crystals, 33 mg, 33%) and diastereomer B of the title compound (lower spot in TLC (ethyl acetate), white crystals, 27 mg, 27%) were obtained.

Diastereomer A $^1$H NMR (DMSO-d$_6$, 400 MHz): δ=1.3-1.6 (m, 2H), 1.39 (d, 3H, J=7 Hz), 2.00 (s, 3H), 2.2-2.3 (m, 1H), 2.4-2.5 (m, 1H), 4.67 (q, 2H, J=9 Hz), 5.05 (quint, 1H, J=7 Hz), 6.54 (s, 1H), 7.0-7.2 (m, 2H), 7.3-7.5 (m, 2H), 8.75 (d, 1H, J=8 Hz), 12.39 (s, 1H).

MS: 424.13[M+H]$^+$

Diastereomer B $^1$H NMR (DMSO-d$_6$, 400 MHz): δ=1.3-1.5 (m, 2H), 1.40 (d, 3H, J=7 Hz), 1.97 (s, 3H), 2.2-2.3 (m, 1H), 2.4-2.5 (m, 1H), 4.64 (q, 2H, J=9 Hz), 5.05 (quint, 1H, J=7 Hz), 6.53 (s, 1H), 7.0-7.2 (m, 2H), 7.3-7.5 (m, 2H), 8.76 (d, 1H, J=9 Hz), 12.39 (s, 1H).

MS: 424.15[M+H]$^+$

Example 2

Trans-2-(1H-benzo[d]imidazol-2-yl)-N—((S)-1-(5-(2,2,2-trifluoroethoxy)thiophen-2-yl)ethyl)cyclopropane-1-carboxamide

[Chemical Formula 29]

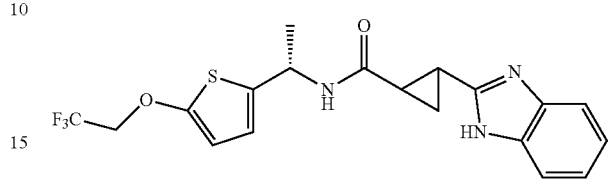

According to a technique similar to that of Example 1, diastereomer A of the title compound (upper spot in TLC (ethyl acetate), white powder, 17 mg, 15%) and diastereomer B of the title compound (lower spot in TLC (ethyl acetate), white powder, 5 mg, 4%) were obtained using (S)-1-(5-(2,2,2-trifluoroethoxy)thiophen-2-yl)ethan-1-amine (61 mg, 0.27 mmol) synthesized in Reference Example 2-2.

Diastereomer A $^1$H NMR (CDCl$_3$, 400 MHz): δ=1.53 (d, 3H, J=7 Hz), 1.6-1.8 (m, 2H), 2.3-2.4 (m, 1H), 2.6-2.8 (m, 1H), 4.34 (q, 2H, J=8 Hz), 5.25 (quint, 1H, J=7 Hz), 6.1-6.2 (m, 1H), 6.18 (d, 1H, J=4 Hz), 6.60 (dd, 1H, J=1, 4 Hz), 7.1-7.3 (m, 2H), 7.4-7.6 (m, 2H). 1H portion is not observable.

MS: 410.15[M+H]$^+$

Diastereomer B $^1$H NMR (CDCl$_3$, 400 MHz): δ=1.56 (d, 3H, J=7 Hz), 1.7-1.8 (m, 2H), 2.1-2.3 (m, 1H), 2.5-2.7 (m, 1H), 4.1-4.3 (m, 2H), 5.21 (quint, 1H, J=7 Hz), 5.97 (d, 1H, J=4 Hz), 6.21 (d, 1H, J=8 Hz), 6.47 (d, 1H, J=4 Hz), 7.2-7.2 (m, 2H), 7.4-7.6 (m, 2H) 0.1H portion is not observable.

MS: 410.13[M+H]$^+$

Example 3

Trans-2-(1H-benzo[d]imidazol-2-yl)-N—((R)-1-(5-(2,2,2-trifluoroethoxy)thiophen-2-yl)ethyl)cyclopropane-1-carboxamide

[Chemical Formula 30]

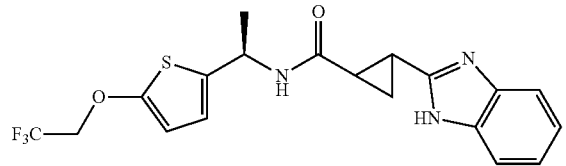

According to a technique similar to that of Example 1, diastereomer A of the title compound (upper spot in TLC (ethyl acetate), white powder, 20 mg, 16%) and diastereomer B of the title compound (lower spot in TLC (ethyl acetate), pale yellow powder, 32 mg, 25%) were obtained using (R)-1-(5-(2,2,2-trifluoroethoxy)thiophen-2-yl)ethan-1-amine (70 mg, 0.31 mmol) synthesized in Reference Example 3-2.

Diastereomer A

¹H NMR (CDCl₃, 400 MHz): δ=1.54 (d, 3H, J=7 Hz), 1.6-1.8 (m, 2H), 2.2-2.3 (m, 1H), 2.6-2.7 (m, 1H), 4.35 (q, 2H, J=8 Hz), 5.25 (quint, 1H, J=7 Hz), 6.04 (d, 1H, J=8 Hz), 6.19 (d, 1H, J=4 Hz), 6.61 (d, 1H, J=4 Hz), 7.2-7.3 (m, 2H), 7.4-7.6 (m, 2H). 1H portion is not observable.

MS: 410.13[M+H]⁺

Diastereomer B

¹H NMR (CDCl₃, 400 MHz): δ=1.56 (d, 3H, J=7 Hz), 1.7-1.8 (m, 2H), 2.1-2.3 (m, 1H), 2.5-2.7 (m, 1H), 4.1-4.3 (m, 2H), 5.20 (quint, 1H, J=7 Hz), 5.96 (d, 1H, J=4 Hz), 6.21 (d, 1H, J=8 Hz), 6.46 (d, 1H, J=4 Hz), 7.1-7.3 (m, 2H), 7.4-7.6 (m, 2H) 0.1H portion is not observable.

MS: 410.12[M+H]⁺

Example 4

Trans-2-(1-methyl-1H-benzo[d]imidazol-2-yl)-N—((R)-1-(5-(2,2,2-trifluoroethoxy)thiophen-2-yl)ethyl)cyclopropane-1-carboxamide

[Chemical Formula 31]

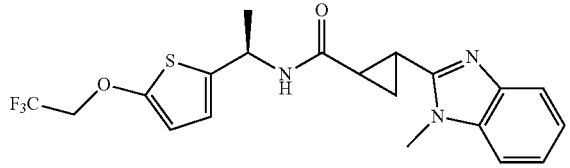

According to a technique similar to that of Example 1, diastereomer A of the title compound (upper spot in TLC (ethyl acetate), pale yellow crystals, 20 mg, 19%) and diastereomer B of the title compound (lower spot in TLC (ethyl acetate), yellow crystals, 24 mg, 23%) were obtained using ((R)-1-(5-(2,2,2-trifluoroethoxy)thiophen-2-yl)ethan-1-amine hydrochloride (65 mg, 0.25 mmol) synthesized in Reference Example 4 and trans-2-(1-methyl-1H-benzo[d]imidazol-2-yl)cyclopropane-1-carboxylic acid (64 mg, 0.30 mmol).

Diastereomer A

¹H NMR (CDCl₃, 400 MHz): δ=1.4-1.5 (m, 1H), 1.54 (d, 3H, J=7 Hz), 1.7-1.8 (m, 1H), 2.3-2.4 (m, 1H), 2.6-2.7 (m, 1H), 3.85 (s, 3H), 4.35 (q, 2H, J=8 Hz), 5.27 (quint, 1H, J=7 Hz), 6.09 (d, 1H, J=8 Hz), 6.20 (d, 1H, J=4 Hz), 6.61 (dd, 1H, J=1, 4 Hz), 7.2-7.4 (m, 3H), 7.6-7.7 (m, 1H).

MS: 424.13[M+H]⁺

Diastereomer B

¹H NMR (CDCl₃, 400 MHz): δ=1.5-1.6 (m, 1H), 1.56 (d, 3H, J=7 Hz), 1.7-1.8 (m, 1H), 2.3-2.4 (m, 1H), 2.6-2.7 (m, 1H), 3.85 (s, 3H), 4.32 (q, 2H, J=8 Hz), 5.26 (quint, 1H, J=7 Hz), 6.1-6.2 (m, 2H), 6.60 (dd, 1H, J=1, 4 Hz), 7.2-7.4 (m, 3H), 7.6-7.7 (m, 1H).

MS: 424.14[M+H]⁺

Example 5

Trans-2-(1H-benzo[d]imidazol-2-yl)-N—((R)-1-(5-(trifluoromethyl)thiophen-2-yl)ethyl)cyclopropane-1-carboxamide

[Chemical Formula 32]

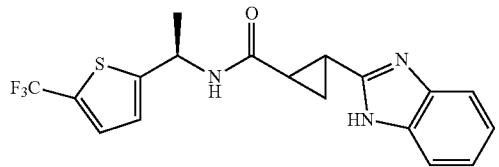

According to a technique similar to that of Example 1, diastereomer A of the title compound (upper spot in TLC (chloroform/methanol=20/1), white powder, 30 mg, 27%) and diastereomer B of the title compound (lower spot in TLC (chloroform/methanol=20/1), white powder, 32 mg, 28%) were obtained using (R)-1-(5-(trifluoromethyl)thiophen-2-yl)ethan-1-amine hydrochloride (70 mg, 0.30 mmol).

Diastereomer A

¹H NMR (CDCl₃, 400 MHz): δ=1.57 (d, 3H, J=7 Hz), 1.6-1.8 (m, 2H), 2.3-2.5 (m, 1H), 2.7-2.8 (m, 1H), 5.3-5.5 (m, 1H), 6.67 (d, 1H, J=8 Hz), 6.91 (d, 1H, J=4 Hz), 7.1-7.7 (m, 5H), 10.60 (br s, 1H).

MS: 380.12[M+H]⁺

Diastereomer B

¹H NMR (CDCl₃, 400 MHz): δ=1.6-1.8 (m, 2H), 1.62 (d, 3H, J=7 Hz), 2.2-2.4 (m, 1H), 2.6-2.7 (m, 1H), 5.3-5.5 (m, 1H), 6.37 (d, 1H, J=8 Hz), 6.87 (d, 1H, J=4 Hz), 7.1-7.3 (m, 3H), 7.3-7.7 (m, 2H), 9.89 (br s, 1H).

MS: 380.13[M+H]⁺

Example 6

Trans-2-(1H-benzo[d]imidazol-2-yl)-N—((R)-1-(5-bromothiophen-2-yl)ethyl)cyclopropane-1-carboxamide

[Chemical Formula 33]

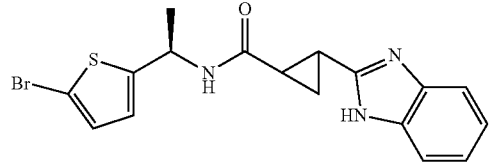

According to a technique similar to that of Example 1, diastereomer A of the title compound (upper spot in TLC (ethyl acetate), pale yellow crystals, 43 mg, 31%) and diastereomer B of the title compound (lower spot in TLC (ethyl acetate), pale yellow crystals, 40 mg, 29%) were obtained using (R)-1-(5-(bromothiophen-2-yl)ethan-1-amine hydrochloride (85 mg, 0.35 mmol).

Diastereomer A

¹H NMR (DMSO-d₆, 400 MHz): δ=1.4-1.6 (m, 2H), 1.43 (d, 3H, J=7 Hz), 2.2-2.3 (m, 1H), 2.4-2.5 (m, 1H), 5.12

(quint, 1H, J=7 Hz), 6.82 (dd, 1H, J=1, 4 Hz), 7.07 (d, 1H, J=4 Hz), 7.0-7.2 (m, 2H), 7.3-7.5 (m, 2H), 8.85 (d, 1H, J=8 Hz), 12.39 (s, 1H).
MS: 390.03[M+H]+
Diastereomer B
$^1$H NMR (DMSO-d$_6$, 400 MHz): δ=1.4-1.6 (m, 2H), 1.44 (d, 3H, J=7 Hz), 2.2-2.3 (m, 1H), 2.4-2.5 (m, 1H), 5.12 (quint, 1H, J=7 Hz), 6.8 (dd, 1H, J=1, 4 Hz), 7.04 (d, 1H, J=4 Hz), 7.0-7.2 (m, 2H), 7.3-7.5 (m, 2H), 8.85 (d, 1H, J=8 Hz), 12.39 (s, 1H).
MS: 390.03[M+H]+

Example 7

Trans-2-(1H-benzo[d]imidazol-2-yl)-N—((S)-1-(2-(2,2,2-trifluoroethoxy)thiazol-5-yl)ethyl)cyclopropane-1-carboxamide

[Chemical Formula 7]

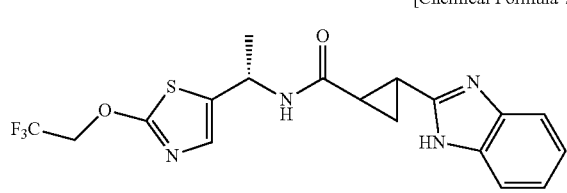

According to a technique similar to that of Example 1, diastereomer A of the title compound (upper spot in TLC (ethyl acetate), pale yellow powder, 9 mg, 21%) and diastereomer B of the title compound (lower spot in TLC (ethyl acetate), pale yellow powder, 8 mg, 19%) were obtained using (S)-1-(2-(2,2,2-trifluoroethoxy)thiazol-5-yl)ethan-1-amine (22 mg, 0.10 mmol) synthesized in Reference Example 5-2.
Diastereomer A
$^1$H NMR (CDCl$_3$, 400 MHz): δ=1.56 (d, 3H, J=7 Hz), 1.6-1.8 (m, 2H), 2.2-2.4 (m, 1H), 2.6-2.7 (m, 1H), 4.7-4.9 (m, 2H), 5.26 (quint, 1H, J=7 Hz), 6.28 (d, 1H, J=8 Hz), 6.99 (s, 1H), 7.2-7.3 (m, 2H), 7.4-7.7 (m, 2H) 0.1H portion is not observable.
MS: 411.13[M+H]+
Diastereomer B
$^1$H NMR (CDCl$_3$, 400 MHz): δ=1.58 (d, 3H, J=7 Hz), 1.6-1.8 (m, 2H), 2.2-2.3 (m, 1H), 2.5-2.7 (m, 1H), 4.6-4.8 (m, 2H), 5.24 (quint, 1H, J=7 Hz), 6.32 (d, 1H, J=8 Hz), 6.90 (s, 1H), 7.1-7.3 (m, 2H), 7.3-7.7 (m, 2H), 9.89 (br s, 1H).
MS: 411.13[M+H]+

Example 8

Trans-2-(1H-benzo[d]imidazol-2-yl)-N—((R)-1-(2-(2,2,2-trifluoroethoxy)thiazol-5-yl)ethyl)cyclopropane-1-carboxamide

[Chemical Formula 35]

According to a technique similar to that of Example 1, diastereomer A of the title compound (upper spot in TLC (ethyl acetate), white powder, 5 mg, 17%) and diastereomer B of the title compound (lower spot in TLC (ethyl acetate), white powder, 40 mg, 15%) were obtained using (R)-1-(2-(2,2,2-trifluoroethoxy)thiazol-5-yl)ethan-1-amine (14 mg, 0.07 mmol) synthesized in Reference Example 6-2.
Diastereomer A
$^1$H NMR (CDCl$_3$, 400 MHz): δ=1.56 (d, 3H, J=7 Hz), 1.6-1.8 (m, 2H), 2.2-2.4 (m, 1H), 2.6-2.7 (m, 1H), 4.7-4.9 (m, 2H), 5.2-5.3 (m, 1H), 6.15 (d, 1H, J=8 Hz), 6.99 (d, 1H, J=Hz), 7.2-7.3 (m, 2H), 7.3-7.7 (m, 2H), 9.49 (br s, 1H).
MS: 411.13[M+H]+
Diastereomer B
$^1$H NMR (CDCl$_3$, 400 MHz): δ=1.58 (d, 3H, J=7 Hz), 1.6-1.8 (m, 2H), 2.2-2.4 (m, 1H), 2.5-2.7 (m, 1H), 4.6-4.8 (m, 2H), 5.2-5.3 (m, 1H), 6.29 (d, 1H, J=8 Hz), 6.92 (d, 1H, J=1 Hz), 7.2-7.3 (m, 2H), 7.4-7.6 (m, 2H). 1H portion is not observable.
MS: 411.12[M+H]+

Example 9

Trans-2-(1H-benzo[d]imidazol-2-yl)-N—((R)-1-(5-(3,3,3-trifluoropropyl)-1H-pyrazol-4-yl)ethyl)cyclopropane-1-carboxamide

[Chemical Formula 36]

According to a technique similar to that of Example 1, a diastereomer mixture of the title compound (white powder, 31 mg, 51%) was obtained using (R)-1-(1-(3,3,3-trifluoropropyl)-1H-pyrazol-4-yl)ethan-1-amine hydrochloride (38 mg, 0.15 mmol) synthesized in Reference Example 7-3.
Diastereomer mixture (1:1)
$^1$H NMR (CDCl$_3$, 400 MHz): δ=1.46 (d, 1.5H, J=7 Hz), 1.51 (d, 1.5H, J=7 Hz), 1.6-1.8 (m, 2H), 2.2-2.4 (m, 1H), 2.4-2.6 (m, 1H), 2.6-2.8 (m, 2H), 4.0-4.2 (m, 1H), 4.30 (t, 1H, J=7 Hz), 5.0-5.2 (m, 1H), 6.37 (d, 0.5H, J=8 Hz), 6.49 (d, 0.5H, J=7 Hz), 7.1-7.8 (m, 6H), 11.09 (br s, 1H).
MS: 392.18[M+H]+

Example 10

Trans-3-(1-(2-(1H-benzo[d]imidazol-2-yl)cyclopropanecarboxamido)ethyl)-1H-indole-1-carboxylic acid tert-butyl ester

[Chemical Formula 37]

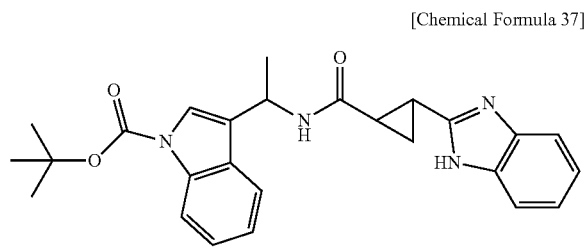 [SMILES: CC(NC(=O)C1CC1c1nc2ccccc2[nH]1)c1cn(C(=O)OC(C)(C)C)c2ccccc12]

According to a technique similar to that of Example 1, the title compound (Rf value=0.5 in TLC (ethyl acetate/hexane=1/1), pale yellow amorphous material, 5 mg, 25%) was obtained using 3-(1-aminoethyl)-1H-indole-1-carboxylic acid tert-butyl ester (7 mg, 0.05 mmol) synthesized in Reference Example 8-2.

$^1$H NMR (CDCl$_3$, 400 MHz): δ=1.5-1.8 (m, 5H), 1.68 (s, 9H), 2.2-2.3 (m, 1H), 2.6-2.8 (m, 1H), 5.4-5.6 (m, 1H), 6.14 (d, 1H, J=8 Hz), 7.1-7.7 (m, 4H), 7.26 (t, 1H, J=7 Hz), 7.35 (t, 1H, J=7 Hz), 7.53 (s, 1H), 7.60 (d, 1H, J=8 Hz), 8.14 (d, 1H, J=7 Hz), 9.81 (br s, 1H).

MS: 445.26[M+H]$^+$

Example 11

Trans-2-(1H-benzo[d]imidazol-2-yl)-N—((R)-1-(5-bromothiazol-2-yl)ethyl)cyclopropane-1-carboxamide

[Chemical Formula 38]

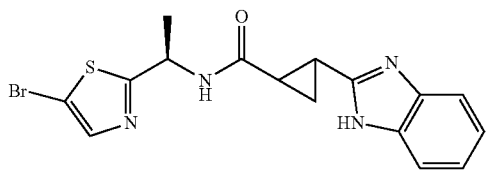

According to a technique similar to that of Example 1, diastereomer A of the title compound (upper spot in TLC (ethyl acetate), white crystals, 12 mg, 15%) and diastereomer B of the title compound (lower spot in TLC (ethyl acetate), pale yellow crystals, 3.6 mg, 5%) were obtained using (R)-1-(5-(bromothiazol-2-yl)ethan-1-amine hydrochloride (50 mg, 0.21 mmol).

Diastereomer A $^1$H NMR (DMSO-d$_6$, 400 MHz): δ=1.48 (d, 3H, J=7 Hz), 1.5-1.6 (m, 2H), 2.3-2.4 (m, 1H), 2.4-2.6 (m, 1H), 5.12 (quint, 1H, J=7 Hz), 7.1-7.2 (m, 2H), 7.44 (br s, 2H), 7.80 (s, 1H), 9.11 (d, 1H, J=8 Hz) 0.1H portion is not observable.

MS: 391.05[M+H]$^+$

Diastereomer B $^1$H NMR (DMSO-d$_6$, 400 MHz): δ=1.49 (d, 3H, J=7 Hz), 1.5-1.6 (m, 2H), 2.3-2.4 (m, 1H), 2.4-2.6 (m, 1H), 5.15 (quint, 1H, J=7 Hz), 7.0-7.2 (m, 2H), 7.4-7.6 (m, 2H), 7.78 (s, 1H), 9.12 (d, 1H, J=7 Hz), 12.43 (br s, 1H).

MS: 391.04[M+H]$^+$

Example 12

(R)-1H-benzo[d]imidazol-2-yl)-N—((R)-1-(5-(2,2,2-trifluoroethoxy)thiophen-2-yl)ethyl)pyrrolidine-3-carboxamide

[Chemical Formula 39]

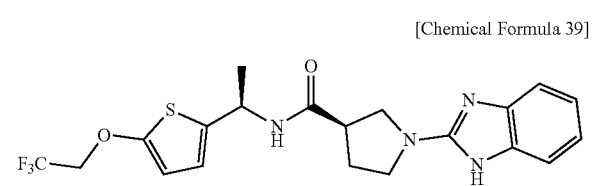 [SMILES: C[C@@H](NC(=O)[C@@H]1CCN(c2nc3ccccc3[nH]2)C1)c1ccc(OCC(F)(F)F)s1]

(R)—N—((R)-1-(5-(2,2,2-trifluoroethoxy)thiophen-2-yl)ethyl)pyrrolidine-3-carboxamide hydrochloride (20 mg, 0.056 mmol) synthesized in Reference Example 9-2 and 2-chloro-1H-benzo[d]imidazole (10 mg, 0.067 mmol) were dissolved in DME (1 mL), and N,N-diisopropylethylamine (19 L, 0.11 mmol) was added to the solution. The mixture was heated to reflux for one day at 120° C. After completion of the reaction, water was added to the mixture, and the mixture was extracted with ethyl acetate. The organic layer was washed with saturated brine and was dried over anhydrous sodium sulfate. Insoluble matters were filtered, and then the solvent was distilled off under reduced pressure. A residue thus obtained was purified by silica gel column chromatography (ethyl acetate:methanol) (concentration gradient: 0% to 20%), and thus the title compound (brown powder, 11 mg, 46%) was obtained.

$^1$H NMR (CD$_3$OD, 400 MHz): δ=1.52 (d, 3H, J=6 Hz), 2.2-2.3 (m, 2H), 3.1-3.2 (m, 1H), 3.5-3.8 (m, 4H), 4.51 (q, 2H, J=9 Hz), 5.1-5.2 (m, 1H), 6.25 (d, 1H, J=4 Hz), 6.62 (d, 1H, J=3 Hz), 6.9-7.0 (m, 2H), 7.2-7.3 (m, 2H). 2H portion is not observable.

MS: 439.16[M+H]$^+$

Example 13

(R)-1-(benzo[d]thiazol-2-yl)-N—((R)-1-(5-(2,2,2-trifluoroethoxy)thiophen-2-yl)ethyl)pyrrolidine-3-carboxamide

[Chemical Formula 40]

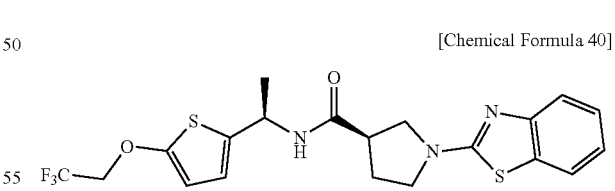

According to a technique similar to that of Example 12, the title compound (pale yellow amorphous material, 15 mg, 60%) was obtained using (R)—N—((R)-1-(5-(2,2,2-trifluoroethoxy)thiophen-2-yl)ethyl)pyrrolidine-3-carboxamide hydrochloride (20 mg, 0.056 mmol) synthesized in Reference Example 9-2 and 2-chloro-1H-benzo[d]thiazole (11 mg, 0.067 mmol).

$^1$H NMR (CD$_3$OD, 400 MHz): δ=1.54 (d, 3H, J=7 Hz), 2.2-2.5 (m, 2H), 3.0-3.1 (m, 1H), 3.5-3.7 (m, 1H), 3.7-3.9 (m, 3H), 4.33 (q, 2H, J=8 Hz), 5.23 (quint, 1H, J=8 Hz), 5.80

(d, 1H, J=8 Hz), 6.17 (d, 1H, J=4 Hz), 6.58 (dd, 1H, J=1, 4 Hz), 7.0-7.1 (m, 1H), 7.2-7.3 (m, 1H), 7.5-7.6 (m, 2H).

MS: 456.12[M+H]$^+$

Example 14

(S)-1-(2-(tert-butylamino)-2-oxoethyl)-N—((R)-1-(5-(2,2,2-trifluoroethoxy)thiophen-2-yl)ethyl)pyrrolidine-3-carboxamide hydrochloride

[Chemical Formula 41]

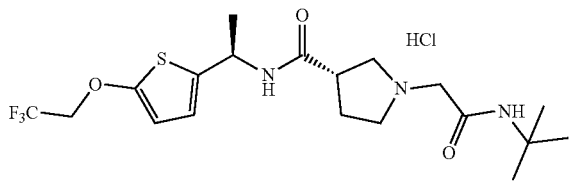

(S)—N—((R)-1-(5-(2,2,2-trifluoroethoxy)thiophen-2-yl)ethyl)pyrrolidine-3-carboxamide hydrochloride (45 mg, 0.13 mmol) synthesized in Reference Example 10-2, N-(tert-butyl)-2-chloroacetamide (23 mg, 0.15 mmol), potassium carbonate (71 mg, 0.51 mmol), and potassium iodide (64 mg, 0.39 mmol) were suspended in acetonitrile (1.3 mL), and the suspension liquid was stirred for one day at room temperature. DMF (0.5 mL) was added to the suspension liquid, and the mixture was stirred for another one hour. Subsequently, water was added to the reaction liquid, and the mixture was extracted with ethyl acetate. The organic layer was washed with saturated brine and was dried over anhydrous sodium sulfate. Insoluble matters were filtered, and then the solvent was distilled off under reduced pressure. A residue thus obtained was purified by silica gel column chromatography (hexane:ethyl acetate) (concentration gradient: 30% to 80%), and an oily material was obtained. The oily material thus obtained was dissolved in methanol, 2 N hydrochloric acid-methanol (110 L) was added thereto, and the mixture was stirred for a while. The reaction liquid was concentrated under reduced pressure, and diethyl ether was added to the residue to obtain a suspension liquid. The suspension liquid was filtered, and crystals thus obtained were dried. Thus, the title compound (pale yellow crystals, 42 mg, 71%) was obtained.

$^1$H NMR (CDCl$_3$, 400 MHz): δ=1.39 (s, 9H), 1.54 (d, 3H, J=7 Hz), 2.2-2.5 (m, 2H), 3.1-4.2 (m, 7H), 4.33 (q, 2H, J=8 Hz), 5.1-5.2 (m, 1H), 6.16 (d, 1H, J=4 Hz), 6.58 (d, 1H, J=4 Hz), 6.73 (d, 1H, J=7 Hz), 7.68 (s, 1H), 12.39 (br s, 1H).

MS: 434.20[M−H]$^-$

Example 15

(R)-1-(2-(tert-butylamino)-2-oxoethyl)-N—((R)-1-(5-(2,2,2-trifluoroethoxy)thiophen-2-yl)ethyl)pyrrolidine-3-carboxamide hydrochloride

[Chemical Formula 42]

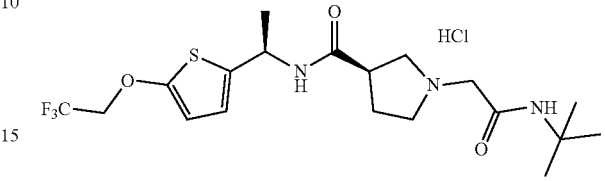

According to a technique similar to that of Example 14, the title compound (pale yellow crystals, 31 mg, 62%) was obtained using (R)—N—((R)-1-(5-(2,2,2-trifluoroethoxy)thiophen-2-yl)ethyl)pyrrolidine-3-carboxamide hydrochloride (38 mg, 0.11 mmol) synthesized in Reference Example 9-2.

$^1$H NMR (CDCl$_3$, 400 MHz): δ=1.39 (s, 9H), 1.55 (d, 3H, J=6 Hz), 2.3-2.5 (m, 2H), 3.2-3.9 (m, 7H), 4.34 (q, 2H, J=8 Hz), 5.0-5.3 (m, 1H), 6.17 (d, 1H, J=4 Hz), 6.59 (d, 1H, J=3 Hz), 6.80 (br s, 1H), 7.65 (br s, 1H), 12.36 (br s, 1H).

MS: 434.19[M−H]$^-$

Example 16

(R)-1-(2-oxoethyl-2-(thiazol-2-ylamino)ethyl)-N—((R)-1-(5-(2,2,2-trifluoroethoxy)thiophen-2-yl)ethyl)pyrrolidine-3-carboxamide

[Chemical Formula 43]

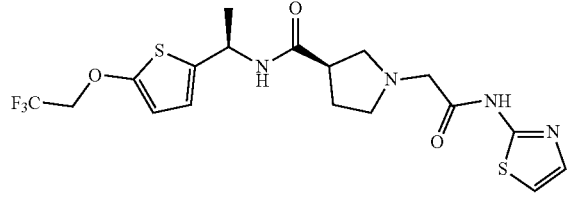

(R)—N—((R)-1-(5-(2,2,2-trifluoroethoxy)thiophen-2-yl)ethyl)pyrrolidine-3-carboxamide hydrochloride (45 mg, 0.13 mmol) synthesized in Reference Example 9-2, 2-chloro-N-(thiazol-2-yl)-2-acetamide (27 mg, 0.15 mmol), potassium carbonate (69 mg, 0.50 mmol), and potassium iodide (62 mg, 0.37 mmol) were dissolved in acetonitrile (1.3 mL), and the solution was stirred for three days at room temperature. Water was added to the reaction liquid, and the mixture was extracted with ethyl acetate. The organic layer was washed with saturated brine and was dried over anhydrous sodium sulfate. Insoluble matters were filtered, and then the solvent was distilled off under reduced pressure. A residue thus obtained was purified by silica gel column chromatography (hexane:ethyl acetate) (concentration gradient: 60% to 100%), and thus the title compound (white crystals, 37 mg, 77%) was obtained.

$^1$H NMR (CDCl$_3$, 400 MHz): δ=1.55 (d, 3H, J=7 Hz), 2.15 (q, 2H, J=7 Hz), 2.8-3.0 (m, 5H), 3.41 (d, 1H, J=17 Hz), 3.47 (d, 1H, J=17 Hz), 4.32 (q, 2H, J=8 Hz), 5.2-5.3 (m, 1H), 5.77 (d, 1H, J=9 Hz), 6.16 (d, 1H, J=4 Hz), 6.59 (dd, 1H, J=1, 4 Hz), 6.99 (d, 1H, J=4 Hz), 7.46 (d, 1H, J=4 Hz), 10.44 (br s, 1H).

MS: 463.13[M+H]$^+$

Example 17

(R)-1-(2-oxoethyl-2-(phenylamino)ethyl)-N—((R)-1-(5-(2,2,2-trifluoroethoxy)thiophen-2-yl)ethyl)pyrrolidine-3-carboxamide hydrochloride

[Chemical Formula 44]

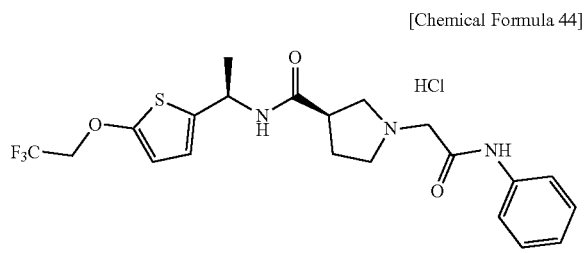 [SMILES: C[C@@H](NC(=O)[C@@H]1CCN(CC(=O)Nc2ccccc2)C1)c1ccc(OCC(F)(F)F)s1 ; Cl]

According to a technique similar to that of Example 14, the title compound (pale yellow crystals, 37 mg, 67%) was obtained using (R)—N—((R)-1-(5-(2,2,2-trifluoroethoxy)thiophen-2-yl)ethyl)pyrrolidine-3-carboxamide hydrochloride (40 mg, 0.11 mmol) synthesized in Reference Example 9-2 and 2-chloro-N-phenylacetamide (23 mg, 0.14 mmol).

$^1$H NMR (DMSO-d$_6$, 400 MHz): δ=1.42 (d, 3H, J=7 Hz), 1.9-2.4 (m, 2H), 2.9-4.0 (m, 5H), 4.1-4.4 (m, 2H), 4.78 (q, 2H, J=9 Hz), 5.01 (quint, 1H, J=7 Hz), 6.35 (d, 1H, J=4 Hz), 6.62 (dd, 1H, J=1, 4 Hz), 7.12 (t, 1H, J=7 Hz), 7.36 (t, 2H, J=7 Hz), 7.61 (d, 2H, J=7 Hz), 10.50 (br s, 1H), 10.73 (s, 1H).

MS: 456.14[M+H]$^+$

Example 18

(R)-1-(3,3-dimethylbutyl)-N—((R)-1-(5-(2,2,2-trifluoroethoxy)thiophen-2-yl)ethyl)pyrrolidine-3-carboxamide hydrochloride

[Chemical Formula 45]

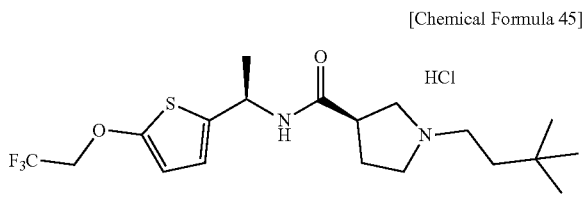 [SMILES: C[C@@H](NC(=O)[C@@H]1CCN(CCC(C)(C)C)C1)c1ccc(OCC(F)(F)F)s1 ; Cl]

(R)—N—((R)-1-(5-(2,2,2-trifluoroethoxy)thiophen-2-yl)ethyl)pyrrolidine-3-carboxamide hydrochloride (45 mg, 0.13 mmol) synthesized in Reference Example 9-2, 3,3-dimethylbutanal (23 mg, 0.15 mmol), and N,N-diisopropylamine (64 mg, 0.39 mmol) were dissolved in chloroform (1.3 mL), and the solution was stirred for a while. Subsequently, sodium triacetoxyborohydride (23 mg, 0.15 mmol) was added to the solution, and the mixture was stirred for three days at room temperature. A saturated aqueous solution of sodium hydrogen carbonate was added to the reaction liquid, and the mixture was extracted with ethyl acetate. The organic layer was washed with saturated brine and was dried over anhydrous sodium sulfate. Insoluble matters were filtered, and then the solvent was distilled off under reduced pressure. A residue thus obtained was purified by silica gel column chromatography (hexane:ethyl acetate) (concentration gradient: 80% to 100%), and a colorless oily material was obtained. The oily material thus obtained was dissolved in methanol, 2 N hydrochloric acid-methanol was added to the solution, and the mixture was stirred for a while. The reaction liquid was concentrated under reduced pressure, and diethyl ether was added to the concentrate to obtain a suspension liquid. The suspension liquid was filtered, and crystals thus obtained were dried. Thus, the title compound (pale yellow crystals, 27 mg, 87%) was obtained.

$^1$H NMR (CDCl$_3$, 400 MHz): δ=0.95 (s, 9H), 1.56 (d, 3H, J=6 Hz), 1.7-1.8 (m, 2H), 2.1-2.7 (m, 2H), 2.9-3.3 (m, 4H), 3.3-3.6 (m, 1H), 3.6-4.0 (m, 2H), 4.33 (q, 2H, J=8 Hz), 5.0-5.3 (m, 1H), 6.16 (d, 1H, J=3 Hz), 6.60 (d, 1H, J=3 Hz), 7.10 (br s, 1H), 12.00 (br s, 1H).

MS: 407.25[M+H]$^+$

Example 19

2-(3,5-Difluorophenyl)-N—((R)-1-(5-(2,2,2-trifluoroethoxy)thiophen-2-yl)ethyl)cyclopropane-1-carboxamide

[Chemical Formula 46]

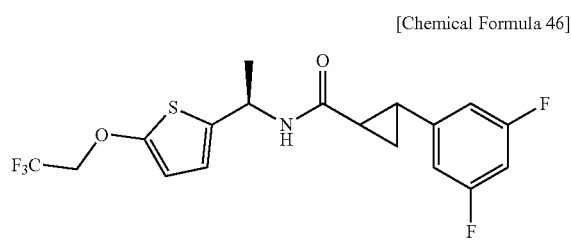 [SMILES: C[C@@H](NC(=O)C1CC1c1cc(F)cc(F)c1)c1ccc(OCC(F)(F)F)s1]

According to a technique similar to that of Example 1, diastereomer A of the title compound (upper spot in TLC (hexane/ethyl acetate=1/1), white crystals, 38 mg, 38%) and diastereomer B of the title compound (lower spot in TLC (hexane/ethyl acetate=1/1), white crystals, 18 mg, 25%) were obtained using (R)-1-(5-(2,2,2-trifluoroethoxy)thiophen-2-yl)ethan-1-amine hydrochloride (65 mg, 0.25 mmol) synthesized in Reference Example 4 and trans-2-(3,5-difluorophenyl)cyclopropane-1-carboxylic acid (74 mg, 0.37 mmol).

Diastereomer A $^1$H NMR (DMSO-d$_6$, 400 MHz): δ=1.2-1.4 (m, 2H), 1.39 (d, 3H, J=7 Hz), 1.8-2.0 (m, 1H), 2.3-2.4 (m, 1H), 4.78 (q, 2H, J=9 Hz), 5.03 (quint, 1H, J=7 Hz), 6.35 (d, 1H, J=4 Hz), 6.60 (dd, 1H, J=1, 4 Hz), 6.9-7.1 (m, 3H), 8.62 (d, 1H, J=Hz).

MS: 404.16[M–H]$^-$

Diastereomer B $^1$H NMR (DMSO-d$_6$, 400 MHz): δ=1.2-1.5 (m, 2H), 1.40 (d, 3H, J=7 Hz), 1.9-2.0 (m, 1H), 2.3-2.4 (m, 1H), 4.76 (q, 2H, J=9 Hz), 5.02 (quint, 1H, J=7 Hz), 6.34 (d, 1H, J=4 Hz), 6.59 (dd, 1H, J=1, 4 Hz), 6.8-7.1 (m, 3H), 8.61 (d, 1H, J=8 Hz).

MS: 404.16[M–H]$^-$

Example 20

Trans-2-(1-methyl-1H-imidazol-2-yl)-N—((R)-1-(5-(2,2,2-trifluoroethoxy)thiophen-2-yl)ethyl)cyclopropane-1-carboxamide

[Chemical Formula 47]

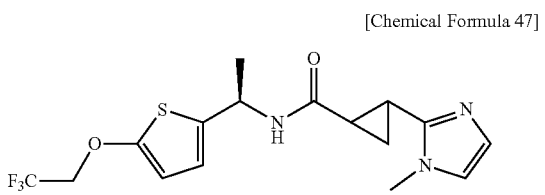 [SMILES: C[C@@H](NC(=O)C1CC1c1nccn1C)c1ccc(OCC(F)(F)F)s1]

According to a technique similar to that of Example 1, a diastereomer mixture of the title compound (pale yellow solid, 43 mg, 65%) was obtained using (R)-1-(5-(2,2,2-trifluoroethoxy)thiophen-2-yl)ethan-1-amine hydrochloride (47 mg, 0.18 mmol) synthesized in Reference Example 4 and a crude form of trans-2-(1-methyl-1H-imidazol-2-yl)cyclopropane-1-carboxylic acid (0.18 mmol) synthesized in Reference Example 70-2.

Diastereomer mixture (1:1)
$^1$H NMR (CDCl$_3$, 400 MHz): δ=1.2-1.4 (m, 1H), 1.5-1.7 (m, 1H), 1.53 (d, 1.5H, J=7 Hz), 1.54 (d, 1.5H, J=6 Hz), 2.0-2.2 (m, 1H), 2.3-2.5 (m, 1H), 3.66 (s, 1.5H), 3.68 (s, 1.5H), 4.2-4.4 (m, 2H), 5.2-5.3 (m, 1H), 6.1-6.3 (m, 2H), 6.5-6.5 (m, 1H), 6.7-6.9 (m, 2H).
MS: 374.13[M+H]$^+$

Example 21

Trans-2-(1H-indol-3-yl)-N—((R)-1-(5-(2,2,2-trifluoroethoxy)thiophen-2-yl)ethyl)cyclopropane-1-carboxamide

[Chemical Formula 48]

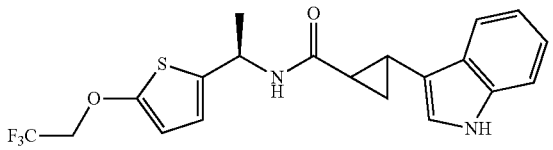

According to a technique similar to that of Example 1, diastereomer A of the title compound (upper spot in TLC (hexane/ethyl acetate=1/1), white crystals, 14 mg, 32%) and diastereomer B of the title compound (lower spot in TLC (hexane/ethyl acetate=1/1, pale yellow crystals, 12 mg, 32%) were obtained using (R)-1-(5-(2,2,2-trifluoroethoxy)thiophen-2-yl)ethan-1-amine hydrochloride (36 mg, 0.14 mmol) synthesized in Reference Example 4 and trans-2-(1H-indol-3-yl)cyclopropane-1-carboxylic acid (33 mg, 0.16 mmol).

Diastereomer A
$^1$H NMR (CDCl$_3$, 400 MHz): δ=1.2-1.4 (m, 1H), 1.5-1.7 (m, 5H), 2.6-2.7 (m, 1H), 4.34 (q, 2H, J=8 Hz), 5.2-5.4 (m, 1H), 5.81 (d, 1H, J=8 Hz), 6.19 (d, 1H, J=4 Hz), 6.61 (dd, 1H, J=1, 4 Hz), 6.94 (d, 1H, J=2 Hz), 7.14 (dt, 1H, J=1, 8 Hz), 7.22 (dt, 1H, J=1, 8 Hz), 7.36 (d, 1H, J=8 Hz), 7.66 (d, 1H, J=7 Hz), 7.94 (br s, 1H).
MS: 431.13[M+Na]$^+$ Diastereomer B
$^1$H NMR (CDCl$_3$, 400 MHz): δ=1.2-1.4 (m, 1H), 1.5-1.7 (m, 2H), 1.55 (d, 3H, J=7 Hz), 2.5-2.7 (m, 1H), 4.34 (q, 2H, J=8 Hz), 5.2-5.4 (m, 1H), 5.84 (d, 1H, J=8 Hz), 6.20 (d, 1H, J=4 Hz), 6.61 (dd, 1H, J=1, 4 Hz), 6.92 (d, 1H, J=2 Hz), 7.0-7.3 (m, 2H), 7.35 (d, 1H, J=8 Hz), 7, 6 Hz), 7.97 (br s, 1H).
MS: 431.13[M+Na]$^+$

Example 22

Trans-2-(1-methyl-1H-indazol-6-yl)-N—((R)-1-(5-(2,2,2-trifluoroethoxy)thiophen-2-yl)ethyl)cyclopropanecarboxamide

[Chemical Formula 49]

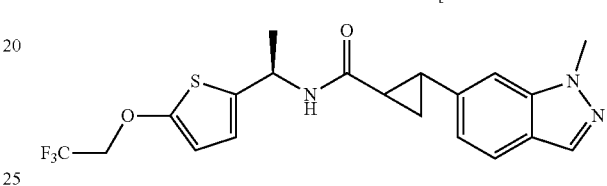

According to a technique similar to that of Example 1, diastereomer A of the title compound (Rf value=0.3 in TLC (ethyl acetate/hexane=1/1), white solid, 2 mg, 4%) was obtained using (R)-1-(5-(2,2,2-trifluoroethoxy)thiophen-2-yl)ethan-1-amine hydrochloride (40 mg, 0.14 mmol) synthesized in Reference Example 4 and trans-2-(1-methyl-1H-indazol-6-yl)cyclopropane-1-carboxylic acid (31 mg, 0.14 mmol).

Diastereomer A
$^1$H NMR (CDCl$_3$, 400 MHz): δ=1.3-1.4 (m, 1H), 1.5-1.8 (m, 5H), 2.6-2.7 (m, 1H), 4.04 (s, 3H), 4.34 (q, 2H, J=8 Hz), 5.29 (quint, 1H, J=7 Hz), 5.81 (d, 1H, J=8 Hz), 6.19 (d, 1H, J=4 Hz), 6.61 (d, 1H, J=4 Hz), 6.84 (d, 1H, J=9 Hz), 7.13 (s, 1H), 7.62 (d, 1H, J=9 Hz), 7.91 (s, 1H).
MS: 424.16[M+H]$^+$

Example 23

Trans-2-(pyridin-2-yl)-N—((R)-1-(5-(2,2,2-trifluoroethoxy)thiophen-2-yl)ethyl)cyclopropane-1-carboxamide

[Chemical Formula 50]

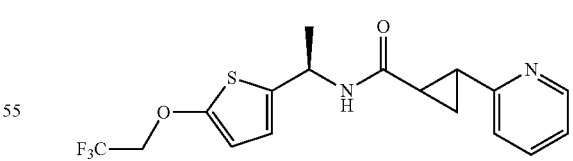

According to a technique similar to that of Example 1, diastereomer A of the title compound (upper spot in TLC (ethyl acetate/hexane=1/1), white solid, 14 mg, 13%) and diastereomer B of the title compound (lower spot in TLC (ethyl acetate/hexane=1/1), white solid, 12 mg, 10%) were obtained using (R)-1-(5-(2,2,2-trifluoroethoxy)thiophen-2-yl)ethan-1-amine hydrochloride (80 mg, 0.31 mmol) synthesized in Reference Example 4 and trans-2-(pyridin-2-yl)cyclopropane-1-carboxylic acid (50 mg, 0.31 mmol).

Diastereomer A

¹H NMR (CDCl₃, 400 MHz): δ=1.4-1.7 (m, 2H), 1.52 (d, 3H, J=7 Hz), 2.0-2.1 (m, 1H), 2.5-2.7 (m, 1H), 4.34 (q, 2H, J=8 Hz), 5.2-5.3 (m, 1H), 5.83 (d, 1H, J=8 Hz), 6.18 (d, 1H, J=4 Hz), 6.58 (dd, 1H, J=1, 4 Hz), 7.08 (ddd, 1H, J=2, 5, 8 Hz), 7.2-7.3 (m, 1H), 7.56 (dt, 1H, J=2, 8 Hz), 8.4-8.5 (m, 1H).

MS: 371.12[M+H]⁺

Diastereomer B

¹H NMR (CDCl₃, 400 MHz): δ=1.4-1.7 (m, 5H), 1.9-2.1 (m, 1H), 2.5-2.7 (m, 1H), 4.32 (q, 2H, J=8 Hz), 5.26 (quint, 1H, J=7 Hz), 5.82 (d, 1H, J=8 Hz), 6.16 (d, 1H, J=4 Hz), 6.58 (dd, 1H, J=1, 4 Hz), 7.07 (ddd, 1H, J=2, 5, 8 Hz), 7.2-7.3 (m, 1H), 7.55 (dt, 1H, J=2, 8 Hz), 8.4-8.5 (m, 1H).

MS: 371.13[M+H]⁺

Example 24

(3R)-1-(1-oxo-1-(phenylamino)propan-2-yl)-N—((R)-1-(5-(2,2,2-trifluoroethoxy)thiophen-2-yl)ethyl)pyrrolidine-3-carboxamide

[Chemical Formula 51]

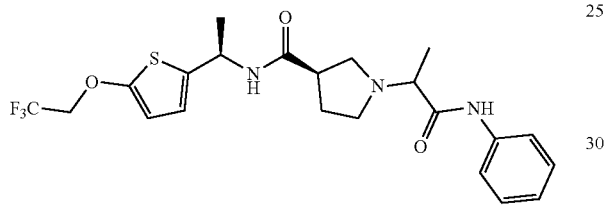

According to a technique similar to that of Example 14, the title compound (colorless oily material, 6 mg, 23%) was obtained using (R)—N—((R)-1-(5-(2,2,2-trifluoroethoxy)thiophen-2-yl)ethyl)pyrrolidine-3-carboxamide hydrochloride (20 mg, 0.056 mmol) synthesized in Reference Example 9-2 and 2-bromo-N-phenylpropanamide (15 mg, 0.067 mmol).

¹H NMR (CDCl₃, 400 MHz): δ=1.36 (d, 1.8H, J=7 Hz), 1.41 (d, 1.2H, J=7 Hz), 1.54 (d, 3H, J=7 Hz), 2.0-2.2 (m, 2H), 2.5-2.9 (m, 3H), 2.9-3.2 (m, 2.4H), 3.30 (q, 0.6H, J=7 Hz), 4.1-4.3 (m, 2H), 5.25 (quint, 1H, J=7 Hz), 5.74 (d, 0.4H), 5.82 (d, 0.6H), 6.12 (dd, 1H, J=4, 8 Hz), 6.5-6.6 (m, 1H), 7.08 (t, 1H, J=7 Hz), 7.2-7.4 (m, 2H), 7.6-7.7 (m, 2H), 9.27 (br s, 1H).

MS: 470.19[M+H]⁺

Example 25

Trans-5-((1R)-1-(2-(1H-benzo[d]imidazol-2-yl)cyclopropane-1-carboxamido)ethyl)thiophene-2-carboxylic acid tert-butyl ester

[Chemical Formula 52]

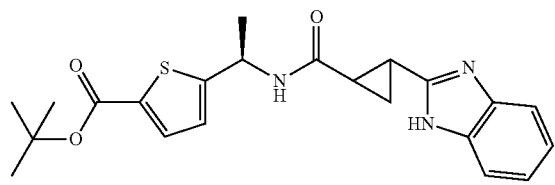

According to a technique similar to that of Example 1, diastereomer A of the title compound (upper spot in TLC (hexane/ethyl acetate=1/3), white powder, 81 mg, 17%) and diastereomer B of the title compound (lower spot in TLC (hexane/ethyl acetate=1/3), white amorphous material, 35 mg, 7%) were obtained using (R)-5-(1-aminoethyl)thiophene-2-carboxylic acid tert-butyl ester (300 mg, 1.14 mmol) and trans-2-(1H-benzo[d]imidazol-2-yl)cyclopropane-1-carboxylic acid (230 mg, 1.14 mmol).

Diastereomer A (1S,2S)

¹H NMR (CDCl₃, 400 MHz): δ=1.5-1.6 (m, 12H), 1.7-1.8 (m, 2H), 2.3-2.5 (m, 1H), 2.7-2.9 (m, 1H), 5.31 (q, 1H, J=7 Hz), 6.88 (dd, 1H, J=1, 4 Hz), 6.97 (d, 1H, J=8 Hz), 6.19 (d, 1H, J=4 Hz), 7.1-7.3 (m, 2H), 7.3-7.9 (m, 2H), 11.3 (br s, 1H).

MS: 412.19[M+H]⁺

Diastereomer B (1R,2R)

¹H NMR (CDCl₃, 400 MHz): δ=1.51 (s, 9H), 1.58 (d, 3H, J=7 Hz), 1.7-1.9 (m, 1H), 1.9-2.0 (m, 1H), 2.2-2.3 (m, 1H), 2.4-2.5 (m, 1H), 5.31 (q, 1H, J=7 Hz), 6.52 (dd, 1H, J=1, 4 Hz), 6.63 (d, 1H, J=4 Hz), 7.1-7.2 (m, 2H), 7.2-7.7 (m, 2H), 8.15 (d, 1H, J=7 Hz), 11.4 (br s, 1H).

MS: 412.20[M+H]⁺

Example 26

Trans-5-((1R)-1-(2-(1H-benzo[d]imidazol-2-yl)cyclopropane-1-carboxamido)ethyl)thiophene-2-carboxylic acid

[Chemical Formula 53]

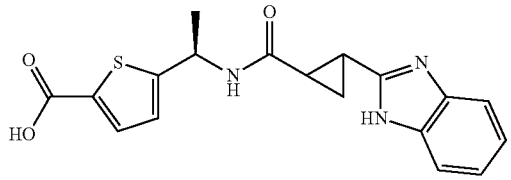

Diastereomer A (78 mg, 0.19 mmol) of trans-5-((1R)-1-(2-(1H-benzo[d]imidazol-2-yl)cyclopropane-1-carboxamido)ethyl)thiophene-2-carboxylic acid tert-butyl ester synthesized in Example 25 was dissolved in chloroform (3.0 mL), and under ice cooling, trifluoroacetic acid (44 L, 0.57 mmol) was added to the solution. The mixture was stirred for 6 hours at room temperature, and then a saturated aqueous solution of sodium hydrogen carbonate and water were added to the reaction liquid. The mixture was stirred for a while, and the mixture was extracted with a liquid mixture of chloroform and methanol. The organic layer was washed with saturated brine and was dried over anhydrous sodium sulfate. Insoluble matters were filtered, and then the solvent was distilled off under reduced pressure. A crude form thus obtained was washed with diethyl ether and then was dried. Thus, the title compound (white powder, 65 mg, 97%) was obtained.

¹H NMR (CDCl₃, 400 MHz): δ=1.58 (d, 3H, J=7 Hz), 1.7-1.9 (m, 2H), 2.4-2.5 (m, 1H), 2.8-2.9 (m, 1H), 5.33 (q, 1H, J=7 Hz), 7.04 (dd, 1H, J=1, 4 Hz), 7.4-7.6 (m, 2H), 6.63 (d, 1H, J=4 Hz), 7.6-7.7 (m, 2H). 3H portion is not observable.

MS: 354.17[M−H]⁻

Example 27

Trans-5-((1R)-1-(2-(1H-benzo[d]imidazol-2-yl)cyclopropane-1-carboxamido)ethyl)thiophene-2-carboxylic acid

[Chemical Formula 54]

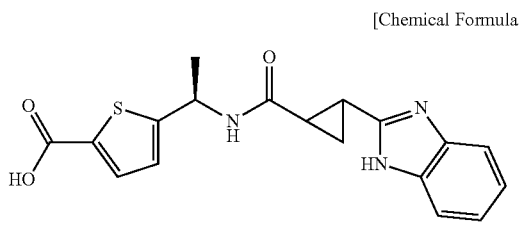

According to a technique similar to that of Example 26, the title compound (light brown powder, 22 mg, 81%) was obtained using diastereomer B (31 mg, 0.075 mmol) of trans-5-((1R)-1-(2-(1H-benzo[d]imidazol-2-yl)cyclopropane-1-carboxamido)ethyl)thiophene-2-carboxylic acid tert-butyl ester synthesized in Example 25.

$^1$H NMR (CDCl$_3$, 400 MHz): δ=1.59 (d, 3H, J=7 Hz), 1.7-1.9 (m, 2H), 2.4-2.5 (m, 1H), 2.7-2.9 (m, 1H), 5.32 (q, 1H, J=7 Hz), 7.03 (d, 1H, J=3 Hz), 7.4-7.6 (m, 2H), 7.6-7.7 (m, 3H). 3H portion is not observable.

MS: 356.13[M+H]$^+$

Example 28

Trans-2-(1H-imidazo[4,5-c]pyridin-2-yl)-N—((R)-1-(5-(2,2,2-trifluoroethoxy)thiophen-2-yl)ethyl)cyclopropane-1-carboxamide

[Chemical Formula 55]

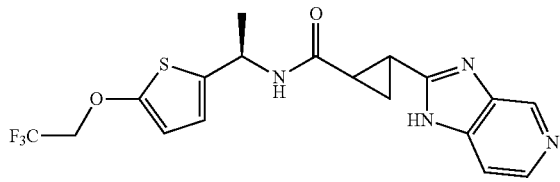

According to a technique similar to that of Example 1, a diastereomer mixture of the title compound (white solid, 45 mg, 71%) was obtained using (R)-1-(5-(2,2,2-trifluoroethoxy)thiophen-2-yl)ethan-1-amine hydrochloride (40 mg, 0.15 mmol) synthesized in Reference Example 4 and trans-2-(1H-imidazo[4,5-c]pyridin-2-yl)cyclopropane-1-carboxylic acid (84 mg, 0.15 mmol) synthesized in Reference Example 59-2.

Diastereomer mixture (1:1)

$^1$H NMR (CD$_3$OD, 400 MHz): δ=1.50 (d, 1.5H, J=7 Hz), 1.52 (d, 1.5H, J=7 Hz), 1.6-1.7 (m, 2H), 2.2-2.4 (m, 1H), 2.6-2.7 (m, 1H), 4.50 (q, 1H, J=8 Hz), 4.53 (q, 1H, J=8 Hz), 5.1-5.2 (m, 1H), 6.24 (d, 0.5H, J=4 Hz), 6.27 (d, 0.5H, J=4 Hz), 6.6-6.7 (m, 1H), 7.53 (br s, 1H), 8.2-8.3 (m, 1H), 7.73 (br s, 1H). 2H portion is not observable.

MS: 411.14[M+H]$^+$

Example 29

Trans-2-(1-methyl-1H-indol-3-yl)-N—((R)-1-(5-(2,2,2-trifluoroethoxy)thiophen-2-yl)ethyl)cyclopropane-1-carboxamide

[Chemical Formula 56]

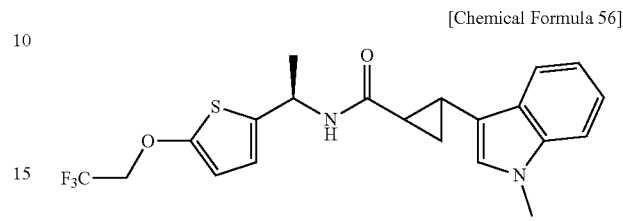

According to a technique similar to that of Example 1, diastereomer A of the title compound (upper spot in TLC (ethyl acetate/hexane=1/1), 20 mg, 36%) as a white solid and diastereomer B of the title compound (lower spot in TLC (ethyl acetate/hexane=1/1), 22 mg, 39%) as a white solid were obtained using (R)-1-(5-(2,2,2-trifluoroethoxy)thiophen-2-yl)ethan-1-amine hydrochloride (34 mg, 0.13 mmol) synthesized in Reference Example 4 and trans-2-(1-methyl-1H-indol-3-yl)cyclopropane-1-carboxylic acid (28 mg, 0.13 mmol).

Diastereomer A $^1$H NMR (CDCl$_3$, 400 MHz): δ=1.2-1.3 (m, 1H), 1.5-1.7 (m, 2H), 1.57 (d, 3H, J=7 Hz), 2.5-2.7 (m, 1H), 3.73 (s, 3H), 4.34 (q, 2H, J=8 Hz), 5.2-5.4 (m, 1H), 5.79 (d, 1H, J=8 Hz), 6.19 (d, 1H, J=4 Hz), 6.61 (dd, 1H, J=1, 4 Hz), 6.79 (s, 1H), 7.1-7.3 (m, 3H), 7.64 (d, 1H, J=8 Hz).

MS: 423.17[M+H]$^+$

Diastereomer B $^1$H NMR (CDCl$_3$, 400 MHz): δ=1.2-1.7 (m, 1H), 1.55 (d, 3H, J=7 Hz), 2.5-2.7 (m, 1H), 3.72 (s, 3H), 4.35 (q, 2H, J=8 Hz), 5.32 (quint, 1H, J=7 Hz), 5.79 (d, 1H, J=9 Hz), 6.20 (d, 1H, J=4 Hz), 6.61 (dd, 1H, J=1, 4 Hz), 6.78 (s, 1H), 7.0-7.3 (m, 3H), 7.63 (d, 1H, J=8 Hz).

MS: 423.16[M+H]$^+$

Example 30

Trans-5-((1R)-1-(2-(1H-benzo[d]imidazol-2-yl)cyclopropane-1-carboxamido)ethyl)thiophene-2-carboxamide

[Chemical Formula 57]

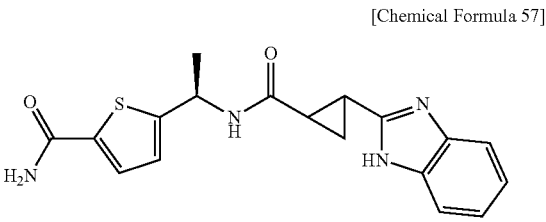 [SMILES: C[C@@H](NC(=O)C1CC1c1nc2ccccc2[nH]1)c1ccc(C(N)=O)s1]

According to a technique similar to that of Example 1, the title compound (white powder, 3 mg, 19%) was obtained using trans-5-((1R)-1-(2-(1H-benzo[d]imidazol-2-yl)cyclopropane-1-carboxamido)ethyl)thiophene-2-carboxylic acid (16 mg, 0.045 mmol) synthesized in Example 26 and ammonium acetate (14 mg, 0.18 mmol).

$^1$H NMR (CD$_3$OD, 400 MHz): δ=1.44 (d, 3H, J=6 Hz), 1.4-1.5 (m, 2H), 2.2-2.4 (m, 1H), 2.6-2.7 (m, 1H), 5.18 (q, 1H, J=7 Hz), 6.96 (d, 1H, J=4 Hz), 7.0-7.2 (m, 2H), 7.3-7.5 (m, 3H), 7.57 (d, 1H, J=4 Hz), 7.90 (br s, 1H). 2H portion is not observable.

MS: 355.13[M+H]$^+$

Example 31

Trans-2-(4-phenyl-1H-imidazol-2-yl)-N—((R)-1-(5-(2,2,2-trifluoroethoxy)thiophen-2-yl)ethyl)cyclopropane-1-carboxamide

[Chemical Formula 58]

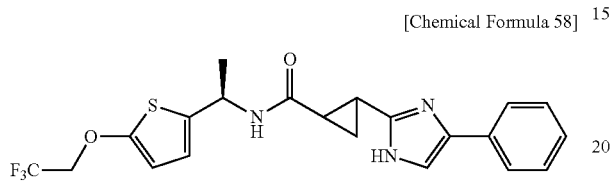

According to a technique similar to that of Example 1, diastereomer A of the title compound (upper spot in TLC (ethyl acetate/hexane=9/1), pale yellow powder, 6 mg, 10%) and diastereomer B of the title compound (lower spot in TLC (ethyl acetate/hexane=9/1), pale yellow powder, 4 mg, 6%) were obtained using (R)-1-(5-(2,2,2-trifluoroethoxy)thiophen-2-yl)ethan-1-amine hydrochloride (37 mg, 0.14 mmol) synthesized in Reference Example 4 and a crude form of trans-2-(4-phenyl-1H-imidazol-2-yl)cyclopropane-1-carboxylic acid (0.14 mmol) synthesized in Reference Example 63.

Diastereomer A $^1$H NMR (CD$_3$OD, 400 MHz): δ=1.4-1.6 (m, 2H), 1.50 (d, 3H, J=7 Hz), 2.0-2.2 (m, 1H), 2.4-2.6 (m, 1H), 4.53 (q, 2H, J=8 Hz), 5.15 (q, 1H, J=7 Hz), 6.26 (d, 1H, J=4 Hz), 6.61 (d, 1H, J=4 Hz), 7.1-7.4 (m, 4H), 7.5-7.8 (m, 2H). 2H portion is not observable.

MS: 436.18[M+H]$^+$

Diastereomer B $^1$H NMR (CD$_3$OD, 400 MHz): δ=1.4-1.6 (m, 2H), 1.52 (d, 3H, J=7 Hz), 2.0-2.2 (m, 1H), 2.4-2.6 (m, 1H), 4.51 (q, 2H, J=8 Hz), 5.14 (q, 1H, J=7 Hz), 6.24 (d, 1H, J=4 Hz), 6.62 (dd, 1H, J=1, 4 Hz), 7.1-7.4 (m, 4H), 7.5-7.7 (m, 2H). 2H portion is not observable.

MS: 436.16[M+H]$^+$

Example 32

Trans-5-((1R)-1-(2-(1H-benzo[d]imidazol-2-yl)cyclopropane-1-carboxamido)ethyl)-N,N-diethylthiophene-2-carboxamide

[Chemical Formula 59]

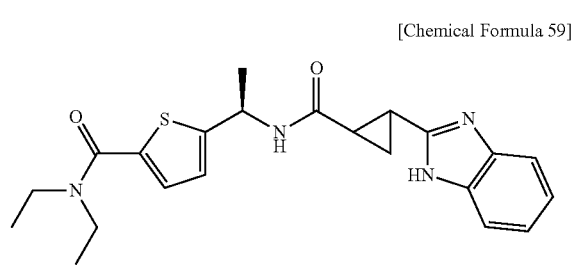 [SMILES: CCN(CC)C(=O)c1ccc([C@@H](C)NC(=O)C2CC2c2nc3ccccc3[nH]2)s1]

According to a technique similar to that of Example 1, the title compound (white powder, 15 mg, 52%) was obtained using trans-5-((1R)-1-(2-(1H-benzo[d]imidazol-2-yl)cyclopropane-1-carboxamido)ethyl)thiophene-2-carboxylic acid (25 mg, 0.070 mmol) synthesized in Example 26 and diethylamine (9 μL, 0.084 mmol).

$^1$H NMR (CDCl$_3$, 400 MHz): δ=1.21 (t, 6H, J=7 Hz), 1.62 (d, 3H, J=7 Hz), 1.6-1.7 (m, 2H), 2.1-2.3 (m, 1H), 2.5-2.6 (m, 1H), 3.47 (q, 4H, J=7 Hz), 5.19 (q, 1H, J=7 Hz), 6.78 (dd, 1H, J=1, 4 Hz), 6.91 (d, 1H, J=4 Hz), 7.1-7.3 (m, 3H), 7.4-7.6 (m, 2H). 1H portion is not observable.

MS: 409.24[M–H]$^-$

Example 33

Trans-2-(1H-benzo[d]imidazol-2-yl)-N—((R)-1-(5-(pyrrolidine-1-carbonyl)thiophen-2-yl)ethyl)cyclopropane-1-carboxamide

[Chemical Formula 60]

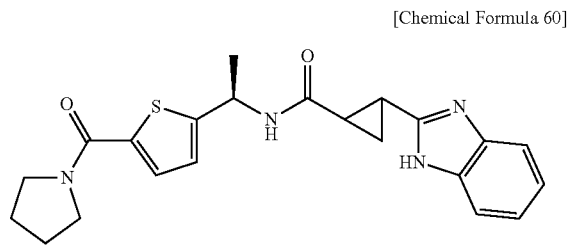 [SMILES: C[C@@H](NC(=O)C1CC1c1nc2ccccc2[nH]1)c1ccc(C(=O)N2CCCC2)s1]

According to a technique similar to that of Example 1, the title compound (white powder, 20 mg, 87%) was obtained using trans-5-((1R)-1-(2-(1H-benzo[d]imidazol-2-yl)cyclopropane-1-carboxamido)ethyl)thiophene-2-carboxylic acid (25 mg, 0.070 mmol) synthesized in Example 26 and pyrrolidine (7 μL, 0.084 mmol).

$^1$H NMR (CD$_3$OD, 400 MHz): δ=1.56 (d, 3H, J=7 Hz), 1.5-1.7 (m, 2H), 1.9-2.1 (m, 4H), 2.2-2.3 (m, 1H), 2.5-2.7 (m, 1H), 3.5-3.7 (m, 2H), 3.7-3.9 (m, 2H), 5.31 (q, 1H, J=7 Hz), 7.02 (d, 1H, J=4 Hz), 7.1-7.2 (m, 2H), 7.3-7.6 (m, 3H). 2H portion is not observable.

MS: 407.22[M–H]$^-$

Example 34

Trans-2-(quinolin-2-yl)-N—((R)-1-(5-(2,2,2-trifluoroethoxy)thiophen-2-yl)ethyl)cyclopropane-1-carboxamide

[Chemical Formula 61]

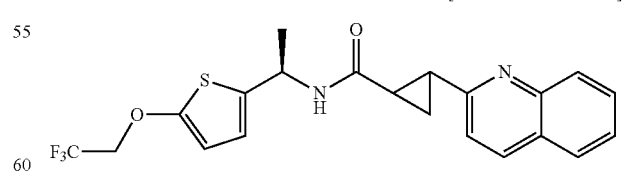

According to a technique similar to that of Example 1, diastereomer A of the title compound (upper spot in TLC (ethyl acetate/hexane=2/3), white solid, 6 mg, 9%) and diastereomer B of the title compound (lower spot in TLC (ethyl acetate/hexane=2/3), white solid, 16 mg, 25%) were obtained using (R)-1-(5-(2,2,2-trifluoroethoxy)thiophen-2- yl)ethan-1-amine hydrochloride (40 mg, 0.15 mmol) synthesized in Reference Example 4 and trans-2-(quinolin-2-yl)cyclopropane-1-carboxylic acid (33 mg, 0.15 mmol).

Diastereomer A $^1$H NMR (CDCl$_3$, 400 MHz): δ=1.51 (d, 3H, J=7 Hz), 1.6-1.8 (m, 2H), 2.2-2.3 (m, 1H), 2.7-2.8 (m, 1H), 4.35 (q, 2H, J=8 Hz), 5.28 (quint, 1H, J=7 Hz), 5.91 (d, 1H, J=7 Hz), 6.19 (d, 1H, J=4 Hz), 6.61 (dd, 1H, J=1, 4 Hz), 7.39 (d, 1H, J=8 Hz), 7.4-7.5 (m, 1H), 7.6-7.7 (m, 1H), 7.76 (d, 1H, J=8 Hz), 7.90 (d, 1H, J=9 Hz), 8.04 (d, 1H, J=9 Hz).

MS: 421.13[M+H]$^+$

Diastereomer B $^1$H NMR (CDCl$_3$, 400 MHz): δ=1.5-1.8 (m, 5H), 2.2-2.3 (m, 1H), 2.7-2.8 (m, 1H), 4.31 (q, 2H, J=8 Hz), 5.28 (quint, 1H, J=7 Hz), 5.90 (d, 1H, J=9 Hz), 6.15 (d, 1H, J=4 Hz), 6.59 (dd, 1H, J=1, 4 Hz), 7.38 (d, 1H, J=8 Hz), 7.4-7.5 (m, 1H), 7.6-7.7 (m, 1H), 7.76 (d, 1H, J=8 Hz), 7.89 (d, 1H, J=8 Hz), 8.03 (d, 1H, J=9 Hz).

MS: 421.12[M+H]$^+$

Example 35

Trans-2-(3H-imidazo[4,5-b]pyridin-2-yl)-N—((R)-1-(5-(2,2,2-trifluoroethoxy)thiophen-2-yl)ethyl)cyclopropane-1-carboxamide

[Chemical Formula 62]

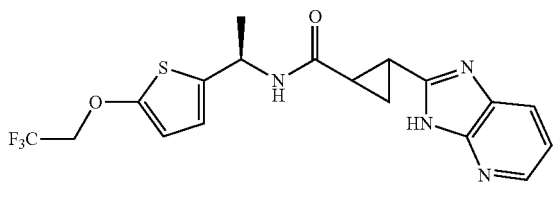

According to a technique similar to that of Example 1, diastereomer A (Rf value=0.7 in TLC (methanol/ethyl acetate=1/9), white solid, 5 mg, 23%) of the title compound was obtained using (R)-1-(5-(2,2,2-trifluoroethoxy)thiophen-2-yl)ethan-1-amine hydrochloride (14 mg, 0.05 mmol) synthesized in Reference Example 4 and a crude form of trans-2-(3H-imidazo[4,5-b]pyridin-2-yl)cyclopropane-1-carboxylic acid (0.05 mmol) synthesized in Reference Example 57-2.

$^1$H NMR (CD$_3$OD, 400 MHz): δ=1.50 (d, 3H, J=7 Hz), 1.6-1.7 (m, 2H), 2.2-2.4 (m, 1H), 2.6-2.7 (m, 1H), 4.53 (q, 2H, J=8 Hz), 5.15 (q, 1H, J=7 Hz), 6.27 (d, 1H, J=4 Hz), 6.62 (dd, 1H, J=1, 4 Hz), 7.25 (dd, 1H, J=5, 8 Hz), 7.8-8.0 (m, 1H), 8.1-8.4 (m, 1H). 2H portion is not observable.

MS: 411.10[M+H]$^+$

Example 36

(R)-1-(2-(adamantan-1-ylamino)-2-oxoethyl)-N—((R)-1-(5-(2,2,2-trifluoroethoxy)thiophen-2-yl)ethyl)pyrrolidine-3-carboxamide

[Chemical Formula 63]

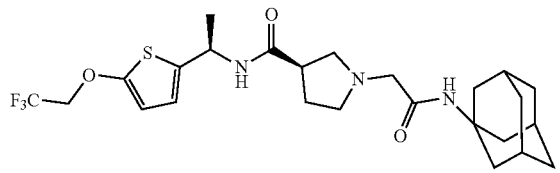

According to a technique similar to that of Example 14, the title compound (white crystals, 20 mg, 67%) was obtained using (R)—N—((R)-1-(5-(2,2,2-trifluoroethoxy)thiophen-2-yl)ethyl)pyrrolidine-3-carboxamide hydrochloride (21 mg, 0.059 mmol) synthesized in Reference Example 9-2 and N-(adamantan-1-yl)-2-chloroacetamide (13 mg, 0.059 mmol).

$^1$H NMR (CDCl$_3$, 400 MHz): δ=1.53 (d, 3H, J=7 Hz), 1.6-1.7 (m, 6H), 1.9-2.0 (m, 6H), 2.0-2.2 (m, 5H), 2.5-2.6 (m, 1H), 2.6-2.7 (m, 1H), 2.7-2.9 (m, 2H), 2.9-3.0 (m, 1H), 3.02 (d, 1H, J=16 Hz), 3.10 (d, 1H, J=16 Hz), 4.33 (q, 2H, J=8 Hz), 5.1-5.3 (m, 1H), 5.93 (d, 1H, J=8 Hz), 6.17 (d, 1H, J=4 Hz), 6.57 (dd, 1H, J=1, 4 Hz), 6.67 (br s, 1H).

MS: 514.23[M+H]$^+$

Example 37

(R)-1-(2-oxo-2-(pyrazin-2-ylamino)ethyl)-N—((R)-1-(5-(2,2,2-trifluoroethoxy)thiophen-2-yl)ethyl)pyrrolidine-3-carboxamide

[Chemical Formula 64]

According to a technique similar to that of Example 14, the title compound (white powder, 30 mg, quant.) was obtained using (R)—N—((R)-1-(5-(2,2,2-trifluoroethoxy)thiophen-2-yl)ethyl)pyrrolidine-3-carboxamide hydrochloride (21 mg, 0.059 mmol) synthesized in Reference Example 9-2 and 2-chloro-N-(pyrazin-2-yl)acetamide (10 mg, 0.059 mmol).

$^1$H NMR (CDCl$_3$, 400 MHz): δ=1.54 (d, 3H, J=7 Hz), 2.1-2.2 (m, 2H), 2.8-3.0 (m, 5H), 3.35 (d, 1H, J=17 Hz), 3.42 (d, 1H, J=16 Hz), 4.32 (q, 2H, J=8 Hz), 5.2-5.3 (m, 1H), 5.82 (d, 1H, J=8 Hz), 6.15 (d, 1H, J=4 Hz), 6.58 (dd, 1H, J=1, 4 Hz), 8.27 (dd, 1H, J=1, 3 Hz), 8.35 (d, 1H, J=3 Hz), 9.55 (br s, 1H), 9.56 (d, 1H, J=1 Hz).

MS: 458.15[M+H]$^+$

Example 38

Trans-2-(1-benzyl-1H-imidazol-2-yl)-N—((R)-1-(5-(2,2,2-trifluoroethoxy)thiophen-2-yl)ethyl)cyclopropane-1-carboxamide

[Chemical Formula 65]

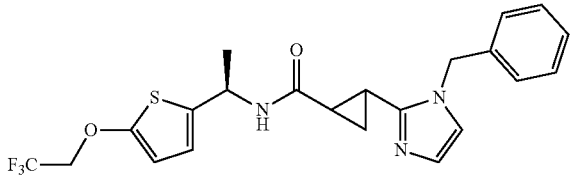

According to a technique similar to that of Example 1, diastereomer A of the title compound (upper spot in TLC (ethyl acetate), white solid, 37 mg, 49%) and diastereomer B of the title compound (lower spot in TLC (ethyl acetate), white solid, 25 mg, 33%) were obtained using (R)-1-(5-(2,2,2-trifluoroethoxy)thiophen-2-yl)ethan-1-amine hydrochloride (44 mg, 0.17 mmol) synthesized in Reference Example 4 and a crude form of trans-2-(1-benzyl-1H-imidazol-2-yl)cyclopropane-1-carboxylic acid (0.34 mmol) synthesized in Reference Example 73-2.

Diastereomer A $^1$H NMR (CDCl$_3$, 400 MHz): δ=1.2-1.6 (m, 2H), 1.47 (d, 3H, J=7 Hz), 1.9-2.1 (m, 1H), 2.3-2.5 (m, 1H), 4.33 (q, 2H, J=8 Hz), 5.1-5.3 (m, 3H), 5.98 (d, 1H, J=8 Hz), 6.17 (d, 1H, J=4 Hz), 6.57 (dd, 1H, J=1, 4 Hz), 6.86 (d, 1H, J=1 Hz), 6.91 (d, 1H, J=1 Hz), 7.0-7.1 (m, 2H), 7.2-7.3 (m, 3H).

MS: 450.13[M+H]$^+$

Diastereomer B $^1$H NMR (CDCl$_3$, 400 MHz): δ=1.3-1.4 (m, 1H), 1.5-1.6 (m, 1H), 1.51 (d, 3H, J=6 Hz), 1.9-2.1 (m, 1H), 2.3-2.5 (m, 1H), 4.32 (q, 2H, J=8 Hz), 5.16 (s, 2H), 5.20 (quint, 1H, J=7 Hz), 6.00 (d, 1H, J=7 Hz), 6.16 (d, 1H, J=4 Hz), 6.55 (d, 1H, J=4 Hz), 6.84 (s, 1H), 6.90 (s, 1H), 7.0-7.1 (m, 2H), 7.2-7.4 (m, 3H).

MS: 450.14[M+H]$^+$

Example 39

Trans-2-(4-(pyridin-2-yl)-1H-imidazol-2-yl)-N—((R)-1-(5-(2,2,2-trifluoroethoxy)thiophen-2-yl)ethyl)cyclopropane-1-carboxamide

[Chemical Formula 66]

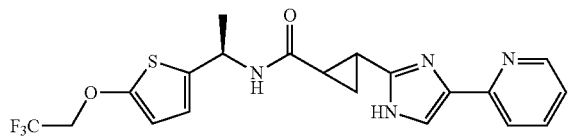

According to a technique similar to that of Example 1, a diastereomer mixture of the title compound (pale yellow solid, 12 mg, 13%) was obtained using (R)-1-(5-(2,2,2-trifluoroethoxy)thiophen-2-yl)ethan-1-amine hydrochloride (55 mg, 0.21 mmol) synthesized in Reference Example 4 and a crude form of trans-2-(4-(pyridin-2-yl)-1H-imidazol-2-yl)cyclopropane-1-carboxylic acid (0.21 mmol) synthesized in Reference Example 71.

Diastereomer mixture (1:1)

$^1$H NMR (CD$_3$OD, 400 MHz): δ=1.4-1.6 (m, 2H), 1.50 (d, 1.5H, J=7 Hz), 1.51 (d, 1.5H, J=7 Hz), 2.0-2.1 (m, 0.5H), 2.3-2.5 (m, 0.5H), 4.32 (q, 1H, J=8 Hz), 5.16 (s, 1H), 5.20 (quint, 0.5H, J=7 Hz), 6.00 (d, 0.5H, J=7 Hz), 6.16 (d, 0.5H, J=4 Hz), 6.55 (d, 0.5H, J=4 Hz), 6.84 (s, 0.5H), 6.90 (s, 0.5H), 7.0-7.1 (m, 1H), 7.2-7.4 (m, 2H). 2H portion is not observable.

MS: 437.14[M+H]$^+$

Example 40

Trans-2-(benzo[d]oxazol-2-yl)-N—((R)-1-(5-(2,2,2-trifluoroethoxy)thiophen-2-yl)ethyl)cyclopropane-1-carboxamide

[Chemical Formula 67]

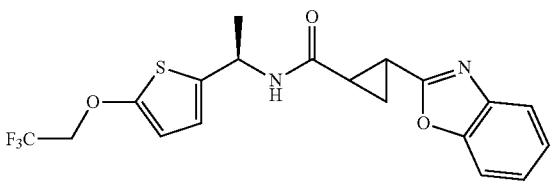

According to a technique similar to that of Example 1, diastereomer A of the title compound (upper spot in TLC (hexane/ethyl acetate=1/5), pale yellow crystals, 26 mg, 26%) and diastereomer B of the title compound (lower spot in TLC (hexane/ethyl acetate=1/5), pale yellow crystals, 26 mg, 26%) were obtained using (R)-1-(5-(2,2,2-trifluoroethoxy)thiophen-2-yl)ethan-1-amine hydrochloride (65 mg, 0.25 mmol) synthesized in Reference Example 4 and a crude form of trans-2-(benzo[d]oxazol-2-yl)cyclopropane-1-carboxylic acid (87 mg) synthesized in Reference Example 67-2.

Diastereomer A $^1$H NMR (DMSO-d$_6$, 400 MHz): δ=1.41 (d, 3H, J=7 Hz), 1.5-1.6 (m, 2H), 2.3-2.6 (m, 2H), 4.79 (q, 2H, J=9 Hz), 5.05 (quint, 1H, J=7 Hz), 6.36 (d, 1H, J=4 Hz), 6.62 (dd, 1H, J=1, 4 Hz), 7.3-7.4 (m, 2H), 7.6-7.7 (m, 2H), 8.83 (d, 1H, J=8 Hz).

MS: 409.18[M–H]$^-$

Diastereomer B $^1$H NMR (DMSO-d$_6$, 400 MHz): δ=1.42 (d, 3H, J=7 Hz), 1.5-1.6 (m, 2H), 2.3-2.6 (m, 2H), 4.77 (q, 2H, J=9 Hz), 5.05 (quint, 1H, J=7 Hz), 6.35 (d, 1H, J=4 Hz), 6.62 (dd, 1H, J=1, 4 Hz), 7.3-7.4 (m, 2H), 7.6-7.7 (m, 2H), 8.84 (d, 1H, J=8 Hz).

MS: 409.18[M–H]$^-$

Example 41

(R)—N—((R)-1-(5-(2,2,2-trifluoroethoxy)thiophen-2-yl)ethyl)-1-(5-(trifluoromethyl)pyridin-2-yl)pyrrolidine-3-carboxamide

[Chemical Formula 68]

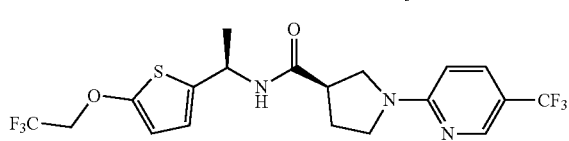

According to a technique similar to that of Example 12, the title compound (white powder, 16 mg, 62%) was obtained using (R)—N—((R)-1-(5-(2,2,2-trifluoroethoxy)thiophen-2-yl)ethyl)pyrrolidine-3-carboxamide hydrochloride (20 mg, 0.056 mmol) synthesized in Reference Example 9-2 and 2-chloro-5-(trifluoromethyl)pyridine (10 mg, 0.056 mmol).

$^1$H NMR (CDCl$_3$, 400 MHz): δ=1.54 (d, 3H, J=6 Hz), 2.2-2.5 (m, 2H), 2.9-3.1 (m, 1H), 3.4-3.6 (m, 1H), 3.6-3.9 (m, 3H), 4.33 (q, 2H, J=8 Hz), 5.2-5.3 (m, 1H), 5.76 (d, 1H, J=7 Hz), 6.17 (d, 1H, J=3 Hz), 6.38 (d, 1H, J=9 Hz), 6.58 (d, 1H, J=3 Hz), 7.61 (d, 1H, J=8 Hz), 8.37 (br s, 1H).

MS: 466.16[M−H]$^-$

Example 42

(R)-1-(2-((3,5-dichlorophenyl)amino)-2-oxoethyl)-N—((R)-1-(5-(2,2,2-trifluoroethoxy)thiophen-2-yl)ethyl)pyrrolidine-3-carboxamide

[Chemical Formula 69]

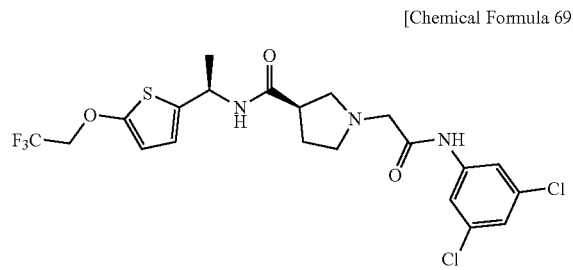 [SMILES: C[C@@H](NC(=O)[C@@H]1CCN(CC(=O)Nc2cc(Cl)cc(Cl)c2)C1)c1ccc(OCC(F)(F)F)s1]

According to a technique similar to that of Example 14, the title compound (white powder, 14 mg, 26%) was obtained using (R)—N—((R)-1-(5-(2,2,2-trifluoroethoxy)thiophen-2-yl)ethyl)pyrrolidine-3-carboxamide hydrochloride (36 mg, 0.10 mmol) synthesized in Reference Example 9-2 and 2-chloro-N-(3,5-dichlorophenyl)acetamide (24 mg, 0.10 mmol).

$^1$H NMR (CDCl$_3$, 400 MHz): δ=1.56 (d, 3H, J=7 Hz), 2.0-2.3 (m, 2H), 2.4-2.6 (m, 1H), 2.6-2.7 (m, 1H), 2.7-2.8 (m, 1H), 3.0-3.2 (m, 3H), 3.46 (d, 1H, J=17 Hz), 4.28 (q, 2H, J=8 Hz), 5.2-5.3 (m, 1H), 5.71 (d, 1H, J=8 Hz), 6.13 (d, 1H, J=4 Hz), 6.61 (d, 1H, J=4 Hz), 7.07 (s, 1H), 7.77 (s, 2H), 9.88 (br s, 1H).

MS: 524.08[M+H]$^+$

Example 43

(R)-1-(3,3-dimethyl-2-oxobutyl)-N—((R)-1-(5-(2,2,2-trifluoroethoxy)thiophen-2-yl)ethyl)pyrrolidine-3-carboxamide

[Chemical Formula 70]

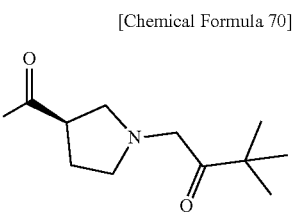

According to a technique similar to that of Example 14, the title compound (yellow oily material, 4.5 mg, 11%) was obtained using (R)—N—((R)-1-(5-(2,2,2-trifluoroethoxy)thiophen-2-yl)ethyl)pyrrolidine-3-carboxamide hydrochloride (36 mg, 0.10 mmol) synthesized in Reference Example 9-2 and 1-chloropinacoline (14 mg, 0.10 mmol).

$^1$H NMR (CDCl$_3$, 400 MHz): δ=1.16 (s, 9H), 1.57 (d, 3H, J=7 Hz), 1.9-2.0 (m, 1H), 2.1-2.3 (m, 1H), 2.3-2.5 (m, 1H), 2.5-2.6 (m, 1H), 2.8-2.9 (m, 1H), 2.9-3.0 (m, 1H), 3.02 (dd, 1H, J=2, 9 Hz), 3.48 (d, 1H, J=18 Hz), 3.68 (d, 1H, J=18 Hz), 4.33 (q, 2H, J=8 Hz), 5.18 (quint, 1H, J=7 Hz), 6.16 (d, 1H, J=4 Hz), 6.55 (dd, 1H, J=1, 4 Hz), 7.73 (d, 1H, J=8 Hz).

MS: 421.17[M+H]$^+$

Example 44

Trans-2-(1H-benzo[d]imidazol-2-yl)-N—((R)-2-methyl-1-(5-(2,2,2-trifluoroethoxy)thiophen-2-yl)propyl)cyclopropane-1-carboxamide

[Chemical Formula 71]

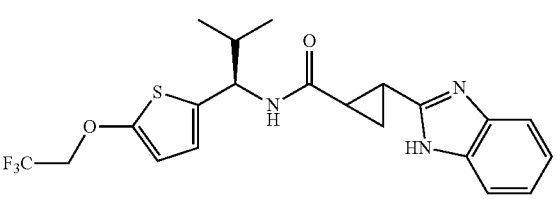

According to a technique similar to that of Example 1, diastereomer A of the title compound (Rf value=0.4 in TLC (ethyl acetate/hexane=2/1), white solid, 12 mg, 16%) was obtained using a crude form of (R)-2-methyl-1-(5-(2,2,2-trifluoroethoxy)thiophen-2-yl)propan-1-amine hydrochloride (0.17 mmol) synthesized in Reference Example 17-2 and trans-2-(1H-benzo[d]imidazol-2-yl)cyclopropane-1-carboxylic acid (35 mg, 0.17 mmol).

Diastereomer A $^1$H NMR (CDCl$_3$, 400 MHz): δ=0.90 (d, 3H, J=7 Hz), 0.94 (d, 3H, J=6 Hz), 1.6-1.8 (m, 2H), 1.9-2.1 (m, 1H), 2.3-2.4 (m, 1H), 2.6-2.8 (m, 1H), 4.34 (q, 2H, J=8 Hz), 4.92 (t, 1H, J=8 Hz), 6.19 (d, 1H, J=4 Hz), 6.23 (d, 1H, J=9 Hz), 6.55 (d, 1H, J=4 Hz), 7.2-7.8 (m, 4H), 10.13 (br s, 1H).

MS: 438.15[M+H]$^+$

Example 45

Trans-N—((R)-1-(5-bromothiophen-2-yl)ethyl)-2-(quinolin-2-yl)cyclopropane-1-carboxamide

[Chemical Formula 72]

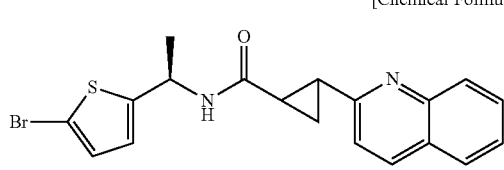

According to a technique similar to that of Example 1, diastereomer A of the title compound (Rf value=0.7 in TLC (ethyl acetate/hexane=1/1), white solid, 3 mg, 9%) was obtained using (R)-1-(5-(bromothiophen-2-yl)ethan-1-amine hydrochloride (20 mg, 0.08 mmol) and trans-2-(quinolin-2-yl)cyclopropane-1-carboxylic acid (18 mg, 0.08 mmol).

Diastereomer A $^1$H NMR (CDCl$_3$, 400 MHz): δ=1.54 (d, 3H, J=7 Hz), 1.6-1.8 (m, 2H), 2.2-2.3 (m, 1H), 2.7-2.8 (m, 1H), 5.35 (quint, 1H, J=7 Hz), 5.94 (d, 1H, J=8 Hz), 6.74 (dd, 1H, J=1, 4 Hz), 6.90 (d, 1H, J=4 Hz), 7.39 (d, 1H, J=9 Hz), 7.4-7.5 (m, 1H), 7.6-7.7 (m, 1H), 7.77 (dd, 1H, J=1, 8 Hz), 7.90 (d, 1H, J=9 Hz), 8.04 (d, 1H, J=8 Hz).

MS: 401.05[M+H]$^+$

Example 46

(1S,2S)-2-(4-(pyridin-2-yl)-1H-imidazol-2-yl)-N—((R)-1-(5-(2,2,2-trifluoroethoxy)thiophen-2-yl)ethyl)cyclopropane-1-carboxamide

[Chemical Formula 73]

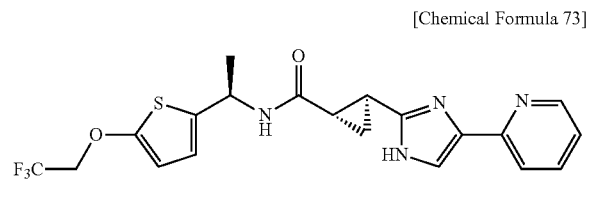 [SMILES: C[C@@H](NC(=O)[C@H]1C[C@@H]1c1nc(-c2ccccn2)c[nH]1)c1ccc(OCC(F)(F)F)s1]

According to a technique similar to that of Example 1, the title compound (pale yellow solid, 17 mg, 17%) was obtained using (R)-1-(5-(2,2,2-trifluoroethoxy)thiophen-2-yl)ethan-1-amine hydrochloride (60 mg, 0.23 mmol) synthesized in Reference Example 4 and a crude form of (1S,2S)-2-(4-(pyridin-2-yl)-1H-imidazol-2-yl)cyclopropane-1-carboxylic acid (0.23 mmol) synthesized in Reference Example 66-3.

$^1$H NMR (CDCl$_3$, 400 MHz): δ=1.4-1.7 (m, 2H), 1.53 (d, 3H, J=7 Hz), 1.9-2.1 (m, 1H), 2.5-2.6 (m, 1H), 4.34 (q, 2H, J=8 Hz), 5.27 (quint, 1H, J=7 Hz), 5.98 (d, 1H, J=8 Hz), 6.19 (d, 1H, J=4 Hz), 6.60 (dd, 1H, J=1, 4 Hz), 7.0-7.2 (m, 1H), 7.3-7.7 (m, 2H), 7.67 (dt, 1H, J=1, 8 Hz), 8.50 (d, 1H, J=4 Hz), 10.17 (br s, 1H).

MS: 437.12[M+H]$^+$

Example 47

(3R)-1-(1-((adamantan-1-yl)amino)-1-oxopropan-2-yl)-N—((R)-1-(2-(2,2,2-trifluoroethoxy)thiazol-5-yl)ethyl)pyrrolidine-3-carboxamide

[Chemical Formula 74]

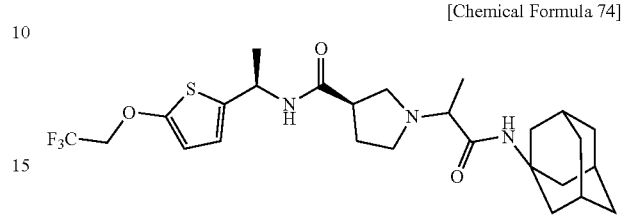

According to a technique similar to that of Example 16, a diastereomer mixture of the title compound (white crystals, 34 mg, 40%) was obtained using (R)—N—((R)-1-(2-(2,2,2-trifluoroethoxy) thiazol-5-yl)ethyl)pyrrolidine-3-carboxamide (50 mg, 0.15 mmol) synthesized in Reference Example 12-2 and N-(adamantan-1-yl)-2-bromopropanamide (53 mg, 0.19 mmol).

Diastereomer mixture (1:1)

$^1$H NMR (CDCl$_3$, 400 MHz): δ=1.27 (d, 1.5H, J=7 Hz), 1.28 (d, 1.5H, J=7 Hz), 1.558 (d, 1.5H, J=7 Hz), 1.564 (d, 1.5H, J=7 Hz), 1.68 (s, 6H), 1.9-2.1 (m, 11H), 2.4-3.0 (m, 6H), 4.7-4.9 (m, 2H), 5.23 (quint, 1H, J=7 Hz), 6.21 (d, 0.5H, J=9 Hz), 6.21 (d, 0.5 H, J=8 Hz), 6.36 (s, 0.5H), 6.42 (s, 0.5H), 6.96 (s, 1H).

MS: 529.27[M+H]$^+$

Example 48

Trans-2-(1-methyl-1H-indol-3-yl)-N—((R)-1-(2-(2,2,2-trifluoroethoxy)thiazol-5-yl)ethyl)cyclopropane-1-carboxamide

[Chemical Formula 75]

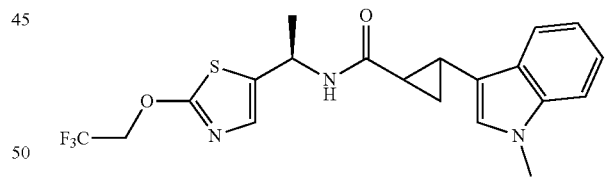

According to a technique similar to that of Example 1, diastereomer A of the title compound (Rf value=0.7 in TLC (ethyl acetate/hexane=1/1), white solid, 20 mg, 16%) was obtained using (R)-1-(2-(2,2,2-trifluoroethoxy)thiazol-5-yl)ethan-1-amine hydrochloride (80 mg, 0.30 mmol) synthesized in Reference Example 6-2 and trans-2-(1-methyl-1H-indol-3-yl)cyclopropane-1-carboxylic acid (32 mg, 0.30 mmol).

Diastereomer A $^1$H NMR (DMSO-d$_6$, 400 MHz): δ=1.1-1.4 (m, 2H), 1.46 (d, 3H, J=7 Hz), 1.7-1.9 (m, 1H), 2.2-2.4 (m, 1H), 3.71 (s, 3H), 5.0-5.2 (m, 1H). 5.10 (q, 1H, J=9 Hz), 7.0-7.2 (m, 4H), 7.38 (d, 1H, J=8 Hz), 7.51 (d, 1H, J=8 Hz), 8.67 (d, 1H, J=8 Hz).

MS: 424.13[M+H]$^+$

Example 49

Trans-2-(1H-indol-3-yl)-N—((R)-1-(2-(2,2,2-trifluoroethoxy)thiazol-5-yl)ethyl)cyclopropane-1-carboxamide

[Chemical Formula 76]

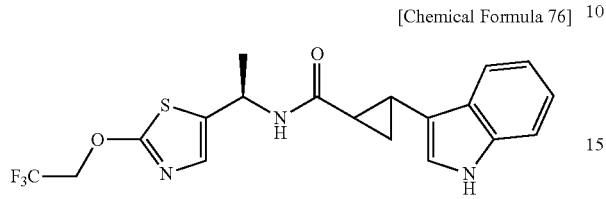

According to a technique similar to that of Example 1, diastereomer A of the title compound (Rf value=0.5 in TLC (ethyl acetate/hexane=1/1), white solid, 43 mg, 35%) was obtained using (R)-1-(2-(2,2,2-trifluoroethoxy)thiazol-5-yl)ethan-1-amine hydrochloride (80 mg, 0.30 mmol) synthesized in Reference Example 6-2 and trans-2-(1H-indol-3-yl)cyclopropane-1-carboxylic acid (61 mg, 0.30 mmol).

Diastereomer A $^1$H NMR (DMSO-d$_6$, 400 MHz): δ=1.1-1.4 (m, 2H), 1.47 (d, 3H, J=7 Hz), 1.7-1.9 (m, 1H), 2.2-2.4 (m, 1H), 3.71 (s, 3H), 5.0-5.2 (m, 1H). 5.10 (q, 1H, J=9 Hz), 6.9-7.2 (m, 4H), 7.33 (d, 1H, J=8 Hz), 7.49 (d, 1H, J=8 Hz), 8.65 (d, 1H, J=8 Hz), 10.85 (s, 1H).

MS: 410.10[M+H]$^+$

Example 50

(1S,2S)-2-(1H-benzo[d]imidazol-2-yl)-N—((R)-2-methyl-1-(5-(trifluoromethyl)thiophen-2-yl)propyl)cyclopropane-1-carboxamide

[Chemical Formula 77]

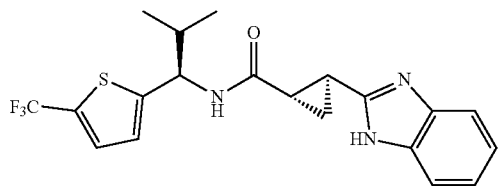

According to a technique similar to that of Example 89, the title compound (white powder, 66 mg, 83%) was obtained using (R)-2-methyl-1-(5-(trifluoromethyl)thiophen-2-yl)propan-1-amine hydrochloride (51 mg, 0.20 mmol) synthesized in Reference Example 19-2.

$^1$H NMR (CD$_3$OD, 400 MHz): δ=0.90 (d, 3H, J=6 Hz), 1.00 (d, 3H, J=6 Hz), 1.5-1.7 (m, 2H), 2.1-2.2 (m, 1H), 2.3-2.4 (m, 1H), 2.5-2.6 (m, 1H), 4.97 (d, 1H, J=8 Hz), 7.01 (d, 1H, J=4 Hz), 7.1-7.2 (m, 2H), 7.3-7.4 (m, 1H), 7.46 (br s, 2H). 2H portion is not observable.

MS: 408.12[M+H]$^+$

Example 51

(1S,2S)-2-(1H-benzo[d]imidazol-2-yl)-N—((R)-1-(4-methyl-2-(2,2,2-trifluoroethoxy)thiazol-5-yl)ethyl)cyclopropane-1-carboxamide

[Chemical Formula 78]

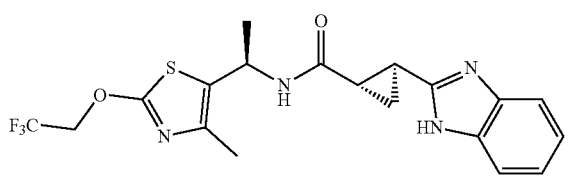

According to a technique similar to that of Example 89, the title compound (white powder, 33 mg, 47%) was obtained using (R)-1-(4-methyl-2-(2,2,2-trifluoroethoxy)thiazol-5-yl)ethan-1-amine (40 mg, 0.17 mmol) synthesized in Reference Example 13-6.

$^1$H NMR (CD$_3$OD, 400 MHz): δ=1.45 (d, 3H, J=7 Hz), 1.5-1.6 (m, 2H), 2.1-2.2 (m, 4H), 2.5-2.6 (m, 1H), 4.8-4.9 (m, 2H), 5.22 (q, 1H, J=7 Hz), 7.1-7.2 (m, 2H), 7.4-7.5 (m, 2H). 2H portion is not observable.

MS: 425.12[M+H]$^+$

Example 52

(1S,2S)-2-(1H-benzo[d]imidazol-2-yl)-N—((R)-1-(quinolin-2-yl)ethyl)cyclopropane-1-carboxamide

[Chemical Formula 79]

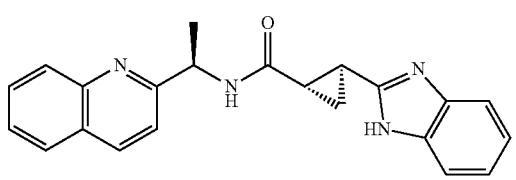

According to a technique similar to that of Example 89, the title compound (white powder, 26 mg, 43%) was obtained using (R)-1-(quinolin-2-yl)ethan-1-amine (35 mg, 0.17 mmol).

$^1$H NMR (CD$_3$OD, 400 MHz): δ=1.5-1.7 (m, 5H), 2.3-2.4 (m, 1H), 2.5-2.6 (m, 1H), 5.23 (q, 1H, J=8 Hz), 7.1-7.2 (m, 2H), 7.47 (br s, 2H), 7.5-7.6 (m, 2H), 7.75 (dd, 1H, J=2, 8 Hz), 7.90 (d, 1H, J=8 Hz), 8.03 (d, 1H, J=9 Hz), 8.32 (d, 1H, J=9 Hz). 2H portion is not observable.

MS: 357.17[M+H]$^+$

Example 53

Trans-2-(5-chloro-1H-benzo[d]imidazol-2-yl)-N—((R)-1-(5-(2,2,2-trifluoroethoxy)thiophen-2-yl)ethyl)cyclopropane-1-carboxamide

[Chemical Formula 80]

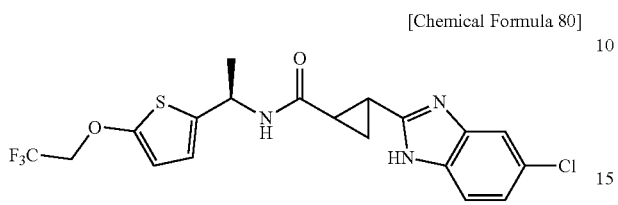

According to a technique similar to that of Example 1, diastereomer A of the title compound (upper spot in TLC (hexane/ethyl acetate=1/9), white crystals, 31 mg, 31%) and diastereomer B of the title compound (lower spot in TLC (hexane/ethyl acetate=1/9), white crystals, 36 mg, 35%) were obtained using (R)-1-(5-(2,2,2-trifluoroethoxy)thiophen-2-yl)ethan-1-amine hydrochloride (60 mg, 0.23 mmol) synthesized in Reference Example 4 and trans-2-(5-chloro-1H-benzo[d]imidazol-2-yl)cyclopropane-1-carboxylic acid (65 mg, 0.28 mmol) synthesized in Reference Example 55-2.

Diastereomer A
$^1$H NMR (DMSO-d$_6$, 400 MHz): δ=1.40 (d, 3H, J=7 Hz), 1.4-1.5 (m, 2H), 2.2-2.3 (m, 1H), 2.4-2.5 (m, 1H), 4.78 (q, 2H, J=9 Hz), 5.04 (quint, 1H, J=7 Hz), 6.35 (d, 1H, J=4 Hz), 6.61 (dd, 1H, J=1, 4 Hz), 7.13 (dd, 1H, J=2, 8 Hz), 7.45 (d, 1H, J=9 Hz), 7.50 (d, 1H, J=2 Hz), 8.76 (d, 1H, J=8 Hz) 0.1H portion is not observable.
MS: 442.15[M–H]$^-$ Diastereomer B
$^1$H NMR (DMSO-d$_6$, 400 MHz): δ=1.4-1.6 (m, 2H), 1.41 (d, 3H, J=7 Hz), 2.2-2.7 (m, 2H), 4.76 (q, 2H, J=9 Hz), 4.9-5.1 (m, 1H), 6.33 (d, 1H, J=4 Hz), 6.60 (d, 1H, J=4 Hz), 7.12 (d, 1H, J=8 Hz), 7.44 (d, 1H, J=8 Hz), 7.49 (s, 1H), 8.76 (d, 1H, J=8 Hz). 1H portion is not observable.
MS: 442.15[M–H]$^-$

Example 54

Trans-2-(1-ethyl-1H-benzo[d]imidazol-2-yl)-N—((R)-1-(5-(2,2,2-trifluoroethoxy)thiophen-2-yl)ethyl)cyclopropane-1-carboxamide

[Chemical Formula 81]

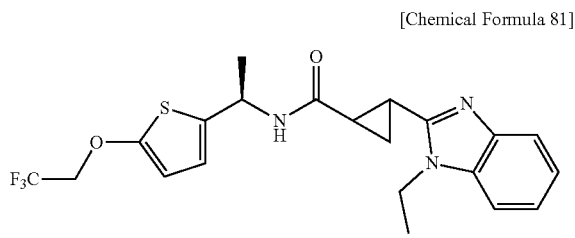 [SMILES: CCn1c(C2CC2C(=O)N[C@H](C)c2ccc(OCC(F)(F)F)s2)nc2ccccc21]

According to a technique similar to that of Example 1, diastereomer A of the title compound (Rf value=0.65 in TLC (ethyl acetate/hexane=9/1), white crystals, 39 mg, 38%) was obtained using (R)-1-(5-(2,2,2-trifluoroethoxy)thiophen-2-yl)ethan-1-amine hydrochloride (60 mg, 0.23 mmol) synthesized in Reference Example 4 and a crude form of trans-2-(1-ethyl-1H-benzo[d]imidazol-2-yl)cyclopropane-1-carboxylic acid (100 mg) synthesized in Reference Example 54-3.

Diastereomer A
$^1$H NMR (DMSO-d$_6$, 400 MHz): δ=1.32 (t, 3H, J=7 Hz), 1.4-1.5 (m, 2H), 1.41 (d, 3H, J=7 Hz), 2.2-2.3 (m, 1H), 2.5-2.6 (m, 1H), 4.2-4.4 (m, 2H), 4.79 (q, 2H, J=9 Hz), 5.08 (quint, 1H, J=7 Hz), 6.36 (d, 1H, J=4 Hz), 6.61 (dd, 1H, J=1, 4 Hz), 7.1-7.3 (m, 2H), 7.4-7.6 (m, 2H), 8.79 (d, 1H, J=8 Hz).
MS: 438.15[M+H]$^+$

Example 55

(1S,2S)—N—((R)-1-(benzo[d][1,3]dioxol-5-yl)ethyl)-2-(1H-benzo[d]imidazol-2-yl)cyclopropane-1-carboxamide

[Chemical Formula 82]

According to a technique similar to that of Example 89, the title compound (white powder, 55 mg, 91%) was obtained using (R)-1-(benzo[d][1,3]dioxol-5-yl)ethan-1-amine (35 mg, 0.17 mmol).
$^1$H NMR (CD$_3$OD, 400 MHz): δ=1.39 (d, 3H, J=8 Hz), 1.5-1.6 (m, 2H), 2.2-2.3 (m, 1H), 2.5-2.6 (m, 1H), 4.9-5.0 (m, 1H), 5.90 (s, 2H), 6.7-6.9 (m, 3H), 7.1-7.2 (m, 2H), 7.4-7.5 (m, 2H). 2H portion is not observable.
MS: 350.15[M+H]$^+$

Example 56

Trans-2-(1H-benzo[d]imidazol-2-yl)-N—((R)-1-(5-(morpholine-4-carbonyl)thiophen-2-yl)ethyl)cyclopropane-1-carboxamide

[Chemical Formula 83]

According to a technique similar to that of Example 1, the title compound (white crystals, 9 mg, 46%) was obtained using trans-5-((1R)-1-(2-(1H-benzo[d]imidazol-2-yl)cyclopropane-1-carboxamido)ethyl)thiophene-2-carboxylic acid (16 mg, 0.045 mmol) synthesized in Example 26 and morpholine (5 μL, 0.054 mmol).

¹H NMR (CD₃OD, 400 MHz): δ=1.47 (d, 3H, J=7 Hz), 1.4-1.6 (m, 2H), 2.1-2.2 (m, 1H), 2.4-2.6 (m, 1H), 3.5-3.7 (m, 8H), 5.23 (q, 1H, J=7 Hz), 6.90 (d, 1H, J=4 Hz), 7.0-7.2 (m, 2H), 7.17 (d, 1H, J=4 Hz), 7.3-7.5 (m, 2H). 2H portion is not observable.
MS: 425.16[M+H]⁺

Example 57

Trans-2-(1-ethyl-1H-benzo[d]imidazol-2-yl)-N—((R)-1-(2-(2,2,2-trifluoroethoxy)thiazol-5-yl)ethyl)cyclopropane-1-carboxamide

[Chemical Formula 84]

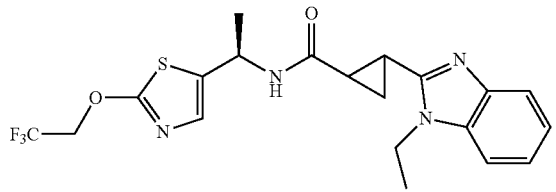

According to a technique similar to that of Example 1, diastereomer A of the title compound (upper spot in TLC (hexane/ethyl acetate=3/7), white crystals, 3 mg, 5%) and diastereomer B of the title compound (lower spot in TLC (hexane/ethyl acetate=3/7), white crystals, 3 mg, 5%) were obtained using (R)-1-(2-(2,2,2-trifluoroethoxy)thiazol-5-yl)ethan-1-amine (27 mg, 0.12 mmol) synthesized in Reference Example 6-2 and a crude form of trans-2-(1-ethyl-1H-benzo[d]imidazol-2-yl)cyclopropane-1-carboxylic acid (52 mg) synthesized in Reference Example 54-3.

Diastereomer A
¹H NMR (DMSO-d₆, 400 MHz): δ=1.32 (t, 3H, J=7 Hz), 1.4-1.5 (m, 2H), 1.45 (d, 3H, J=6 Hz), 2.2-2.3 (m, 1H), 2.4-2.6 (m, 1H), 4.34 (q, 2H, J=7 Hz), 5.0-5.2 (m, 3H), 7.10 (s, 1H), 7.1-7.3 (m, 2H), 7.4-7.6 (m, 2H), 8.80 (d, 1H, J=8 Hz).
MS: 439.16[M+H]⁺

Diastereomer B
¹H NMR (DMSO-d₆, 400 MHz): δ=1.26 (t, 3H, J=7 Hz), 1.4-1.5 (m, 2H), 1.46 (d, 3H, J=6 Hz), 2.1-2.3 (m, 1H), 2.4-2.6 (m, 1H), 4.2-4.5 (m, 2H), 4.9-5.3 (m, 3H), 7.08 (s, 1H), 7.1-7.3 (m, 2H), 7.4-7.6 (m, 2H), 8.89 (d, 1H, J=7 Hz).
MS: 439.15[M+H]⁺

Example 58

(1S,2S)—N—((R)-1-(1H-indol-6-yl)ethyl)-2-(1H-benzo[d]imidazol-2-yl)cyclopropane-1-carboxamide

[Chemical Formula 85]

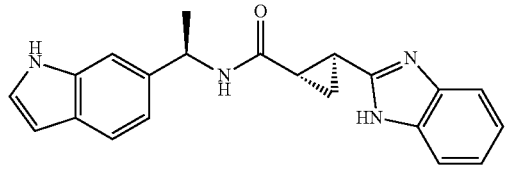

According to a technique similar to that of Example 89, the title compound (white powder, 50 mg, 68%) was obtained using (R)-1-(1H-indol-6-yl)ethan-1-amine (34 mg, 0.21 mmol).
¹H NMR (CD₃OD, 400 MHz): δ=1.50 (d, 3H, J=7 Hz), 1.5-1.6 (m, 2H), 2.2-2.3 (m, 1H), 2.5-2.6 (m, 1H), 5.12 (q, 1H, J=7 Hz), 6.39 (dd, 1H, J=1, 3 Hz), 7.01 (dd, 1H, J=2, 8 Hz), 7.1-7.2 (m, 3H), 7.36 (s, 1H), 7.4-7.5 (m, 2H), 7.50 (d, 1H, J=8 Hz) 0.3H portion is not observable.
MS: 367.15[M+Na]⁺

Example 59

(1S,2S)-2-(1H-benzo[d]imidazol-2-yl)-N—((R)-cyclohexyl(5-(trifluoromethyl)thiophen-2-yl)methyl)cyclopropane-1-carboxamide

[Chemical Formula 86]

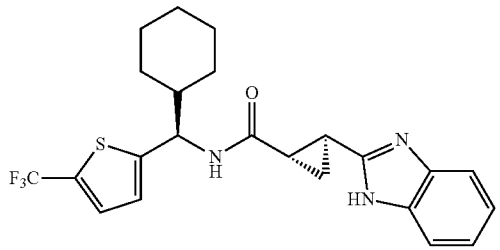

According to a technique similar to that of Example 89, the title compound (white powder, 55 mg, 78%) was obtained using (R)-cyclohexyl(5-(trifluoromethyl)thiophen-2-yl)methanamine (42 mg, 0.16 mmol) synthesized in Reference Example 21-2.
¹H NMR (CD₃OD, 400 MHz): δ=0.9-1.3 (m, 5H), 1.5-1.9 (m, 8H), 2.2-2.3 (m, 1H), 2.5-2.6 (m, 1H), 4.97 (d, 1H, J=9 Hz), 6.99 (d, 1H, J=4 Hz), 7.1-7.2 (m, 2H), 7.3-7.4 (m, 1H), 7.46 (br s, 2H). 2H portion is not observable.
MS: 448.16[M+H]⁺

Example 60

Trans-2-(1H-benzo[d]imidazol-2-yl)-N—((R)-1-(5-(3,3-difluoropyrrolidine-1-carbonyl)thiophen-2-yl)ethyl)cyclopropane-1-carboxamide

[Chemical Formula 87]

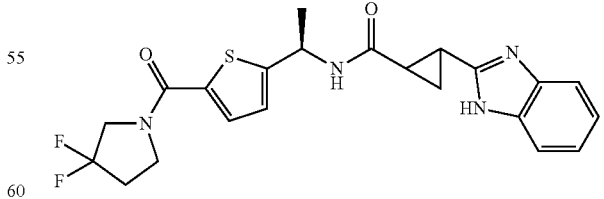

According to a technique similar to that of Example 1, the title compound (white crystals, 12 mg, 52%) was obtained using trans-5-((1R)-1-(2-(1H-benzo[d]imidazol-2-yl)cyclopropane-1-carboxamido)ethyl)thiophene-2-carboxylic acid (18 mg, 0.051 mmol) synthesized in Example 26 and 3,3-difluoropyrrolidine hydrochloride (9 mg, 0.061 mmol).

¹H NMR (CD₃OD, 400 MHz): δ=1.47 (d, 3H, J=7 Hz), 1.4-1.6 (m, 2H), 2.1-2.3 (m, 1H), 2.3-2.6 (m, 3H), 3.6-4.2 (m, 4H), 5.23 (q, 1H, J=7 Hz), 6.95 (dd, 1H, J=1, 4 Hz), 7.0-7.2 (m, 2H), 7.3-7.5 (m, 3H). 2H portion is not observable.
MS: 445.20[M+H]⁺

Example 61

Trans-2-(1H-benzo[d]imidazol-2-yl)-N—((R)-1-(5-(piperidine-1-carbonyl)thiophen-2-yl)ethyl)cyclopropane-1-carboxamide

[Chemical Formula 88]

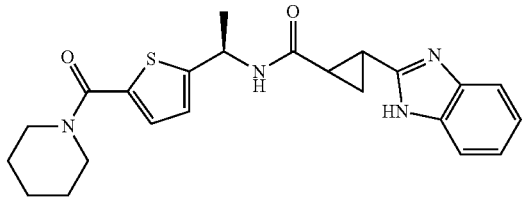

According to a technique similar to that of Example 1, the title compound (white crystals, 11 mg, 50%) was obtained using trans-5-((1R)-1-(2-(1H-benzo[d]imidazol-2-yl)cyclopropane-1-carboxamido)ethyl)thiophene-2-carboxylic acid (18 mg, 0.051 mmol) synthesized in Example 26 and piperidine (6 μL, 0.061 mmol).
¹H NMR (DMSO-d₆, 400 MHz): δ=1.4-1.7 (m, 8H), 1.46 (d, 3H, J=7 Hz), 2.2-2.6 (m, 2H), 3.5-3.7 (m, 4H), 5.20 (quint, 1H, J=7 Hz), 6.95 (d, 1H, J=4 Hz), 7.0-7.2 (m, 2H), 7.02 (d, 1H, J=4 Hz), 7.3-7.6 (m, 2H), 8.90 (d, 1H, J=8 Hz), 12.41 (br s, 1H).
MS: 421.26[M−H]⁻

Example 62

Trans-5-((1R)-1-(2-(1H-benzo[d]imidazol-2-yl)cyclopropane-1-carboxamido)ethyl)-N-(4-fluorophenyl)-N-methylthiophene-2-carboxamide

[Chemical Formula 89]

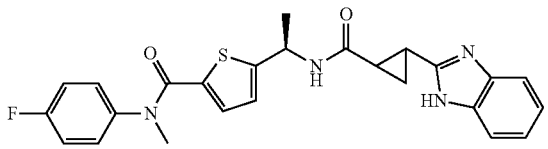

According to a technique similar to that of Example 1, the title compound (pale yellow crystals, 5 mg, 21%) was obtained using trans-5-((1R)-1-(2-(1H-benzo[d]imidazol-2-yl)cyclopropane-1-carboxamido)ethyl)thiophene-2-carboxylic acid (18 mg, 0.051 mmol) synthesized in Example 26 and 4-fluoro-N-methylaniline (8 mg, 0.061 mmol).
¹H NMR (DMSO-d₆, 400 MHz): δ=1.3-1.5 (m, 2H), 1.36 (d, 3H, J=7 Hz), 2.2-2.3 (m, 1H), 2.4-2.5 (m, 1H), 3.30 (s, 3H), 5.07 (quint, 1H, J=7 Hz), 6.42 (d, 1H, J=4 Hz), 6.73 (d, 1H, J=4 Hz), 7.1-7.2 (m, 2H), 7.2-7.6 (m, 6H), 8.81 (d, 1H, J=8 Hz), 12.40 (br s, 1H).
MS: 463.18[M+H]⁺

Example 63

(1S,2S)-2-(1H-benzo[d]imidazol-2-yl)-N—((R)-1-(5-fluoro-1H-indol-2-yl)ethyl)cyclopropane-1-carboxamide

[Chemical Formula 90]

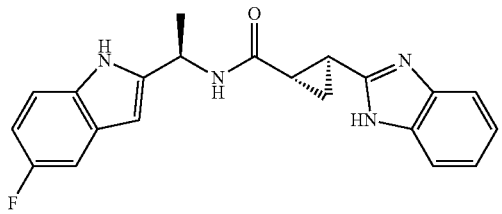

According to a technique similar to that of Example 89, the title compound (white powder, 53 mg, 85%) was obtained using (R)-1-(5-fluoro-1H-indol-2-yl)ethan-1-amine (30 mg, 0.17 mmol).
¹H NMR (CD₃OD, 400 MHz): δ=1.57 (d, 3H, J=7 Hz), 1.6-1.7 (m, 2H), 2.2-2.3 (m, 1H), 2.5-2.6 (m, 1H), 5.25 (q, 1H, J=7 Hz), 6.31 (s, 1H), 6.81 (ddd, 1H, J=2, 9, 9 Hz), 7.11 (dd, 1H, J=2, 10 Hz), 7.1-7.2 (m, 2H), 7.25 (dd, 1H, J=5, 9 Hz), 7.45 (br s, 2H). 3H portion is not observable.
MS: 363.17[M+H]⁺

Example 64

Trans-2-(5-chloro-1H-benzo[d]imidazol-2-yl)-N—((R)-1-(2-(2,2,2-trifluoroethoxy)thiazol-5-yl)ethyl)cyclopropane-1-carboxamide

[Chemical Formula 91]

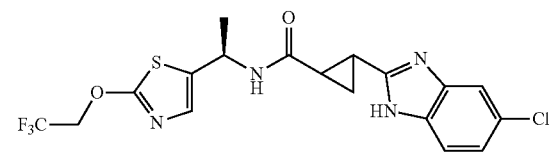

According to a technique similar to that of Example 1, diastereomer A of the title compound (upper spot in TLC (hexane/ethyl acetate=1/4), white crystals, 34 mg, 26%) and diastereomer B of the title compound (lower spot in TLC (hexane/ethyl acetate=1/4), white crystals, 22 mg, 17%) were obtained using (R)-1-(2-(2,2,2-trifluoroethoxy)thiazol-5-yl)ethan-1-amine (65 mg, 0.29 mmol) synthesized in Reference Example 6-2 and trans-2-(5-chloro-1H-benzo[d]imidazol-2-yl)cyclopropane-1-carboxylic acid (82 mg, 0.34 mmol) synthesized in Reference Example 55-2.

Diastereomer A

¹H NMR (DMSO-d₆, 400 MHz): δ=1.4-1.5 (m, 2H), 1.44 (d, 3H, J=7 Hz), 2.2-2.3 (m, 1H), 2.4-2.5 (m, 1H), 5.0-5.2 (m, 3H), 7.09 (s, 1H), 7.13 (dd, 1H, J=2, 8 Hz), 7.45 (d, 1H, J=8 Hz), 7.50 (s, 1H), 8.85 (d, 1H, J=8 Hz). 1H portion is not observable.
MS: 443.14[M−H]⁻

Diastereomer B

¹H NMR (DMSO-d₆, 400 MHz): δ=1.4-1.5 (m, 2H), 1.45 (d, 3H, J=7 Hz), 2.2-2.3 (m, 1H), 2.4-2.5 (m, 1H), 5.0-5.2 (m, 3H), 7.08 (s, 1H), 7.13 (dd, 1H, J=2, 8 Hz), 7.44 (d, 1H, J=8 Hz), 7.50 (s, 1H), 8.85 (d, 1H, J=8 Hz), 12.60 (br s, 1H).

MS: 443.18[M–H]⁻

Example 65

(1S,2S)-2-(1H-benzo[d]imidazol-2-yl)-N—((R)-1-(5-fluorobenzofuran-2-yl)ethyl)cyclopropane-1-carboxamide

[Chemical Formula 92]

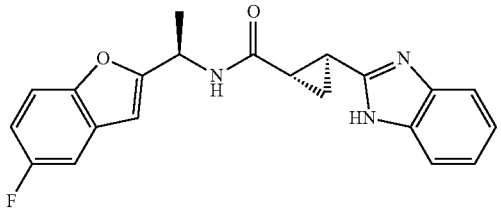

According to a technique similar to that of Example 89, the title compound (white powder, 54 mg, 88%) was obtained using (R)-1-(5-fluorobenzofuran-2-yl)ethan-1-amine (30 mg, 0.17 mmol) synthesized in Reference Example 23-3.

¹H NMR (CD₃OD, 400 MHz): δ=1.55 (d, 3H, J=7 Hz), 1.6-1.7 (m, 2H), 2.2-2.3 (m, 1H), 2.5-2.6 (m, 1H), 5.25 (q, 1H, J=7 Hz), 6.65 (s, 1H), 6.99 (ddd, 1H, J=3, 9, 9 Hz), 7.1-7.2 (m, 2H), 7.24 (dd, 1H, J=3, 9 Hz), 7.42 (dd, 1H, J=4, 9 Hz), 7.45 (br s, 2H). 2H portion is not observable.

MS: 364.14[M+H]⁺

Example 66

(1S,2S)-2-(1H-benzo[d]imidazol-2-yl)-N—((R)-1-(5-fluorobenzo[b]thiophen-2-yl)ethyl)cyclopropane-1-carboxamide

[Chemical Formula 93]

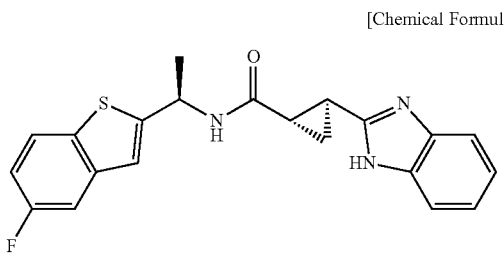

According to a technique similar to that of Example 89, the title compound (white powder, 37 mg, 65%) was obtained using (R)-1-(5-fluorobenzo[b]thiophen-2-yl)ethan-1-amine (29 mg, 0.15 mmol) synthesized in Reference Example 40-2.

¹H NMR (CD₃OD, 400 MHz): δ=1.6-1.7 (m, 5H), 2.2-2.3 (m, 1H), 2.5-2.6 (m, 1H), 5.38 (q, 1H, J=7 Hz), 7.07 (ddd, 1H, J=2, 9, 9 Hz), 7.1-7.2 (m, 2H), 7.22 (s, 1H), 7.44 (dd, 1H, J=2, 10 Hz), 7.46 (br s, 2H), 7.78 (dd, 1H, J=5, 9 Hz). 2H portion is not observable.

MS: 380.14[M+H]⁺

Example 67

Trans-2-(1H-benzo[d]imidazol-2-yl)-N—((R)-1-(5-(2,2-dimethylpyrrolidine-1-carbonyl)thiophen-2-yl)ethyl)cyclopropane-1-carboxamide

[Chemical Formula 94]

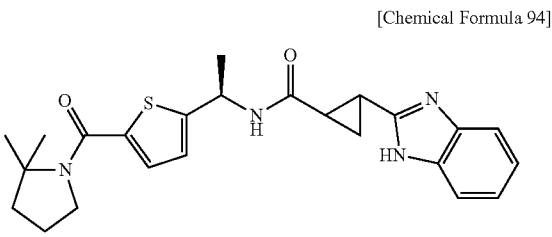 [SMILES: C[C@@H](NC(=O)C1CC1c1nc2ccccc2[nH]1)c1ccc(C(=O)N2CCCC2(C)C)s1]

According to a technique similar to that of Example 1, the title compound (pale yellow crystals, 8 mg, 38%) was obtained using trans-5-((1R)-1-(2-(1H-benzo[d]imidazol-2-yl)cyclopropane-1-carboxamido)ethyl)thiophene-2-carboxylic acid (18 mg, 0.051 mmol) synthesized in Example 26 and 2,2-dimethylpyrrolidine hydrochloride (8 mg, 0.061 mmol).

¹H NMR (DMSO-d₆, 400 MHz): δ=1.3-1.6 (m, 11H), 1.7-1.9 (m, 4H), 2.2-2.4 (m, 1H), 2.4-2.6 (m, 1H), 3.76 (t, 2H, J=6 Hz), 5.18 (quint, 1H, J=7 Hz), 6.94 (d, 1H, J=4 Hz), 7.0-7.2 (m, 2H), 7.35 (d, 1H, J=4 Hz) 7.4-7.5 (m, 2H), 8.88 (d, 1H, J=8 Hz), 12.40 (br s, 1H).

MS: 437.23[M+H]⁺

Example 68

Trans-2-(1H-benzo[d]imidazol-2-yl)-N—((R)-1-(5-(4-methylpiperazine-1-carbonyl)thiophen-2-yl)ethyl)cyclopropane-1-carboxamide

[Chemical Formula 95]

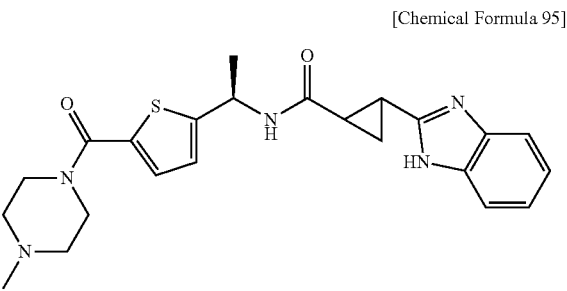 [SMILES: C[C@@H](NC(=O)C1CC1c1nc2ccccc2[nH]1)c1ccc(C(=O)N2CCN(C)CC2)s1]

According to a technique similar to that of Example 1, the title compound (pale yellow crystals, 11 mg, 52%) was obtained using trans-5-((1R)-1-(2-(1H-benzo[d]imidazol-2-yl)cyclopropane-1-carboxamido)ethyl)thiophene-2-carboxylic acid (18 mg, 0.051 mmol) synthesized in Example 26 and N-methylpiperazine (6 mg, 0.061 mmol).

¹H NMR (DMSO-d₆, 400 MHz): δ=1.4-1.6 (m, 2H), 1.46 (d, 3H, J=7 Hz), 2.20 (s, 3H), 2.2-2.4 (m, 5H), 2.4-2.5 (m, 1H), 3.6-3.7 (m, 4H), 5.20 (quint, 1H, J=7 Hz), 6.96 (d, 1H, J=4 Hz), 7.1-7.2 (m, 2H), 7.24 (d, 1H, J=4 Hz), 7.4-7.5 (m, 2H), 8.91 (d, 1H, J=8 Hz), 12.41 (br s, 1H).

MS: 438.21[M+H]⁺

Example 69

(1S,2S)-2-(1H-benzo[d]imidazol-2-yl)-N—((R)-cyclopropyl(5-(trifluoromethyl)thiophen-2-yl)methyl)cyclopropane-1-carboxamide

[Chemical Formula 96]

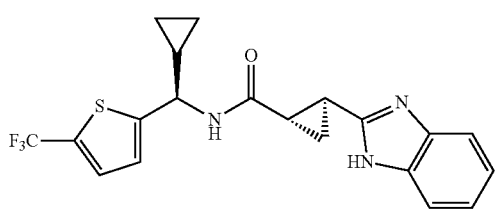

According to a technique similar to that of Example 89, the title compound (pale yellow powder, 7.0 mg, 52%) was obtained using (R)-cyclopropyl(5-(trifluoromethyl) thiophen-2-yl)methanamine (7.2 mg, 0.033 mmol) synthesized in Reference Example 18-3.

$^1$H NMR (CD$_3$OD, 400 MHz): δ=0.4-0.5 (m, 2H), 0.6-0.8 (m, 2H), 1.2-1.4 (m, 1H), 1.6-1.7 (m, 2H), 2.2-2.3 (m, 1H), 2.5-2.6 (m, 1H), 4.52 (d, 1H, J=10 Hz), 7.0-7.1 (min, H), 7.1-7.2 (m, 2H), 7.3-7.4 (m, 1H), 7.46 (br s, 2H). 2H portion is not observable.

MS: 428.13[M+Na]$^+$

Example 70

(1S,2S)-2-(1H-benzo[d]imidazol-2-yl)-N—((R)-1-(2,3-dihydrobenzo[b][1,4]dioxin-6-yl)ethyl)cyclopropane-1-carboxamide

[Chemical Formula 97]

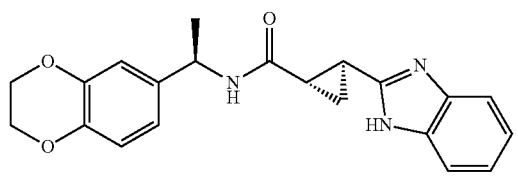

According to a technique similar to that of Example 89, the title compound (white powder, 51 mg, 87%) was obtained using (R)-1-(2,3-dihydrobenzo[b][1,4]dioxin-6-yl)ethan-1-amine (29 mg, 0.16 mmol).

$^1$H NMR (CDCl$_3$, 400 MHz): δ=1.39 (d, 3H, J=7 Hz), 1.6-1.7 (m, 2H), 2.3-2.4 (m, 1H), 2.8-2.9 (m, 1H), 4.23 (s, 4H), 5.02 (q, 1H, J=7 Hz), 6.7-6.9 (m, 3H), 7.1-7.2 (m, 2H), 7.45 (br s, 2H). 2H portion is not observable.

MS: 386.17[M+Na]$^+$

Example 71

Trans-2-(5-methoxy-1H-benzo[d]imidazol-2-yl)-N—((R)-1-(5-(2,2,2-trifluoroethoxy)thiophen-2-yl)ethyl)cyclopropane-1-carboxamide

[Chemical Formula 98]

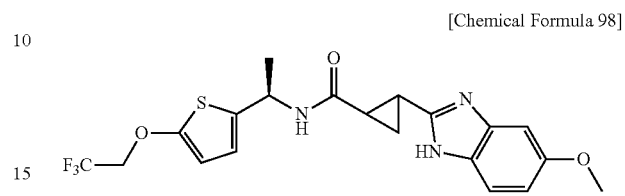

According to a technique similar to that of Example 1, diastereomer A of the title compound (upper spot in TLC (hexane/ethyl acetate=1/9), white crystals, 47 mg, 35%) and diastereomer B of the title compound (lower spot in TLC (hexane/ethyl acetate=1/9), white crystals, 44 mg, 33%) were obtained using (R)-1-(5-(2,2,2-trifluoroethoxy)thiophen-2-yl)ethan-1-amine hydrochloride (80 mg, 0.31 mmol) synthesized in Reference Example 4 and trans-2-(5-methoxy-1H-benzo[d]imidazol-2-yl)cyclopropane-1-carboxylic acid (85 mg, 0.37 mmol) synthesized in Reference Example 56-2.

Diastereomer A $^1$H NMR (DMSO-d$_6$, 400 MHz): δ=1.3-1.5 (m, 2H), 1.40 (d, 3H, J=7 Hz), 2.1-2.3 (m, 1H), 2.3-2.5 (m, 1H), 3.74 (s, 1.2H), 3.78 (s, 1.8H), 4.78 (q, 2H, J=9 Hz), 5.04 (quint, 1H, J=7 Hz), 6.35 (d, 1H, J=4 Hz), 6.61 (d, 1H, J=4 Hz), 6.7-6.8 (m, 1H), 6.90 (s, 0.6H), 7.01 (s, 0.4H), 7.27 (s, 0.4H), 7.34 (s, 0.6H), 8.75 (d, 1H, J=8 Hz), 12.2-12.3 (m, 1H).

MS: 438.21[M–H]$^-$

Diastereomer B $^1$H NMR (DMSO-d$_6$, 400 MHz): δ=1.3-1.5 (m, 2H), 1.41 (d, 3H, J=7 Hz), 2.1-2.3 (m, 1H), 2.3-2.5 (m, 1H), 3.75 (s, 3H), 4.76 (q, 2H, J=9 Hz), 5.04 (quint, 1H, J=7 Hz), 6.33 (d, 1H, J=4 Hz), 6.60 (d, 1H, J=4 Hz), 6.7-6.8 (m, 1H), 6.90 (s, 0.6H), 7.01 (s, 0.4H), 7.27 (s, 0.4H), 7.34 (s, 0.6H), 8.75 (d, 1H, J=8 Hz), 12.1-12.4 (m, 1H).

MS: 438.19[M–H]$^-$

Example 72

(1S,2S)-2-(1H-benzo[d]imidazol-2-yl)-N—((R)-1-(3-cyclopropyl-1,2,4-oxadiazol-5-yl)ethyl)cyclopropane-1-carboxamide

[Chemical Formula 99]

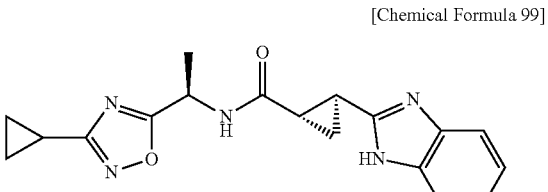

According to a technique similar to that of Example 89, the title compound (white powder, 51 mg, 87%) was obtained using (R)-1-(3-cyclopropyl-1,2,4-oxadiazol-5-yl)ethan-1-amine hydrochloride (33 mg, 0.17 mmol) synthesized in Reference Example 16-2.

¹H NMR (CD₃OD, 400 MHz): δ=0.9-1.1 (m, 4H), 1.54 (d, 3H, J=7 Hz), 1.6-1.7 (m, 2H), 2.0-2.1 (m, 1H), 2.2-2.3 (m, 1H), 2.5-2.6 (m, 1H), 5.20 (q, 1H, J=7 Hz), 7.1-7.2 (m, 2H), 7.46 (br s, 2H). 2H portion is not observable.

MS: 338.16[M+H]⁺

Example 73

(1S,2S)-2-(1H-benzo[d]imidazol-2-yl)-N—((R)-1-(2,2-difluorobenzo[d][1,3]dioxol-5-yl)ethyl)cyclopropane-1-carboxamide

[Chemical Formula 100]

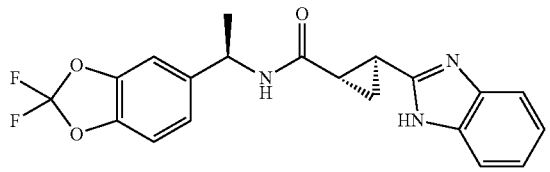

According to a technique similar to that of Example 89, the title compound (white powder, 43 mg, 75%) was obtained using (R)-1-(2,2-difluorobenzo[d][1,3]dioxol-5-yl)ethan-1-amine (30 mg, 0.15 mmol).

¹H NMR (CD₃OD, 400 MHz): δ=1.44 (d, 3H, J=7 Hz), 1.5-1.6 (m, 2H), 2.2-2.3 (m, 1H), 2.5-2.6 (m, 1H), 5.01 (q, 1H, J=7 Hz), 7.1-7.2 (m, 5H), 7.4-7.5 (m, 2H). 2H portion is not observable.

MS: 386.13[M+H]⁺

Example 74

(1S,2S)-2-(1H-benzo[d]imidazol-2-yl)-N—((R)-1-(5-cyclopropylfuran-2-yl)ethyl)cyclopropane-1-carboxamide

[Chemical Formula 101]

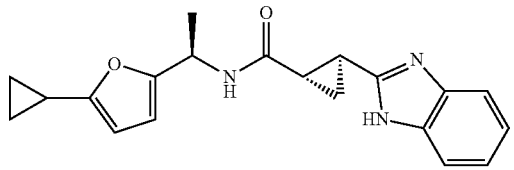

According to a technique similar to that of Example 89, the title compound (white powder, 42 mg, 78%) was obtained using (R)-1-(5-cyclopropylfuran-2-yl)ethan-1-amine (24 mg, 0.16 mmol) synthesized in Reference Example 15-2.

¹H NMR (CD₃OD, 400 MHz): δ=0.6-0.7 (m, 2H), 0.8-0.9 (m, 2H), 1.41 (d, 3H, J=8 Hz), 1.5-1.6 (m, 2H), 1.8-1.9 (m, 1H), 2.2-2.3 (m, 1H), 2.5-2.6 (m, 1H), 5.04 (q, 1H, J=8 Hz), 5.88 (d, 1H, J=3 Hz), 6.07 (d, 1H, J=3 Hz), 7.1-7.2 (m, 2H), 7.46 (br s, 2H). 2H portion is not observable.

MS: 358.17[M+Na]⁺

Example 75

Trans-2-(1H-benzo[d]imidazol-2-yl)-N—((R)-1-(5-(piperazine-1-carbonyl)thiophen-2-yl)ethyl)cyclopropane-1-carboxamide

[Chemical Formula 102]

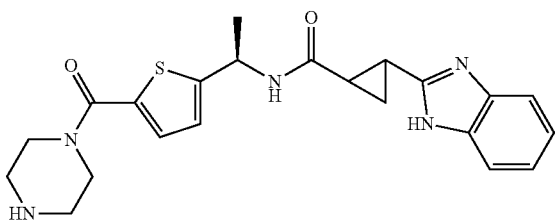

According to a technique similar to that of Example 1, trans-4-(5-((1R)-1-(2-(1H-benzo[d]imidazol-2-yl)cyclopropane-1-carboxamido)ethyl)thiophene-2-carbonyl)piperazine-1-carboxylic acid tert-butyl ester (12.3 mg, 23%) was obtained using trans-5-((1R)-1-(2-(1H-benzo[d]imidazol-2-yl)cyclopropane-1-carboxamido)ethyl)thiophene-2-carboxylic acid (36 mg, 0.10 mmol) synthesized in Example 26 and 1-(tert-butoxycarbonyl)piperazine (23 mg, 0.12 mmol). Subsequently, according to a technique similar to that of Reference Example 12-2, the title compound (white crystals, 2.1 mg, 21%) was obtained using trans-4-(5-((1R)-1-(2-(1H-benzo[d]imidazol-2-yl)cyclopropane-1-carboxamido)ethyl)thiophene-2-carbonyl)piperazine-1-carboxylic acid tert-butyl ester (12.3 mg, 0.023 mmol) synthesized in Reference Example 12-2.

¹H NMR (DMSO-d₆, 400 MHz): δ=1.4-1.6 (m, 2H), 1.46 (d, 3H, J=7 Hz), 2.2-2.5 (m, 2H), 2.6-2.8 (m, 4H), 3.5-3.6 (m, 4H), 5.20 (quint, 1H, J=7 Hz), 6.95 (d, 1H, J=4 Hz), 7.1-7.2 (m, 2H), 7.22 (d, 1H, J=4 Hz), 7.3-7.5 (m, 2H), 8.90 (d, 1H, J=8 Hz), 12.41 (s, 1H). 1H portion is not observable.

MS: 424.19[M+H]⁺

Example 76

(1S,2S)-2-(1H-benzo[d]imidazol-2-yl)-N—((R)-1-(benzofuran-2-yl)ethyl)cyclopropane-1-carboxamide

[Chemical Formula 103]

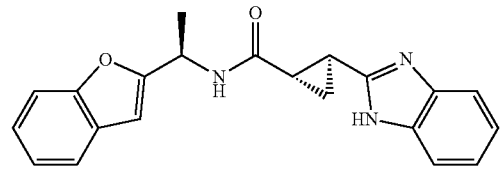

According to a technique similar to that of Example 89, the title compound (white powder, 53 mg, 80%) was obtained using (R)-1-(benzofuran-2-yl)ethan-1-amine (31 mg, 0.19 mmol).

¹H NMR (CD₃OD, 400 MHz): δ=1.56 (d, 3H, J=7 Hz), 1.6-1.7 (m, 2H), 2.2-2.3 (m, 1H), 2.6-2.7 (m, 1H), 5.27 (q, 1H, J=7 Hz), 6.65 (s, 1H), 7.1-7.3 (m, 4H), 7.43 (dd, 1H, J=1, 7 Hz), 7.45 (br s, 2H), 7.53 (dd, 1H, J=1, 7 Hz). 2H portion is not observable.

MS: 368.16[M+Na]⁺

Example 77

Trans-2-(5-chloro-1H-benzo[d]imidazol-2-yl)-N—((R)-1-(3-cyclopropyl-1,2,4-oxadiazol-5-yl)ethyl)cyclopropane-1-carboxamide

[Chemical Formula 104]

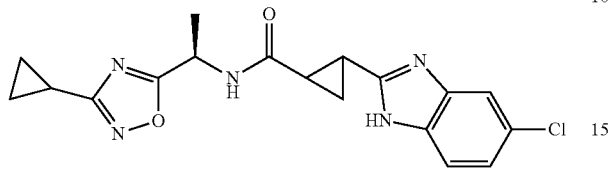

According to a technique similar to that of Example 1, diastereomer A of the title compound (upper spot in TLC (hexane/ethyl acetate=1/3), white powder, 28 mg, 47%) and diastereomer B of the title compound (lower spot in TLC (hexane/ethyl acetate=1/3), white powder, 25 mg, 42%) were obtained using (R)-1-(3-cyclopropyl-1,2,4-oxadiazol-5-yl)ethan-1-amine hydrochloride (30 mg, 0.16 mmol) synthesized in Reference Example 16-2 and trans-2-(5-chloro-1H-benzo[d]imidazol-2-yl)cyclopropane-1-carboxylic acid (45 mg, 0.19 mmol) synthesized in Reference Example 55-2.

Diastereomer A $^1$H NMR (CDCl$_3$, 400 MHz): δ=1.0-1.1 (m, 4H), 1.5-1.8 (m, 5H), 2.0-2.2 (m, 1H), 2.3-2.4 (m, 1H), 2.6-2.7 (m, 1H), 5.33 (q, 1H, J=7 Hz), 6.56 (d, 1H, J=7 Hz), 7.20 (dd, 1H, J=2, 9 Hz), 7.3-7.7 (m, 2H). 1H portion is not observable.

MS: 372.14[M+H]$^+$

Diastereomer B $^1$H NMR (CDCl$_3$, 400 MHz): δ=0.6-0.8 (m, 1H), 0.8-1.0 (m, 3H), 1.5-1.6 (m, 3H), 1.7-1.9 (m, 3H), 2.2-2.3 (m, 1H), 2.4-2.6 (m, 1H), 5.31 (quint, 1H, J=7 Hz), 6.74 (d, 1H, J=8 Hz), 7.17 (dd, 1H, J=2, 9 Hz), 7.3-7.7 (m, 1H), 10.0-10.0.2 (m, 1H). 1H portion is not observable.

MS: 372.14[M+H]$^+$

Example 78

(1S,2S)-2-(1H-benzo[d]imidazol-2-yl)-N—((R)-1-(2,3-dihydrobenzofuran-5-yl)ethyl)cyclopropane-1-carboxamide

[Chemical Formula 105]

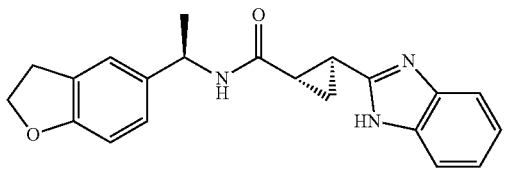

According to a technique similar to that of Example 89, the title compound (white powder, 46 mg, 78%) was obtained using (R)-1-(2,3-dihydrobenzofuran-5-yl)ethan-1-amine (28 mg, 0.17 mmol) synthesized in Reference Example 45-2.

$^1$H NMR (CD$_3$OD, 400 MHz): δ=1.41 (d, 3H, J=7 Hz), 1.5-1.6 (m, 2H), 2.2-2.3 (m, 1H), 2.5-2.6 (m, 1H), 3.17 (t, 2H, J=9 Hz), 4.51 (t, 2H, J=9 Hz), 4.96 (q, 1H, J=7 Hz), 6.66 (d, 1H, J=8 Hz), 7.05 (d, 1H, J=8 Hz), 7.1-7.2 (m, 3H), 7.45 (br s, 2H). 2H portion is not observable.

MS: 370.16[M+Na]$^+$

Example 79

(1S,2S)-2-(1H-benzo[d]imidazol-2-yl)-N—((R)-1-(5-methoxybenzofuran-2-yl)ethyl)cyclopropane-1-carboxamide

[Chemical Formula 106]

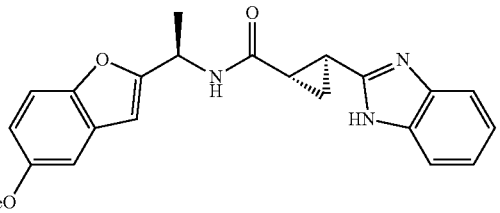

According to a technique similar to that of Example 89, the title compound (white powder, 49 mg, 73%) was obtained using (R)-1-(5-methoxybenzofuran-2-yl)ethan-1-amine (34 mg, 0.18 mmol) synthesized in Reference Example 32-3.

$^1$H NMR (CD$_3$OD, 400 MHz): δ=1.54 (d, 3H, J=7 Hz), 1.6-1.7 (m, 2H), 2.2-2.3 (m, 1H), 2.6-2.7 (m, 1H), 3.80 (s, 3H), 5.24 (q, 1H, J=7 Hz), 6.59 (s, 1H), 6.84 (dd, 1H, J=2, 9 Hz), 7.04 (d, 1H, J=2 Hz), 7.1-7.2 (m, 2H), 7.31 (d, 1H, J=9 Hz), 7.4-7.5 (m, 2H). 2H portion is not observable.

MS: 398.15[M+Na]$^+$

Example 80

(1S,2S)-2-(1H-benzo[d]imidazol-2-yl)-N-(1-(furo[3,2-b]pyridin-2-yl)ethyl)cyclopropane-1-carboxamide

[Chemical Formula 107]

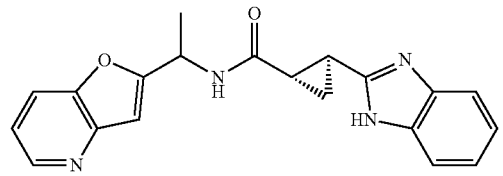

According to a technique similar to that of Example 89, a diastereomer mixture of the title compound (pale yellow powder, 99 mg, 81%) was obtained using 1-(furo[3,2-b]pyridin-2-yl)ethan-1-amine (57 mg, 0.35 mmol) synthesized in Reference Example 38-3.

Diastereomer mixture (0.6:0.4)

$^1$H NMR (CD$_3$OD, 400 MHz): δ=1.5-1.7 (m, 5H), 2.2-2.4 (m, 1H), 2.5-2.7 (m, 1H), 5.3-5.4 (m, 1H), 6.81 (s, 0.4H), 6.83 (s, 0.6H), 7.1-7.2 (m, 2H), 7.3-7.4 (m, 1H), 7.47 (br s, 2H), 7.8-8.0 (m, 1H), 8.4-8.5 (m, 1H). 2H portion is not observable.

MS: 369.13[M+Na]$^+$

Example 81

(1S,2S)-2-(5-chloro-1H-benzo[d]imidazol-2-yl)-N—((R)-1-(5-fluorobenzofuran-2-yl)ethyl)cyclopropane-1-carboxamide

[Chemical Formula 108]

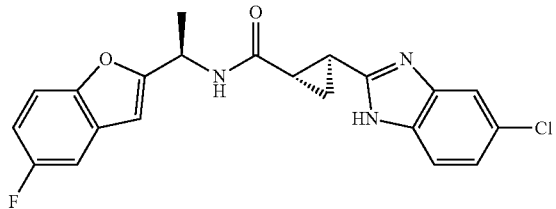

According to a technique similar to that of Example 1, the title compound (white powder, 44 mg, 63%) was obtained using (R)-1-(5-fluorobenzofuran-2-yl)ethan-1-amine (31 mg, 0.18 mmol) synthesized in Reference Example 23-3 and (1S,2S)-2-(5-chloro-1H-benzo[d]imidazol-2-yl)cyclopropane-1-carboxylic acid (49 mg, 0.21 mmol) synthesized in Reference Example 65-2.

$^1$H NMR (CD$_3$OD, 400 MHz): δ=1.55 (d, 3H, J=7 Hz), 1.6-1.7 (m, 2H), 2.2-2.3 (m, 1H), 2.5-2.6 (m, 1H), 5.25 (q, 1H, J=7 Hz), 6.65 (s, 1H), 6.99 (ddd, 1H, J=2, 8, 8 Hz), 7.1-7.3 (m, 2H), 7.4-7.5 (m, 3H). 2H portion is not observable.

MS: 396.05[M−H]$^-$

Example 82

(1S,2S)-2-(1H-benzo[d]imidazol-2-yl)-N—((R)-1-(5-chlorobenzofuran-2-yl)ethyl)cyclopropane-1-carboxamide

[Chemical Formula 109]

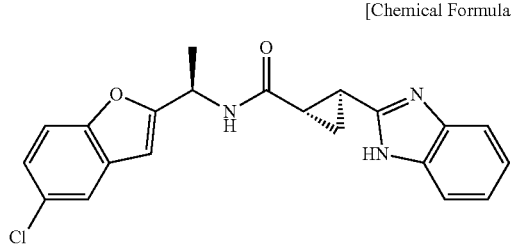

According to a technique similar to that of Example 89, the title compound (white powder, 44 mg, 67%) was obtained using (R)-1-(5-chlorobenzofuran-2-yl)ethan-1-amine (34 mg, 0.173 mmol).

$^1$H NMR (CD$_3$OD, 400 MHz): δ=1.55 (d, 3H, J=7 Hz), 1.6-1.7 (m, 2H), 2.2-2.3 (m, 1H), 2.6-2.7 (m, 1H), 5.26 (q, 1H, J=7 Hz), 6.65 (s, 1H), 7.1-7.2 (m, 2H), 7.23 (dd, 1H, J=2, 9 Hz), 7.42 (d, 1H, J=9 Hz), 7.46 (br s, 2H), 7.54 (d, 1H, J=2 Hz). 2H portion is not observable.

MS: 380.11[M+H]$^+$

Example 83

(1S,2S)-2-(1H-benzo[d]imidazol-2-yl)-N—((R)-1-(5-(3,3-difluoroazetidine-1-carbonyl)thiophen-2-yl)ethyl)cyclopropane-1-carboxamide

[Chemical Formula 110]

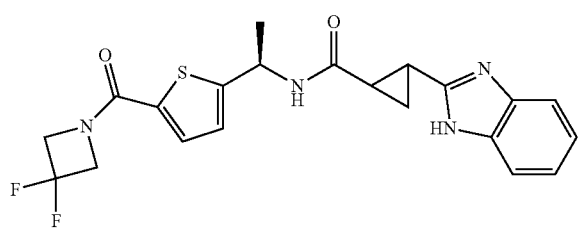

According to a technique similar to that of Example 1, the title compound (white crystals, 8 mg, 41%) was obtained using trans-5-((1R)-1-(2-(1H-benzo[d]imidazol-2-yl)cyclopropane-1-carboxamido)ethyl)thiophene-2-carboxylic acid (18 mg, 0.051 mmol) synthesized in Example 26 and 3,3-difluoroazetidine hydrochloride (9 mg, 0.061 mmol).

$^1$H NMR (DMSO-d$_6$, 400 MHz): δ=1.4-1.6 (m, 2H), 1.46 (d, 3H, J=7 Hz), 2.2-2.5 (m, 2H), 4.2-5.3 (m, 4H), 5.21 (quint, 1H, J=7 Hz), 7.04 (d, 1H, J=4 Hz), 7.1-7.2 (m, 2H), 7.3-7.6 (m, 2H), 7.41 (d, 1H, J=4 Hz), 8.93 (d, 1H, J=8 Hz), 12.42 (br s, 1H).

MS: 431.12[M+H]$^+$

Example 84

5-((R)-1-((1S,2S)-2-(1H-benzo[d]imidazol-2-yl)cyclopropane-1-carboxamido)ethyl)-N,N-dimethyl-thiophene-2-carboxamide

[Chemical Formula 111]

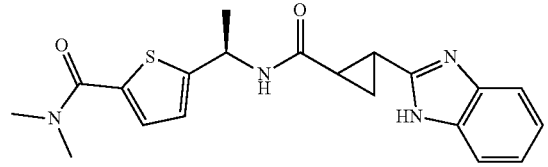

According to a technique similar to that of Example 1, trans-5-((1R)-1-(2-(1H-benzo[d]imidazol-2-yl)cyclopropane-1-carboxamido)ethyl)thiophene-2-carboxylic acid (20 mg, 0.056 mmol) synthesized in Example 26 and N,N-dimethylamine (2.0 M ethanol solution) (34 μL, 0.068 mmol) were dissolved in ethanol (0.6 mL), and DMT-MM (20 mg, 0.073 mmol) was added to the solution. The mixture was stirred overnight. A saturated aqueous solution of sodium hydrogen carbonate was added to the reaction liquid, and the mixture was stirred for a while. Subsequently, the mixture was extracted with ethyl acetate. The organic layer was washed sequentially with a saturated aqueous solution of ammonium chloride and saturated brine, and the organic layer was dried over anhydrous sodium sulfate. Insoluble matters were filtered, and then the solvent was distilled off under reduced pressure. A residue thus obtained was purified by silica gel column chromatography (ethyl acetate:methanol) (concentration gradient: 0% to 10%) and recrystallization (hexane:ethyl acetate), and thus the title compound (white crystals, 16 mg, 75%) was obtained.

$^1$H NMR (DMSO-d$_6$, 400 MHz): δ=1.4-1.6 (m, 2H), 1.46 (d, 3H, J=7 Hz), 2.2-2.5 (m, 2H), 3.10 (br s, 6H), 5.20 (quint, 1H, J=7 Hz), 6.96 (d, 1H, J=4 Hz), 7.0-7.2 (m, 2H), 7.3-7.6 (m, 2H), 7.34 (d, 1H, J=4 Hz), 8.90 (d, 1H, J=8 Hz), 12.41 (br s, 1H).

MS: 383.14[M+H]$^+$

Example 85

Trans-2-(6-chloro-3H-imidazo[4,5-b]pyridin-2-yl)-N—((R)-1-(5-(2,2,2-trifluoroethoxy)thiophen-2-yl)ethyl)cyclopropane-1-carboxamide

[Chemical Formula 112]

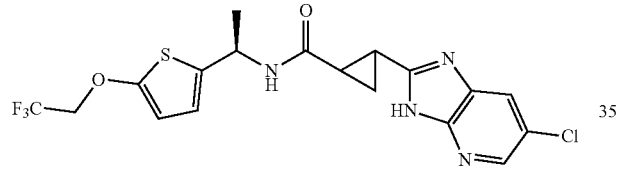

According to a technique similar to that of Example 1, diastereomer A of the title compound (upper spot in TLC (ethyl acetate), white crystals, 8 mg, 11%) and diastereomer B of the title compound (lower spot in TLC (ethyl acetate), white crystals, 23 mg, 34%) were obtained using (R)-1-(5-(2,2,2-trifluoroethoxy)thiophen-2-yl)ethan-1-amine hydrochloride (40 mg, 0.15 mmol) synthesized in Reference Example 4 and trans-2-(6-chloro-3H-imidazo[4,5-b]pyridin-2-yl)cyclopropane-1-carboxylic acid (44 mg, 0.18 mmol) synthesized in Reference Example 58-2.

Diastereomer A $^1$H NMR (DMSO-d$_6$, 400 MHz): δ=1.40 (d, 3H, J=7 Hz), 1.4-1.6 (m, 2H), 2.2-2.5 (m, 2H), 4.78 (q, 2H, J=9 Hz), 5.04 (quint, 1H, J=7 Hz), 6.35 (d, 1H, J=4 Hz), 6.61 (d, 1H, J=3 Hz), 8.00 (d, 1H, J=2 Hz), 8.24 (d, 1H, J=2 Hz), 8.79 (d, 1H, J=8 Hz), 13.07 (br s, 1H).

MS: 445.05[M+H]$^+$

Diastereomer B $^1$H NMR (DMSO-d$_6$, 400 MHz): δ=1.4-1.6 (m, 2H), 1.42 (d, 3H, J=7 Hz), 2.3-2.5 (m, 2H), 4.76 (q, 2H, J=9 Hz), 5.04 (quint, 1H, J=7 Hz), 6.34 (d, 1H, J=4 Hz), 6.60 (dd, 1H, J=1, 4 Hz), 8.00 (d, 1H, J=2 Hz), 8.24 (d, 1H, J=2 Hz), 8.80 (d, 1H, J=8 Hz), 12.96 (br s, 1H).

MS: 443.02[M−H]$^−$

Example 86

(1S,2S)-2-(1H-benzo[d]imidazol-2-yl)-N—((R)-1-(1-methyl-1H-indol-6-yl)ethyl)cyclopropane-1-carboxamide

[Chemical Formula 113]

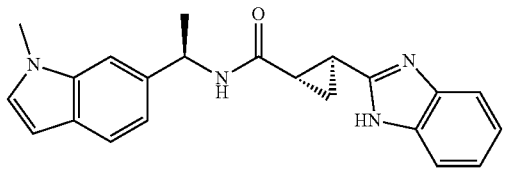

According to a technique similar to that of Example 89, the title compound (white powder, 35 mg, 54%) was obtained using (R)-1-(1-methyl-1H-indol-6-yl)ethan-1-amine (31 mg, 0.18 mmol) synthesized in Reference Example 44-2.

$^1$H NMR (CD$_3$OD, 400 MHz): δ=1.52 (d, 3H, J=7 Hz), 1.6-1.7 (m, 2H), 2.2-2.3 (m, 1H), 2.5-2.6 (m, 1H), 3.80 (s, 3H), 5.16 (q, 1H, J=7 Hz), 6.37 (d, 1H, J=3 Hz), 7.04 (dd, 1H, J=2, 8 Hz), 7.11 (d, 1H, J=3 Hz), 7.1-7.2 (m, 2H), 7.33 (s, 1H), 7.46 (br s, 2H), 7.49 (d, 1H, J=8 Hz). 2H portion is not observable.

MS: 359.18[M+H]$^+$

Example 87

(1S,2S)—N—((R)-1-(5-(azepane-1-carbonyl)thiophen-2-yl)ethyl)-2-(1H-benzo[d]imidazol-2-yl)cyclopropane-1-carboxamide

[Chemical Formula 114]

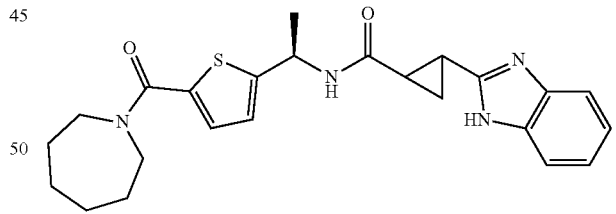

According to a technique similar to that of Example 1, the title compound (white crystals, 3 mg, 10%) was obtained using trans-5-((1R)-1-(2-(1H-benzo[d]imidazol-2-yl)cyclopropane-1-carboxamido)ethyl)thiophene-2-carboxylic acid (20 mg, 0.056 mmol) synthesized in Example 26 and hexamethylenimine (8 μL, 0.068 mmol).

$^1$H NMR (DMSO-d$_6$, 400 MHz): δ=1.4-1.8 (m, 10H), 1.46 (d, 3H, J=7 Hz), 2.2-2.5 (m, 2H), 3.5-3.7 (m, 4H), 5.20 (quint, 1H, J=7 Hz), 6.95 (d, 1H, J=3 Hz), 7.1-7.2 (m, 2H), 7.26 (d, 1H, J=4 Hz), 7.4-7.5 (m, 2H), 8.89 (d, 1H, J=8 Hz), 12.41 (br s, 1H).

MS: 437.20[M+H]$^+$

Example 88

(1S,2S)-2-(1H-benzo[d]imidazol-2-yl)-N—((R)-1-(5,7-difluorobenzofuran-2-yl)ethyl)cyclopropane-1-carboxamide

[Chemical Formula 115]

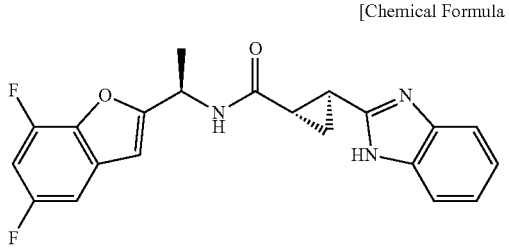

According to a technique similar to that of Example 89, the title compound (white powder, 44 mg, 68%) was obtained using (R)-1-(5,7-difluorobenzofuran-2-yl)ethan-1-amine (34 mg, 0.17 mmol) synthesized in Reference Example 28-3.

$^1$H NMR (CD$_3$OD, 400 MHz): δ=1.57 (d, 3H, J=7 Hz), 1.6-1.7 (m, 2H), 2.2-2.3 (m, 1H), 2.6-2.7 (m, 1H), 5.27 (q, 1H, J=7 Hz), 6.74 (d, 1H, J=3 Hz), 6.93 (ddd, 1H, J=2, 8, 10 Hz), 7.12 (dd, 1H, J=2, 8 Hz), 7.1-7.2 (m, 2H), 7.46 (br s, 2H). 2H portion is not observable.

MS: 382.14[M+H]$^+$

Example 89

(1S,2S)-2-(1H-benzo[d]imidazol-2-yl)-N—((R)-1-(2-phenylthiazol-5-yl)ethyl)cyclopropane-1-carboxamide

[Chemical Formula 116]

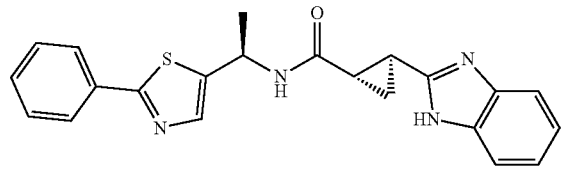

According to a technique similar to that of Example 1, the title compound (white crystals, 4 mg, 16%) was obtained using (R)-1-(2-phenylthiazol-5-yl)ethan-1-amine (12 mg, 0.059 mmol) synthesized in Reference Example 53-2 and (1S,2S)-2-(1H-benzo[d]imidazol-2-yl)cyclopropane-1-carboxylic acid (14 mg, 0.071 mmol) synthesized in Reference Example 62-2.

$^1$H NMR (DMSO-d$_6$, 400 MHz): δ=1.4-1.6 (m, 2H), 1.53 (d, 3H, J=7 Hz), 2.2-2.3 (m, 1H), 2.4-2.5 (m, 1H), 5.29 (quint, 1H, J=7 Hz), 7.1-7.2 (m, 2H), 7.4-7.6 (m, 5H), 7.76 (s, 1H), 7.8-8.0 (m, 2H), 8.96 (d, 1H, J=8 Hz), 12.42 (br s, 1H).

MS: 389.13[M+H]$^+$

Example 90

Trans-2-(benzo[d]oxazol-2-yl)-N—((R)-1-(2-(2,2,2-trifluoroethoxy)thiazol-5-yl)ethyl)cyclopropane-1-carboxamide

[Chemical Formula 117]

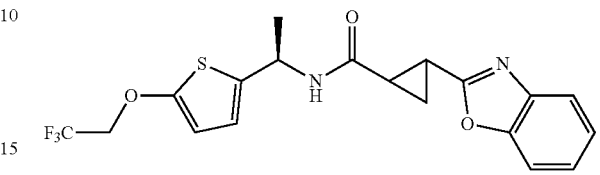

According to a technique similar to that of Example 1, diastereomer A of the title compound (upper spot in TLC (hexane/ethyl acetate=1/1), pale yellow powder, 30 mg, 31%) and diastereomer B of the title compound (lower spot in TLC (hexane/ethyl acetate=1/1), pale yellow powder, 29 mg, 30%) were obtained using (R)-1-(2-(2,2,2-trifluoroethoxy) thiazol-5-yl)ethan-1-amine (53 mg, 0.23 mmol) synthesized in Reference Example 6-2 and a crude form of trans-2-(benzo[d]oxazol-2-yl)cyclopropane-1-carboxylic acid (100 mg) synthesized in Reference Example 67-2.

Diastereomer A $^1$H NMR (DMSO-d$_6$, 400 MHz): δ=1.46 (d, 3H, J=7 Hz), 1.5-1.6 (m, 2H), 2.3-2.5 (m, 1H), 2.5-2.6 (m, 1H), 5.0-5.2 (m, 3H), 7.11 (s, 1H), 7.3-7.4 (m, 2H), 7.6-7.7 (m, 2H), 8.91 (d, 1H, J=8 Hz).

MS: 410.08[M–H]$^-$

Diastereomer B $^1$H NMR (DMSO-d$_6$, 400 MHz): δ=1.46 (d, 3H, J=7 Hz), 1.5-1.6 (m, 2H), 2.3-2.6 (m, 2H), 5.0-5.2 (m, 3H), 7.10 (s, 1H), 7.3-7.4 (m, 2H), 7.6-7.7 (m, 2H), 8.92 (d, 1H, J=8 Hz).

MS: 410.07[M–H]$^-$

Example 91

(1S,2S)-2-(1H-benzo[d]imidazol-2-yl)-N—((R)-1-(5,6-difluorobenzofuran-2-yl)ethyl)cyclopropane-1-carboxamide

[Chemical Formula 118]

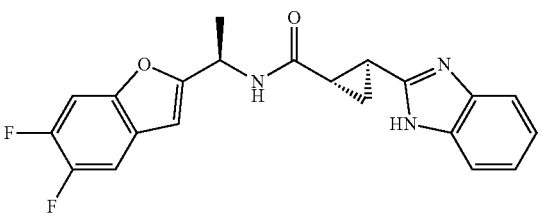

According to a technique similar to that of Example 89, the title compound (white powder, 49 mg, 75%) was obtained using (R)-1-(5,6-difluorobenzofuran-2-yl)ethan-1-amine (34 mg, 0.17 mmol) synthesized in Reference Example 29-3.

$^1$H NMR (CD$_3$OD, 400 MHz): δ=1.54 (d, 3H, J=7 Hz), 1.6-1.7 (m, 2H), 2.2-2.3 (m, 1H), 2.6-2.7 (m, 1H), 5.24 (q, 1H, J=7 Hz), 6.67 (s, 1H), 7.1-7.2 (m, 2H), 7.4-7.6 (m, 4H). 2H portion is not observable.

MS: 382.13[M+H]$^+$

Example 92

(1S,2S)-2-(1H-benzo[d]imidazol-2-yl)-N—((R)-1-(4,6-difluorobenzofuran-2-yl)ethyl)cyclopropane-1-carboxamide

[Chemical Formula 119]

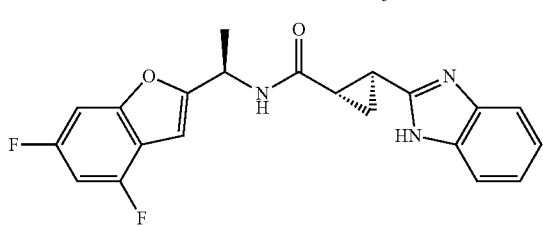

According to a technique similar to that of Example 89, the title compound (white powder, 42 mg, 65%) was obtained using (R)-1-(4,6-difluorobenzofuran-2-yl)ethan-1-amine (34 mg, 0.17 mmol) synthesized in Reference Example 30-3.

$^1$H NMR (CD$_3$OD, 400 MHz): δ=1.55 (d, 3H, J=7 Hz), 1.6-1.7 (m, 2H), 2.2-2.3 (m, 1H), 2.6-2.7 (m, 1H), 5.25 (q, 1H, J=7 Hz), 6.73 (s, 1H), 6.86 (ddd, 1H, J=2, 10.10 Hz), 7.1-7.2 (m, 3H), 7.49 (br s, 2H). 2H portion is not observable.

MS: 382.13[M+H]$^+$

Example 93

(1S,2S)-2-(1H-benzo[d]imidazol-2-yl)-N—((R)-1-(pyrazolo[1,5-a]pyridin-2-yl)ethyl)cyclopropane-1-carboxamide

[Chemical Formula 120]

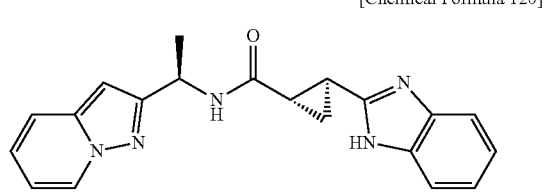

According to a technique similar to that of Example 89, the title compound (white powder, 20 mg, 33%) was obtained using (R)-1-(pyrazolo[1,5-a]pyridin-2-yl)ethan-1-amine (28 mg, 0.17 mmol) synthesized in Reference Example 43-2.

$^1$H NMR (CD$_3$OD, 400 MHz): δ=1.57 (d, 3H, J=7 Hz), 1.6-1.7 (m, 2H), 2.3-2.4 (m, 1H), 2.6-2.7 (m, 1H), 5.31 (q, 1H, J=7 Hz), 6.50 (s, 1H), 6.83 (ddd, 1H, J=1, 7, 7 Hz), 7.1-7.2 (m, 3H), 7.4-7.5 (m, 2H), 7.57 (d, 1H, J=9 Hz), 8.44 (dd, 1H, J=1, 7 Hz). 2H portion is not observable.

MS: 368.14[M+Na]$^+$

Example 94

(1S,2S)-2-(1H-benzo[d]imidazol-2-yl)-N—((R)-1-(5-(4,4-difluoropiperidine-1-carbonyl)thiophen-2-yl)ethyl)cyclopropane-1-carboxamide

[Chemical Formula 121]

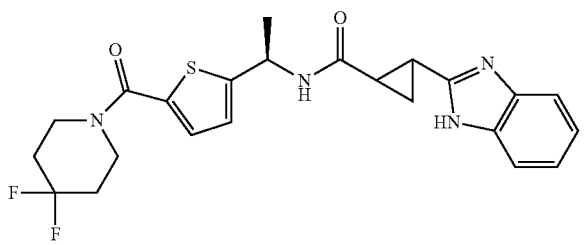

According to a technique similar to that of Example 1, the title compound (pale yellow crystals, 19 mg, 74%) was obtained using trans-5-((1R)-1-(2-(1H-benzo[d]imidazol-2-yl)cyclopropane-1-carboxamido)ethyl)thiophene-2-carboxylic acid (20 mg, 0.056 mmol) synthesized in Example 26 and 4,4-difluoropiperidine hydrochloride (11 mg, 0.068 mmol).

$^1$H NMR (DMSO-d$_6$, 400 MHz): δ=1.4-1.6 (m, 2H), 1.46 (d, 3H, J=7 Hz), 2.0-2.2 (m, 4H), 2.2-2.5 (m, 2H), 3.7-3.8 (m, 4H), 5.21 (quint, 1H, J=7 Hz), 6.97 (d, 1H, J=4 Hz), 7.0-7.2 (m, 2H), 7.32 (d, 1H, J=4 Hz), 7.3-7.5 (m, 2H), 8.91 (d, 1H, J=8 Hz), 12.40 (s, 1H).

MS: 457.15[M−H]$^-$

Example 95

(1S,2S)-2-(1H-benzo[d]imidazol-2-yl)-N-((1R)-1-(5-(3-fluoropiperidine-1-carbonyl)thiophen-2-yl)ethyl)cyclopropane-1-carboxamide

[Chemical Formula 122]

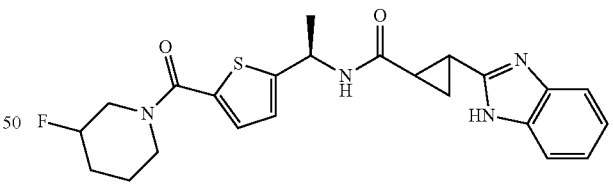

According to a technique similar to that of Example 1, the title compound (pale yellow crystals, 25 mg, 57%) was obtained using trans-5-((1R)-1-(2-(1H-benzo[d]imidazol-2-yl)cyclopropane-1-carboxamido)ethyl)thiophene-2-carboxylic acid (35 mg, 0.099 mmol) synthesized in Example 26 and 3-fluoropiperidine hydrochloride (17 mg, 0.12 mmol).

$^1$H NMR (DMSO-d$_6$, 400 MHz): δ=1.4-2.0 (m, 6H), 1.46 (d, 3H, J=7 Hz), 2.2-2.4 (m, 1H), 2.4-2.5 (m, 1H), 3.0-3.7 (m, 2H), 3.9-4.2 (m, 2H), 4.7-4.9 (m, 1H), 5.21 (quint, 1H, J=7 Hz), 6.96 (d, 1H, J=4 Hz), 7.1-7.2 (m, 2H), 7.23 (d, 1H, J=4 Hz), 7.3-7.6 (m, 2H), 8.91 (d, 1H, J=8 Hz), 12.40 (br s, 1H).

MS: 439.15[M−H]$^-$

Example 96

(1S,2S)-2-(1H-benzo[d]imidazol-2-yl)-N—((R)-1-(7-fluorobenzofuran-2-yl)ethyl)cyclopropane-1-carboxamide

[Chemical Formula 123]

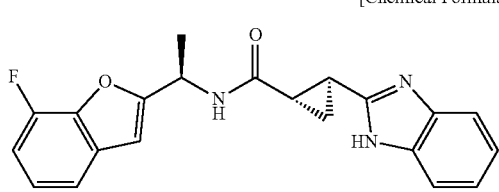

According to a technique similar to that of Example 89, the title compound (white powder, 58 mg, 94%) was obtained using (R)-1-(7-fluorobenzofuran-2-yl)ethan-1-amine (30 mg, 0.17 mmol) synthesized in Reference Example 26-3.

$^1$H NMR (CD$_3$OD, 400 MHz): δ=1.59 (d, 3H, J=7 Hz), 1.6-1.7 (m, 2H), 2.3-2.4 (m, 1H), 2.6-2.7 (m, 1H), 5.30 (q, 1H, J=7 Hz), 6.72 (dd, 1H, J=1, 3 Hz), 7.03 (ddd, 1H, J=1, 8, 11 Hz), 7.1-7.2 (m, 3H), 7.34 (dd, 1H, J=1, 8 Hz), 7.46 (br s, 2H). 2H portion is not observable.

MS: 386.11[M+Na]$^+$

Example 97

(1S,2S)-2-(1H-benzo[d]imidazol-2-yl)-N—((R)-1-(4-fluorobenzofuran-2-yl)ethyl)cyclopropane-1-carboxamide

[Chemical Formula 124]

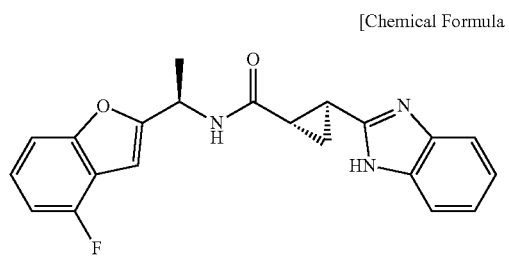

According to a technique similar to that of Example 89, the title compound (white powder, 50 mg, 81%) was obtained using (R)-1-(4-fluorobenzofuran-2-yl)ethan-1-amine (31 mg, 0.17 mmol) synthesized in Reference Example 25-3.

$^1$H NMR (CD$_3$OD, 400 MHz): δ=1.58 (d, 3H, J=7 Hz), 1.6-1.7 (m, 2H), 2.3-2.4 (m, 1H), 2.6-2.7 (m, 1H), 5.28 (q, 1H, J=7 Hz), 6.74 (s, 1H), 6.94 (dd, 1H, J=8, 8 Hz), 7.1-7.3 (m, 4H), 7.46 (br s, 2H). 2H portion is not observable.

MS: 386.12[M+Na]$^+$

Example 98

Trans-N—((R)-1-(5-fluorobenzofuran-2-yl)ethyl)-2-(1H-indol-3-yl)cyclopropane-1-carboxamide

[Chemical Formula 125]

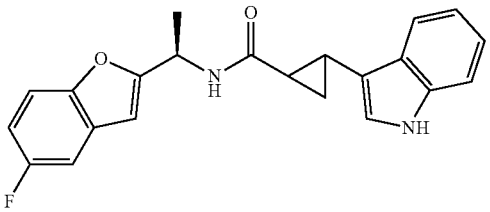

According to a technique similar to that of Example 1, diastereomer A of the title compound (upper spot in TLC (ethyl acetate/hexane=1/1), pale yellow powder, 2.4 mg, 2%) and diastereomer B of the title compound (lower spot in TLC (ethyl acetate/hexane=1/1), pale yellow powder, 12 mg, 9%) were obtained using (R)-1-(5-fluorobenzofuran-2-yl)ethan-1-amine (61 mg, 0.34 mmol) synthesized in Reference Example 23-3 and trans-2-(1H-indol-3-yl)cyclopropane-1-carboxylic acid (82 mg, 0.41 mmol).

Diastereomer A $^1$H NMR (CD$_3$OD, 400 MHz): δ=1.2-1.3 (m, 1H), 1.4-1.5 (m, 1H), 1.60 (d, 3H, J=7 Hz), 1.8-1.9 (m, 1H), 2.4-2.5 (m, 1H), 5.30 (q, 1H, J=7 Hz), 6.65 (s, 1H), 6.9-7.1 (m, 4H), 7.23 (dd, 1H, J=3, 9 Hz), 7.31 (d, 1H, J=8 Hz), 7.41 (dd, 1H, J=4, 9 Hz), 7.57 (d, 1H, J=8 Hz). 2H portion is not observable.

MS: 385.13[M+Na]$^+$

Diastereomer B $^1$H NMR (CD$_3$OD, 400 MHz): δ=1.2-1.3 (m, 1H), 1.5-1.6 (m, 1H), 1.57 (d, 3H, J=7 Hz), 1.8-1.9 (m, 1H), 2.4-2.5 (m, 1H), 5.31 (q, 1H, J=7 Hz), 6.67 (s, 1H), 6.9-7.1 (m, 4H), 7.25 (dd, 1H, J=3, 9 Hz), 7.30 (d, 1H, J=8 Hz), 7.44 (dd, 1H, J=4, 9 Hz), 7.53 (d, 1H, J=8 Hz). 2H portion is not observable.

MS: 385.12[M+Na]$^+$

Example 99

(1S,2S)-2-(1H-benzo[d]imidazol-2-yl)-N-(1-(furo[3,2-c]pyridin-2-yl)ethyl)cyclopropane-1-carboxamide

[Chemical Formula 126]

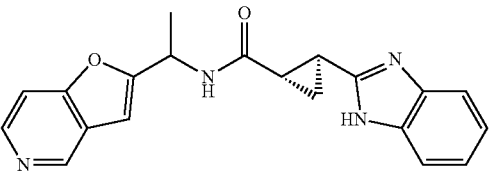

According to a technique similar to that of Example 89, a diastereomer mixture of the title compound (pale yellow powder, 37 mg, 54%) was obtained using 1-(furo[3,2-c]pyridin-2-yl)ethan-1-amine (33 mg, 0.20 mmol) synthesized in Reference Example 39-4.

$^1$H NMR (CD$_3$OD, 400 MHz): δ=1.5-1.7 (m, 5H), 2.2-2.4 (m, 1H), 2.5-2.7 (m, 1H), 5.2-5.4 (m, 1H), 6.84 (s, 0.4H), 6.85 (s, 0.6H), 7.1-7.2 (m, 2H), 7.46 (br s, 2H), 7.5-7.6 (m, 1H), 8.3-8.4 (m, 1H), 8.80 (s, 0.4H), 8.83 (s, 0.6H). 2H portion is not observable.

MS: 347.14[M+H]+

Example 100

(1S,2S)-2-(1H-benzo[d]imidazol-2-yl)-N—((R)-1-(6-fluorobenzofuran-2-yl)ethyl)cyclopropane-1-carboxamide

[Chemical Formula 127]

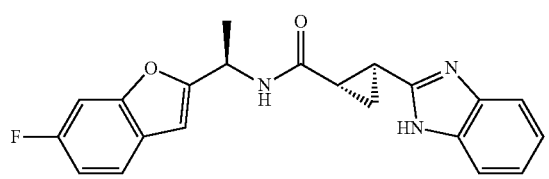

According to a technique similar to that of Example 89, the title compound (white powder, 40 mg, 65%) was obtained using (R)-1-(6-fluorobenzofuran-2-yl)ethan-1-amine (30 mg, 0.17 mmol) synthesized in Reference Example 27-4.

$^1$H NMR (CD$_3$OD, 400 MHz): δ=1.56 (d, 3H, J=7 Hz), 1.6-1.7 (m, 2H), 2.2-2.3 (m, 1H), 2.6-2.7 (m, 1H), 5.26 (q, 1H, J=7 Hz), 6.66 (s, 1H), 7.00 (ddd, 1H, J=2, 9, 9 Hz), 7.1-7.2 (m, 2H), 7.24 (dd, 1H, J=2, 9 Hz), 7.4-7.5 (m, 2H), 7.51 (dd, 1H, J=6, 9 Hz). 2H portion is not observable.

MS: 364.13[M+H]+

Example 101

(1S,2S)-2-(1H-benzo[d]imidazol-2-yl)-N—((R)-1-(5-fluoro-3-methylbenzofuran-2-yl)ethyl)cyclopropane-1-carboxamide

[Chemical Formula 128]

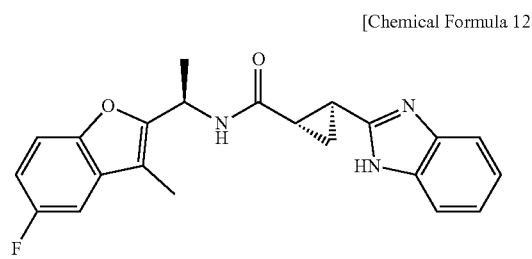

According to a technique similar to that of Example 89, the title compound (white powder, 50 mg, 77%) was obtained using (R)-1-(5-fluoro-3-methylbenzofuran-2-yl)ethan-1-amine (33 mg, 0.17 mmol) synthesized in Reference Example 31-3.

$^1$H NMR (CD$_3$OD, 400 MHz): δ=1.5-1.6 (m, 5H), 2.2-2.3 (m, 4H), 2.5-2.6 (m, 1H), 5.34 (q, 1H, J=7 Hz), 6.99 (ddd, 1H, J=2, 9, 9 Hz), 7.1-7.2 (m, 3H), 7.37 (dd, 1H, J=4, 9 Hz), 7.46 (br s, 2H). 2H portion is not observable.

MS: 400.14[M+Na]+

Example 102

(1S,2S)-2-(1-ethyl-1H-benzo[d]imidazol-2-yl)-N—((R)-1-(5-fluorobenzofuran-2-yl)ethyl)cyclopropane-1-carboxamide

[Chemical Formula 129]

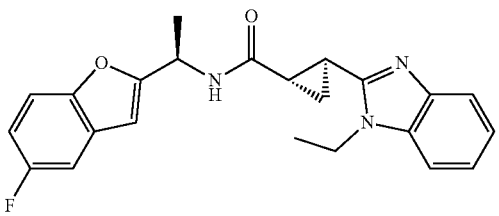

According to a technique similar to that of Example 1, the title compound (white crystals, 98 mg, 86%) was obtained using (R)-1-(5-fluorobenzofuran-2-yl)ethan-1-amine (52 mg, 0.31 mmol) synthesized in Reference Example 23-3 and a crude form of (1S,2S)-2-(1-ethyl-1H-benzo[d]imidazol-2-yl)cyclopropane-1-carboxylic acid (125 mg) synthesized in Reference Example 63-2.

$^1$H NMR (DMSO-d$_6$, 400 MHz): δ=1.33 (t, 3H, J=7 Hz), 1.4-1.6 (m, 2H), 1.48 (d, 3H, J=7 Hz), 2.3-2.4 (m, 1H), 2.5-2.6 (m, 1H), 4.3-4.4 (m, 2H), 5.21 (quint, 1H, J=7 Hz), 6.74 (s, 1H), 7.0-7.3 (m, 3H), 7.41 (dd, 1H, J=2, 9 Hz), 7.52 (t, 1H, J=8 Hz), 7.58 (dd, 1H, J=4, 8 Hz), 8.90 (d, 1H, J=8 Hz), 12.40 (br s, 1H).

MS: 392.17[M+H]+

Example 103

Trans-N—((R)-1-(5-fluorobenzofuran-2-yl)ethyl)-2-(1-methyl-1H-indazol-6-yl)cyclopropane-1-carboxamide

[Chemical Formula 130]

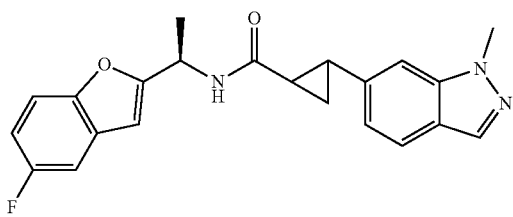

According to a technique similar to that of Example 1, diastereomer A of the title compound (upper spot in TLC (hexane/ethyl acetate=1/1), pale yellow powder, 30 mg, 31%) and diastereomer B of the title compound (lower spot in TLC (hexane/ethyl acetate=1/1), pale yellow powder, 29 mg, 30%) were obtained using (R)-1-(5-fluorobenzofuran-2-yl)ethan-1-amine (82 mg, 0.46 mmol) synthesized in Reference Example 23-3 and trans-2-(1-methyl-1H-indazol-6-yl)cyclopropane-1-carboxylic acid (119 mg, 0.55 mmol).

Diastereomer A $^1$H NMR (DMSO-d$_6$, 400 MHz): δ=1.3-1.5 (m, 2H), 1.47 (d, 3H, J=7 Hz), 2.0-2.1 (m, 1H), 2.4-2.5 (m, 1H), 4.01 (s, 3H), 5.19 (quint, 1H, J=7 Hz), 6.72 (s, 1H), 6.90 (d d, 1H, J=1, 9 Hz), 7.11 (dt, 1H, J=3, 9 Hz), 7.41 (dd, 1H, J=3, 9 Hz), 7.43 s, 1H), 7.58 (dd, 1H, J=4, 9 Hz), 7.65 (d, 1H, J=9 Hz), 7.97 (s, 1H), 8.74 d, 1H, J=8 Hz).

MS: 376.13[M−H]⁻

Diastereomer B

¹H NMR (DMSO-d₆, 400 MHz): δ=1.3-1.5 (m, 2H), 1.48 (d, 3H, J=7 Hz), 2.0-2.1 (m, 1H), 2.4-2.5 (m, 1H), 3.99 (s, 3H), 5.18 (quint, 1H, J=7 Hz), 6.72 (s, 1H), 6.88 (d d, 1H, J=1, 9 Hz), 7.08 (dt, 1H, J=3, 9 Hz), 7.34 (dd, 1H, J=3, 9 Hz), 7.42 (s, 1H), 7.55 (dd, 1H, J=4, 9 Hz), 7.64 (d, 1H, J=8 Hz), 7.95 (s, 1H), 8.74 d, 1H, J=8 Hz).

MS: 376.13[M−H]⁻

Example 104

(1S,2S)-2-(1H-benzo[d]imidazol-2-yl)-N-(1-(5-fluorobenzo[d]thiazol-2-yl)ethyl)cyclopropane-1-carboxamide

[Chemical Formula 131]

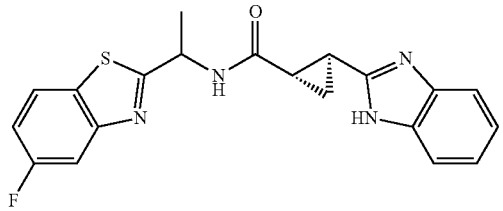

According to a technique similar to that of Example 89, the title compound (Rf value=0.3 in TLC (ethyl acetate/hexane=3/1), pale yellow powder, 46 mg, 71%) was obtained using 1-(5-fluorobenzo[d]thiazol-2-yl)ethan-1-amine (33 mg, 0.17 mmol).

¹H NMR (CD₃OD, 400 MHz): δ=1.6-1.7 (m, 5H), 2.3-2.4 (m, 1H), 2.6-2.7 (m, 1H), 5.41 (q, 1H, J=7 Hz), 7.1-7.3 (m, 3H), 7.47 (br s, 2H), 7.65 (dd, 1H, J=2, 10 Hz), 7.96 (dd, 1H, J=5, 9 Hz). 2H portion is not observable.

MS: 381.10[M+H]⁺

Example 105

(1S,2S)-2-(1H-benzo[d]imidazol-2-yl)-N—((R)-1-(5-fluorobenzo[d]oxazol-2-yl)ethyl)cyclopropane-1-carboxamide

[Chemical Formula 132]

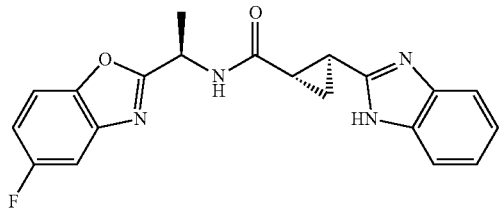

According to a technique similar to that of Example 89, the title compound (white powder, 42 mg, 66%) was obtained using (R)-1-(5-fluorobenzo[d]oxazol-2-yl)ethan-1-amine (31 mg, 0.17 mmol) synthesized in Reference Example 42-4.

¹H NMR (CD₃OD, 400 MHz): δ=1.6-1.7 (m, 5H), 2.3-2.4 (m, 1H), 2.6-2.7 (m, 1H), 5.31 (q, 1H, J=7 Hz), 7.1-7.2 (m, 3H), 7.40 (dd, 1H, J=2, 8 Hz), 7.47 (br s, 2H), 7.61 (dd, 1H, J=4, 9 Hz). 2H portion is not observable.

MS: 387.12[M+Na]⁺

Example 106

Trans-2-(5-methyl-3H-imidazo[4,5-b]pyridin-2-yl)-N—((R)-1-(5-(2,2,2-trifluoroethoxy)thiophen-2-yl)ethyl)cyclopropane-1-carboxamide

[Chemical Formula 133]

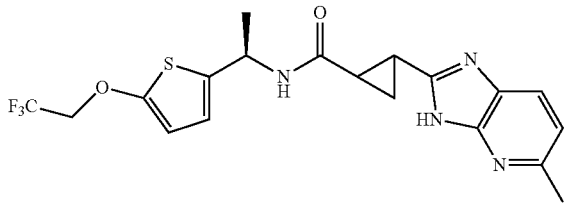

According to a technique similar to that of Example 1, diastereomer A of the title compound (upper spot in TLC (ethyl acetate/methanol=9/1), white crystals, 24 mg, 23%) and diastereomer B of the title compound (lower spot in TLC (ethyl acetate/methanol=9/1), white crystals, 34 mg, 32%) were obtained using (R)-1-(5-(2,2,2-trifluoroethoxy)thiophen-2-yl)ethan-1-amine hydrochloride (65 mg, 0.25 mmol) synthesized in Reference Example 4 and a crude form of trans-2-(5-methyl-3H-imidazo[4,5-b]pyridin-2-yl)cyclopropane-1-carboxylic acid (108 mg) synthesized in Reference Example 60-2.

Diastereomer A

¹H NMR (DMSO-d₆, 400 MHz): δ=1.3-1.6 (m, 2H), 1.40 (d, 3H, J=7 Hz), 2.2-2.3 (m, 1H), 2.4-2.5 (m, 4H), 4.78 (q, 2H, J=9 Hz), 5.05 (quint, 1H, J=7 Hz), 6.36 (d, 1H, J=4 Hz), 6.61 (d, 1H, J=4 Hz), 7.01 (d, 1H, J=8 Hz), 7.71 (d, 1H, J=8 Hz), 8.77 (d, 1H, J=8 Hz), 12.72 (br s, 1H).

MS: 423.11[M−H]⁻

Diastereomer B

¹H NMR (DMSO-d₆, 400 MHz): δ=1.4-1.5 (m, 2H), 1.42 (d, 3H, J=7 Hz), 2.2-2.6 (m, 5H), 4.75 (q, 2H, J=9 Hz), 5.05 (quint, 1H, J=7 Hz), 6.33 (d, 1H, J=3 Hz), 6.60 (d, 1H, J=3 Hz), 7.01 (d, 1H, J=8 Hz), 7.70 (d, 1H, J=8 Hz), 8.77 (d, 1H, J=8 Hz), 12.72 (br s, 1H).

MS: 423.11[M−H]⁻

Example 107

(1S,2S)-2-(1H-benzo[d]imidazol-2-yl)-N—((R)-1-(5-cyanobenzofuran-2-yl)ethyl)cyclopropane-1-carboxamide

[Chemical Formula 134]

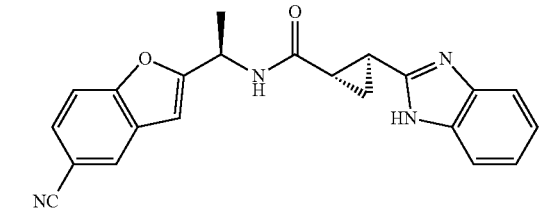

According to a technique similar to that of Example 89, the title compound (white powder, 30 mg, 58%) was obtained using (R)-2-(1-aminoethyl)benzofuran-5-carbonitrile (26 mg, 0.14 mmol) synthesized in Reference Example 33-4.

$^1$H NMR (CD$_3$OD, 400 MHz): δ=1.58 (d, 3H, J=7 Hz), 1.6-1.7 (m, 2H), 2.2-2.3 (m, 1H), 2.6-2.7 (m, 1H), 5.30 (q, 1H, J=7 Hz), 6.80 (s, 1H), 7.1-7.2 (m, 2H), 7.4-7.5 (m, 2H), 7.61 (dd, 1H, J=2, 9 Hz), 7.65 (d, 1H, J=9 Hz), 8.01 (d, 1H, J=2 Hz). 2H portion is not observable.

MS: 393.14[M+Na]$^+$

Example 108

Trans-2-(5-chlorobenzo[d]oxazol-2-yl)-N—((R)-1-(5-fluorobenzofuran-2-yl)ethyl)cyclopropane-1-carboxamide

[Chemical Formula 135]

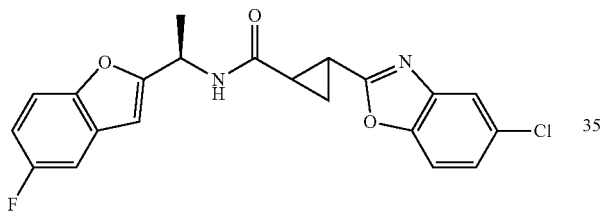

According to a technique similar to that of Example 1, diastereomer A of the title compound (upper spot in TLC (ethyl acetate/hexane=1/1), white powder, 8 mg, 29%) and diastereomer B of the title compound (lower spot in TLC (ethyl acetate/hexane=1/1), white powder, 9 mg, 32%) were obtained using a crude form of (R)-1-(5-fluorobenzofuran-2-yl)ethan-1-amine hydrochloride (0.08 mmol) synthesized in Reference Example 77-1 and a crude form of trans-2-(5-chlorobenzo[d]oxazol-2-yl)cyclopropane-1-carboxylic acid lithium salt (0.07 mmol) synthesized in Reference Example 68-2.

Diastereomer A $^1$H NMR (CDCl$_3$, 400 MHz): δ=1.59 (d, 3H, J=7 Hz), 1.6-1.9 (m, 2H), 2.1-2.3 (m, 1H), 2.7-2.9 (m, 1H), 5.38 (quint, 1H, J=7 Hz), 6.08 (d, 1H, J=8 Hz), 6.57 (s, 1H), 6.99 (dt, 1H, J=3, 9 Hz), 7.18 (dd, 1H, J=3, 9 Hz), 7.2-7.3 (m, 3H), 7.59 (d, 1H, J=2 Hz).

MS: 397.08[M−H]$^−$

Diastereomer B $^1$H NMR (CDCl$_3$, 400 MHz): δ=1.61 (d, 3H, J=7 Hz), 1.6-1.9 (m, 2H), 2.1-2.3 (m, 1H), 2.7-2.8 (m, 1H), 5.38 (quint, 1H, J=7 Hz), 6.08 (d, 1H, J=9 Hz), 6.56 (s, 1H), 6.97 (dt, 1H, J=3, 9 Hz), 7.16 (dd, 1H, J=3, 9 Hz), 7.2-7.4 (m, 3H), 7.57 (d, 1H, J=2 Hz).

MS: 397.09[M−H]$^−$

Example 109

(1S,2S)-2-(1H-benzo[d]imidazol-2-yl)-N—((R)-1-(5-(trifluoromethyl)benzofuran-2-yl)ethyl)cyclopropane-1-carboxamide

[Chemical Formula 136]

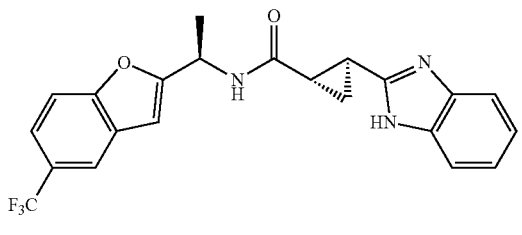

According to a technique similar to that of Example 89, the title compound (white powder, 58 mg, 82%) was obtained using (R)-1-(5-(trifluoromethyl)benzofuran-2-yl)ethan-1-amine (39 mg, 0.17 mmol) synthesized in Reference Example 34-3.

$^1$H NMR (CD$_3$OD, 400 MHz): δ=1.59 (d, 3H, J=7 Hz), 1.6-1.7 (m, 2H), 2.2-2.3 (m, 1H), 2.6-2.7 (m, 1H), 5.31 (q, 1H, J=7 Hz), 6.81 (s, 1H), 7.1-7.2 (m, 2H), 7.47 (br s, 2H), 7.56 (dd, 1H, J=2, 9 Hz), 7.63 (d, 1H, J=9 Hz), 7.91 (s, 1H). 2H portion is not observable.

MS: 436.12[M+Na]$^+$

Example 110

(1S,2S)-2-(1-ethyl-1H-benzo[d]imidazol-2-yl)-N—((R)-1-(6-fluorobenzofuran-2-yl)ethyl)cyclopropane-1-carboxamide

[Chemical Formula 137]

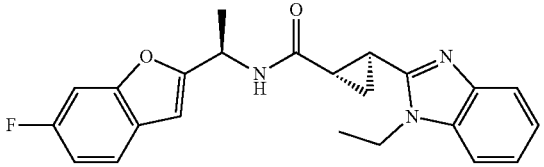

According to a technique similar to that of Example 1, the title compound (pale yellow powder, 36 mg, 57%) was obtained using (R)-1-(6-fluorobenzofuran-2-yl)ethan-1-amine (29 mg, 0.16 mmol) synthesized in Reference Example 27-4 and (1S,2S)-2-(1-ethyl-1H-benzo[d]imidazol-2-yl)cyclopropane-1-carboxylic acid (48 mg, 0.21 mmol) synthesized in Reference Example 63-2.

$^1$H NMR (CD$_3$OD, 400 MHz): δ=1.44 (t, 3H, J=7 Hz), 1.58 (d, 3H, J=7 Hz), 1.6-1.7 (m, 2H), 2.2-2.3 (m, 1H), 2.6-2.7 (m, 1H), 4.40 (q, 2H, J=7 Hz), 5.28 (q, 1H, J=7 Hz), 6.67 (s, 1H), 7.00 (ddd, 1H, J=2, 8, 10 Hz), 7.2-7.3 (m, 3H), 7.4-7.6 (m, 3H). 1H portion is not observable.

MS: 414.15[M+Na]$^+$

Example 111

(1S,2S)-2-(1H-benzo[d]imidazol-2-yl)-N—((S)-1-(5-fluorobenzofuran-2-yl)ethyl)cyclopropane-1-carboxamide

[Chemical Formula 138]

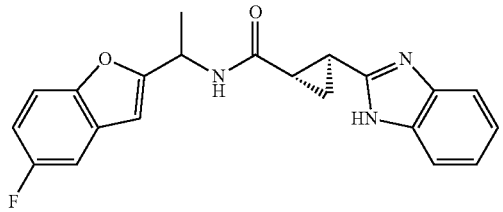

According to a technique similar to that of Example 89, the title compound (white powder, 20 mg, 56%) was obtained using (S)-1-(5-fluorobenzofuran-2-yl)ethan-1-amine (20 mg, 0.11 mmol) synthesized in Reference Example 24 and (1S,2S)-2-(1H-benzo[d]imidazol-2-yl)cyclopropane-1-carboxylic acid (20 mg, 0.099 mmol) synthesized in Reference Example 62-2.

$^1$H NMR (CDCl$_3$, 400 MHz): δ=1.5-1.6 (m, 3H), 1.6-1.8 (m, 2H), 2.2-2.3 (m, 1H), 2.5-2.7 (m, 1H), 5.36 (quint, 1H, J=7 Hz), 6.20 (d, 1H, J=8 Hz), 6.52 (s, 1H), 6.94 (ddd, 1H, J=3, 9, 9 Hz), 7.13 (dd, 1H, J=2, 8), 7.2-7.4 (m, 4H), 7.6-7.7 (m, 1H), 9.29 (br s, 1H).

MS: 364.15[M+H]$^+$

Example 112

Trans-N—((R)-1-(5-fluorobenzofuran-2-yl)ethyl)-2-((4-fluorophenoxy)methyl)cyclopropane-1-carboxamide

[Chemical Formula 139]

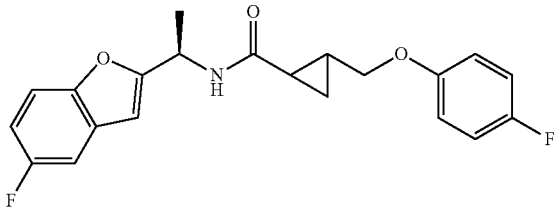

According to a technique similar to that of Example 1, diastereomer A of the title compound (upper spot in TLC (ethyl acetate/hexane=1/1), white powder, 14 mg, 34%) and diastereomer B of the title compound (lower spot in TLC (ethyl acetate/hexane=1/1), white powder, 15 mg, 36%) were obtained using a crude form of (R)-1-(5-fluorobenzofuran-2-yl)ethan-1-amine hydrochloride (0.11 mmol) synthesized in Reference Example 77-1 and a crude form of trans-2-((4-fluorophenoxy)methyl)cyclopropane-1-carboxylic acid lithium salt (0.19 mmol) synthesized in Reference Example 74-3.

Diastereomer A $^1$H NMR (CDCl$_3$, 400 MHz): δ=0.8-1.0 (m, 1H), 1.31 (quint, 1H, J=5 Hz), 1.45 (quint, 1H, J=5 Hz), 1.59 (d 3H, J=7 Hz), 1.8-2.0 (m, 1H), 3.78 (dd, 1H, J=5, 10 Hz), 4.03 (dd, 1H, J=5, 10 Hz), 5.36 (quint, 1H, J=7 Hz), 5.94 (d, 1H, J=8 Hz), 6.54 (s, 1H), 6.7-7.1 (m, 5H), 7.17 (dd, 1H, J=3, 8 Hz), 7.36 (dd, 1H, J=4, 9 Hz).

MS: 370.13[M–H]$^-$

Diastereomer B $^1$H NMR (CDCl$_3$, 400 MHz): δ=0.9-1.0 (m, 1H), 1.32 (quint, 1H, J=5 Hz), 1.46 (quint, 1H, J=5 Hz), 1.58 (d 3H, J=7 Hz), 1.8-2.0 (m, 1H), 3.79 (dd, 1H, J=7, 10 Hz), 3.99 (dd, 1H, J=6, 10 Hz), 5.36 (quint, 1H, J=7 Hz), 5.94 (d, 1H, J=8 Hz), 6.54 (s, 1H), 6.7-7.1 (m, 5H), 7.18 (dd, 1H, J=3, 8 Hz), 7.37 (dd, 1H, J=4, 9 Hz).

MS: 370.14[M–H]$^-$

Example 113

(1S,2S)-2-(1H-benzo[d]imidazol-2-yl)-N-((5-fluorobenzofuran-2-yl)methyl)cyclopropane-1-carboxamide

[Chemical Formula 140]

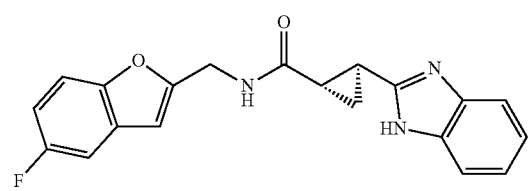

According to a technique similar to that of Example 1, the title compound (white powder, 70 mg, 71%) was obtained using (5-fluorobenzofuran-2-yl)methanamine (46 mg, 0.28 mmol) synthesized in Reference Example 37-2 and (1S,2S)-2-(1H-benzo[d]imidazol-2-yl)cyclopropane-1-carboxylic acid (85 mg, 0.42 mmol) synthesized in Reference Example 62-2.

$^1$H NMR (DMSO-d$_6$, 400 MHz): δ=1.4-1.6 (m, 2H), 2.32 (ddd, 1H, J=4, 6, 8 Hz), 2.4-2.6 (m, 1H), 4.4-4.6 (m, 2H), 6.74 (d, 1H, J=1 Hz), 7.0-7.2 (m, 3H), 7.3-7.5 (m, 3H), 7.56 (dd, 1H, J=4, 9 Hz), 8.93 (dd, 1H, J=6, 6 Hz), 12.41 (br s, 1H).

MS: 350.14[M+H]

Example 114

(1S,2S)-2-(1H-benzo[d]imidazol-2-yl)-N—((R)-1-(6-fluorobenzo[d]oxazol-2-yl)ethyl)cyclopropane-1-carboxamide

[Chemical Formula 141]

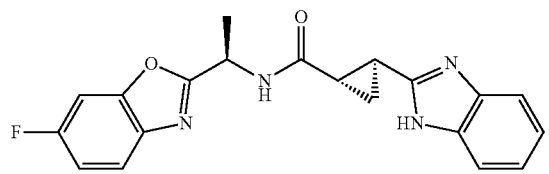

According to a technique similar to that of Example 89, the title compound (white powder, 52 mg, 82%) was obtained using (R)-1-(6-fluorobenzo[d]oxazol-2-yl)ethan-1-amine (31 mg, 0.17 mmol).

¹H NMR (CD₃OD, 400 MHz): δ=1.6-1.7 (m, 5H), 2.3-2.4 (m, 1H), 2.6-2.7 (m, 1H), 5.31 (q, 1H, J=7 Hz), 7.1-7.2 (m, 3H), 7.44 (dd, 1H, J=3, 8 Hz), 7.46 (br s, 2H), 7.66 (dd, 1H, J=5, 9 Hz). 2H portion is not observable.

MS: 387.14[M+Na]⁺

Example 115

(1S,2S)-2-(1H-benzo[d]imidazol-2-yl)-N—((S)-2-methyl-1-(5-(trifluoromethyl)thiophen-2-yl)propyl)cyclopropane-1-carboxamide

[Chemical Formula 142]

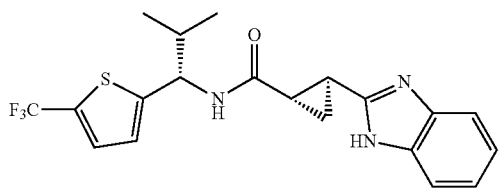

According to a technique similar to that of Example 1, the title compound (pale yellow crystals, 18 mg, 54%) was obtained using (S)-2-methyl-1-(5-(trifluoromethyl)thiophen-2-yl)propan-1-amine (18 mg, 0.081 mmol) synthesized in Reference Example 20 and (1S,2S)-2-(1H-benzo[d]imidazol-2-yl)cyclopropane-1-carboxylic acid (20 mg, 0.097 mmol) synthesized in Reference Example 62-2.

¹H NMR (DMSO-d₆, 400 MHz): δ=0.85 (d, 3H, J=6 Hz), 0.93 (d, 3H, J=7 Hz), 1.4-1.6 (m, 2H), 2.0-2.2 (m, 1H), 2.3-2.5 (m, 2H), 4.97 (t, 1H, J=8 Hz), 7.0-7.2 (m, 3H), 7.3-7.5 (m, 2H), 7.56 (d, 1H, J=2 Hz), 8.82 (d, 1H, J=9 Hz), 12.36 (br s, 1H).

MS: 408.14[M+H]⁺

Example 116

(1S,2S)-2-(1H-benzo[d]imidazol-2-yl)-N—((S)-cyclohexyl(5-(trifluoromethyl)thiophen-2-yl)methyl)cyclopropane-1-carboxamide

[Chemical Formula 143]

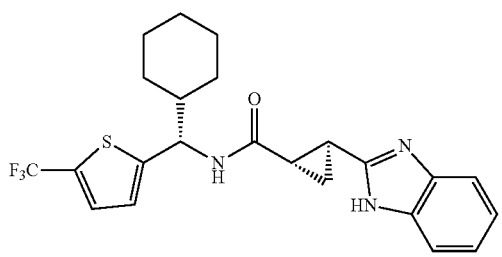

According to a technique similar to that of Example 1, the title compound (pale yellow crystals, 15 mg, 10%) was obtained using (S)-cyclohexyl(5-(trifluoromethyl)thiophen-2-yl)methanamine (28 mg, 0.11 mmol) synthesized in Reference Example 22 and (1S,2S)-2-(1H-benzo[d]imidazol-2-yl)cyclopropane-1-carboxylic acid (26 mg, 0.13 mmol) synthesized in Reference Example 62-2.

¹H NMR (DMSO-d₆, 400 MHz): δ=0.9-1.3 (m, 5H), 1.4-1.8 (m, 8H), 2.3-2.5 (m, 2H), 4.97 (t, 1H, J=9 Hz), 7.0-7.2 (m, 3H), 7.3-7.5 (m, 2H), 7.55 (d, 1H, J=2 Hz), 8.82 (d, 1H, J=9 Hz), 12.35 (br s, 1H).

MS: 448.16[M+H]⁺

Example 117

N—((R)-1-(5-fluorobenzofuran-2-yl)ethyl)-2-(imidazo[1,5-a]pyridin-3-yl)cyclopropane-1-carboxamide

[Chemical Formula 144]

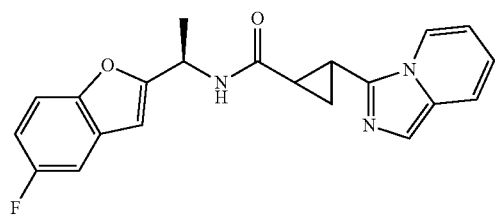

According to a technique similar to that of Example 1, diastereomer A of the title compound (upper spot in TLC (hexane/ethyl acetate=1/3), pale yellow powder, 17 mg, 26%) and diastereomer B of the title compound (lower spot in TLC (hexane/ethyl acetate=1/3), white powder, 24 mg, 36%) were obtained using (R)-1-(5-fluorobenzofuran-2-yl)ethan-1-amine (32 mg, 0.18 mmol) synthesized in Reference Example 23-3 and a crude form of 2-(imidazo[1,5-a]pyridin-3-yl)cyclopropane-1-carboxylic acid (75 mg) synthesized in Reference Example 69-3.

Diastereomer A

¹H NMR (CD₃OD, 400 MHz): δ=1.52 (ddd, 1H, J=4, 6, 8 Hz), 1.59 (d, 3H, J=7 Hz), 1.64 (ddd, 1H, J=4, 5, 9 Hz), 2.16 (ddd, 1H, J=4, 5, 8 Hz), 2.72 (ddd, 1H, J=4, 6, 9 Hz), 5.29 (q, 1H, J=7 Hz), 6.67 (s, 1H), 6.73 (ddd, 1H, J=1, 6, 7 Hz), 6.80 (ddd, 1H, J=1, 6, 9 Hz), 7.00 (td, 1H, J=3, 9 Hz), 7.25 (dd, 1H, J=3, 9 Hz), 7.27 (s, 1H), 7.42 (dd, 1H, J=4, 9 Hz), 7.50 (td, 1H, J=1, 9 Hz), 8.16 (dd, 1H, J=1, 7 Hz). 1H portion is not observable.

MS: 364.16[M+H]⁺

Diastereomer B

¹H NMR (CD₃OD, 400 MHz): δ=1.54 (ddd, 1H, J=4, 6, 9 Hz), 1.59 (d, 3H, J=7 Hz), 1.66 (ddd, 1H, J=4, 5, 9 Hz), 2.13 (ddd, 1H, J=4, 5, 9 Hz), 2.69 (ddd, 1H, J=4, 6, 9 Hz), 5.30 (q, 1H, J=7 Hz), 6.64 (ddd, 1H, J=1, 6, 7 Hz), 6.68 (t, 1H, J=1 Hz), 6.78 (ddd, 1H, J=1, 6, 9 Hz), 7.00 (td, 1H, J=3, 9 Hz), 7.2-7.3 (m, 2H), 7.43 (dd, 1H, J=4, 9 Hz), 7.48 (dt, 1H, J=1, 9 Hz), 8.09 (dd, 1H, J=1, 7 Hz). 1H portion is not observable.

MS: 364.16[M+H]⁺

Example 118

(1S,2S)-2-(5-fluoro-1H-benzo[d]imidazol-2-yl)-N—((R)-1-(5-(2,2,2-trifluoroethoxy)thiophen-2-yl)ethyl)cyclopropane-1-carboxamide

[Chemical Formula 145]

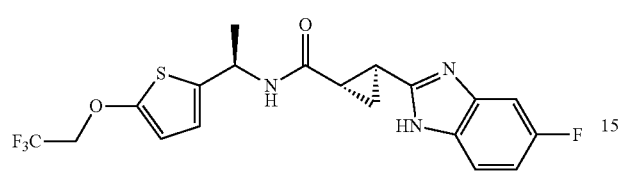

According to a technique similar to that of Example 1, the title compound (pale yellow crystals, 21 mg, 36%) was obtained using (R)-1-(5-(2,2,2-trifluoroethoxy)thiophen-2-yl)ethan-1-amine hydrochloride (35 mg, 0.13 mmol) synthesized in Reference Example 4 and (1S,2S)-2-(5-fluoro-1H-benzo[d]imidazol-2-yl)cyclopropane-1-carboxylic acid (35 mg, 0.16 mmol) synthesized in Reference Example 64-2.

$^1$H NMR (DMSO-d$_6$, 400 MHz): δ=1.3-1.5 (m, 2H), 1.40 (d, 3H, J=7 Hz), 2.2-2.3 (m, 1H), 2.4-2.5 (m, 1H), 4.78 (q, 2H, J=9 Hz), 5.04 (quint, 1H, 7 Hz), 6.35 (d, 1H, J=4 Hz), 6.61 (d, 1H, J=3 Hz), 6.69 (t, 1H, J=9 Hz), 7.2-7.3 (m, 1H), 7.3-7.5 (m, 1H), 8.74 (d, 1H, J=8 Hz), 12.50 (br s, 1H).

MS: 426.09[M−H]$^−$

Example 119

(1S,2S)-2-(1H-benzo[d]imidazol-2-yl)-N—((R)-1-(6-fluorobenzo[b]thiophen-2-yl)ethyl)cyclopropane-1-carboxamide

[Chemical Formula 146]

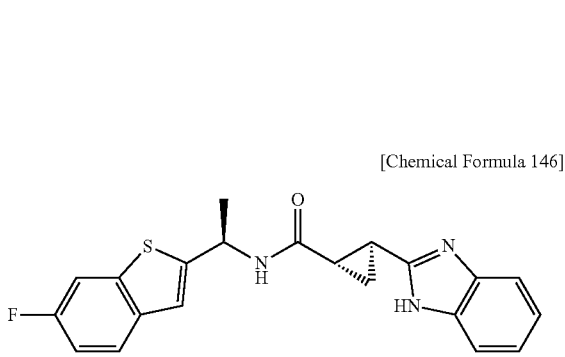 [SMILES: C[C@@H](NC(=O)[C@H]1C[C@@H]1c1nc2ccccc2[nH]1)c1nc2ccc(F)cc2o1]

According to a technique similar to that of Example 89, the title compound (white powder, 59 mg, 94%) was obtained using (R)-1-(6-fluorobenzo[b]thiophen-2-yl)ethan-1-amine (32 mg, 0.17 mmol).

$^1$H NMR (CD$_3$OD, 400 MHz): δ=1.6-1.7 (m, 5H), 2.2-2.3 (m, 1H), 2.6-2.7 (m, 1H), 5.36 (q, 1H, J=7 Hz), 7.11 (ddd, 1H, J=2, 9, 9 Hz), 7.2-7.3 (m, 3H), 7.46 (br s, 2H), 7.56 (dd, 1H, J=2, 9 Hz), 7.71 (dd, 1H, J=5, 9 Hz). 2H portion is not observable.

MS: 402.10[M+Na]$^+$

Example 120

(1S,2S)-2-(1H-benzo[d]imidazol-2-yl)-N—((R)-1-(6-fluorobenzo[b]thiophen-2-yl)-2-methylpropyl)cyclopropane-1-carboxamide

[Chemical Formula 147]

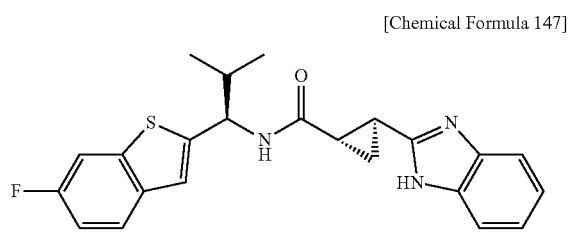

According to a technique similar to that of Example 89, the title compound (white powder, 57 mg, 83%) was obtained using (R)-1-(6-fluorobenzo[b]thiophen-2-yl)-2-methylpropan-1-amine (38 mg, 0.17 mmol) synthesized in Reference Example 41-3.

$^1$H NMR (CD$_3$OD, 400 MHz): δ=0.94 (d, 3H, J=7 Hz), 1.04 (d, 3H, J=7 Hz), 1.5-1.6 (m, 2H), 2.1-2.2 (m, 1H), 2.3-2.4 (m, 1H), 2.6-2.7 (m, 1H), 5.00 (d, 1H, J=8 Hz), 7.11 (ddd, 1H, J=2, 9, 9 Hz), 7.2-7.3 (m, 3H), 7.4-7.5 (m, 2H), 7.57 (dd, 1H, J=2, 9 Hz), 7.72 (dd, 1H, J=6, 9 Hz). 2H portion is not observable.

MS: 430.13[M+Na]$^+$

Example 121

(R)—N—((R)-1-(5-fluorobenzofuran-2-yl)ethyl)-1-(5-(trifluoromethyl)pyridin-2-yl)pyrrolidine-3-carboxamide

[Chemical Formula 148]

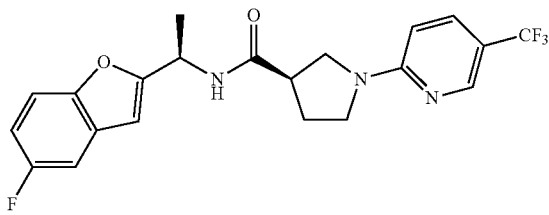

A crude form of (R)—N—((R)-1-(5-fluorobenzofuran-2-yl)ethyl)pyrrolidine-3-carboxamide hydrochloride (10 mg, 0.03 mmol) synthesized in Reference Example 77-3, 2-chloro-5-(trifluoromethyl)pyridine (7 mg, 0.04 mmol), and potassium carbonate (10 mg, 0.07 mmol) were suspended in DMF (1 mL), and the suspension was stirred for 5 hours at room temperature. A saturated aqueous solution of sodium hydrogen carbonate was added to the reaction liquid, and the mixture was stirred for a while. Subsequently, the mixture was extracted with ethyl acetate. The organic layer was dried over anhydrous sodium sulfate, and insoluble matters were filtered. Subsequently, the solvent was distilled off under reduced pressure. A residue thus obtained was purified by silica gel column chromatography (hexane ethyl acetate) (concentration gradient: 30% to 60%), and thus the title compound (white powder, 11 mg, 82%) was obtained.

$^1$H NMR (CDCl$_3$, 400 MHz): δ=1.60 (d, 3H, J=7 Hz), 2.2-2.5 (m, 2H), 3.05 (quint, 1H, J=8 Hz), 3.4-3.6 (m, 1H), 3.7-3.9 (m, 3H), 5.37 (quint, 1H, J=7 Hz), 5.89 (d, 1H, J=9 Hz), 6.37 (d, 1H, J=9 Hz), 6.54 (s, 1H), 6.99 (dt, 1H, J=3, 9 Hz), 7.17 (dd, 1H, J=3, 8 Hz), 7.35 (dd, 1H, J=4, 9 Hz), 7.60 (dd, 1H, J=3, 9 Hz), 8.37 (s, 1H).
MS: 420.14[M−H]$^-$ Example 122

Trans-2-(4-chloro-1H-benzo[d]imidazol-2-yl)-N—((R)-1-(5-(2,2,2-trifluoroethoxy)thiophen-2-yl)ethyl)cyclopropane-1-carboxamide

[Chemical Formula 149]

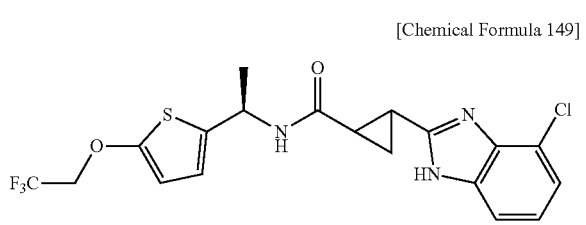 [SMILES: C[C@@H](NC(=O)C1CC1c1nc2c(Cl)cccc2[nH]1)c1ccc(OCC(F)(F)F)s1]

According to a technique similar to that of Example 1, diastereomer A of the title compound (upper spot in TLC (hexane/ethyl acetate=1/9), pale yellow crystals, 38 mg, 44%) and diastereomer B of the title compound (lower spot in TLC (hexane/ethyl acetate=1/9), pale yellow crystals, 25 mg, 29%) were obtained using (R)-1-(5-(2,2,2-trifluoroethoxy)thiophen-2-yl)ethan-1-amine hydrochloride (50 mg, 0.19 mmol) synthesized in Reference Example 4 and a crude form of trans-2-(4-chloro-1H-benzo[d]imidazol-2-yl)cyclopropane-1-carboxylic acid (109 mg) synthesized in Reference Example 61-2.
Diastereomer A
$^1$H NMR (DMSO-d$_6$, 400 MHz): δ=1.53 (d, 3H, J=7 Hz), 1.6-1.8 (m, 2H), 2.2-2.5 (m, 1H), 2.7-2.8 (m, 1H), 4.34 (q, 2H, J=9 Hz), 5.30 (quint, 1H, J=7 Hz), 6.1-6.3 (m, 2H), 6.60 (d, 1H, J=4 Hz), 7.1-7.6 (m, 3H), 10.28 (br s, 0.6H), 10.46 (br s, 0.4H).
MS: 442.08[M−H]$^-$
Diastereomer B
$^1$H NMR (DMSO-d$_6$, 400 MHz): δ=1.3-1.6 (m, 5H), 2.2-2.6 (m, 2H), 4.7-4.8 (m, 2H), 5.0-5.1 (m, 1H), 6.2-6.4 (m, 1H), 6.5-6.7 (m, 1H), 7.0-7.6 (m, 3H), 8.7-8.9 (m, 1H), 12.82 (br s, 1H).
MS: 442.07[M−H]$^-$ Example 123

(1S,2S)-2-(1H-benzo[d]imidazol-2-yl)-N—((R)-1-(6-(trifluoromethyl)benzofuran-2-yl)ethyl)cyclopropane-1-carboxamide

[Chemical Formula 150]

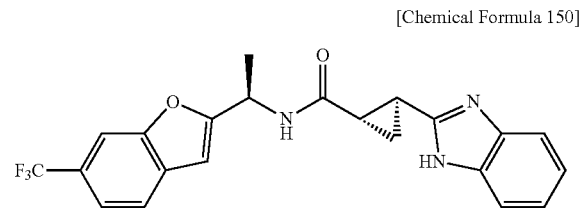 [SMILES: C[C@@H](NC(=O)[C@H]1C[C@@H]1c1nc2ccccc2[nH]1)c1cc2ccc(C(F)(F)F)cc2o1]

According to a technique similar to that of Example 89, the title compound (white powder, 50 mg, 70%) was obtained using (R)-1-(6-(trifluoromethyl)benzofuran-2-yl)ethan-1-amine (39 mg, 0.17 mmol) synthesized in Reference Example 35-3.
$^1$H NMR (CD$_3$OD, 400 MHz): δ=1.59 (d, 3H, J=7 Hz) 1.6-1.7 (m, 2H), 2.3-2.4 (m, 1H), 2.6-2.7 (m, 1H), 5.31 (q, 1H, J=7 Hz), 6.79 (s, 1H), 7.1-7.2 (m, 2H), 7.46 (br s, 2H), 7.50 (d, 1H, J=8 Hz), 7.73 (d, 1H, J=8 Hz), 7.79 (s, 1H). 2H portion is not observable.
MS: 436.14[M+Na]$^+$ Example 124

(1S,2S)-2-(1H-benzo[d]imidazol-2-yl)-N—((R)-1-(6-fluorobenzofuran-2-yl)-2-methylpropyl)cyclopropane-1-carboxamide

[Chemical Formula 151]

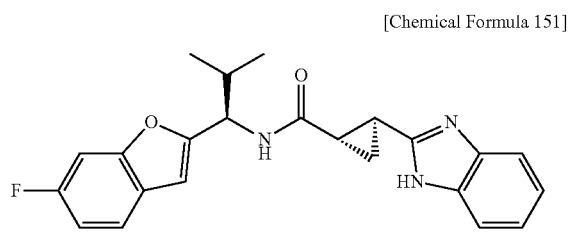 [SMILES: CC(C)[C@@H](NC(=O)[C@H]1C[C@@H]1c1nc2ccccc2[nH]1)c1cc2ccc(F)cc2o1]

According to a technique similar to that of Example 89, the title compound (white powder, 50 mg, 75%) was obtained using (R)-1-(6-fluorobenzofuran-2-yl)-2-methylpropan-1-amine (35 mg, 0.17 mmol) synthesized in Reference Example 36-2.
$^1$H NMR (CD$_3$OD, 400 MHz): δ=0.92 (d, 3H, J=6 Hz), 1.01 (d, 3H, J=6 Hz), 1.5-1.7 (m, 2H), 2.2-2.3 (m, 1H), 2.3-2.4 (m, 1H), 2.6-2.7 (m, 1H), 4.93 (d, 1H, J=8 Hz), 6.65 (s, 1H), 7.01 (ddd, 1H, J=2, 9, 11 Hz), 7.1-7.2 (m, 2H), 7.24 (dd, 1H, J=2, 9 Hz), 7.47 (br s, 2H), 7.52 (dd, 1H, J=6, 9 Hz). 2H portion is not observable.
MS: 414.16[M+Na]$^+$ Example 125

(1S,2S)-2-(5-fluoro-1H-benzo[d]imidazol-2-yl)-N—((R)-1-(5-fluorobenzofuran-2-yl)ethyl)cyclopropane-1-carboxamide

[Chemical Formula 152]

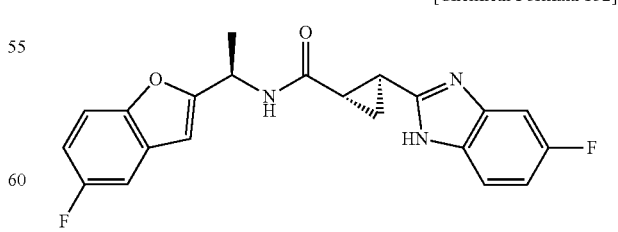

According to a technique similar to that of Example 1, the title compound (white crystals, 42 mg, 68%) was obtained using (R)-1-(5-fluorobenzofuran-2-yl)ethan-1-amine (29 mg, 0.16 mmol) synthesized in Reference Example 23-3 and a crude form of (1S,2S)-2-(5-fluoro-1H-benzo[d]imidazol-2-yl)cyclopropane-1-carboxylic acid (110 mg) synthesized in Reference Example 64-2.

$^1$H NMR (DMSO-$d_6$, 400 MHz): δ=1.4-1.6 (m, 5H), 2.2-2.6 (m, 2H), 5.18 (quint, 1H, J=7 Hz), 6.73 (s, 1H), 6.97 (t, 1H, J=9 Hz), 7.11 (t, 1H, J=8 Hz), 7.26 (d, 1H, J=9 Hz), 7.3-7.5 (m, 2H), 7.58 (dd, 1H, J=4, 9 Hz), 8.87 (d, 1H, J=8 Hz), 12.54 (br s, 1H).

MS: 380.13[M−H]$^−$

Example 126

(R)-1-(benzo[d]thiazol-2-yl)-N—((R)-1-(5-fluorobenzofuran-2-yl)ethyl)pyrrolidine-3-carboxamide

[Chemical Formula 153]

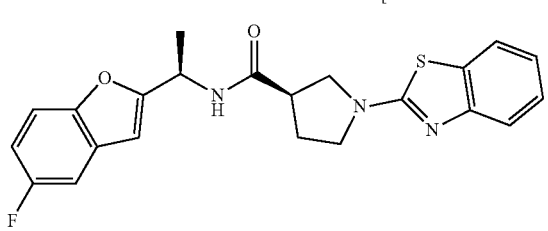

According to a technique similar to that of Example 121, the title compound (white powder, 5 mg, 35%) was obtained using a crude form of (R)—N—((R)-1-(5-fluorobenzofuran-2-yl)ethyl)pyrrolidine-3-carboxamide hydrochloride (10 mg, 0.03 mmol) synthesized in Reference Example 77-3 and 2-chlorobenzothiazole (7 mg, 0.04 mmol).

$^1$H NMR (CDCl$_3$, 400 MHz): δ=1.59 (d, 3H, J=7 Hz), 2.2-2.5 (m, 2H), 3.09 (quint, 1H, J=8 Hz), 3.5-3.9 (m, 4H), 5.37 (quint, 1H, J=7 Hz), 5.95 (d, 1H, J=8 Hz), 6.53 (s, 1H), 6.98 (dt, 1H, J=3, 9 Hz), 7.07 (t, 1H, J=8 Hz), 7.16 (dd, 1H, J=3, 8 Hz), 7.2-7.4 (m, 1H), 7.35 (dd, 1H, J=4, 9 Hz), 7.5-7.7 (m, 2H).

MS: 410.15[M+H]$^+$

Example 127

(1S,2S)-2-(1H-benzo[d]imidazol-2-yl)-N-(1-(6-fluoro-1H-benzo[d]imidazol-2-yl)ethyl)cyclopropane-1-carboxamide

[Chemical Formula 154]

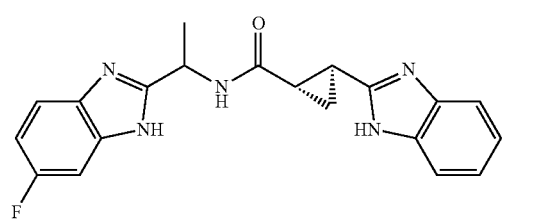

According to a technique similar to that of Example 1, diastereomer A of the title compound (upper spot in TLC (ethyl acetate/methanol=10/1), white powder, 16 mg, 14%) and diastereomer B of the title compound (lower spot in TLC (ethyl acetate/methanol=10/1), white powder, 50 mg, 44%) were obtained using 1-(5-fluoro-1H-benzo[d]imidazol-2-yl)ethan-1-amine (67 mg, 0.37 mmol) and (1S,2S)-2-(1H-benzo[d]imidazol-2-yl)cyclopropane-1-carboxylic acid (63 mg, 0.31 mmol) synthesized in Reference Example 62-2.

Diastereomer A $^1$H NMR (DMSO-$d_6$, 400 MHz): δ=1.4-1.6 (m, 5H), 2.3-2.6 (m, 2H), 5.18 (quint, 1H, J=7 Hz), 7.01 (dd, 1H, J=9, 9 Hz), 7.0-7.6 (m, 6H), 8.93 (d, 1H, J=8 Hz), 12.38 (br s, 2H).

MS: 364.15[M+H]$^+$

Diastereomer B $^1$H NMR (DMSO-$d_6$, 400 MHz): δ=1.4-1.6 (m, 5H), 2.3-2.6 (m, 2H), 5.19 (quint, 1H, J=7 Hz), 6.98 (dd, 1H, J=8, 8 Hz), 7.0-7.6 (m, 6H), 8.93 (d, 1H, J=7 Hz), 12.37 (br s, 2H).

MS: 364.17[M+H]$^+$

Example 128

(1S,2S)-2-(1H-benzo[d]imidazol-2-yl)-N-(1-(5-fluorobenzofuran-2-yl)cyclopropyl)cyclopropane-1-carboxamide

[Chemical Formula 155]

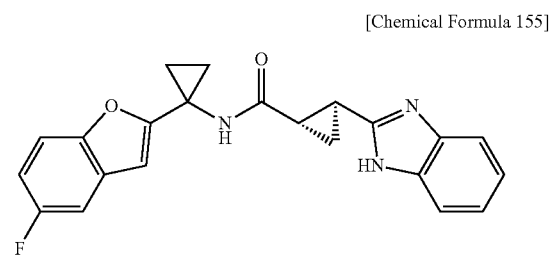 [SMILES: O=C(NC1(c2cc3cc(F)ccc3o2)CC1)[C@H]1C[C@@H]1c1nc2ccccc2[nH]1]

According to a technique similar to that of Example 89, the title compound (white powder, 36 mg, 35%) was obtained using 1-(5-fluorobenzofuran-2-yl)cyclopropan-1-amine (52 mg, 0.27 mmol) synthesized in Reference Example 46-2.

$^1$H NMR (CD$_3$OD, 400 MHz): δ=1.2-1.3 (m, 2H), 1.5-1.7 (m, 4H), 2.2-2.3 (m, 1H), 2.6-2.7 (m, 1H), 6.55 (s, 1H), 6.92 (ddd, 1H, J=3, 9, 9 Hz), 7.1-7.2 (m, 3H), 7.33 (dd, 1H, J=4, 9 Hz), 7.47 (br s, 2H). 2H portion is not observable.

MS: 398.11[M+Na]$^+$

Example 129

(1S,2S)-2-(1H-benzo[d]imidazol-2-yl)-N—((R)-1-(6-fluorobenzofuran-2-yl)ethyl)-N-methylcyclopropane-1-carboxamide

[Chemical Formula 156]

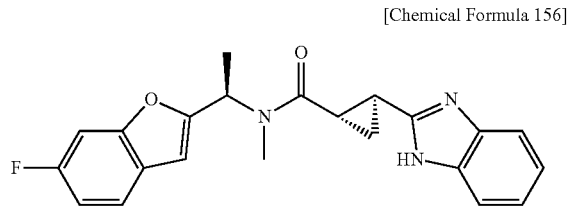

According to a technique similar to that of Example 89, the title compound (white powder, 48 mg, 74%) was obtained using (R)-1-(6-fluorobenzofuran-2-yl)-N-methyl-ethan-1-amine (33 mg, 0.17 mmol) synthesized in Reference Example 78-2.

¹H NMR (CD₃OD, 400 MHz): δ=1.56 (d, 2.1H, J=7 Hz), 1.6-1.8 (m, 2.9H), 2.6-2.7 (m, 1.7H), 2.80 (s, 0.9H), 2.9-3.0 (m, 0.3H), 3.00 (s, 2.1H), 5.73 (q, 0.3H, J=7 Hz), 6.00 (q, 0.7H, J=7 Hz), 6.73 (s, 0.3H), 6.80 (s, 0.7H), 6.95 (ddd, 0.3H, J=2, 9, 10 Hz), 7.0-7.1 (m, 1H), 7.1-7.2 (m, 2H), 7.25 (dd, 0.7H, J=2, 9 Hz), 7.43 (dd, 0.3H, J=6, 9 Hz), 7.47 (br s, 2H), 7.54 (dd, 0.7H, J=6, 9 Hz). 1H portion is not observable.

MS: 400.15[M+Na]⁺

Example 130

Trans-N1-((R)-1-(5-fluorobenzofuran-2-yl)ethyl)-N2-(3-(trifluoromethyl)phenyl)cyclopropane-1,2-dicarboxamide

[Chemical Formula 157]

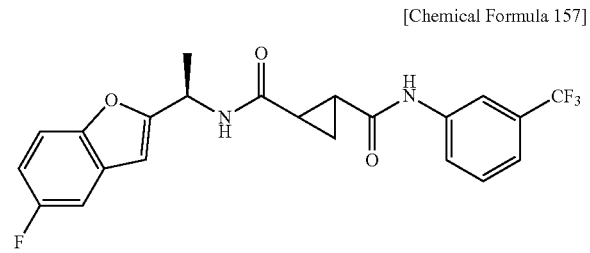 [SMILES: C[C@@H](NC(=O)C1CC1C(=O)Nc1cccc(C(F)(F)F)c1)c1cc2cc(F)ccc2o1]

According to a technique similar to that of Example 1, diastereomer A of the title compound (upper spot in TLC (ethyl acetate/hexane=1/1), white powder, 13 mg, 28%) and diastereomer B of the title compound (lower spot in TLC (ethyl acetate/hexane=1/1), white powder, 12 mg, 24%) were obtained using (R)-1-(5-fluorobenzofuran-2-yl)ethan-1-amine hydrochloride (0.11 mmol) synthesized in Reference Example 77-1 and a crude form of trans-2-((3-(trifluoromethyl)phenyl)carbamoyl)cyclopropane-1-carboxylic acid (75 mg, 0.27 mmol) synthesized in Reference Example 75-2.

Diastereomer A

¹H NMR (CDCl₃, 400 MHz): δ=1.4-1.6 (m, 2H), 1.60 (d, 3H, J=7 Hz), 2.0-2.2 (m, 1H), 2.2-2.3 (m, 1H), 5.35 (quint, 1H, J=7 Hz), 6.22 (d, 1H, J=8 Hz), 6.54 (s, 1H), 6.99 (dt, 1H, J=3, 9 Hz), 7.17 (dd, 1H, J=3, 8 Hz), 7.3-7.5 (m, 3H), 7.65 (d, 1H, J=7 Hz), 7.90 (s, 1H), 8.09 (s, 1H).

MS: 433.14[M−H]⁻

Diastereomer B

¹H NMR (DMSO-d₆, 400 MHz): δ=1.2-1.3 (m, 2H), 1.47 (d, 3H, J=7 Hz), 2.1-2.2 (m, 1H), 2.2-2.3 (m, 1H), 5.15 (quint, 1H, J=7 Hz), 6.74 (s, 1H), 7.09 (dt, 1H, J=3, 9 Hz), 7.3-7.5 (m, 2H), 7.5-7.6 (m, 2H), 7.73 (d, 1H, J=9 Hz), 8.08 (s, 1H), 8.90 (d, 1H, J=8 Hz), 10.70 (s, 1H).

MS: 433.16[M−H]⁻

Example 131

N—((R)-1-(5-fluorobenzofuran-2-yl)ethyl)-1-(3-(trifluoromethyl)phenyl)pyrrolidine-3-carboxamide

[Chemical Formula 158]

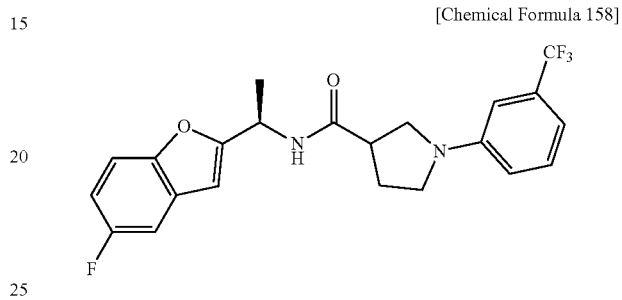

A crude form of (R)—N—((R)-1-(5-fluorobenzofuran-2-yl)ethyl)pyrrolidine-3-carboxamide hydrochloride (15 mg, 0.05 mmol) synthesized in Reference Example 77-3, 1-bromo-3-(trifluoromethyl)benzene (9 mg, 0.05 mmol), tris(dibenzylideneacetone)dipalladium (0) (4 mg, 0.01 mmol), BINAP (7 mg, 0.01 mmol), and sodium tert-butoxide (14 mg, 0.14 mmol) were suspended in toluene (1 mL), subsequently the suspension was purged with nitrogen, and the suspension was stirred for 6 hours at 85° C. Water was added to the reaction liquid, and the mixture was stirred for a while. Subsequently, the mixture was extracted with ethyl acetate. The organic layer was dried over anhydrous sodium sulfate, and insoluble matters were filtered. Subsequently, the solvent was distilled off under reduced pressure. A residue thus obtained was purified by silica gel column chromatography (hexane:ethyl acetate) (concentration gradient: 20% to 50%), and thus, diastereomer A of the title compound (upper spot in TLC (ethyl acetate/hexane=1/1), light brown powder, 4 mg, 20%) and diastereomer B of the title compound (lower spot in ethyl acetate/hexane=1/1), light brown powder, 4 mg, 21%) were obtained.

Diastereomer A

¹H NMR (CDCl₃, 400 MHz): δ=1.60 (d, 3H, J=7 Hz), 2.2-2.4 (m, 2H), 3.06 (quint, 1H, J=8 Hz), 3.38 (q, 1H, J=8 Hz), 3.52 (dt, 1H, J=5, 8 Hz), 3.58 (d, 2H, J=8 Hz), 5.38 (quint, 1H, J=7 Hz), 5.93 (d, 1H, J=7 Hz), 6.55 (s, 1H), 6.71 (dd, 1H, J=2, 8 Hz), 6.75 (s, 1H), 6.93 (d, 1H, J=8 Hz), 6.99 (dt, 1H, J=3, 9 Hz), 7.18 (dd, 1H, J=3, 9 Hz), 7.2-7.4 (m, 2H).

MS: 419.15[M−H]⁻

Diastereomer B

¹H NMR (CDCl₃, 400 MHz): δ=1.59 (d, 3H, J=7 Hz), 2.3-2.4 (m, 2H), 3.3-3.6 (m, 4H), 5.38 (quint, 1H, J=7 Hz), 5.94 (d, 1H, J=9 Hz), 6.55 (s, 1H), 6.69 (dd, 1H, J=2, 8 Hz), 6.74 (s, 1H), 6.93 (d, 1H, J=7 Hz), 6.99 (dt, 1H, J=3, 9 Hz), 7.18 (dd, 1H, J=3, 9 Hz), 7.2-7.4 (m, 2 MS: 419.16 [M−H]⁻

Example 132

(1S,2S)-2-(1H-benzo[d]imidazol-2-yl)-N—((R)-1-(3,6-difluorobenzo[b]thiophen-2-yl)ethyl)cyclopropane-1-carboxamide

[Chemical Formula 159]

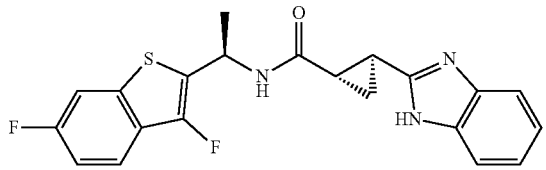

According to a technique similar to that of Example 89, the title compound (white powder, 52 mg, 78%) was obtained using (R)-1-(3,6-difluorobenzo[b]thiophen-2-yl)ethan-1-amine (36 mg, 0.17 mmol) synthesized in Reference Example 47-4.

$^1$H NMR (CD$_3$OD, 400 MHz): δ=1.5-1.7 (m, 5H), 2.2-2.3 (m, 1H), 2.5-2.6 (m, 1H), 5.46 (q, 1H, J=7 Hz), 7.1-7.2 (m, 2H), 7.23 (ddd, 1H, J=2, 8, 8 Hz), 7.46 (br s, 2H), 7.59 (ddd, 1H, J=2, 2, 9 Hz), 7.69 (dd, 1H, J=5, 8 Hz). 2H portion is not observable.

MS: 420.11[M+Na]$^+$

Example 133

(1S,2S)-2-(1H-benzo[d]imidazol-2-yl)-N-(1-(5-fluoro-1-methyl-1H-indol-2-yl)ethyl)cyclopropane-1-carboxamide

[Chemical Formula 160]

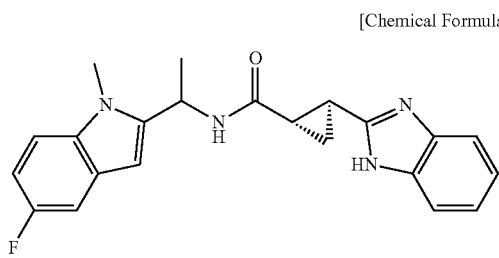

According to a technique similar to that of Example 89, diastereomer A of the title compound (upper spot in TLC (ethyl acetate), white powder, 34 mg, 51%) and diastereomer B of the title compound (lower spot in TLC (ethyl acetate), white powder, 27 mg, 40%) were obtained using 1-(5-fluoro-1-methyl-1H-indol-2-yl)ethan-1-amine (34 mg, 0.18 mmol) synthesized in Reference Example 48-3.

Diastereomer A $^1$H NMR (CD$_3$OD, 400 MHz): δ=1.6-1.7 (m, 5H), 2.2-2.3 (m, 1H), 2.6-2.7 (m, 1H), 3.71 (s, 3H), 5.36 (q, 1H, J=7 Hz), 6.45 (s, 1H), 6.90 (ddd, 1H, J=3, 9, 9 Hz), 7.1-7.2 (m, 3H), 7.31 (dd, 1H, J=4, 9 Hz), 7.46 (br s, 2H). 2H portion is not observable.

MS: 375.17[M−H]$^-$

Diastereomer B $^1$H NMR (CD$_3$OD, 400 MHz): δ=1.6-1.7 (m, 5H), 2.2-2.3 (m, 1H), 2.6-2.7 (m, 1H), 3.70 (s, 3H), 5.35 (q, 1H, J=7 Hz), 6.44 (s, 1H), 6.88 (ddd, 1H, J=3, 9, 9 Hz), 7.1-7.2 (m, 3H), 7.28 (dd, 1H, J=4, 9 Hz), 7.44 (br s, 2H). 2H portion is not observable.

MS: 375.17[M−H]$^-$

Example 134

(1S,2S)-2-(1H-benzo[d]imidazol-2-yl)-N—((R)-1-(5-fluorobenzofuran-2-yl)ethyl-2,2,2-d$_3$)cyclopropane-1-carboxamide

[Chemical Formula 161]

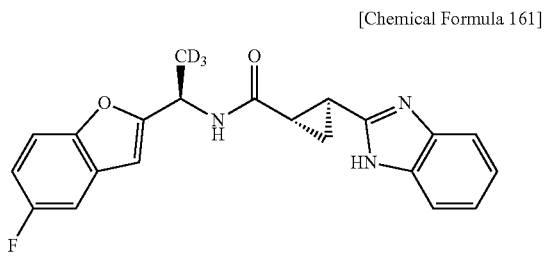 [SMILES: [2H]C([2H])([2H])[C@@H](NC(=O)[C@H]1C[C@@H]1c1nc2ccccc2[nH]1)c1cc2cc(F)ccc2o1]

According to a technique similar to that of Example 1, the title compound (white crystals, 46 mg, 60%) was obtained using (R)-1-(5-fluorobenzofuran-2-yl)ethan-2,2,2-d$_3$-1-amine (38 mg, 0.21 mmol) synthesized in Reference Example 49-2 and (1S,2S)-2-(1H-benzo[d]imidazol-2-yl)cyclopropane-1-carboxylic acid (51 mg, 0.25 mmol) synthesized in Reference Example 62-2.

$^1$H NMR (DMSO-d$_6$, 400 MHz): δ=1.4-1.6 (m, 2H), 2.2-2.6 (m, 2H), 5.16 (d, 1H, J=8 Hz), 6.73 (s, 1H), 7.0-7.2 (m, 3H), 7.3-7.6 (m, 3H), 7.58 (dd, 1H, J=4, 9 Hz), 8.86 (d, 1H, J=8 Hz), 12.39 (br s, 1H).

MS: 365.16[M−H]$^-$

Example 135

(1S,2S)-2-(1H-benzo[d]imidazol-2-yl)-N—((S)-1-(5-fluorobenzofuran-2-yl)ethyl-2,2,2-d$_3$)cyclopropane-1-carboxamide

[Chemical Formula 162]

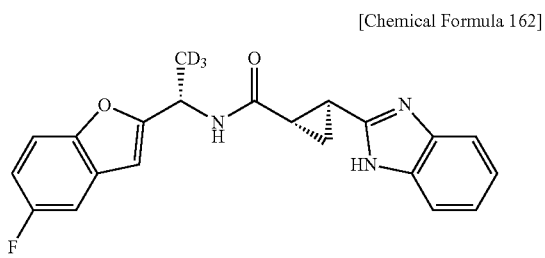 [SMILES: [2H]C([2H])([2H])[C@H](NC(=O)[C@H]1C[C@@H]1c1nc2ccccc2[nH]1)c1cc2cc(F)ccc2o1]

According to a technique similar to that of Example 1, the title compound (white crystals, 46 mg, 60%) was obtained using (S)-1-(5-fluorobenzofuran-2-yl)ethan-2,2,2-d$_3$-1-amine (41 mg, 0.23 mmol) synthesized in Reference Example 50 and (1S,2S)-2-(1H-benzo[d]imidazol-2-yl)cyclopropane-1-carboxylic acid (55 mg, 0.27 mmol) synthesized in Reference Example 62-2.

$^1$H NMR (DMSO-d$_6$, 400 MHz): δ=1.4-1.6 (m, 2H), 2.3-2.6 (m, 2H), 5.16 (d, 1H, J=8 Hz), 6.72 (s, 1H), 7.0-7.2 (m, 3H), 7.3-7.5 (m, 3H), 7.55 (dd, 1H, J=4, 9 Hz), 8.88 (d, 1H, J=8 Hz), 12.40 (br s, 1H).

MS: 365.16[M−H]$^-$

Example 136

Trans-N—((R)-1-(5-fluorobenzofuran-2-yl)ethyl)-2-((3-(trifluoromethyl)phenoxy)methyl)cyclopropane-1-carboxamide

[Chemical Formula 163]

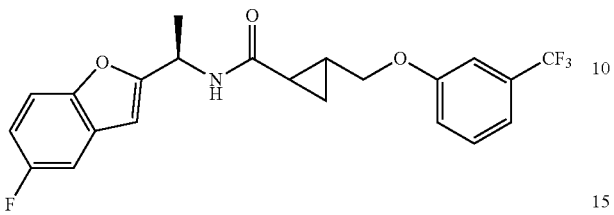

According to a technique similar to that of Example 112, diastereomer A of the title compound (upper spot in TLC (ethyl acetate/hexane=1/1), white powder, 5 mg, 11%) and diastereomer B of the title compound (lower spot in TLC (ethyl acetate/hexane=1/1), white powder, 10 mg, 20%) were obtained using a crude form of (R)-1-(5-fluorobenzofuran-2-yl)ethan-1-amine hydrochloride (0.11 mmol) synthesized in Reference Example 77-1 and a crude form of trans-2-((4-fluorophenoxy)methyl)cyclopropane-1-carboxylic acid (0.19 mmol) synthesized in Reference Example 76-2.

Diastereomer A
$^1$H NMR (DMSO-$d_6$, 400 MHz): δ=0.8-0.9 (m, 1H), 0.9-1.1 (m, 1H), 1.47 (d, 3H, J=7 Hz), 1.6-1.8 (m, 2H), 3.95 (dd, 1H, J=7, 10 Hz), 4.08 (dd, 1H, J=6, 10 Hz), 5.14 (quint, 1H, J=7 Hz), 6.70 (s, 1H), 7.10 (dt, 1H, J=3, 9 Hz), 7.2-7.3 (m, 3H), 7.40 (dt, 1H, J=3, 9 Hz), 7.52 (t, 1H, J=8 Hz), 7.57 (dd, 1H, =4, 9 Hz), 8.74 (d, 1H, J=8 Hz).
MS: 422.16[M+H]$^+$ Diastereomer B
$^1$H NMR (DMSO-$d_6$, 400 MHz): δ=0.8-0.9 (m, 1H), 0.9-1.1 (m, 1H), 1.42 (d, 3H, J=7 Hz), 1.5-1.8 (m, 2H), 3.90 (dd, 1H, J=7, 10 Hz), 4.04 (dd, 1H, J=6, 10 Hz), 5.10 (quint, 1H, J=7 Hz), 6.66 (s, 1H), 7.07 (dt, 1H, J=3, 9 Hz), 7.1-7.3 (m, 3H), 7.36 (dt, 1H, J=3, 9 Hz), 7.46 (t, 1H, J=8 Hz), 7.53 (dd, 1H, J=4, 9 Hz), 8.70 (d, 1H, J=8 Hz).
MS: 422.15[M+H]$^+$

Example 137

(1S,2S)-2-(1H-benzo[d]imidazol-2-yl)-N—((R)-1-(5-fluorobenzofuran-2-yl)butyl)cyclopropane-1-carboxamide

[Chemical Formula 164]

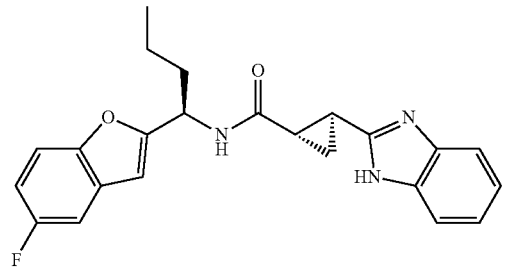

According to a technique similar to that of Example 1, the title compound (white crystals, 70 mg, 93%) was obtained using (R)-1-(5-fluorobenzofuran-2-yl)butan-1-amine (40 mg, 0.19 mmol) synthesized in Reference Example 51-2 and (1S,2S)-2-(1H-benzo[d]imidazol-2-yl)cyclopropane-1-carboxylic acid (47 mg, 0.23 mmol) synthesized in Reference Example 62-2.
$^1$H NMR (DMSO-$d_6$, 400 MHz): 0.89 (t, 3H, J=7 Hz), 1.2-1.5 (m, 4H), 1.6-2.0 (m, 2H), 2.3-2.6 (m, 2H), 5.0-5.2 (m, 1H), 6.73 (s, 1H), 7.0-7.2 (m, 3H), 7.3-7.7 (m, 4H), 8.81 (d, 1H, J=8 Hz), 12.41 (br s, 1H).
MS: 390.17[M−H]$^-$

Example 138

(1S,2S)-2-(1H-benzo[d]imidazol-2-yl)-N—((S)-1-(5-fluorobenzofuran-2-yl)butyl)cyclopropane-1-carboxamide

[Chemical Formula 165]

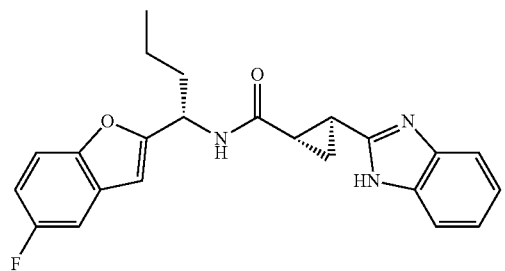

According to a technique similar to that of Example 1, the title compound (white crystals, 50 mg, 66%) was obtained using (S)-1-(5-fluorobenzofuran-2-yl)butan-1-amine (40 mg, 0.19 mmol) synthesized in Reference Example 52 and (1S,2S)-2-(1H-benzo[d]imidazol-2-yl)cyclopropane-1-carboxylic acid (47 mg, 0.23 mmol) synthesized in Reference Example 62-2.
$^1$H NMR (DMSO-$d_6$, 400 MHz): δ=0.91 (t, 3H, J=8 Hz), 1.2-1.6 (m, 4H), 1.7-1.9 (m, 2H), 2.3-2.6 (m, 2H), 5.09 (q, 1H, J=8 Hz), 6.72 (s, 1H), 7.0-7.2 (m, 3H), 7.3-7.6 (m, 4H), 8.83 (d, 1H, J=8 Hz), 12.37 (br s, 1H).
MS: 390.14[M−H]$^-$

Example 139

(1S,2S)-2-(1-ethyl-1H-benzo[d]imidazol-2-yl)-N-(1-(6-fluoro-1H-benzo[d]imidazol-2-yl)ethyl)cyclopropane-1-carboxamide

[Chemical Formula 166]

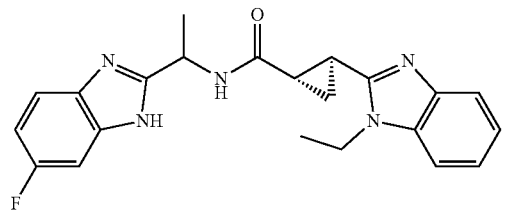

According to a technique similar to that of Example 1, diastereomer A of the title compound (upper spot in TLC (ethyl acetate/methanol=10/1), white powder, 33 mg, 45%) and diastereomer B of the title compound (lower spot in TLC (ethyl acetate/methanol=10/1), white powder, 34 mg, 43%) were obtained using 1-(5-fluoro-1H-benzo[d]imidazol-2-yl)ethan-1-amine (34 mg, 0.19 mmol) and a crude form of (1S,2S)-2-(1-ethyl-1H-benzo[d]imidazol-2-yl)cyclopropane-1-carboxylic acid (87 mg) synthesized in Reference Example 63-2.

Diastereomer A $^1$H NMR (DMSO-$d_6$, 400 MHz): δ=1.33 (t, 3H, J=7 Hz), 1.4-1.6 (m, 5H), 2.3-2.4 (m, 1H), 2.5-2.6 (m, 1H), 4.36 (dq, 2H, J=2, 7 Hz), 5.23 (quint, 1H, J=7 Hz), 6.9-7.1 (m, 1H), 7.1-7.4 (m, 3H), 7.4-7.6 (m, 3H), 8.97 (d, 1H, J=8 Hz), 12.41 (br s, 1H).

MS: 392.18[M+H]$^+$

Diastereomer B $^1$H NMR (DMSO-$d_6$, 400 MHz): δ=5:1.25 (t, 3H, J=7 Hz), 1.4-1.6 (m, 5H), 2.41 (ddd, 1H, J=4, 6, 8 Hz), 2.4-2.6 (m, 1H), 4.31 (dq, 2H, J=3, 7 Hz), 5.21 (quint, 1H, J=7 Hz), 6.9-7.6 (m, 7H), 8.97 (d, 1H, J=8 Hz), 12.38 (br s, 1H).

MS: 392.18[M+H]$^+$

Example 140

Pharmacological Test 1

(Test Method)

Construction of Stable Cells Expressing Human Cav3.2 Channels (1) A sequence produced by incorporating HindIII site and kozak sequence (GCCACC) into the 5'-terminal side of human Cav3.2 channel ORF (Open Reading Frame) gene and incorporating Kpnl site into the 3'-terminal side was incorporated into pcDNA3.1(+) (Thermo-Fisher Scientific, Inc., #V790-20), and the plasmid was transfected into HEK293 cells (ATCC No. CRL-1573) according to the protocol of FuGENE (registered trademark) HD Transfection Reagent (PROMEGA #E2311).

(2) Method for Measuring Intracellular Calcium Concentration

In the present measurement system, buffer A and buffer B having different potassium ion concentrations were used in order to evaluate the state-dependent Cav3.2 inhibitory action of a test compound.

Stable cell line expressing human Cav3.2 channels, which had been produced in (1), was seeded in a 96-well plate using DMEM medium including 10% FBS, and the cells were cultured for 48 hours under the conditions of 37° C. and 5% $CO_2$. Subsequently, the medium was removed, and various wells that had been washed with a base buffer were treated with 80 μL of a fluorescent dye solution containing a mixed liquid of 22 μg of calcium fluorescence indicator Fluo-4 AM (Dojindo Laboratories Co., Ltd., #F311), 20 μL of DMSO, 1 L of 10% Pluronic F-127 (Thermo-Fisher Scientific, Inc., #P6866), and 4 mL of a base buffer. The cells were left to stand for 45 minutes at room temperature in the dark, and then the cells were washed with buffer A or buffer B. Solutions having various test compound concentrations and respectively containing buffer A or buffer B were added to the respective wells, the respective solutions containing DMSO at the same final concentration as that of the test compound as negative control, or containing the test compound dissolved in 100% DMSO at a final concentration of 0.1%. The cells were left to stand for another 15 minutes at room temperature in the dark, and the cells were analyzed using the following method using a microplate reader, EnVision (PerkinElmer, Inc.). First, the background fluorescence for each well was measured, subsequently an ionophore was added to the well, and the fluorescence of the baseline was measured. Subsequently, buffer A or buffer B containing added KCl at a concentration of 83.8 mM or 91.8 mM was added to each well, and an increase in fluorescence caused by a calcium influx generated by that stimulus was measured for 10 seconds. The percentage inhibition was calculated from the maximum fluorescence increment from the baseline, and the logarithmic value of the test compound concentration and the inhibitory activity were plotted to calculate the $IC_{50}$ value. The analysis was carried out by measuring the fluorescence at 510 nm emitted when the cells were irradiated with exciting light at 485 nm.

(Buffer Composition)

Base buffer: 140 mM NaCl, 5 mM KCl, 1 mM $MgCl_2$, 0.5 mM $CaCl_2$, 10 mM Glucose, and 10 mM HEPES, pH 7.3

Buffer A: Equilibrium potential of potassium: −92 mV

Buffer B: Equilibrium potential of potassium: −110 mV (Test Results)

The test results are presented in Table 1.

TABLE 1

| Test compound | Inhibitory action of buffer A (inactivated state) | Inhibitory action of buffer B (resting state or closed state) |
|---|---|---|
| Example 1A | +++ | + |
| Example 1B | ++ | NT |
| Example 2A | ++ | + |
| Example 2B | ++ | + |
| Example 3A | ++++ | + |
| Example 3B | ++ | ++ |
| Example 4A | ++++ | + |
| Example 4B | ++ | + |
| Example 5A | +++ | +++ |
| Example 5B | ++ | ++ |
| Example 6A | +++ | ++ |
| Example 6B | ++ | + |
| Example 7A | ++ | + |
| Example 7B | ++ | + |
| Example 8A | +++ | + |
| Example 8B | + | NT |
| Example 9 | + | NT |
| Example 10 | +++ | +++ |
| Example 11A | ++ | + |
| Example 11B | + | NT |
| Example 12 | +++ | ++ |
| Example 13 | + | NT |
| Example 14 | ++ | ++ |
| Example 15 | +++ | ++ |
| Example 16 | +++ | ++ |
| Example 17 | +++ | ++ |
| Example 18 | ++ | ++ |

$IC_{50} ≤ 0.1$ μM; ++++, $0.1$ μM$<IC_{50}≤1$ μM; +++, $1$ μM$<IC_{50}≤10$ μM; ++, $10$ μM$<IC_{50}$; +, not tested; NT As is obvious from Table 1, it was found that the compounds of the present invention have excellent voltage-dependent T-type calcium channel inhibitory action.

Furthermore, it was found that diastereomer A of Example 1, diastereomers A and B of Example 2, diastereomer A of Example 3, diastereomers A and B of Example 4, diastereomers A and B of Example 6, diastereomers A and B of Example 7, diastereomer A described in Example 8, diastereomer A of Example 11, and diastereomers A of Example 12 and Examples 15 to 17; in particular, diastereomer A of Example 1, diastereomer A of Example 3, diastereomer A of Example 4, and diastereomer A described in Example 8, have superior voltage-dependent T-type calcium channel inhibitory action in an inactivated state, compared to a resting state or closed state.

Example 141

Pharmacological Test 2

(Test Method)

A test was carried out in the same manner as in the test described in Example 140.

(Test Results)

The results for a test on the inhibitory action of buffer A are described in Tables 2 to 6.

TABLE 2

| Test compound | Inhibitory action of buffer A (inactivated state) | Test compound | Inhibitory action of buffer A (inactivated state) |
|---|---|---|---|
| Example 19A | + | Example 19B | + |
| Example 20 | ++ | | |
| Example 21A | +++ | Example 21B | +++ |
| Example 22A | +++ | Example 22B | +++ |
| Example 23A | ++ | Example 23B | + |
| Example 24 | +++ | | |
| Example 25A | +++ | Example 25B | ++ |
| Example 26 | +++ | | |
| Example 27 | + | | |
| Example 28 | + | | |
| Example 29A | + | Example 29B | + |
| Example 30 | + | | |
| Example 31A | +++ | Example 31B | +++ |
| Example 32 | +++ | | |
| Example 33 | +++ | | |
| Example 34A | +++ | Example 34B | +++ |
| Example 35 | ++ | | |
| Example 36 | ++++ | | |
| Example 37 | ++ | | |
| Example 38A | + | Example 38B | + |
| Example 39 | +++ | | |
| Example 40A | + | Example 40B | + |

TABLE 3

| | | | |
|---|---|---|---|
| Example 41 | ++ | | |
| Example 42 | ++++ | | |
| Example 43 | +++ | | |
| Example 44 | ++++ | | |
| Example 45 | +++ | | |
| Example 46 | +++ | | |
| Example 47 | ++++ | | |
| Example 48 | ++++ | | |
| Example 49 | ++++ | | |
| Example 50 | +++ | | |
| Example 51 | +++ | | |
| Example 52 | +++ | | |
| Example 53A | ++++ | Example 53B | +++ |
| Example 54 | ++++ | | |
| Example 55 | +++ | | |
| Example 56 | ++ | | |
| Example 57A | +++ | Example 57B | ++ |
| Example 58 | +++ | | |
| Example 59 | +++ | | |
| Example 60 | +++ | | |
| Example 61 | +++ | | |
| Example 62 | +++ | | |
| Example 63 | ++++ | | |
| Example 64A | ++++ | Example 64B | ++ |
| Example 65 | ++++ | | |
| Example 66 | ++++ | | |
| Example 67 | ++ | | |
| Example 68 | ++ | | |
| Example 69 | +++ | | |

TABLE 4

| | | | |
|---|---|---|---|
| Example 70 | ++ | | |
| Example 71A | +++ | Example 71B | +++ |
| Example 72 | ++ | | |
| Example 73 | +++ | | |
| Example 74 | +++ | | |
| Example 75 | ++ | | |
| Example 76 | +++ | | |
| Example 77A | +++ | Example 77B | ++ |
| Example 78 | +++ | | |
| Example 79 | +++ | | |
| Example 80 | ++ | | |
| Example 81 | ++++ | | |
| Example 82 | ++++ | | |
| Example 83 | +++ | | |
| Example 84 | ++ | | |
| Example 85A | ++ | Example 85B | + |
| Example 86 | ++ | | |
| Example 87 | ++ | | |
| Example 88 | ++++ | | |

TABLE 5

| | | | |
|---|---|---|---|
| Example 89 | +++ | | |
| Example 90A | ++ | Example 90B | ++ |
| Example 91 | ++++ | | |
| Example 92 | ++++ | | |
| Example 93 | ++ | | |
| Example 94 | +++ | | |
| Example 95 | ++ | | |
| Example 96 | +++ | | |
| Example 97 | +++ | | |
| Example 98A | +++ | Example 98B | +++ |
| Example 99 | ++ | | |
| Example 100 | ++++ | | |
| Example 101 | ++++ | | |
| Example 102 | ++++ | | |
| Example 103A | +++ | Example 103B | + |
| Example 104 | ++++ | | |
| Example 105 | +++ | | |
| Example 106A | ++ | Example 106B | ++ |
| Example 107 | +++ | | |
| Example 108A | +++ | Example 108B | +++ |
| Example 109 | +++ | | |
| Example 110 | ++++ | | |

TABLE 6

| | | | |
|---|---|---|---|
| Example 111 | NT | | |
| Example 112A | ++ | Example 112B | +++ |
| Example 113 | ++++ | | |
| Example 114 | +++ | | |
| Example 115 | +++ | | |
| Example 116 | NT | | |
| Example 117A | +++ | Example 117B | ++ |
| Example 118 | ++++ | | |
| Example 119 | ++++ | | |
| Example 120 | +++ | | |
| Example 121 | + | | |
| Example 122A | ++++ | Example 122B | +++ |
| Example 123 | ++++ | | |
| Example 124 | ++++ | | |
| Example 125 | ++++ | | |
| Example 126 | +++ | | |
| Example 127A | +++ | Example 127B | ++ |
| Example 128 | +++ | | |
| Example 129 | +++ | | |
| Example 130A | NT | Example 130B | +++ |
| Example 131 | NT | | |
| Example 132 | NT | | |
| Example 133A | NT | Example 133B | NT |
| Example 134 | NT | | |
| Example 135 | NT | | |
| Example 136A | NT | Example 136B | NT |

$IC_{50} \leq 0.1$ µM; ++++, 0.1 µM<$IC_{50} \leq 1$ µM; +++, 1 µM<$IC_{50} \leq 10$ µM; ++, 10 µM<$IC_{50}$; +, not tested; NT As is obvious from Tables 2 to 6, it was found that the compounds of the present invention have excellent voltage-dependent T-type calcium channel inhibitory action.

Example 142

Pharmacological Test 3
(Test Method)
Electrophysiological Evaluation

Stable cell line expressing human Cav3.2 channels, which had been produced by Test method (1) of Example 140, was seeded in a 10-cm dish using DMEM medium containing 10% FBS, and the cells were cultured for 24 hours or longer under the conditions of 37° C. and 5% $CO_2$. The cells were detached using Accutase and were used after being suspended in ice-cold extracellular solution. The Cav3.2 channel current was measured by the Whole-cell patch-clamp method using an automatic patch-clamp system (Port-a-Patch; Nanion Technologies GmbH, EPC-10; HEKA Elektronik GmbH, Patchmaster; HEKA Elektronik GmbH) and buffers described below. Measurement of the Cav3.2 channel current was carried out at room temperature, and the measurement conditions were set as follows: holding potential: −80 mV, depolarization potential: −20 mV, depolarization time: 100 msec, and depolarization frequency: 10 sec. The Cav3.2 channel current was defined as the peak value of the inward current observed when depolarization occurred at −20 mV.

For a test compound, a DMSO solution was diluted 1,000 times with extracellular solution, and thus a solution having an intended concentration was produced. The test compound was applied using an extracellular perfusion system (Nanion Technologies GmbH) until the Cav3.2 channel current was stabilized, and five concentrations at the maximum from the low-concentration side were cumulatively applied. The inhibition ratio of the test compound was calculated from the current value immediately before the application of the test compound and the change rate of the Cav3.2 channel current after the application of the test compound (conditions for a holding potential of −80 mV: test compound concentration of 0.3 µM, conditions for a holding potential of −100 mV: test compound concentration of 3 µM).

(Buffer Composition)
Extracellular solution: 135 mM NaCl, 4 mM KCl, 1 mM $MgCl_2$, 5 mM $CaCl_2$, 5 mM D-Glucose, and 10 mM HEPES, pH 7.4

Internal solution for electrode: 10 mM NaCl, 10 mM HEPES, 50 mM CsCl, 60 mM CsF, and 20 mM EGTA, pH 7.2

(Test Results)
The test results are presented in Tables 7 and 8.

TABLE 7

| Test compound | Cav3.2 channel current inhibition ratio at 0.3 µM of test compound (holding potential −80 mV) | Cav3.2 channel current inhibition ratio at 3 µM of test compound (holding potential −100 mV) |
|---|---|---|
| RQ-00311651 | 17% | 14% |
| Example 3A | 60% | 13% |
| Example 4A | 58% | NT |
| Example 5A | 59% | NT |
| Example 8A | 1% | 13% |

TABLE 7-continued

| Test compound | Cav3.2 channel current inhibition ratio at 0.3 µM of test compound (holding potential −80 mV) | Cav3.2 channel current inhibition ratio at 3 µM of test compound (holding potential −100 mV) |
|---|---|---|
| Example 15 | 33% | NT |
| Example 17 | 64% | NT |
| Example 22A | 81% | NT |
| Example 25A | 59% | 54% |
| Example 26 | 19% | NT |
| Example 34A | 58% | NT |
| Example 36 | 94% | NT |
| Example 39 | 50% | NT |
| Example 42 | 87% | NT |
| Example 43 | 32% | NT |
| Example 49 | 35% | NT |
| Example 50 | 43% | NT |
| Example 51 | 33% | NT |
| Example 52 | 36% | NT |
| Example 60 | 48% | NT |

TABLE 8

| | Cav3.2 channel current inhibition ratio at 0.3 µM of test compound (holding potential −80 mV) | Cav3.2 channel current inhibition ratio at 3 µM of test compound (holding potential −100 mV) |
|---|---|---|
| Example 61 | 53% | NT |
| Example 62 | 34% | NT |
| Example 63 | 91% | NT |
| Example 64A | 52% | NT |
| Example 65 | 81% | 49% |
| Example 66 | 81% | NT |
| Example 73 | 50% | NT |
| Example 76 | 49% | NT |
| Example 78 | 49% | NT |
| Example 82 | 88% | NT |
| Example 88 | 37% | NT |
| Example 91 | 72% | NT |
| Example 92 | 74% | NT |
| Example 93 | 22% | NT |
| Example 100 | 90% | 52% |
| Example 101 | 73% | NT |
| Example 102 | 74% | NT |
| Example 104 | 52% | NT |
| Example 105 | 58% | NT |
| Example 114 | 32% | NT |
| Example 117A | 70% | NT |

Not test; NT
RQ-00311651: Example 286 of WO 2010/137351 As is obvious from Tables 7 and 8, it was found that the compounds of the present invention have excellent voltage-dependent T-type calcium channel inhibitory action.

Example 143

Pharmacological Test 4
(Test Method)
Evaluation of CYP3A4 Activity Inhibitory Action To a 50 mM potassium phosphate buffer solution (pH 7.4), 5 nM Human CYP3A4BR EasyCYP Bactosomes (Cypex, Ltd.), 50 µM 7-Benzyloxy-4-(trifluoromethyl)-coumarin, cofactor mix (0.0081 mM β-NADP$^+$, 0.4 mM G-6-P, 0.4 mM $MgCl_2$, and 0.2 U/mL G-6-P DH(Y)), and 0.01% Pluronic F-127 were added, and the mixture was incubated for 45 minutes at 37° C. The reaction was initiated by adding the cofactor mix. After the incubation, 0.5 M Tris base/acetonitrile (20:80) was added thereto as a reaction terminating liquid, and the resulting mixture was stirred. Subsequently, the fluorescence intensity (excitation: 405 nm, emission: 535 nm) was measured. The reaction was carried out in duplicate. The results are presented as the inhibition rate at 10 µM of the test compound.

(Test Results)
The test results are presented in Table 9.

TABLE 9

| Test compound | CYP3A4 activity inhibition ratio at 10 µM of test compound |
|---|---|
| TTA-A2 | 55.7% |
| Example 3A | 12.7% |
| Example 4A | 39.6% |
| Example 5A | 13.0% |
| Example 12 | 84.4% |
| Example 15 | 21.9% |
| Example 17 | 31.8% |
| Example 20 | 27.4% |
| Example 21A | 16.9% |
| Example 21B | 23.3% |
| Example 22A | 12.2% |
| Example 24 | 51.1% |
| Example 25 | 8.7% |
| Example 26 | 11.3% |
| Example 31A | 7.0% |
| Example 32 | 23.3% |
| Example 33 | −12.8% |
| Example 34 | 19.6% |
| Example 36 | 81.0% |
| Example 42 | 77.9% |
| Example 43 | 23.6% |
| Example 53 | 3.0% |
| Example 54 | −1.1% |
| Example 57 | −1.4% |
| Example 58 | 53.5% |
| Example 60 | −1.2% |
| Example 61 | 4.5% |
| Example 63 | 45.7% |
| Example 64A | 4.4% |
| Example 65 | 4.2% |
| Example 91 | 20.1% |
| Example 92 | 23.6% |
| Example 100 | 27.9% |
| Example 105 | 21.2% |
| Example 109 | 24.1% |
| Example 114 | 30.0% |
| Example 123 | 11.7% |
| Example 124 | 28.6% |
| Example 125 | 25.0% |
| Example 129 | 56.0% |

TTA-A2: Example 21 of Japanese Patent No. 5269761

It was found that the compounds of the present invention include compounds having weak CYP3A4 activity inhibitory action as well.

Example 144

Pharmacological Test 5
(Test Method)
Mechanical Allodynia in a Mouse Partial Sciatic Nerve Ligation (PSNL) Model Production of a mouse PSNL model was carried out according to the method of Seltzer, et al. A mouse was subjected to inhalation anesthesia with isoflurane. The femoral region of the mouse was shaved and disinfected with isodine. The skin on the thighbone of the mouse was incised, the fascia underneath the skin was cut, and the biceps femoris muscle was divided at a site between the heads of muscles. The sciatic nerve underneath the incision was checked, and then the sciatic nerve was detached without damaging the nerve. The needle of an 8-0 silk suture with a needle was passed through the sciatic nerve so as to penetrate through the nerve, and thus a portion of about ½ to ⅓ of the sciatic nerve was ligated. The skin was sutured, and the mouse was kept for about 7 days. The surgery of a Sham control mouse was performed only for checking of the sciatic nerve, and the skin was sutured.

The measurement of pain threshold was carried out after the mouse was transferred into a cage for measurement and was waited until exploratory behavior had disappeared. Regarding the pain threshold (paw withdrawal filament (g)), the planta pedis of the mouse was stimulated with von Frey filaments (Sttoelting Co.: TOUCH-TEST SENSORY EVALUATOR) having different stimulus intensities, and the presence or absence of an escape reaction was observed. The 50% threshold was calculated by an up-down method by referring to the method of Chaplan, et al. (Quantitative assessment of tactile allodynia in the raw paw. J Neurosci Methods, 53, 1994, 55-63).

For an evaluation of efficacy, diastereomer A of Example 3 was intraperitoneally administered into the PSNL model, and an observation was made for the influence of the compound on the pain threshold by the von Frey filament test.

Figure 2:
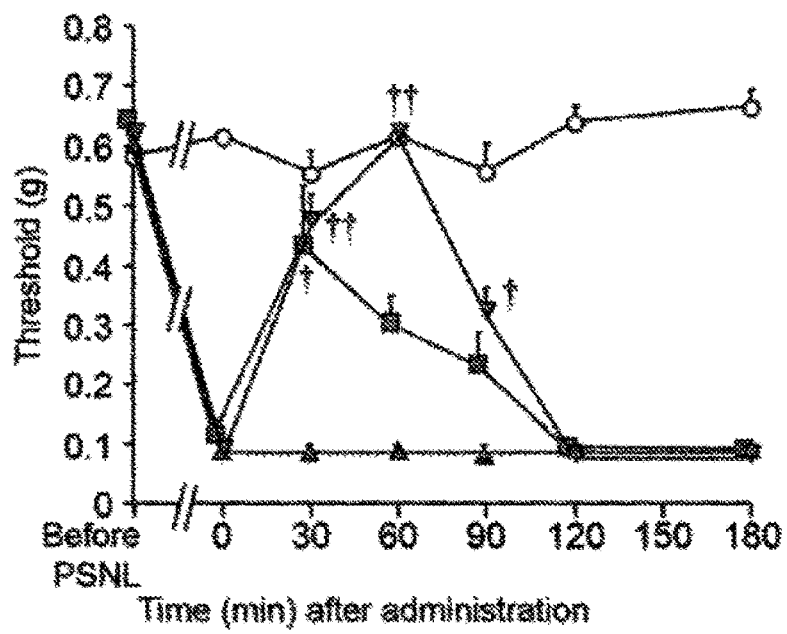
FIG. 2 is a diagram showing the test results for allodynia in a PSNL model using Example 65.

(Test Results)
The results are presented in FIG. 1.
When diastereomer A of Example 3 was intraperitoneally administered at a dose of 20 to 30 mg/kg, the compound suppressed mechanical allodynia statistically significantly compared to the vehicle group.

Example 145

Pharmacological Test 6
(Test Method)
Mechanical Allodynia in Mouse PSNL Model

Production of a mouse PSNL model was carried out according to the method of Seltzer, et al. A mouse was subjected to inhalation anesthesia with isoflurane. The femoral region of the mouse was shaved and disinfected with isodine. The skin on the thighbone of the mouse was incised, the fascia underneath the skin was cut, and the biceps femoris muscle was divided at a site between the heads of muscles. The sciatic nerve underneath the incision was checked, and then the sciatic nerve was detached without damaging the nerve. The needle of an 8-0 silk suture with a needle was passed through the sciatic nerve so as to penetrate through the nerve, and thus a portion of about ½ to ⅓ of the sciatic nerve was ligated. The skin was sutured, and the mouse was kept for about 7 days. The surgery of a Sham control mouse was performed only for checking of the sciatic nerve, and the skin was sutured.

The measurement of pain threshold was carried out after the mouse was transferred into a cage for measurement and was waited until exploratory behavior had disappeared. Regarding the pain threshold (paw withdrawal filament (g)), the planta pedis of the mouse was stimulated with von Frey filaments (Sttoelting Co.: TOUCH-TEST SENSORY EVALUATOR) having different stimulus intensities, and the presence or absence of an escape reaction was observed. The 50% threshold was calculated by an up-down method by referring to the method of Chaplan, et al. (Quantitative assessment of tactile allodynia in the raw paw. J Neurosci Methods, 53, 1994, 55-63).

For an evaluation of efficacy, Example 65 was perorally administered into the PSNL model, and an observation was made for the influence of the compound on the pain threshold by the von Frey filament test.

(Test Results)
The results are presented in FIG. 2.
As is obvious from FIG. 2, when Example 65 was perorally administered at a dose of 10 mg/kg and 30 mg/kg, the compound suppressed mechanical allodynia statistically significantly compared to the vehicle group.

(Data show the mean with S.E.M. for five mice. †P<0.05, ††P<0.01 vs. PSNL+Vehicle.)

INDUSTRIAL APPLICABILITY

The compounds of the present invention can be used as pain treatment drug.

REFERENCE SIGNS LIST

In FIG. 1, the symbol ○ represents Sham+Vehicle.
In FIG. 1, the symbol ● represents PSNL+Vehicle.
In FIG. 1, the symbol ♦ represents PSNL+diastereomer A of Example 3 at a dose of 10 mg/kg.
In FIG. 1, the symbol ■ represents PSNL+diastereomer A of Example 3 at a dose of 20 mg/kg.
In FIG. 1, the symbol ▲ represents PSNL+diastereomer A of Example 3 at a dose of 30 mg/kg.
In FIG. 2, the symbol ○ represents Sham+Vehicle.
In FIG. 2, the symbol ▲ represents PSNL+Vehicle.
In FIG. 2, the symbol ■ represents PSNL+Example 65 at a dose of 10 mg/kg.
In FIG. 2, the symbol ▼ represents PSNL+Example 65 at a dose of 30 mg/kg.

The invention claimed is:

1. A compound represented by the following General Formula (IA), a tautomer or a stereoisomer of the compound, a pharmaceutically acceptable salt thereof, or a solvate thereof:

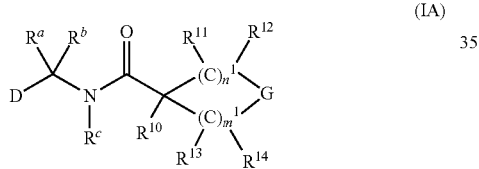

(IA)

wherein D represents a 5-membered heteroaryl group having one to three identical or different heteroatoms selected from the group consisting of an oxygen atom, a nitrogen atom, and a sulfur atom as a ring-constituting element(s), or a fused ring of a 5-membered or 6-membered heterocyclic ring having one or two identical or different heteroatoms selected from the group consisting of an oxygen atom, a nitrogen atom, and a sulfur atom as a ring-constituting element(s) with either a benzene ring or a pyridine ring, the 5-membered heteroaryl group having, as a substituent, at least one selected from the group consisting of a halogen atom, a cyano group, a carboxyl group, an alkyl group having 1 to 8 carbon atoms, a cyclopropyl group, an alkoxy group having 1 to 8 carbon atoms, a phenyl group which may have a substituent, a group represented by the following formula:

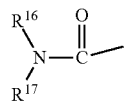

an alkyl group having 1 to 8 carbon atoms and substituted with 1 to 5 halogen atoms, an alkoxy group having 1 to 8 carbon atoms and substituted with 1 to 5 halogen atoms, and a (C1-C8 alkyloxy)carbonyl group, and the fused ring may have as a substituent, at least one selected from the group consisting of a halogen atom, a cyano group, a carboxyl group, an alkyl group having 1 to 8 carbon atoms, a cyclopropyl group, an alkoxy group having 1 to 8 carbon atoms, a phenyl group which may have a substituent, a group represented by the following formula:

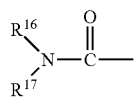

an alkyl group having 1 to 8 carbon atoms and substituted with 1 to 5 halogen atoms, an alkoxy group having 1 to 8 carbon atoms and substituted with 1 to 5 halogen atoms, and a (C1-C8 alkyloxy)carbonyl group, while D is bonded to $C(R^a)(R^b)N$ via a ring-constituting carbon atom;

wherein, $R^{16}$ and $R^{17}$, which may be identical or different, each represent a hydrogen atom, an alkyl group having 1 to 8 carbon atoms, or an aryl group which may have a substituent; or $R^{16}$, $R^{17}$, and the nitrogen atom to which $R^{16}$ and $R^{17}$ are bonded are joined together and represent a saturated nitrogen-containing saturated 4-membered to 7-membered heterocyclic ring which may further have one heteroatom selected from the group consisting of an oxygen atom, a nitrogen atom, and a sulfur atom as a ring-constituting element, and may have a substituent;

$R^a$ represents a hydrogen atom, a cyano group, an alkyl group having 1 to 8 carbon atoms, an alkyl group having 1 to 8 carbon atoms and substituted with 1 to 5 halogen atoms, a 3-membered to 7-membered cycloalkyl group, or a heteroaryl group which may have a substituent, and $R^b$ represents a hydrogen atom or an alkyl group having 1 to 8 carbon atoms;

alternatively, $R^a$, $R^b$, and the carbon atom to which $R^a$ and $R^b$ are bonded are joined together and form a 3-membered to 6-membered cycloalkyl ring;

$R^c$ represents a hydrogen atom or an alkyl group having 1 to 8 carbon atoms;

G represents $CR^{15}(W^1)$ wherein, $W^1$ represents an alkyl group having 1 to 8 carbon atoms substituted with a phenyloxy group which may have any one selected from the group consisting of a trifluoromethyl group, a t-butyl group, and a methoxy group as a substituent of the phenyl group, a phenylaminocarbonyl group which may have any one selected from the group consisting of a trifluoromethyl group, a t-butyl group, and a methoxy group as a substituent of the phenyl group, or a heteroaryl group which may have a substituent;

wherein the heteroaryl group of $W^1$ is selected from imidazole or a fused ring of a 5-membered heteroaryl ring having one or two nitrogen atoms as a ring-constituting element with a 6-membered heteroaryl ring having one or two nitrogen atoms as a ring-constituting element or a benzene ring;

the substituent which may be carried by the heteroaryl group of $W^1$ is a halogen atom, a carboxyl group, a cyano group, a hydroxyl group, an alkyl group having 1 to 8 carbon atoms, an alkoxy group having 1 to 8 carbon atoms, an alkylsulfonyl group having 1 to 8 carbon atoms, an alkyl group having 1 to 8 carbon atoms and substituted with 1 to 5 halogen atoms, an alkoxy group having 1 to 8 carbon atoms and substituted with 1 to 5 halogen atoms, an amino group, an alkylamino group having 1 to 8 carbon atoms, a carboxamide, a phenyl group, a pyridyl group, or an alkyl group having 1 to 5 carbon atoms and substituted with a phenyl group;

$R^{10}$, $R^{11}$, $R^{12}$, $R^{13}$, $R^{14}$, and $R^{15}$, which may be identical or different, each represent a hydrogen atom, a cyano group, a hydroxyl group, a halogen atom, a carboxyl group, an amino group, an alkylamino group having 1 to 8 carbon atoms, a dialkylamino group having 2 to 12 carbon atoms, or an alkyl group having 1 to 8 carbon atoms;

$n^1$ represents 0 and $m^1$ represents 1.

2. The compound according to claim 1, a tautomer or a stereoisomer of the compound, a pharmaceutically acceptable salt thereof, or a solvate thereof,
wherein the 5-membered heteroaryl group for D, having one to three identical or different heteroatoms selected from the group consisting of an oxygen atom, a nitrogen atom, and a sulfur atom as a ring-constituting element(s), is thiophene, thiazole, pyrazole, imidazole, furan, oxazole, oxadiazole, triazole, or pyrrole.

3. The compound according to claim 1, a tautomer or a stereoisomer of the compound, a pharmaceutically acceptable salt thereof, or a solvate thereof,
wherein the 5-membered heteroaryl group for D, having one to three identical or different heteroatoms selected from the group consisting of an oxygen atom, a nitrogen atom, and a sulfur atom, as a ring-constituting element(s), is thiophene or thiazole.

4. The compound according to claim 1, a tautomer or a stereoisomer of the compound, a pharmaceutically acceptable salt thereof, or a solvate thereof,
wherein the fused ring of a 5-membered or 6-membered heterocyclic ring for D, having one or two identical or different heteroatoms selected from the group consisting of an oxygen atom, a nitrogen atom, and a sulfur atom as a ring-constituting element(s) with either a benzene ring or a pyridine ring, is indole, benzofuran, furopyridine, pyrazolopyridine, benzoxazole, benzothiazole, benzimidazole, quinoline, dihydrobenzodioxine, or dihydrobenzofuran.

5. The compound according to claim 1, a tautomer or a stereoisomer of the compound, a pharmaceutically acceptable salt thereof, or a solvate thereof,
wherein the fused ring of a 5-membered or 6-membered heterocyclic ring for D, having one or two identical or different heteroatoms selected from the group consisting of an oxygen atom, a nitrogen atom, and a sulfur atom as a ring-constituting element(s) with either a benzene ring or a pyridine ring, is benzofuran, benzothiophene, or benzoxazole.

6. The compound according to claim 1, a tautomer or a stereoisomer of the compound, a pharmaceutically acceptable salt thereof, or a solvate thereof,
wherein $R^a$ represents an alkyl group having 1 to 8 carbon atoms, and $R^b$ represents a hydrogen atom.

7. The compound according to claim 1, a tautomer or a stereoisomer of the compound, a pharmaceutically acceptable salt thereof, or a solvate thereof,
wherein $R^c$ represents a hydrogen atom.

8. The compound according to claim 1, a tautomer or a stereoisomer of the compound, a pharmaceutically acceptable salt thereof, or a solvate thereof,
wherein $R^{10}$, $R^{11}$, $R^{12}$, $R^{13}$, and $R^{14}$, which may be identical or different, each represent a hydrogen atom, a halogen atom, or a hydroxyl group.

9. The compound according to claim 1, a tautomer or a stereoisomer of the compound, a pharmaceutically acceptable salt thereof, or a solvate thereof,
wherein $R^{10}$, $R^{11}$, $R^{12}$, $R^{13}$, and $R^{14}$ each represent a hydrogen atom.

10. The compound according to claim 1, a tautomer or a stereoisomer of the compound, a pharmaceutically acceptable salt thereof, or a solvate thereof,
wherein $R^{15}$ represents a hydrogen atom.

11. The compound according to claim 1, a tautomer or a stereoisomer of the compound, a pharmaceutically acceptable salt thereof, or a solvate thereof, wherein $W^1$ represents a heteroaryl group which may have a substituent, and $W^1$ is bonded to $C(R^{15})$ via a carbon atom that constitutes the ring of the heteroaryl group.

12. The compound according to claim 1, a tautomer or a stereoisomer of the compound, a pharmaceutically acceptable salt thereof, or a solvate thereof, wherein $W^1$ represents a fused ring of an optionally substituted 5-membered heteroaryl ring with an optionally substituted 6-membered heteroaryl ring or a benzene ring, the 5-membered heteroaryl ring having one or two nitrogen atoms as a ring-constituting element, and the 6-membered heteroaryl ring having one or two nitrogen atoms as a ring-constituting element.

13. The compound according to claim 1, a tautomer or a stereoisomer of the compound, a pharmaceutically acceptable salt thereof, or a solvate thereof,
wherein $W^1$ represents benzimidazole, imidazole, imidazopyridine, or indole, all of which may have a substituent.

14. The compound according to claim 1, a tautomer or a stereoisomer of the compound, a pharmaceutically acceptable salt thereof, or a solvate thereof,
wherein $W^1$ represents benzimidazol-2-yl which may have a substituent, or indol-3-yl which may have a substituent.

15. A compound represented by the following General Formula (I), a tautomer or a stereoisomer of the compound, a pharmaceutically acceptable salt thereof, or a solvate thereof:

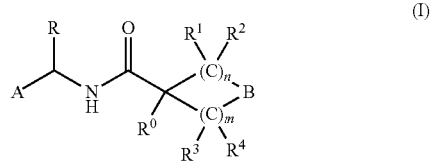

(I)

wherein A represents 5-membered heteroaryl group having one to three identical or different heteroatoms selected from the group consisting of an oxygen atom, a nitrogen atom, and a sulfur atom as a ring-constituting element(s), or a fused ring of a 5-membered or 6-membered heterocyclic ring having one or two identical or different heteroatoms selected from the group consisting of an oxygen atom, a nitrogen atom, and a sulfur atom as a ring-constituting element(s) with either a benzene ring or a pyridine ring, the 5-membered heteroaryl group for A having, as a substituent, at least one selected from the group consisting of a halogen atom, a cyano group, a carboxyl group, an alkyl group having 1 to 8 carbon atoms, a cyclopropyl group, an alkoxy group having 1 to 8 carbon atoms, a phenyl group which may have a substituent, a group represented by the following formula:

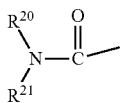

an alkyl group having 1 to 8 carbon atoms and substituted with 1 to 5 halogen atoms, an alkoxy group having 1 to 8 carbon atoms and substituted with 1 to 5 halogen atoms, and a (C1-C8 alkyloxy)carbonyl group, the fused ring may have as a substituent, at least one selected from the group consisting of a halogen atom, a cyano group, a carboxyl group, an alkyl group having 1 to 8 carbon atoms, a cyclopropyl group, an alkoxy group having 1 to 8 carbon atoms, a phenyl group which may have a substituent, a group represented by the following formula:

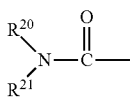

an alkyl group having 1 to 8 carbon atoms and substituted with 1 to 5 halogen atoms, an alkoxy group having 1 to 8 carbon atoms and substituted with 1 to 5 halogen atoms, and a (C1-C8 alkyloxy)carbonyl group, while A is bonded to CH(R)N via a ring-constituting carbon atom;

wherein, $R^{20}$ and $R^{21}$, which may be identical or different, each represent a hydrogen atom, an alkyl group having 1 to 8 carbon atoms, or an aryl group which may have a substituent; or $R^{20}$, $R^{21}$, and the nitrogen atom to which $R^{20}$ and $R^{21}$ are bonded are joined together and represent a saturated nitrogen-containing saturated 4-membered to 7-membered heterocyclic ring which may further have one heteroatom selected from the group consisting of an oxygen atom, a nitrogen atom, and a sulfur atom as a ring-constituting element, and may have a substituent;

R represents a hydrogen atom, a cyano group, an alkyl group having 1 to 8 carbon atoms, a 3-membered to 7-membered cycloalkyl group, or a heteroaryl group which may have a substituent;

B represents $CR^5(Q^1)$;

wherein, $Q^1$ represents an alkyl group having 1 to 8 carbon atoms and substituted with a phenyloxy group which may have any one selected from the group consisting of a trifluoromethyl group, a t-butyl group, and a methoxy group as a substituent for the phenyl group, a phenylaminocarbonyl group which may have any one selected from the group consisting of a trifluoromethyl group, a t-butyl group, and a methoxy group as a substituent for the phenyl group; or a heteroaryl group which may have a substituent;

wherein the heteroaryl group of $Q^1$ is selected from imidazole or a fused ring of a 5-membered heteroaryl ring having one or two nitrogen atoms as a ring-constituting element with a 6-membered heteroaryl ring having one or two nitrogen atoms as a ring-constituting element or a benzene ring;

the substituent which may be carried by the heteroaryl group of $Q^1$ is selected from the group consisting of a halogen atom, a carboxyl group, a cyano group, a hydroxyl group, an alkyl group having 1 to 8 carbon atoms, an alkoxy group having 1 to 8 carbon atoms, an alkylsulfonyl group having 1 to 8 carbon atoms, an alkyl group having 1 to 8 carbon atoms and substituted with 1 to 5 halogen atoms, an alkoxy group having 1 to 8 carbon atoms and substituted with 1 to 5 halogen atoms, an amino group, an alkylamino group having 1 to 8 carbon atoms, a carboxamide, a phenyl group, a pyridyl group, or an alkyl group having 1 to 5 carbon atoms and substituted with a phenyl group;

$R^0$, $R^1$, $R^2$, $R^3$, $R^4$, and $R^5$, which may be identical or different, each represent a hydrogen atom, a cyano group, a hydroxyl group, a halogen atom, a carboxy group, an amino group, an alkylamino group having 1 to 8 carbon atoms, a dialkylamino group having 2 to 12 carbon atoms, or an alkyl group having 1 to 8 carbon atoms;

n represents 0 and m represents 1.

16. The compound according to claim 15, a tautomer or a stereoisomer of the compound, a pharmaceutically acceptable salt thereof, or a solvate thereof, wherein A represents a 5-membered heteroaryl group having one to three identical or different heteroatoms as a ring-constituting element(s), or a fused ring of a 5-membered heteroaryl ring having one to three identical or different heteroatoms as a ring-constituting element(s) with either a benzene ring or a pyridine ring, the 5-membered heteroaryl group and the fused ring having, as a substituent, at least one selected from the group consisting of a halogen atom, a carboxyl group, an alkyl group having 1 to 8 carbon atoms, an alkoxy group having 1 to 8 carbon atoms, a group represented by the following formula:

[Chemical Formula 4]

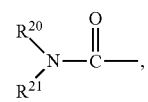

an alkyl group having 1 to 8 carbon atoms and substituted with 1 to 5 halogen atoms, an alkoxy group having 1 to 8 carbon atoms and substituted with 1 to 5 halogen atoms, and a (C1-C8 alkyloxy)carbonyl group, and the fused ring optionally having no substituent;

wherein, $R^{20}$ and $R^{21}$, which may be identical or different, each represent a hydrogen atom, an alkyl group having 1 to 8 carbon atoms, or an aryl group which may have a substituent;

R represents a hydrogen atom, a cyano group, an alkyl group having 1 to 8 carbon atoms, or a heteroaryl group which may have a substituent;

$Q^1$ represents an alkyl group having 1 to 8 carbon atoms and substituted with a phenyloxy group which may have any one selected from the group consisting of a trifluoromethyl group, a t-butyl group, and a methoxy group as a substituent for the phenyl group, or a heteroaryl group which may have a substituent;

wherein the heteroaryl group of $Q^1$ is selected from imidazole or a fused ring of a 5-membered heteroaryl ring having one or two nitrogen atoms as a ring-constituting element with a 6-membered heteroaryl ring having one or two nitrogen atoms as a ring-constituting element or a benzene ring; and $R^0$, $R^1$, $R^2$, $R^3$, $R^4$, and $R^5$, which may be identical or different, each represent a hydrogen atom, a cyano group, a hydroxyl group, a halogen atom, a carboxyl group, an amino group, an alkylamino group having 1 to 8 carbon atoms, or an alkyl group having 1 to 8 carbon atoms.

17. The compound according to claim 15, a tautomer or a stereoisomer of the compound, a pharmaceutically acceptable salt thereof, or a solvate thereof,
wherein the 5-membered heteroaryl group having a substituent for A is thiophene, thiazole, pyrazole, imidazole, furan, oxazole, oxadiazole, triazole, or pyrrole.

18. The compound according to claim 15, a tautomer or a stereoisomer of the compound, a pharmaceutically acceptable salt thereof, or a solvate thereof, wherein A represents thiophene or thiazole, each of which have a substituent.

19. The compound according to claim 15, a tautomer or a stereoisomer of the compound, a pharmaceutically acceptable salt thereof, or a solvate thereof,
wherein the fused ring of a 5-membered or 6-membered heterocyclic ring for A, having one or two identical or different heteroatoms selected from the group consisting of an oxygen atom, a nitrogen atom, and a sulfur atom as a ring-constituting element(s) with either a benzene ring or a pyridine ring, is indole, benzofuran, furopyridine, pyrazolopyridine, benzoxazole, benzothiazole, benzimidazole, quinoline, dihydrobenzodioxine, or dihydrobenzofuran.

20. The compound according to claim 4, a tautomer or a stereoisomer of the compound, a pharmaceutically acceptable salt thereof, or a solvate thereof,
wherein the fused ring of a 5-membered or 6-membered heterocyclic ring for A, having one or two identical or different heteroatoms selected from the group consisting of an oxygen atom, a nitrogen atom, and a sulfur atom as a ring-constituting element(s) with either a benzene ring or a pyridine ring, is benzofuran, benzoxazole, or benzothiophene.

21. The compound according to claim 15, a tautomer or a stereoisomer of the compound, a pharmaceutically acceptable salt thereof, or a solvate thereof,
wherein R represents an alkyl group having 1 to 8 carbon atoms.

22. The compound according to claim 15, a tautomer or a stereoisomer of the compound, a pharmaceutically acceptable salt thereof, or a solvate thereof,
wherein $R^0$, $R^1$, $R^2$, $R^3$, and $R^4$, which may be identical or different, each represent a hydrogen atom, a halogen atom, or a hydroxyl group.

23. The compound according to claim 15, a tautomer or a stereoisomer of the compound, a pharmaceutically acceptable salt thereof, or a solvate thereof,
wherein $R^0$, $R^1$, $R^2$, $R^3$, and $R^4$ each represent a hydrogen atom.

24. The compound according to claim 15, a tautomer or a stereoisomer of the compound, a pharmaceutically acceptable salt thereof, or a solvate thereof,
wherein $R^5$ represents a hydrogen atom.

25. The compound according to claim 15, a tautomer or a stereoisomer of the compound, a pharmaceutically acceptable salt thereof, or a solvate thereof, wherein $Q^1$ represents a heteroaryl group which may have a substituent, and $Q^1$ is bonded to $C(R^5)$ via a carbon atom that constitutes the ring of the heteroaryl group.

26. The compound according to claim 15, a tautomer or a stereoisomer of the compound, a pharmaceutically acceptable salt thereof, or a solvate thereof,
wherein $Q^1$ represents a fused ring of a 5-membered heteroaryl ring having one or two nitrogen atoms as a ring-constituting element with a 6-membered heteroaryl ring having one or two nitrogen atoms as a ring-constituting element or a benzene ring, the fused ring which may have a substituent.

27. The compound according to claim 15, a tautomer or a stereoisomer of the compound, a pharmaceutically acceptable salt thereof, or a solvate thereof, wherein $Q^1$ represents benzimidazole, imidazole, imidazopyridine, or indole, all of which may have a substituent.

28. The compound according to claim 15, a tautomer or a stereoisomer of the compound, a pharmaceutically acceptable salt thereof, or a solvate thereof,
wherein $Q^1$ represents benzimidazol-2-yl or indol-3-yl, each of which may have a substituent.

29. The compound according to claim 15, a tautomer or a stereoisomer of the compound, a pharmaceutically acceptable salt thereof, or a solvate thereof,
wherein the substituent of the heteroaryl group which may have a substituent, represented by $Q^1$, is selected from the group consisting of a halogen atom, a carboxyl group, a cyano group, a hydroxyl group, an alkyl group having 1 to 8 carbon atoms, an alkoxy group having 1 to 8 carbon atoms, an alkylsulfonyl group having 1 to 8 carbon atoms, an alkyl group having 1 to 8 carbon atoms and substituted with 1 to 5 halogen atoms, an alkoxy group having 1 to 8 carbon atoms and substituted with 1 to 5 halogen atoms, an amino group, an alkylamino group having 1 to 8 carbon atoms, and a carboxamide.

30. A compound represented by the following General Formula (II), a tautomer or a stereoisomer of the compound, a pharmaceutically acceptable salt thereof, or a solvate thereof:

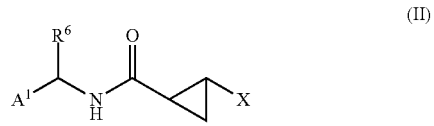

(II)

wherein $A^1$ represents a 5-membered heteroaryl group having one to three identical or different heteroatoms selected from the group consisting of an oxygen atom, a nitrogen atom, and a sulfur atom as a ring-constituting element(s), or a fused ring of a 5-membered or 6-membered heterocyclic ring having one or two identical or different heteroatoms selected from the group consisting of an oxygen atom, a nitrogen atom, and a sulfur atom as a ring-constituting element(s) with either a benzene ring or a pyridine ring, the 5-membered heteroaryl group of $A^1$ having, as a substituent, at least one selected from the group consisting of a halogen atom, a cyano group, a carboxyl group, an alkyl group having 1 to 8 carbon atoms, a cyclopropyl group, an alkoxy group having 1 to 8 carbon atoms, a phenyl group which may have a substituent, a group represented by the following formula:

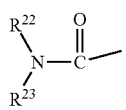

an alkyl group having 1 to 8 carbon atoms and substituted with 1 to 5 halogen atoms, an alkoxy group having 1 to 8 carbon atoms and substituted with 1 to 5 halogen atoms, and a (C1-C8 alkyloxy)carbonyl group, and the fused ring may have as a substituent, at least one selected from the group consisting of a halogen atom, a cyano group, a carboxyl group, an alkyl group having 1 to 8 carbon atoms, a cyclopropyl group, an alkoxy group having 1 to 8 carbon atoms, a phenyl group which may have a substituent, a group represented by the following formula:

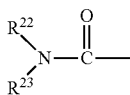

an alkyl group having 1 to 8 carbon atoms and substituted with 1 to 5 halogen atoms, an alkoxy group having 1 to 8 carbon atoms and substituted with 1 to 5 halogen atoms, and a (C1-C8 alkyloxy)carbonyl group, while $A^1$ is bonded to $CH(R^6)N$ via a ring-constituting carbon atom;

wherein, $R^{22}$ and $R^{23}$, which may be identical or different, each represent a hydrogen atom, an alkyl group having 1 to 8 carbon atoms, or an aryl group which may have a substituent; or $R^{22}$, $R^{23}$, and the nitrogen atom to which $R^{22}$ and $R^{23}$ are bonded are joined together and represent a saturated nitrogen-containing saturated 4-membered to 7-membered heterocyclic ring which may further have one heteroatom selected from the group consisting of an oxygen atom, a nitrogen atom, and a sulfur atom as a ring-constituting element, and may have a substituent;

$R^6$ represents a hydrogen atom, a cyano group, an alkyl group having 1 to 8 carbon atoms, a 3-membered to 7-membered cycloalkyl group, or a heteroaryl group which may have a substituent; and X represents a heteroaryl group which may have, as a substituent, any one selected from the group consisting of a halogen atom, a carboxyl group, a cyano group, a hydroxyl group, an alkyl group having 1 to 8 carbon atoms, an alkoxy group having 1 to 8 carbon atoms, an alkylsulfonyl group having 1 to 8 carbon atoms, an alkyl group having 1 to 8 carbon atoms and substituted with 1 to 5 halogen atoms, an alkoxy group having 1 to 8 carbon atoms and substituted with 1 to 5 halogen atoms, an amino group, an alkylamino group having 1 to 8 carbon atoms, a carboxamide, a phenyl group, a pyridyl group, or an alkyl group having 1 to 5 carbon atoms and substituted with a phenyl group, wherein the heteroaryl group of X is selected from imidazole or a fused ring.

31. The compound according to claim 30, a tautomer or a stereoisomer of the compound, a pharmaceutically acceptable salt thereof, or a solvate thereof, wherein the fused ring of a 5-membered or 6-membered heterocyclic ring for $A^1$, having one or two identical or different heteroatoms selected from the group consisting of an oxygen atom, a nitrogen atom, and a sulfur atom as a ring-constituting element(s) with either a benzene ring or a pyridine ring, is indole, benzofuran, furopyridine, pyrazolopyridine, benzoxazole, benzothiazole, benzimidazole, quinoline, dihydrobenzodioxine, or dihydrobenzofuran.

32. The compound according to claim 30, a tautomer or a stereoisomer of the compound, a pharmaceutically acceptable salt thereof, or a solvate thereof, wherein the heteroaryl group having a substituent for $A^1$ is thiophene, thiazole, pyrazole, imidazole, furan, oxazole, oxadiazole, triazole, or pyrrole.

33. The compound according to claim 30, a tautomer or a stereoisomer of the compound, a pharmaceutically acceptable salt thereof, or a solvate thereof,
wherein $A^1$ represents thiophene or thiazole, each of which have a substituent.

34. The compound according to claim 30, a tautomer or a stereoisomer of the compound, a pharmaceutically acceptable salt thereof, or a solvate thereof,
wherein $A^1$ represents thiophene or thiazole, each of which is substituted with at least one alkoxy group having 1 to 4 carbon atoms which is substituted with 1 to 3 halogen atoms.

35. The compound according to claim 30, a tautomer or a stereoisomer of the compound, a pharmaceutically acceptable salt thereof, or a solvate thereof,
wherein $A^1$ represents benzofuran, benzoxazole, or benzothiophene, each of which may have a substituent.

36. The compound according to claim 30, a tautomer or a stereoisomer of the compound, a pharmaceutically acceptable salt thereof, or a solvate thereof,
wherein the heteroaryl group of X is a fused ring, and X is bonded to cyclopropyl via a carbon atom that constitutes a heteroaryl ring of the fused ring.

37. The compound according to claim 30, a tautomer or a stereoisomer of the compound, a pharmaceutically acceptable salt thereof, or a solvate thereof,
wherein the substituent of the fused ring for X is selected from the group consisting of a halogen atom, a carboxyl group, a cyano group, a hydroxyl group, an alkyl group having 1 to 8 carbon atoms, an alkoxy group having 1 to 8 carbon atoms, an alkylsulfonyl group having 1 to 8 carbon atoms, an alkyl group having 1 to 8 carbon atoms and substituted with 1 to 5 halogen atoms, an alkoxy group having 1 to 8 carbon atoms and substituted with 1 to 5 halogen atoms, and a carboxamide.

38. The compound according to claim 30, a tautomer or a stereoisomer of the compound, a pharmaceutically acceptable salt thereof, or a solvate thereof,
wherein X represents a fused ring of a 5-membered heteroaryl ring having one or two nitrogen atoms as a ring-constituting element with a benzene ring, the fused ring which may have a substituent.

39. The compound according to claim 30, a tautomer or a stereoisomer of the compound, a pharmaceutically acceptable salt thereof, or a solvate thereof,
wherein X represents benzimidazol-2-yl which may have a substituent, or indol-3-yl which may have a substituent.

40. The compound according to claim 30, a tautomer or a stereoisomer of the compound, a pharmaceutically acceptable salt thereof, or a solvate thereof,
wherein X represents benzimidazol-2-yl.

41. The compound according to claim 30, a tautomer or a stereoisomer of the compound, a pharmaceutically acceptable salt thereof, or a solvate thereof,
wherein $R^6$ represents a methyl group.

42. A compound selected from the following, a tautomer or a stereoisomer of the compound, a pharmaceutically acceptable salt thereof, or a solvate thereof:

- (1S,2S)-2-(1H-benzo[d]imidazol-2-yl)-N-((R)-1-(4-methyl-5-(2,2,2-trifluoroethoxy)thiophen-2-yl)ethyl)cyclopropane-1-carboxamide,
- (1R,2R)-2-(1H-benzo[d]imidazol-2-yl)-N-((R)-1-(4-methyl-5-(2,2,2-trifluoroethoxy)thiophen-2-yl)ethyl)cyclopropane-1-carboxamide,
- (1S,2S)-2-(1H-benzo[d]imidazol-2-yl)-N-((S)-1-(5-(2,2,2-trifluoroethoxy)thiophen-2-yl)ethyl)cyclopropane-1-carboxamide,
- (1R,2R)-2-(1H-benzo[d]imidazol-2-yl)-N-((S)-1-(5-(2,2,2-trifluoroethoxy)thiophen-2-yl)ethyl)cyclopropane-1-carboxamide,
- (1S,2S)-2-(1H-benzo[d]imidazol-2-yl)-N-((R)-1-(5-(2,2,2-trifluoroethoxy)thiophen-2-yl)ethyl)cyclopropane-1-carboxamide,
- (1R,2R)-2-(1H-benzo[d]imidazol-2-yl)-N-((R)-1-(5-(2,2,2-trifluoroethoxy)thiophen-2-yl)ethyl)cyclopropane-1-carboxamide,
- (1S,2S)-2-(1-methyl-1H-benzo[d]imidazol-2-yl)-N-((R)-1-(5-(2,2,2-trifluoroethoxy)thiophen-2-yl)ethyl)cyclopropane-1-carboxamide,
- (1R,2R)-2-(1-methyl-1H-benzo[d]imidazol-2-yl)-N-((R)-1-(5-(2,2,2-trifluoroethoxy)thiophen-2-yl)ethyl)cyclopropane-1-carboxamide,
- (1S,2S)-2-(1H-benzo[d]imidazol-2-yl)-N-((R)-1-(5-(trifluoromethyl)thiophen-2-yl)ethyl)cyclopropane-1-carboxamide,
- (1R,2R)-2-(1H-benzo[d]imidazol-2-yl)-N-((R)-1-(5-(trifluoromethyl)thiophen-2-yl)ethyl)cyclopropane-1-carboxamide,
- (1S,2S)-2-(1H-benzo[d]imidazol-2-yl)-N-((R)-1-(5-bromothiophen-2-yl)ethyl)cyclopropane-1-carboxamide,
- (1R,2R)-2-(1H-benzo[d]imidazol-2-yl)-N-((R)-1-(5-bromothiophen-2-yl)ethyl)cyclopropane-1-carboxamide,
- (1S,2S)-2-(1H-benzo[d]imidazol-2-yl)-N-((S)-1-(2-(2,2,2-trifluoroethoxy)thiazol-5-yl)ethyl)cyclopropane-1-carboxamide,
- (1R,2R)-2-(1H-benzo[d]imidazol-2-yl)-N-((S)-1-(2-(2,2,2-trifluoroethoxy)thiazol-5-yl)ethyl)cyclopropane-1-carboxamide,
- (1S,2S)-2-(1H-benzo[d]imidazol-2-yl)-N-((R)-1-(2-(2,2,2-trifluoroethoxy)thiazol-2-yl)ethyl)cyclopropane-1-carboxamide,
- (1R,2R)-2-(1H-benzo[d]imidazol-2-yl)-N-((R)-1-(2-(2,2,2-trifluoroethoxy)thiazol-2-yl)ethyl)cyclopropane-1-carboxamide,
- (1S,2S)-2-(1H-benzo[d]imidazol-2-yl)-N-((R)-1-(5-(3,3,3-trifluoropropyl)-1H-pyrazol-4-yl)ethyl)cyclopropane-1-carboxamide,
- (1R,2R)-2-(1H-benzo[d]imidazol-2-yl)-N-((R)-1-(5-(3,3,3-trifluoropropyl)-1H-pyrazol-4-yl)ethyl)cyclopropane-1-carboxamide,
- (1S,2S)-2-(1H-benzo[d]imidazol-2-yl)-N-((R)-1-(5-bromothiazol-2-yl)ethyl)cyclopropane-1-carboxamide, and
- (1R,2R)-2-(1H-benzo[d]imidazol-2-yl)-N-((R)-1-(5-bromothiazol-2-yl)ethyl)cyclopropane-1-carboxamide.

43. A compound selected from the following, a tautomer or a stereoisomer of the compound, a pharmaceutically acceptable salt thereof, or a solvate thereof:

- (1S,2S)-2-(1-methyl-1H-imidazol-2-yl)-N-((R)-1-(5-(2,2,2-trifluoroethoxy)thiophen-2-yl)ethyl)cyclopropane-1-carboxamide,
- (1R,2R)-2-(1-methyl-1H-imidazol-2-yl)-N-((R)-1-(5-(2,2,2-trifluoroethoxy)thiophen-2-yl)ethyl)cyclopropane-1-carboxamide,
- (1S,2S)-2-(1H-indol-3-yl)-N-((R)-1-(5-(2,2,2-trifluoroethoxy)thiophen-2-yl)ethyl)cyclopropane-1-carboxamide,
- (1R,2R)-2-(1H-indol-3-yl)-N-((R)-1-(5-(2,2,2-trifluoroethoxy)thiophen-2-yl)ethyl)cyclopropane-1-carboxamide,
- (1S,2S)-2-(1-methyl-1H-indazol-6-yl)-N-((R)-1-(5-(2,2,2-trifluoroethoxy)thiophen-2-yl)ethyl)cyclopropanecarboxamide,
- (1R,2R)-2-(1-methyl-1H-indazol-6-yl)-N-((R)-1-(5-(2,2,2-trifluoroethoxy)thiophen-2-yl)ethyl)cyclopropanecarboxamide,
- (1S,2S)-5-((1R)-1-(2-(1H-benzo[d]imidazol-2-yl)cyclopropane-1-carboxamido)ethyl)thiophene-2-carboxylic acid tert-butyl ester,
- (1R,2R)-5-((1R)-1-(2-(1H-benzo[d]imidazol-2-yl)cyclopropane-1-carboxamido)ethyl)thiophene-2-carboxylic acid tert-butyl ester,
- (1S,2S)-5-((1R)-1-(2-(1H-benzo[d]imidazol-2-yl)cyclopropane-1-carboxamido)ethyl)thiophene-2-carboxylic acid,
- (1R,2R)-5-((1R)-1-(2-(1H-benzo[d]imidazol-2-yl)cyclopropane-1-carboxamido)ethyl)thiophene-2-carboxylic acid,
- (1S,2S)-2-(1H-imidazo[4,5-c]pyridin-2-yl)-N-((R)-1-(5-(2,2,2-trifluoroethoxy)thiophen-2-yl)ethyl)cyclopropane-1-carboxamide,
- (1R,2R)-2-(1H-imidazo[4,5-c]pyridin-2-yl)-N-((R)-1-(5-(2,2,2-trifluoroethoxy)thiophen-2-yl)ethyl)cyclopropane-1-carboxamide,
- (1S,2S)-2-(1-methyl-1H-indol-3-yl)-N-((R)-1-(5-(2,2,2-trifluoroethoxy)thiophen-2-yl)ethyl)cyclopropane-1-carboxamide,
- (1R,2R)-2-(1-methyl-1H-indol-3-yl)-N-((R)-1-(5-(2,2,2-trifluoroethoxy)thiophen-2-yl)ethyl)cyclopropane-1-carboxamide,
- (1S,2S)-5-((1R)-1-(2-(1H-benzo[d]imidazol-2-yl)cyclopropane-1-carboxamido)ethyl)thiophene-2-carboxamide,
- (1R,2R)-5-((1R)-1-(2-(1H-benzo[d]imidazol-2-yl)cyclopropane-1-carboxamido)ethyl)thiophene-2-carboxamide,
- (1S,2S)-2-(4-phenyl-1H-imidazol-2-yl)-N-((R)-1-(5-(2,2,2-trifluoroethoxy)thiophen-2-yl)ethyl)cyclopropane-1-carboxamide,
- (1R,2R)-2-(4-phenyl-1H-imidazol-2-yl)-N-((R)-1-(5-(2,2,2-trifluoroethoxy)thiophen-2-yl)ethyl)cyclopropane-1-carboxamide,
- (1S,2S)-5-((1R)-1-(2-(1H-benzo[d]imidazol-2-yl)cyclopropane-1-carboxamido)ethyl)-N,N-diethylthiophene-2-carboxamide,
- (1R,2R)-5-((1R)-1-(2-(1H-benzo[d]imidazol-2-yl)cyclopropane-1-carboxamido)ethyl)-N,N-diethylthiophene-2-carboxamide,
- (1S,2S)-2-(1H-benzo[d]imidazol-2-yl)-N-((R)-1-(5-(pyrrolidine-1-carbonyl)thiophen-2-yl)ethyl)cyclopropane-1-carboxamide,
- (1R,2R)-2-(1H-benzo[d]imidazol-2-yl)-N-((R)-1-(5-(pyrrolidine-1-carbonyl)thiophen-2-yl)ethyl)cyclopropane-1-carboxamide,
- (1R,2R)-2-(3H-imidazo[4,5-b]pyridin-2-yl)-N-((R)-1-(5-(2,2,2-trifluoroethoxy)thiophen-2-yl)ethyl)cyclopropane-1-carboxamide, (1S,2S)-2-(3H-imidazo[4,5-b]pyridin-2-yl)-N-((R)-1-(5-(2,2,2-trifluoroethoxy)thiophen-2-yl)ethyl)cyclopropane-1-carboxamide, (1R,2R)-2-(1-benzyl-1H-imidazol-2-yl)-N-((R)-1-(5-(2,2,2-trifluoroethoxy)thiophen-2-yl)ethyl)cyclopropane-1-carboxamide, (1R,2R)-2-(1-benzyl-1H-imidazol-2-yl)-N-((R)-1-(5-(2,2,2-trifluoroethoxy)thiophen-2-yl)ethyl)cyclopropane-1-carboxamide, (1S,2S)-2-(4-(pyridin-2-yl)-1H-imidazol-2-yl)-N-((R)-1-(5-(2,2,2-trifluoroethoxy)thiophen-2-yl)ethyl)cyclopropane-1-carboxamide, (1R,2R)-2-(4-(pyridin-2-yl)-1H-imidazol-2-yl)-N-((R)-1-(5-(2,2,2-trifluoroethoxy)thiophen-2-yl)ethyl)cyclopropane-1-carboxamide, (1S,2S)-2-(benzo[d]oxazol-2-yl)-N-((R)-1-(5-(2,2,2-trifluoroethoxy)thiophen-2-yl)ethyl)cyclopropane-1-carboxamide, (1R,2R)-2-(benzo[d]oxazol-2-yl)-N-((R)-1-(5-(2,2,2-trifluoroethoxy)thiophen-2-yl)ethyl)cyclopropane-1-carboxamide, (1S,2S)-2-(1H-benzo[d]imidazol-2-yl)-N-((R)-2-methyl-1-(5-(2,2,2-trifluoroethoxy)thiophen-2-yl)propyl)cyclopropane-1-carboxamide, (1R,2R)-2-(1H-benzo[d]imidazol-2-yl)-N-((R)-2-methyl-1-(5-(2,2,2-trifluoroethoxy)thiophen-2-yl)propyl)cyclopropane-1-carboxamide, (1S,2S)-N-((R)-1-(5-bromothiophen-2-yl)ethyl)-2-(quinolin-2-yl)cyclopropane-1-carboxamide, (1R,2R)-N-((R)-1-(5-bromothiophen-2-yl)ethyl)-2-(quinolin-2-yl)cyclopropane-1-carboxamide, (1S,2S)-2-(1-methyl-1H-indol-3-yl)-N-((R)-1-(2-(2,2,2-trifluoroethoxy)thiazol-5-yl)ethyl)cyclopropane-1-carboxamide, (1R,2R)-2-(1-methyl-1H-indol-3-yl)-N-((R)-1-(2-(2,2,2-trifluoroethoxy)thiazol-5-yl)ethyl)cyclopropane-1-carboxamide, (1S,2S)-2-(1H-indol-3-yl)-N-((R)-1-(2-(2,2,2-trifluoroethoxy)thiazol-5-yl)ethyl)cyclopropane-1-carboxamide, (1R,2R)-2-(1H-indol-3-yl)-N-((R)-1-(2-(2,2,2-trifluoroethoxy)thiazol-5-yl)ethyl)cyclopropane-1-carboxamide, (1S,2S)-2-(1H-benzo[d]imidazol-2-yl)-N-((R)-2-methyl-1-(5-(trifluoromethyl)thiophen-2-yl)propyl)cyclopropane-1-carboxamide, (1S,2S)-2-(1H-benzo[d]imidazol-2-yl)-N-((R)-1-(4-methyl-2-(2,2,2-trifluoroethoxy)thiazol-5-yl)ethyl)cyclopropane-1-carboxamide, (1S,2S)-2-(1H-benzo[d]imidazol-2-yl)-N-((R)-1-(quinolin-2-yl)ethyl)cyclopropane-1-carboxamide, (1S,2S)-2-(5-chloro-1H-benzo[d]imidazol-2-yl)-N-((R)-1-(5-(2,2,2-trifluoroethoxy)thiophen-2-yl)ethyl)cyclopropane-1-carboxamide, (1R,2R)-2-(5-chloro-1H-benzo[d]imidazol-2-yl)-N-((R)-1-(5-(2,2,2-trifluoroethoxy)thiophen-2-yl)ethyl)cyclopropane-1-carboxamide, (1S,2S)-2-(1-ethyl-1H-benzo[d]imidazol-2-yl)-N-((R)-1-(5-(2,2,2-trifluoroethoxy)thiophen-2-yl)ethyl)cyclopropane-1-carboxamide, (1R,2R)-2-(1-ethyl-1H-benzo[d]imidazol-2-yl)-N-((R)-1-(5-(2,2,2-trifluoroethoxy)thiophen-2-yl)ethyl)cyclopropane-1-carboxamide, (1S,2S)-N-((R)-1-(benzo[d][1,3]dioxol-5-yl)ethyl)-2-(1H-benzo[d]imidazol-2-yl)cyclopropane-1-carboxamide, (1S,2S)-2-(1H-benzo[d]imidazol-2-yl)-N-((R)-1-(5-(morpholine-4-carbonyl)thiophen-2-yl)ethyl)cyclopropane-1-carboxamide, (1R,2R)-2-(1H-benzo[d]imidazol-2-yl)-N-((R)-1-(5-(morpholine-4-carbonyl)thiophen-2-yl)ethyl)cyclopropane-1-carboxamide, (1S,2S)-2-(1-ethyl-1H-benzo[d]imidazol-2-yl)-N-((R)-1-(2-(2,2,2-trifluoroethoxy)thiazol-5-yl)ethyl)cyclopropane-1-carboxamide, (1R,2R)-2-(1-ethyl-1H-benzo[d]imidazol-2-yl)-N-((R)-1-(2-(2,2,2-trifluoroethoxy)thiazol-5-yl)ethyl)cyclopropane-1-carboxamide, (1S,2S)-N-((R)-1-(1H-indol-6-yl)ethyl)-2-(1H-benzo[d]imidazol-2-yl)cyclopropane-1-carboxamide, (1S,2S)-2-(1H-benzo[d]imidazol-2-yl)-N-((R)-cyclohexyl(5-(trifluoromethyl)thiophen-2-yl)methyl)cyclopropane-1-carboxamide, (1S,2S)-2-(1H-benzo[d]imidazol-2-yl)-N-((R)-1-(5-(3,3-difluoropyrrolidine-1-carbonyl)thiophen-2-yl)ethyl)cyclopropane-1-carboxamide, (1R,2R)-2-(1H-benzo[d]imidazol-2-yl)-N-((R)-1-(5-(3,3-difluoropyrrolidine-1-carbonyl)thiophen-2-yl)ethyl)cyclopropane-1-carboxamide, (1S,2S)-2-(1H-benzo[d]imidazol-2-yl)-N-((R)-1-(5-(piperidine-1-carbonyl)thiophen-2-yl)ethyl)cyclopropane-1-carboxamide, (1R,2R)-2-(1H-benzo[d]imidazol-2-yl)-N-((R)-1-(5-(piperidine-1-carbonyl)thiophen-2-yl)ethyl)cyclopropane-1-carboxamide, (1S,2S)-5-((1R)-1-(2-(1H-benzo[d]imidazol-2-yl)cyclopropane-1-carboxamido)ethyl)-N-(4-fluorophenyl)-N-methylthiophene-2-carboxamide, (1R,2R)-5-((1R)-1-(2-(1H-benzo[d]imidazol-2-yl)cyclopropane-1-carboxamido)ethyl)-N-(4-fluorophenyl)-N-methylthiophene-2-carboxamide, (1S,2S)-2-(1H-benzo[d]imidazol-2-yl)-N-((R)-1-(5-fluoro-1H-indol-2-yl)ethyl)cyclopropane-1-carboxamide, (1S,2S)-2-(5-chloro-1H-benzo[d]imidazol-2-yl)-N-((R)-1-(2-(2,2,2-trifluoroethoxy)thiazol-5-yl)ethyl)cyclopropane-1-carboxamide, (1R,2R)-2-(5-chloro-1H-benzo[d]imidazol-2-yl)-N-((R)-1-(2-(2,2,2-trifluoroethoxy)thiazol-5-yl)ethyl)cyclopropane-1-carboxamide, (1S,2S)-2-(1H-benzo[d]imidazol-2-yl)-N-((R)-1-(5-fluorobenzofuran-2-yl)ethyl)cyclopropane-1-carboxamide, (1S,2S)-2-(1H-benzo[d]imidazol-2-yl)-N-((R)-1-(5-fluorobenzo[b]thiophen-2-yl)ethyl)cyclopropane-1-carboxamide, (1S,2S)-2-(1H-benzo[d]imidazol-2-yl)-N-((R)-1-(5-(2,2-dimethylpyrrolidine-1-carbonyl)thiophen-2-yl)ethyl)cyclopropane-1-carboxamide, (1R,2R)-2-(1H-benzo[d]imidazol-2-yl)-N-((R)-1-(5-(2,2-dimethylpyrrolidine-1-carbonyl)thiophen-2-yl)ethyl)cyclopropane-1-carboxamide, (1S,2S)-2-(1H-benzo[d]imidazol-2-yl)-N-((R)-1-(5-(4-methylpiperazine-1-carbonyl)thiophen-2-yl)ethyl)cyclopropane-1-carboxamide, (1R,2R)-2-(1H-benzo[d]imidazol-2-yl)-N-((R)-1-(5-(4-methylpiperazine-1-carbonyl)thiophen-2-yl)ethyl)cyclopropane-1-carboxamide, (1S,2S)-2-(1H-benzo[d]imidazol-2-yl)-N-((R)-cyclopropyl(5-(trifluoromethyl)thiophen-2-yl)methyl)cyclopropane-1-carboxamide, (1S,2S)-2-(1H-benzo[d]imidazol-2-yl)-N-((R)-1-(2,3-dihydrobenzo[b][1,4]dioxin-6-yl)ethyl)cyclopropane-1-carboxamide, (1S,2S)-2-(5-methoxy-1H-benzo[d]imidazol-2-yl)-N-((R)-1-(5-(2,2,2-trifluoroethoxy)thiophen-2-yl)ethyl)cyclopropane-1-carboxamide,
(1R,2R)-2-(5-methoxy-1H-benzo[d]imidazol-2-yl)-N-((R)-1-(5-(2,2,2-trifluoroethoxy)thiophen-2-yl)ethyl)cyclopropane-1-carboxamide,
(1S,2S)-2-(1H-benzo[d]imidazol-2-yl)-N-((R)-1-(3-cyclopropyl-1,2,4-oxadiazol-5-yl)ethyl)cyclopropane-1-carboxamide,
(1S,2S)-2-(1H-benzo[d]imidazol-2-yl)-N-((R)-1-(2,2-difluorobenzo[d][1,3]dioxol-5-yl)ethyl)cyclopropane-1-carboxamide,
(1S,2S)-2-(1H-benzo[d]imidazol-2-yl)-N-((R)-1-(5-cyclopropylfuran-2-yl)ethyl)cyclopropane-1-carboxamide,
(1S,2S)-2-(1H-benzo[d]imidazol-2-yl)-N-((R)-1-(5-(piperazine-1-carbonyl)thiophen-2-yl)ethyl)cyclopropane-1-carboxamide,
(1R,2R)-2-(1H-benzo[d]imidazol-2-yl)-N-((R)-1-(5-(piperazine-1-carbonyl)thiophen-2-yl)ethyl)cyclopropane-1-carboxamide,
(1S,2S)-2-(1H-benzo[d]imidazol-2-yl)-N-((R)-1-(benzofuran-2-yl)ethyl)cyclopropane-1-carboxamide,
(1S,2S)-2-(5-chloro-1H-benzo[d]imidazol-2-yl)-N-((R)-1-(3-cyclopropyl-1,2,4-oxadiazol-5-yl)ethyl)cyclopropane-1-carboxamide,
(1R,2R)-2-(5-chloro-1H-benzo[d]imidazol-2-yl)-N-((R)-1-(3-cyclopropyl-1,2,4-oxadiazol-5-yl)ethyl)cyclopropane-1-carboxamide,
(1S,2S)-2-(1H-benzo[d]imidazol-2-yl)-N-((R)-1-(2,3-dihydrobenzofuran-5-yl)ethyl)cyclopropane-1-carboxamide,
(1S,2S)-2-(1H-benzo[d]imidazol-2-yl)-N-((R)-1-(5-methoxybenzofuran-2-yl)ethyl)cyclopropane-1-carboxamide,
(1S,2S)-2-(1H-benzo[d]imidazol-2-yl)-N-((R)-1-(furo[3,2-b]pyridin-2-yl)ethyl)cyclopropane-1-carboxamide,
(1S,2S)-2-(1H-benzo[d]imidazol-2-yl)-N-((S)-1-(furo[3,2-b]pyridin-2-yl)ethyl)cyclopropane-1-carboxamide,
(1S,2S)-2-(5-chloro-1H-benzo[d]imidazol-2-yl)-N-((R)-1-(5-fluorobenzofuran-2-yl)ethyl)cyclopropane-1-carboxamide,
(1S,2S)-2-(1H-benzo[d]imidazol-2-yl)-N-((R)-1-(5-chlorobenzofuran-2-yl)ethyl)cyclopropane-1-carboxamide,
(1S,2S)-2-(1H-benzo[d]imidazol-2-yl)-N-((R)-1-(5-(3,3-difluoroazetidine-1-carbonyl)thiophen-2-yl)ethyl)cyclopropane-1-carboxamide,
(1R,2R)-2-(1H-benzo[d]imidazol-2-yl)-N-((R)-1-(5-(3,3-difluoroazetidine-1-carbonyl)thiophen-2-yl)ethyl)cyclopropane-1-carboxamide,
5-((R)-1-((1S,2S)-2-(1H-benzo[d]imidazol-2-yl)cyclopropane-1-carboxamido)ethyl)-N,N-dimethylthiophene-2-carboxamide,
5-((R)-1-((1R,2R)-2-(1H-benzo[d]imidazol-2-yl)cyclopropane-1-carboxamido)ethyl)-N,N-dimethylthiophene-2-carboxamide,
(1S,2S)-2-(6-chloro-3H-imidazo[4,5-b]pyridin-2-yl)-N-((R)-1-(5-(2,2,2-trifluoroethoxy)thiophen-2-yl)ethyl)cyclopropane-1-carboxamide,
(1R,2R)-2-(6-chloro-3H-imidazo[4,5-b]pyridin-2-yl)-N-((R)-1-(5-(2,2,2-trifluoroethoxy)thiophen-2-yl)ethyl)cyclopropane-1-carboxamide,
(1S,2S)-2-(1H-benzo[d]imidazol-2-yl)-N-((R)-1-(1-methyl-1H-indol-6-yl)ethyl)cyclopropane-1-carboxamide,
(1S,2S)-N-((R)-1-(5-(azepane-1-carbonyl)thiophen-2-yl)ethyl)-2-(1H-benzo[d]imidazol-2-yl)cyclopropane-1-carboxamide,
(1R,2R)-N-((R)-1-(5-(azepane-1-carbonyl)thiophen-2-yl)ethyl)-2-(1H-benzo[d]imidazol-2-yl)cyclopropane-1-carboxamide,
(1S,2S)-2-(1H-benzo[d]imidazol-2-yl)-N-((R)-1-(5,7-difluorobenzofuran-2-yl)ethyl)cyclopropane-1-carboxamide,
(1S,2S)-2-(1H-benzo[d]imidazol-2-yl)-N-((R)-1-(2-phenylthiazol-5-yl)ethyl)cyclopropane-1-carboxamide,
(1S,2S)-2-(benzo[d]oxazol-2-yl)-N-((R)-1-(2-(2,2,2-trifluoroethoxy)thiazol-5-yl)ethyl)cyclopropane-1-carboxamide,
(1R,2R)-2-(benzo[d]oxazol-2-yl)-N-((R)-1-(2-(2,2,2-trifluoroethoxy)thiazol-5-yl)ethyl)cyclopropane-1-carboxamide,
(1S,2S)-2-(1H-benzo[d]imidazol-2-yl)-N-((R)-1-(5,6-difluorobenzofuran-2-yl)ethyl)cyclopropane-1-carboxamide,
(1S,2S)-2-(1H-benzo[d]imidazol-2-yl)-N-((R)-1-(4,6-difluorobenzofuran-2-yl)ethyl)cyclopropane-1-carboxamide,
(1S,2S)-2-(1H-benzo[d]imidazol-2-yl)-N-((R)-1-(pyrazolo[1,5-a]pyridin-2-yl)ethyl)cyclopropane-1-carboxamide,
(1S,2S)-2-(1H-benzo[d]imidazol-2-yl)-N-((R)-1-(5-(4,4-difluoropiperidine-1-carbonyl)thiophen-2-yl)ethyl)cyclopropane-1-carboxamide,
(1R,2R)-2-(1H-benzo[d]imidazol-2-yl)-N-((R)-1-(5-(4,4-difluoropiperidine-1-carbonyl)thiophen-2-yl)ethyl)cyclopropane-1-carboxamide,
(1S,2S)-2-(1H-benzo[d]imidazol-2-yl)-N-((1R)-1-(5-(3-fluoropiperidine-1-carbonyl)thiophen-2-yl)ethyl)cyclopropane-1-carboxamide,
(1R,2R)-2-(1H-benzo[d]imidazol-2-yl)-N-((1R)-1-(5-(3-fluoropiperidine-1-carbonyl)thiophen-2-yl)ethyl)cyclopropane-1-carboxamide,
(1S,2S)-2-(1H-benzo[d]imidazol-2-yl)-N-((R)-1-(7-fluorobenzofuran-2-yl)ethyl)cyclopropane-1-carboxamide,
(1S,2S)-2-(1H-benzo[d]imidazol-2-yl)-N-((R)-1-(4-fluorobenzofuran-2-yl)ethyl)cyclopropane-1-carboxamide,
(1S,2S)-N-((R)-1-(5-fluorobenzofuran-2-yl)ethyl)-2-(1H-indol-3-yl)cyclopropane-1-carboxamide,
(1R,2R)-N-((R)-1-(5-fluorobenzofuran-2-yl)ethyl)-2-(1H-indol-3-yl)cyclopropane-1-carboxamide,
(1S,2S)-2-(1H-benzo[d]imidazol-2-yl)-N-((R)-1-(furo[3,2-c]pyridin-2-yl)ethyl)cyclopropane-1-carboxamide,
(1S,2S)-2-(1H-benzo[d]imidazol-2-yl)-N-((S)-1-(furo[3,2-c]pyridin-2-yl)ethyl)cyclopropane-1-carboxamide,
(1S,2S)-2-(1H-benzo[d]imidazol-2-yl)-N-((R)-1-(6-fluorobenzofuran-2-yl)ethyl)cyclopropane-1-carboxamide,
(1S,2S)-2-(1H-benzo[d]imidazol-2-yl)-N-((R)-1-(5-fluoro-3-methylbenzofuran-2-yl)ethyl)cyclopropane-1-carboxamide,
(1S,2S)-2-(1-ethyl-1H-benzo[d]imidazol-2-yl)-N-((R)-1-(5-fluorobenzofuran-2-yl)ethyl)cyclopropane-1-carboxamide,
(1S,2S)-N-((R)-1-(5-fluorobenzofuran-2-yl)ethyl)-2-(1-methyl-1H-indazol-6-yl)cyclopropane-1-carboxamide,
(1R,2R)-N-((R)-1-(5-fluorobenzofuran-2-yl)ethyl)-2-(1-methyl-1H-indazol-6-yl)cyclopropane-1-carboxamide,
(1S,2S)-2-(1H-benzo[d]imidazol-2-yl)-N-((R)-1-(5-fluorobenzo[d]thiazol-2-yl)ethyl)cyclopropane-1-carboxamide, (1S,2S)-2-(1H-benzo[d]imidazol-2-yl)-N-((S)-1-(5-fluorobenzo[d]thiazol-2-yl)ethyl)cyclopropane-1-carboxamide, (1S,2S)-2-(1H-benzo[d]imidazol-2-yl)-N-((R)-1-(5-fluorobenzo[d]oxazol-2-yl)ethyl)cyclopropane-1-carboxamide, (1S,2S)-2-(5-methyl-3H-imidazo[4,5-b]pyridin-2-yl)-N-((R)-1-(5-(2,2,2-trifluoroethoxy)thiophen-2-yl)ethyl)cyclopropane-1-carboxamide, (1R,2R)-2-(5-methyl-3H-imidazo[4,5-b]pyridin-2-yl)-N-((R)-1-(5-(2,2,2-trifluoroethoxy)thiophen-2-yl)ethyl)cyclopropane-1-carboxamide, (1S,2S)-2-(1H-benzo[d]imidazol-2-yl)-N-((R)-1-(5-cyanobenzofuran-2-yl)ethyl)cyclopropane-1-carboxamide, (1S,2S)-2-(5-chlorobenzo[d]oxazol-2-yl)-N-((R)-1-(5-fluorobenzofuran-2-yl)ethyl)cyclopropane-1-carboxamide, (1R,2R)-2-(5-chlorobenzo[d]oxazol-2-yl)-N-((R)-1-(5-fluorobenzofuran-2-yl)ethyl)cyclopropane-1-carboxamide, (1S,2S)-2-(1H-benzo[d]imidazol-2-yl)-N-((R)-1-(5-(trifluoromethyl)benzofuran-2-yl)ethyl)cyclopropane-1-carboxamide, (1S,2S)-2-(1-ethyl-1H-benzo[d]imidazol-2-yl)-N-((R)-1-(6-fluorobenzofuran-2-yl)ethyl)cyclopropane-1-carboxamide, (1S,2S)-2-(1H-benzo[d]imidazol-2-yl)-N-((S)-1-(5-fluorobenzofuran-2-yl)ethyl)cyclopropane-1-carboxamide, (1S,2S)-2-(1H-benzo[d]imidazol-2-yl)-N-((5-fluorobenzofuran-2-yl)methyl)cyclopropane-1-carboxamide, (1S,2S)-2-(1H-benzo[d]imidazol-2-yl)-N-((R)-1-(6-fluorobenzo[d]oxazol-2-yl)ethyl)cyclopropane-1-carboxamide, (1S,2S)-2-(1H-benzo[d]imidazol-2-yl)-N-((S)-2-methyl-1-(5-(trifluoromethyl)thiophen-2-yl)propyl)cyclopropane-1-carboxamide, (1S,2S)-2-(1H-benzo[d]imidazol-2-yl)-N-((S)-cyclohexyl(5-(trifluoromethyl)thiophen-2-yl)methyl)cyclopropane-1-carboxamide, (1S,2S)-N-((R)-1-(5-fluorobenzofuran-2-yl)ethyl)-2-(imidazo[1,5-a]pyridin-3-yl)cyclopropane-1-carboxamide, (1R,2R)-N-((R)-1-(5-fluorobenzofuran-2-yl)ethyl)-2-(imidazo[1,5-a]pyridin-3-yl)cyclopropane-1-carboxamide, (1S,2R)-N-((R)-1-(5-fluorobenzofuran-2-yl)ethyl)-2-(imidazo[1,5-a]pyridin-3-yl)cyclopropane-1-carboxamide, (1R,2S)-N-((R)-1-(5-fluorobenzofuran-2-yl)ethyl)-2-(imidazo[1,5-a]pyridin-3-yl)cyclopropane-1-carboxamide, (1S,2S)-2-(5-fluoro-1H-benzo[d]imidazol-2-yl)-N-((R)-1-(5-(2,2,2-trifluoroethoxy)thiophen-2-yl)ethyl)cyclopropane-1-carboxamide, (1S,2S)-2-(1H-benzo[d]imidazol-2-yl)-N-((R)-1-(6-fluorobenzo[b]thiophen-2-yl)ethyl)cyclopropane-1-carboxamide, (1S,2S)-2-(1H-benzo[d]imidazol-2-yl)-N-((R)-1-(6-fluorobenzo[b]thiophen-2-yl)-2-methylpropyl)cyclopropane-1-carboxamide, (1S,2S)-2-(4-chloro-1H-benzo[d]imidazol-2-yl)-N-((R)-1-(5-(2,2,2-trifluoroethoxy)thiophen-2-yl)ethyl)cyclopropane-1-carboxamide, (1R,2R)-2-(4-chloro-1H-benzo[d]imidazol-2-yl)-N-((R)-1-(5-(2,2,2-trifluoroethoxy)thiophen-2-yl)ethyl)cyclopropane-1-carboxamide, (1S,2S)-2-(1H-benzo[d]imidazol-2-yl)-N-((R)-1-(6-(trifluoromethyl)benzofuran-2-yl)ethyl)cyclopropane-1-carboxamide, (1S,2S)-2-(1H-benzo[d]imidazol-2-yl)-N-((R)-1-(6-fluorobenzofuran-2-yl)-2-methylpropyl)cyclopropane-1-carboxamide, (1S,2S)-2-(5-fluoro-1H-benzo[d]imidazol-2-yl)-N-((R)-1-(5-fluorobenzofuran-2-yl)ethyl)cyclopropane-1-carboxamide, (1S,2S)-2-(1H-benzo[d]imidazol-2-yl)-N-((R)-1-(6-fluoro-1H-benzo[d]imidazol-2-yl)ethyl)cyclopropane-1-carboxamide, (1S,2S)-2-(1H-benzo[d]imidazol-2-yl)-N-((S)-1-(6-fluoro-1H-benzo[d]imidazol-2-yl)ethyl)cyclopropane-1-carboxamide, (1S,2S)-2-(1H-benzo[d]imidazol-2-yl)-N-((R)-1-(6-fluorobenzofuran-2-yl)ethyl)-N-methylcyclopropane-1-carboxamide, (1S,2S)-2-(1H-benzo[d]imidazol-2-yl)-N-((R)-1-(3,6-difluorobenzo[b]thiophen-2-yl)ethyl)cyclopropane-1-carboxamide, (1S,2S)-2-(1H-benzo[d]imidazol-2-yl)-N-((R)-1-(5-fluoro-1-methyl-1H-indol-2-yl)ethyl)cyclopropane-1-carboxamide, (1S,2S)-2-(1H-benzo[d]imidazol-2-yl)-N-((S)-1-(5-fluoro-1-methyl-1H-indol-2-yl)ethyl)cyclopropane-1-carboxamide, (1S,2S)-2-(1H-benzo[d]imidazol-2-yl)-N-((R)-1-(5-fluorobenzofuran-2-yl)ethyl-2,2,2-d$_3$)cyclopropane-1-carboxamide, (1S,2S)-2-(1H-benzo[d]imidazol-2-yl)-N-((S)-1-(5-fluorobenzofuran-2-yl)ethyl-2,2,2-d$_3$)cyclopropane-1-carboxamide, (1S,2S)-2-(1H-benzo[d]imidazol-2-yl)-N-((R)-1-(5-fluorobenzofuran-2-yl)butyl)cyclopropane-1-carboxamide, (1S,2S)-2-(1H-benzo[d]imidazol-2-yl)-N-((S)-1-(5-fluorobenzofuran-2-yl)butyl)cyclopropane-1-carboxamide, (1S,2S)-2-(1-ethyl-1H-benzo[d]imidazol-2-yl)-N-((R)-1-(6-fluoro-1H-benzo[d]imidazol-2-yl)ethyl)cyclopropane-1-carboxamide, and (1S,2S)-2-(1-ethyl-1H-benzo[d]imidazol-2-yl)-N-((S)-1-(6-fluoro-1H-benzo[d]imidazol-2-yl)ethyl)cyclopropane-1-carboxamide.

44. A pharmaceutical composition comprising:
the compound according to claim 1, a tautomer or a stereoisomer of the compound, a pharmaceutically acceptable salt thereof, or a solvate thereof, as an active ingredient; and
a pharmaceutically acceptable carrier.

45. The compound, a pharmaceutically acceptable salt thereof, or a solvate thereof according to claim 42, wherein the compound is selected from:

(1S,2S)-2-(1H-benzo[d]imidazol-2-yl)-N-((R)-1-(5-(2,2,2-trifluoroethoxy)thiophen-2-yl)ethyl)cyclopropane-1-carboxamide, and (1R,2R)-2-(1H-benzo[d]imidazol-2-yl)-N-((R)-1-(5-(2,2,2-trifluoroethoxy)thiophen-2-yl)ethyl)cyclopropane-1-carboxamide.

46. The compound, a pharmaceutically acceptable salt thereof, or a solvate thereof according to claim 43, wherein the compound is (1S,2S)-2-(1H-benzo[d]imidazol-2-yl)-N-((R)-1-(5-fluorobenzofuran-2-yl)ethyl)cyclopropane-1-carboxamide.

47. The compound, a pharmaceutically acceptable salt thereof, or a solvate thereof according to claim 43, wherein the compound is (1S,2S)-2-(1H-benzo[d]imidazol-2-yl)-N-((R)-1-(6-fluorobenzofuran-2-yl)ethyl)cyclopropane-1-carboxamide.

48. The compound, a pharmaceutically acceptable salt thereof, or a solvate thereof according to claim 43, wherein the compound is (1S,2S)-2-(1H-benzo[d]imidazol-2-yl)-N-((R)-1-(2,2-difluorobenzo[d][1,3]dioxol-5-yl)ethyl)cyclopropane-1-carboxamide.

49. The compound, a pharmaceutically acceptable salt thereof, or a solvate thereof according to claim 42, wherein the compound is selected from:
- (1S,2S)-2-(1-methyl-1H-benzo[d]imidazol-2-yl)-N-((R)-1-(5-(2,2,2-trifluoroethoxy)thiophen-2-yl)ethyl)cyclopropane-1-carboxamide, and
- (1R,2R)-2-(1-methyl-1H-benzo[d]imidazol-2-yl)-N-((R)-1-(5-(2,2,2-trifluoroethoxy)thiophen-2-yl)ethyl)cyclopropane-1-carboxamide.

50. The compound, a pharmaceutically acceptable salt thereof, or a solvate thereof according to claim 43, wherein the compound is selected from:
- (1S,2S)-2-(1H-benzo[d]imidazol-2-yl)-N-((R)-1-(4,6-difluorobenzofuran-2-yl)ethyl)cyclopropane-1-carboxamide,
- (1S,2S)-2-(5-chloro-1H-benzo[d]imidazol-2-yl)-N-((R)-1-(5-(2,2,2-trifluoroethoxy)thiophen-2-yl)ethyl)cyclopropane-1-carboxamide,
- (1R,2R)-2-(5-chloro-1H-benzo[d]imidazol-2-yl)-N-((R)-1-(5-(2,2,2-trifluoroethoxy)thiophen-2-yl)ethyl)cyclopropane-1-carboxamide,
- (1S,2S)-2-(1H-benzo[d]imidazol-2-yl)-N-((R)-1-(5-fluoro-1H-indol-2-yl)ethyl)cyclopropane-1-carboxamide,
- (1S,2S)-2-(5-fluoro-1H-benzo[d]imidazol-2-yl)-N-((R)-1-(5-fluorobenzofuran-2-yl)ethyl)cyclopropane-1-carboxamide,
- (1S,2S)-2-(1H-benzo[d]imidazol-2-yl)-N-((R)-1-(6-fluorobenzo[b]thiophen-2-yl)ethyl)cyclopropane-1-carboxamide,
- (1S,2S)-2-(1H-benzo[d]imidazol-2-yl)-N-((R)-1-(5-fluorobenzo[b]thiophen-2-yl)ethyl)cyclopropane-1-carboxamide, and
- (1S,2S)-2-(1H-benzo[d]imidazol-2-yl)-N-((R)-1-(5,6-difluorobenzofuran-2-yl)ethyl)cyclopropane-1-carboxamide.

* * * * *